United States Patent
Isaacs et al.

(10) Patent No.: US 8,513,234 B2
(45) Date of Patent: Aug. 20, 2013

(54) HIV INTEGRASE INHIBITORS

(75) Inventors: Richard C. A. Isaacs, Harleysville, PA (US); Wayne J. Thompson, Lansdale, PA (US); Peter D. Williams, Harleysville, PA (US); Dai-Shi Su, Dresher, PA (US); Shankar Venkatraman, Lansdale, PA (US); Mark W. Embrey, Harleysville, PA (US); Thorsten E. Fisher, Hatfield, PA (US); John S. Wai, Harleysville, PA (US); David C. Dubost, Collegeville, PA (US); Richard G. Ball, Edison, NJ (US); Eric J. Choi, Westfield, NJ (US); Tao Pei, Morganville, NJ (US); Sarah L. Trice, Glenside, PA (US); Neil Campbell, Cherry Hill, NJ (US); Matthew Maddess, Boston, MA (US); Peter E. Maligres, Fanwood, NJ (US); Michael Shevlin, Plainfield, NJ (US); Zhiguo Jake Song, Edison, NJ (US); Dietrich P. Steinhuebel, Boston, MA (US); Neil A. Strotman, Monmouth Junction, NJ (US); Jingjun Yin, Green Brook, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 482 days.

(21) Appl. No.: 12/572,341

(22) Filed: Oct. 2, 2009

(65) Prior Publication Data
US 2010/0087419 A1 Apr. 8, 2010

Related U.S. Application Data

(60) Provisional application No. 61/195,271, filed on Oct. 6, 2008.

(51) Int. Cl.
*C07D 487/12* (2006.01)

(52) U.S. Cl.
USPC ..................................... 514/214.02; 540/579

(58) Field of Classification Search
USPC .................... 514/214.02; 540/579
See application file for complete search history.

(56) References Cited

U.S. PATENT DOCUMENTS

| | | |
|---|---|---|
| 7,037,908 B2 | 5/2006 | Naidu et al. |
| 7,115,601 B2 | 10/2006 | Naidu et al. |
| 7,135,467 B2 | 11/2006 | Walker et al. |
| 7,157,447 B2 | 1/2007 | Naidu et al. |
| 7,169,780 B2 | 1/2007 | Crescenzi et al. |
| 7,173,022 B2 | 2/2007 | Naidu et al. |
| 7,176,196 B2 | 2/2007 | Naidu et al. |
| 7,192,948 B2 | 3/2007 | Banville et al. |
| 7,211,572 B2 | 5/2007 | Miyazaki et al. |
| 7,217,713 B2 | 5/2007 | Crescenzi et al. |
| 7,232,819 B2 | 6/2007 | Di Francesco et al. |
| 7,273,859 B2 | 9/2007 | Naidu |
| 7,279,487 B2 | 10/2007 | Egbertson et al. |
| 7,414,045 B2 | 8/2008 | Crescenzi et al. |
| 7,419,969 B2 | 9/2008 | Naidu et al. |
| 7,435,734 B2 | 10/2008 | Crescenzi et al. |
| 7,494,984 B2 | 2/2009 | Banville et al. |
| 7,504,405 B2 | 3/2009 | Wang et al. |
| 2004/0229909 A1 | 11/2004 | Kiyama et al. |
| 2007/0083045 A1 | 4/2007 | Di Francesco et al. |
| 2007/0111984 A1 | 5/2007 | Naidu et al. |
| 2007/0111985 A1 | 5/2007 | Naidu et al. |

(Continued)

FOREIGN PATENT DOCUMENTS

| EP | 1698628 A1 | 9/2006 |
|---|---|---|
| WO | 2005/061501 A2 | 7/2005 |

(Continued)

OTHER PUBLICATIONS

Ferrara et al. "Synthesis of a hexahydropyrimido[1,2-α]azepine-2-carboxamide derivative useful as an HIV integrase inhibitor", Tetrahedron Letters, 2007, vol. 48, pp. 8379-8382.

(Continued)

*Primary Examiner* — Brenda Coleman
(74) *Attorney, Agent, or Firm* — Sheldon O. Herber; Jeffrey P. Bergman

(57) ABSTRACT

Compounds of Formula I are inhibitors of HIV integrase and inhibitors of HIV replication:

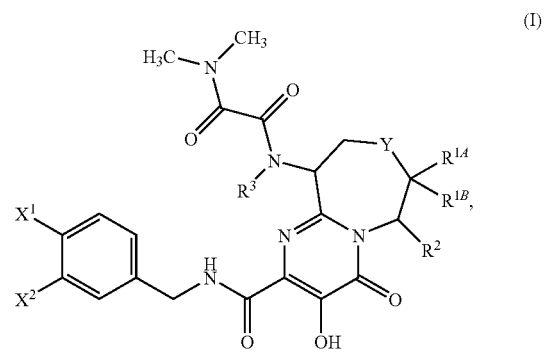

wherein $X^1, X^2, Y, R^{1A}, R^{1B}, R^2$ and $R^3$ are defined herein. The compounds are useful for the prophylaxis or treatment of infection by HIV and the prophylaxis, treatment, or delay in the onset or progression of AIDS. The compounds are employed against HIV infection and AIDS as compounds per se (or as hydrates or solvates thereof) or in the form of pharmaceutically acceptable salts. The compounds and their salts can be employed as ingredients in pharmaceutical compositions, optionally in combination with other antivirals, immunomodulators, antibiotics or vaccines. Processes for making compounds of Formula I and intermediates thereof are also described.

21 Claims, 5 Drawing Sheets

(56) References Cited

U.S. PATENT DOCUMENTS

| | | |
|---|---|---|
| 2007/0112190 A1 | 5/2007 | Naidu |
| 2007/0142635 A1 | 6/2007 | Askin et al. |
| 2007/0149556 A1 | 6/2007 | Mikamiyama et al. |
| 2007/0281917 A1 | 12/2007 | Naidu et al. |
| 2008/0004265 A1 | 1/2008 | Walker et al. |
| 2008/0176869 A1 | 7/2008 | Crescenzi et al. |
| 2008/0249112 A1 | 10/2008 | Wang et al. |
| 2008/0275004 A1 | 11/2008 | Crescenzi et al. |
| 2009/0171082 A1 | 7/2009 | Wang et al. |

FOREIGN PATENT DOCUMENTS

| | | |
|---|---|---|
| WO | 2006/060225 A2 | 6/2006 |
| WO | 2006/103399 A1 | 10/2006 |
| WO | 2007/058646 A1 | 5/2007 |
| WO | 2007/064316 A1 | 6/2007 |

OTHER PUBLICATIONS

Kinzel et al. "The synthesis of tetrahydropyridopyrimidones as a new scaffold for HIV-1 integrase inhibitors", Tetrahedron Letters, 2007, vol. 48, pp. 6552-6555.

Muraglia et al. "Design and Synthesis of Bicyclic Pyrimidinones as Potent and Orally Bioavailable HIV-1 Integrase Inhibitors", Journal of Medicinal Chemistry, 2008, vol. 51, pp. 861-874.

Pearl et al. "A structural model for the retroviral proteases", Nature, 1987 vol. 329, pp. 351-354.

Power et al. "Nucleotide Sequence of SRV-1, a Type D Simian Acquired Immune Deficiency Syndrome Retrovirus", Science, 1986, vol. 231, pp. 1567-1572.

Ratner et al. "Complete nucleotide sequence of the AIDS virus, HTLV-III", Nature, 1985, vol. 313, pp. 277-284.

Toh et al. "Close structural resemblance between putative polymerase of a *Drosophila* transposable genetic element 17.6 and pol gene product of Moloney murine leukaemia virus", The EMBO Journal, 1985, vol. 4, pp. 1267-1272.

HIV INTEGRASE INHIBITORS

CROSS-REFERENCE TO RELATED APPLICATIONS

This application claims the benefit of U.S. Provisional Application No. 61/195,271 (filed Oct. 6, 2008), the disclosure of which is hereby incorporated by reference in its entirety.

FIELD OF THE INVENTION

The present invention is directed to certain 2-{[(substituted benzyl)amino]carbonyl}-3-hydroxy-4-oxo-4,6,7,8,9,10-hexahydropyrimido[1,2-a]azepin-10-yl)-N,N',N'-trialkylethanediamide compounds, certain 2-{[(substituted benzyl)amino]carbonyl}-3-hydroxy-4-oxo-6,7,9,10-tetrahydro-4H-pyrimido[1,2-d][1,4]oxazepin-10-yl)-N N' N'-trialkylethanediamide compounds, and pharmaceutically acceptable salts thereof, their synthesis, and their use as inhibitors of the HIV integrase enzyme. The compounds and pharmaceutically acceptable salts thereof of the present invention are useful in the prophylaxis or treatment of infection by HIV and in the prophylaxis, delay in the onset or progression, or treatment of AIDS.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277 (1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication. The inhibition of integrase in vitro and HIV replication in cells is a direct result of inhibiting the strand transfer reaction catalyzed by the recombinant integrase in vitro in HIV infected cells.

The following references are of interest as background:

Kinzel et al., Tet. Letters 2007, 48(37): pp. 6552-6555 discloses the synthesis of tetrahydropyridopyrimidones as a scaffold for HIV-1 integrase inhibitors.

Ferrara et al., Tet. Letters 2007, 48(37), pp. 8379-8382 discloses the synthesis of a hexahydropyrimido[1,2-a]azepine-2-carboxamide derivative useful as an HIV integrase inhibitor.

Muraglia et al., J. Med. Chem. 2008, 51: 861-874 discloses the design and synthesis of bicyclic pyrimidinones as potent and orally bioavailable HIV-1 integrase inhibitors.

US2004/229909 discloses certain compounds having integrase inhibitory activity.

U.S. Pat. No. 7,232,819 and US 2007/0083045 disclose certain 5,6-dihydroxypyrimidine-4-carboxamides as HIV integrase inhibitors.

U.S. Pat. No. 7,169,780, U.S. Pat. No. 7,217,713, and US 2007/0123524 disclose certain N-substituted 5-hydroxy-6-oxo-1,6-dihydropyrimidine-4-carboxamides as HIV integrase inhibitors.

U.S. Pat. No. 7,279,487 discloses certain hydroxynaphthyridinone carboxamides that are useful as HIV integrase inhibitors.

U.S. Pat. No. 7,135,467 and U.S. Pat. No. 7,037,908 disclose certain pyrimidine carboxamides that are useful as HIV integrase inhibitors.

U.S. Pat. No. 7,211,572 discloses certain nitrogenous condensed ring compounds that are HIV integrase inhibitors.

U.S. Pat. No. 7,414,045 discloses certain tetrahydro-4H-pyrido[1,2-a]pyrimidine carboxamides, hexahydropyrimido[1,2-a]azepine carboxamides, and related compounds that are useful as HIV integrase inhibitors.

WO 2006/103399 discloses certain tetrahydro-4H-pyrimidooxazepine carboaxmides, tetrahydropyrazinopyrimidine carboxamides, hexahydropyrimidodiazepine carboxamides, and related compounds that are useful as HIV integrase inhibitors.

US 2007/0142635 discloses processes for preparing hexahydropyrimido[1,2-a]azepine-2-carboxylates and related compounds.

US 2007/0149556 discloses certain hydroxypyrimidinone derivatives having HIV integrase inhibitory activity.

Various pyrimidinone compounds useful as HIV integrase inhibitors are also disclosed in U.S. Pat. Nos. 7,115,601, 7,157,447, 7,173,022, 7,176,196, 7,192,948, 7,273,859, and 7,419,969.

US 2007/0111984 discloses a series of bicyclic pyrimidinone compounds useful as HIV integrase inhibitors.

SUMMARY OF THE INVENTION

The present invention is directed to certain 2-{[(substituted benzyl)amino]carbonyl}-3-hydroxy-4-oxo-4,6,7,8,9,10-hexahydropyrimido[1,2-a]azepin-10-yl)-N,N',N'-trialkylethanediamide compounds and certain 2-{[(substituted benzyl)amino]carbonyl}-3-hydroxy-4-oxo-6,7,9,10-tetrahydro-4H-pyrimido[1,2-d][1,4]oxazepin-10-yl)-N N' N'-trialkylethanediamide compounds. These compounds (including hydrates and solvates thereof), optionally in the form of pharmaceutically acceptable salts, are useful in the inhibition of HIV integrase, the prevention of infection by HIV, the treatment of infection by HIV and in the prevention, treatment, and delay in the onset or progression of AIDS and/or ARC, either as compounds per se, or as pharmaceutical composition ingredients, whether or not in combination with other HIV/AIDS antivirals, anti-infectives, immunomodulators, antibiotics or vaccines. More particularly, the present invention includes compounds of Formula I and pharmaceutically acceptable salts thereof:

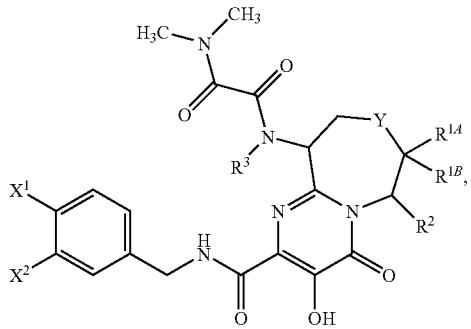

(I)

wherein:
$X^1$ and $X^2$ are each independently H, halogen, or $C_{1-3}$ alkyl, with the proviso that at least one of $X^1$ and $X^2$ is other than H;
Y is $CH_2$ or O;
$R^{1A}$ is H or $C_{1-3}$ alkyl;
$R^{1B}$ is H, $C_{1-3}$ alkyl, or O—$C_{1-4}$ alkyl;
$R^2$ is H or $C_{1-3}$ alkyl; and
$R^3$ is $C_{1-3}$ alkyl;
and provided that:
(C) when Y is O, then $R^{1A}$ and $R^{1B}$ are both H and $R^2$ is $C_{1-3}$ alkyl; and
(D) when Y is $CH_2$, then
(i) $R^2$ is H, $R^{1A}$ is $C_{1-3}$ alkyl and $R^{1B}$ is $C_{1-3}$ alkyl or O—$C_{1-4}$ alkyl;
(ii) $R^2$ is $C_{1-3}$ alkyl, $R^{1A}$ is H, and $R^{1B}$ is H; or
(iii) $R^2$ is H, $R^{1A}$ is H, and $R^{1B}$ is O—$C_{1-4}$ alkyl.

The present invention also includes pharmaceutical compositions containing a compound of Formula I or a pharmaceutically acceptable salt thereof. The present invention further includes methods involving compounds of Formula I for the treatment of AIDS, the delay in the onset or progression of AIDS, the prophylaxis of AIDS, the prophylaxis of infection by HIV, and the treatment of infection by HIV.

Other embodiments, aspects and features of the present invention are either further described in or will be apparent from the ensuing description, examples and appended claims.

DETAILED DESCRIPTION OF THE INVENTION

Figure 1:
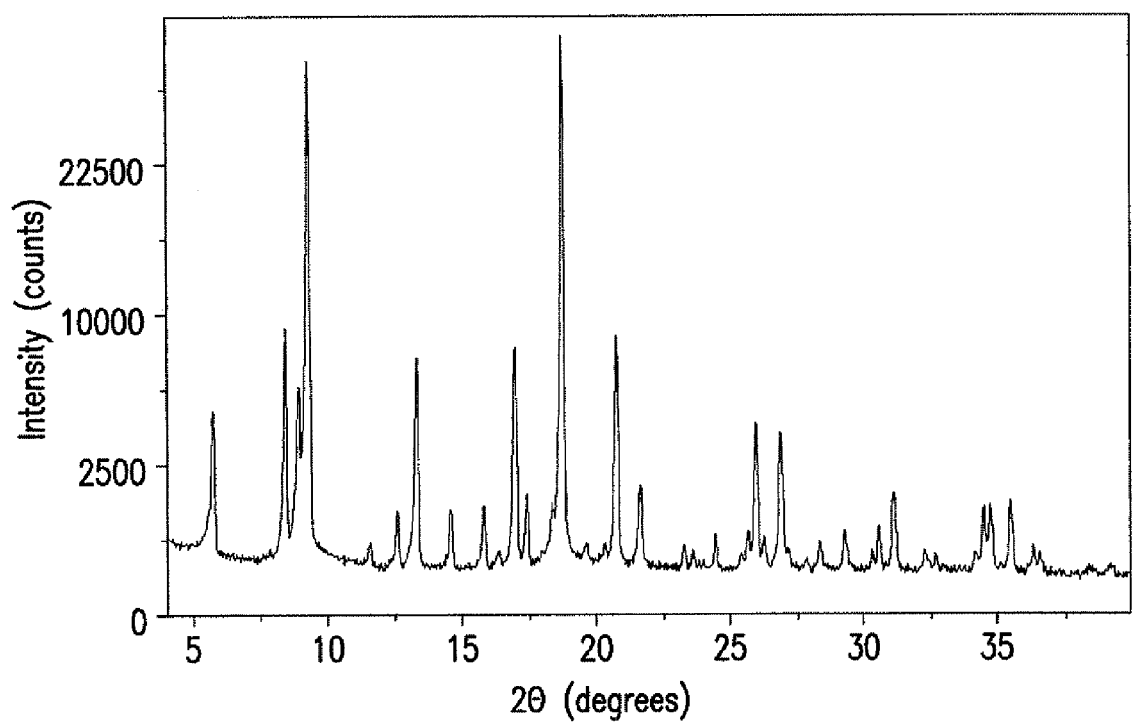
FIG. 1 is the X-ray powder diffraction pattern for the crystalline form of Compound 2A described in Example 2.

The present invention includes compounds of Formula I above (including hydrates and solvates thereof), and pharmaceutically acceptable salts thereof. These compounds are effective inhibitors of wild-type HIV integrase (e.g., HIV-1) and mutant strains thereof, as demonstrated by the results shown in Examples 7 to 9 below. Certain of the compounds have also exhibited advantageous pharmacokinetics in animal models.

A first embodiment of the present invention (alternatively referred to herein as "Embodiment E1") is a compound of Formula I (alternatively and more simply referred to as "Compound I"), or a pharmaceutically acceptable salt thereof; wherein:
$X^1$ is F or $CH_3$;
$X^2$ is H, F, or $CH_3$, and provided that:
(A) when $X^1$ is F, then $X^2$ is H or $CH_3$, and
(B) when $X^1$ is $CH_3$, then $X^2$ is F;
Y is $CH_2$ or O;
$R^{1A}$ is H or $CH_3$;
$R^{1B}$ is H, $CH_3$, or $OCH_3$;
$R^2$ is H, $CH_3$, or $CH_2CH_3$; and
$R^3$ is $CH_3$ or $CH_2CH_3$;
and provided that:
(C) when Y is O, then $R^{1A}$ and $R^{1B}$ are both H, $R^2$ is $CH_3$ or $CH_2CH_3$, and $R^3$ is $CH_3$; and
(D) when Y is $CH_2$, then
(i) $R^2$ is H, $R^3$ is $CH_3$, $R^{1A}$ is $CH_3$ and $R^{1B}$ is $CH_3$ or $OCH_3$;
(ii) $R^2$ is $CH_3$, $R^3$ is $CH_3$, $R^{1A}$ is H, and $R^{1B}$ is H; or
(iii) $R^2$ is H, $R^3$ is $CH_2CH_3$, $R^{1A}$ is H, and $R^{1B}$ is $OCH_3$.

A second embodiment of the present invention (alternatively referred to herein as "Embodiment E2") is a compound of Formula II (alternatively referred to as "Compound II"), or a pharmaceutically acceptable salt thereof:

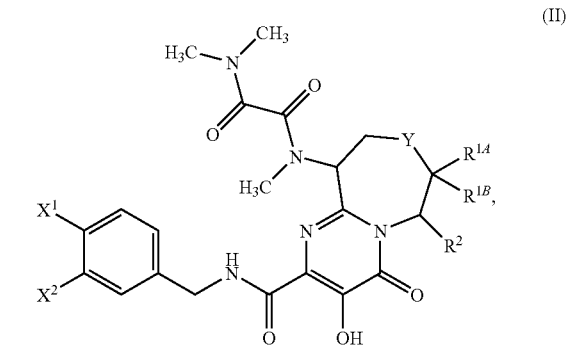

(II)

wherein:
$X^1$ is F or $CH_3$;
$X^2$ is H, F, or $CH_3$, and provided that:
(A) when $X^1$ is F, then $X^2$ is H or $CH_3$, and
(B) when $X^1$ is $CH_3$, then $X^2$ is F;
Y is $CH_2$ or O;
$R^{1A}$ is H or $CH_3$;
$R^{1B}$ is H, $CH_3$, or $OCH_3$; and
$R^2$ is H, $CH_3$, or $CH_2CH_3$;
and provided that:
(C) when Y is O, then $R^{1A}$ and $R^{1B}$ are both H and $R^2$ is $CH_3$ or $CH_2CH_3$; and
(D) when Y is $CH_2$, then
(i) $R^2$ is H, $R^{1A}$ is $CH_3$ and $R^{1B}$ is $CH_3$ or $OCH_3$, or
(ii) $R^2$ is $CH_3$, and $R^{1A}$ is H, and $R^{1B}$ is H.

A third embodiment of the present invention (Embodiment E3) is a compound of Formula II (or "Compound III"), or a pharmaceutically acceptable salt thereof:

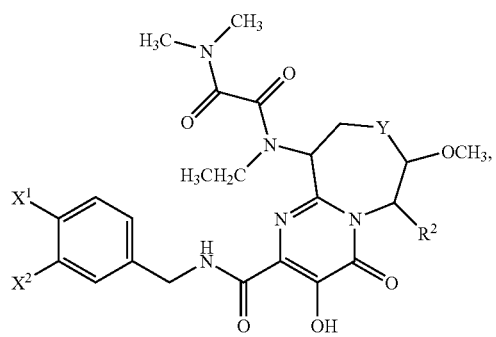

(III)

wherein:
$X^1$ is F or $CH_3$;
$X^2$ is H, F, or $CH_3$, and provided that:
(A) when $X^1$ is F, then $X^2$ is H or $CH_3$, and
(B) when $X^1$ is $CH_3$, then $X^2$ is F; and
$R^2$ is H or $CH_3$.

In an aspect of Embodiment E3, $R^2$ is H.

A fourth embodiment of the present invention (Embodiment E4) is a compound of Formula I (or "Compound I") or Compound II or Compound III, or a pharmaceutically acceptable salt thereof, wherein $X^1$ is F and $X^2$ is H or $CH_3$; and all other variables are as originally defined (i.e., as defined in the Summary of the Invention) or as defined in Embodiment E1 or Embodiment E2 or Embodiment E3. In an aspect of Embodiment E4, $X^1$ is F and $X^2$ is H. In another aspect of Embodiment E4, $X^1$ is F and $X^2$ is $CH_3$.

A fifth embodiment of the present invention (Embodiment E5) is a compound of Formula I or Formula II or Formula III, or a pharmaceutically acceptable salt thereof, wherein $X^1$ is $CH_3$ and $X^2$ is F; and all other variables are as originally defined or as defined in Embodiment E1.

A sixth embodiment of the present invention (Embodiment E6) is a compound of Formula II, or a pharmaceutically acceptable salt thereof, wherein Y is $CH_2$; $R^2$ is H; $R^{1A}$ is $CH_3$; and $R^{1B}$ is $CH_3$ or $OCH_3$; and all other variables are as defined in Embodiment E2.

A seventh embodiment of the present invention (Embodiment E7) is a compound of Formula II, or a pharmaceutically acceptable salt thereof, wherein Y is $CH_2$; $R^2$ is $CH_3$; $R^{1A}$ is H; $R^{1B}$ is H; and all other variables are as defined in Embodiment E2.

An eighth embodiment of the present invention (Embodiment E8) is a compound of Formula II, or a pharmaceutically acceptable salt thereof, wherein Y is O; $R^{1A}$ and $R^{1B}$ are both H; $R^2$ is $CH_3$ or $CH_2CH_3$; and all other variables are as defined in Embodiment E2.

A ninth embodiment of the present invention (Embodiment E9) is a compound of Formula I selected from the group consisting of:

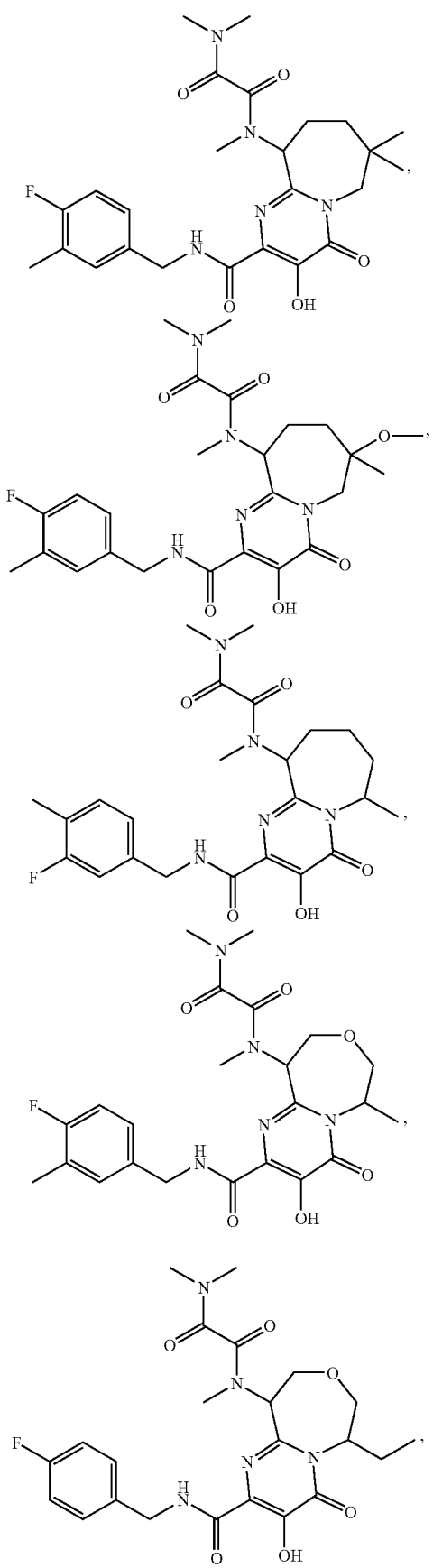

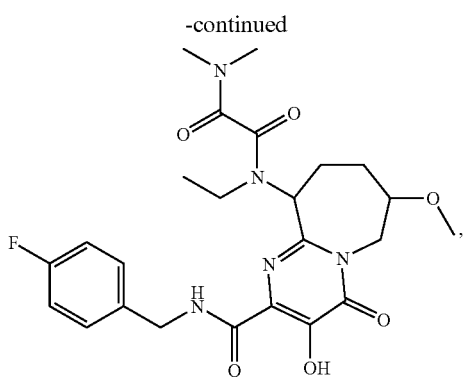

and pharmaceutically acceptable salts thereof.

A tenth embodiment of the present invention (Embodiment E10) is a compound of Formula I or Formula II or Formula II, or a pharmaceutically acceptable salt thereof, wherein the compound is a stereomerically pure compound.

An eleventh embodiment of the present invention (Embodiment E11) is a compound of Formula I, or a pharmaceutically acceptable salt thereof, wherein the compound is a compound as set forth in any of Examples 1 to 6; i.e., the compound is Compound 1A, Compound 1B, Compound 2A, Compound 2B, Compound 2C, Compound 2D, Compound 3A, Compound 3B, Compound 4A, Compound 4B, Compound 4C, Compound 4D, Compound 5A, Compound 5B, Compound 5C, Compound 5D, Compound 6A, or Compound 6B.

A twelfth embodiment of the present invention (Embodiment E12) is a compound of Formula I, or a pharmaceutically acceptable salt thereof, wherein the compound is Compound 1A, Compound 2A, Compound 2D, Compound 4A, Compound 4B, Compound 4C, Compound 5A, Compound 5B, or Compound 6A. In an aspect of this embodiment, the compound is stereomerically pure. Each of the foregoing compounds is a separate aspect of Embodiment E12.

A thirteenth embodiment of the present invention (Embodiment E13) is a compound of Formula I, or a pharmaceutically acceptable salt thereof, which is:

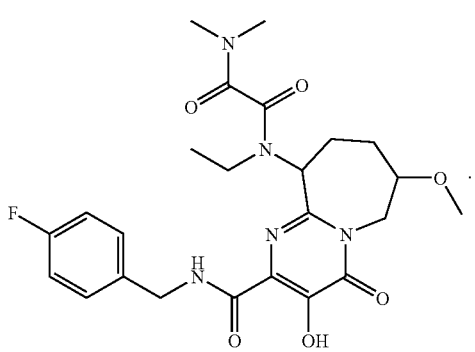 [SMILES: CCN(C(=O)C(=O)N(C)C)C1CCC(OC)Cn2c1nc(C(=O)NCc1ccc(F)cc1)c(O)c2=O]

In an aspect of this embodiment, the compound is Compound 6A:

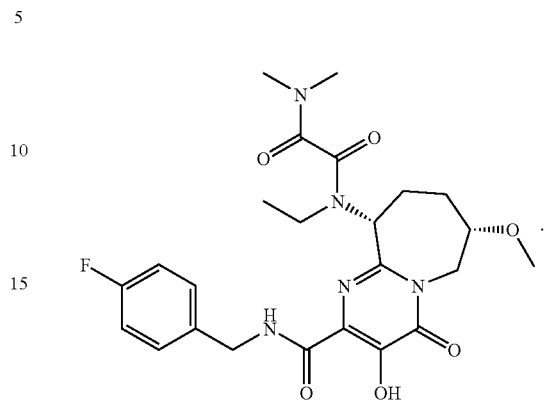

In a feature of this aspect, the compound is stereomerically pure.

A fourteenth embodiment of the present invention (Embodiment E14) is a compound of Formula I, or a pharmaceutically acceptable salt thereof, which is:

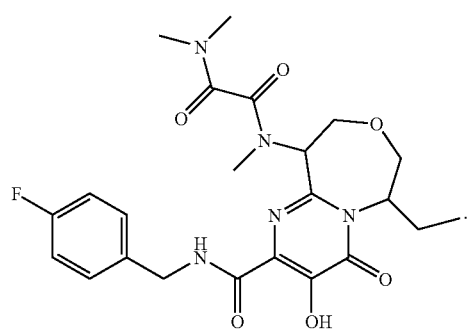 [SMILES: CCC1COCC(N(C)C(=O)C(=O)N(C)C)c2nc(C(=O)NCc3ccc(F)cc3)c(O)c(=O)n21]

In an aspect of this embodiment, the compound is Compound 5A:

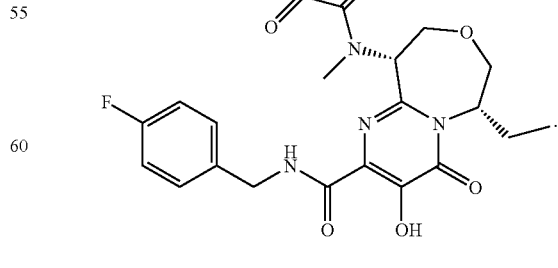

In a feature of this aspect, the compound is stereomerically pure.

A fifteenth embodiment of the present invention (Embodiment E15) is a compound of Formula I, or a pharmaceutically acceptable salt thereof, which is:

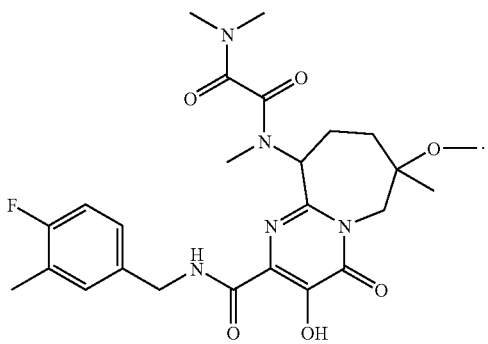 [SMILES: COC1(C)CCC(N(C)C(=O)C(=O)N(C)C)c2nc(C(=O)NCc3ccc(F)c(C)c3)c(O)c(=O)n2C1]

In an aspect of this embodiment, the compound is Compound 2A:

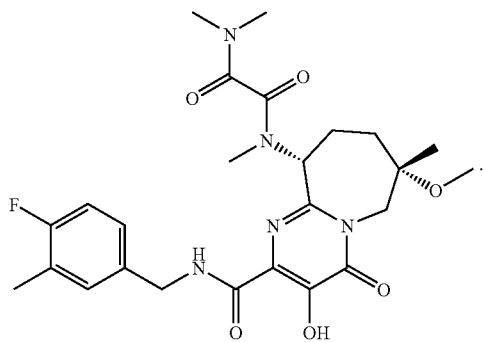 [SMILES: CO[C@@]1(C)CC[C@@H](N(C)C(=O)C(=O)N(C)C)c2nc(C(=O)NCc3ccc(F)c(C)c3)c(O)c(=O)n2C1]

In a feature of this aspect, the compound is stereomerically pure.

A sixteenth embodiment of the present invention (Embodiment E16) is a compound of Formula I, or a pharmaceutically acceptable salt thereof, which is:

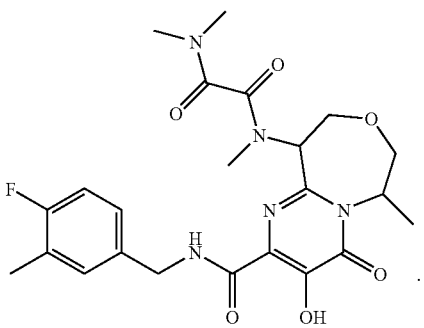 [SMILES: Cc1cc(CNC(=O)c2nc3n(c(=O)c2O)C(C)COCC3N(C)C(=O)C(=O)N(C)C)ccc1F ; "."]

In an aspect of this embodiment, the compound is Compound 4A:

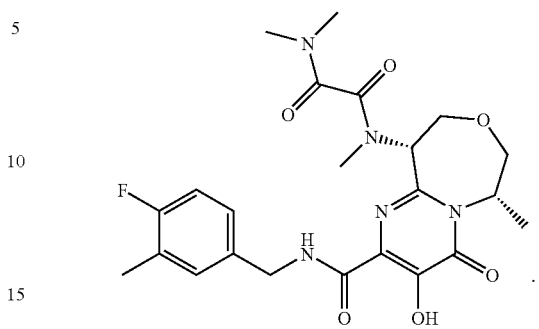

In a feature of this aspect, the compound is stereomerically pure.

As used herein and unless otherwise indicated, the term "stereomerically pure" in reference to a compound of the invention means one stereoisomer of a compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A stereomerically pure compound comprises greater than about 75% by weight of one stereoisomer of the compound and less than about 25% by weight of other stereoisomers (e.g., greater than about 80% of one stereoisomer and less than 20% of the other stereoisomers) of the compound, preferably greater than about 90% by weight of one stereoisomer of the compound and less than about 10% by weight of the other stereoisomers of the compound, more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers (e.g., greater than about 99% of one stereoisomer and less than 1% of the other stereoisomers) of the compound. The level of purity of the compounds and salts can be determined using a standard method of analysis. If more than one method of analysis is employed and the methods provide experimentally significant differences in the level of stereomeric purity determined in a given sample, then the method providing the highest purity level governs.

It is understood that all isomeric forms of the compounds of Formula I, whether isolated or in mixtures, are within the scope of the present invention. Stereomerically pure compounds represent only one facet of the present invention.

A seventeenth embodiment of the present invention (Embodiment E17) is a crystalline form of Compound 2A wherein the crystalline form is characterized by the XRPD, DSC and TGA analysis set forth in Example 2 below. In an aspect of this embodiment, the crystalline Compound 2A is characterized by an X-ray powder diffraction pattern obtained using copper $K_\alpha$ radiation (i.e., the radiation source is a combination of Cu $K_{\alpha 1}$ and $K_{\alpha 2}$ radiation) which comprises 2Θ values (i.e., reflections at 2Θ values) in degrees of about 8.5, 9.3, 13.3, 17.0, 18.8 and 20.8. In this embodiment, and any analogous embodiments which follow, the term "about" is understood to modify each of the 2Θ values. In another aspect of this embodiment, the crystalline Compound 2A is characterized by an X-ray powder diffraction pattern obtained using copper $K_\alpha$ radiation which comprises 2Θ values in degrees of about 5.7, 8.5, 8.9, 9.3, 11.6, 12.6, 13.3, 14.6, 15.9, 16.4, 17.0, 17.5, 18.4, 18.8, 19.7, 20.4, 20.8, 21.7, 23.3, 23.7, 24.5, 25.5, 25.7, 26.0, 26.3, 26.9, 27.9, 28.4, 29.3, 30.4, 30.6, 31.2, 32.3, 32.7, 34.2, 34.5, 34.8, 35.5, 36.4, 36.6, 38.6 and 39.3.

An eighteenth embodiment of the present invention (Embodiment E18) is the crystalline form of Compound 2A wherein the crystalline form is characterized by the PDF trace derived from its X-ray diffraction pattern shown in FIG. 1. The PDF trace provides a fingerprint of the inter-atomic distances that define the crystalline form. A PDF trace can be obtained in the manner described in WO 2005/082050. In one aspect of this embodiment, the crystalline form is characterized by the parts of the PDF trace corresponding to the 2Θ values in degrees of about 8.5, 9.3, 13.3, 17.0, 18.8 and 20.8 in the XRPD. In another aspect of this embodiment, the crystalline form is characterized by the parts of the PDF trace corresponding to the 2Θ values in degrees of about 5.7, 8.5, 8.9, 9.3, 11.6, 12.6, 13.3, 14.6, 15.9, 16.4, 17.0, 17.5, 18.4, 18.8, 19.7, 20.4, 20.8, 21.7, 23.3, 23.7, 24.5, 25.5, 25.7, 26.0, 26.3, 26.9, 27.9, 28.4, 29.3, 30.4, 30.6, 31.2, 32.3, 32.7, 34.2, 34.5, 34.8, 35.5, 36.4, 36.6, 38.6 and 39.3 in the XRPD.

A nineteenth embodiment of the present invention (Embodiment E19) is a crystalline form of Compound 4A wherein the crystalline form is characterized by the XRPD, DSC and TGA analysis set forth in Example 4-1 below. In an aspect of this embodiment, the crystalline Compound 2A is characterized by an X-ray powder diffraction pattern obtained using copper $K_\alpha$ radiation which comprises 2Θ values in degrees of about 6.1, 10.4, 12.9, 13.7, 19.4 and 22.9. In another aspect of this embodiment, the crystalline form of Compound 4A is characterized by an X-ray powder diffraction pattern obtained using copper $K_\alpha$ radiation which comprises 2Θ values in degrees of about 6.1, 10.0, 10.3, 10.4, 12.2, 12.9, 13.7, 14.5, 15.1, 15.5, 17.5, 17.7, 18.3, 18.6, 19.2, 19.4, 20.0, 20.6, 20.9, 21.7, 22.0, 22.3, 22.9, 23.5, 24.0, 25.6, 25.9, 26.5, 27.1, 27.5, 28.5, 29.3, 30.2, 31.1, 31.5, 32.4, 33.1, 33.7, 34.1, 35.8 and 37.4.

A twentieth embodiment of the present invention (Embodiment E20) is a first crystalline form of Compound 5A wherein the crystalline form is characterized by the XRPD, DSC and TGA analysis set forth in Example 5-1 below. In an aspect of this embodiment, the Form I crystalline Compound 5A is characterized by an X-ray powder diffraction pattern obtained using copper $K_\alpha$ radiation which comprises 2Θ values in degrees of about 8.4, 8.6, 18.0, 20.5, 20.8, 25.2, 26.1 and 27.2. In another aspect of this embodiment, the Form I crystalline Compound 5A is characterized by an X-ray powder diffraction pattern obtained using copper $K_\alpha$ radiation which comprises 2Θ values in degrees of about 8.4, 8.6, 10.4, 14.8, 16.0, 16.8, 18.0, 19.5, 20.5, 20.8, 23.0, 24.5, 25.2, 26.1, and 27.2. In another aspect of this embodiment, Form I crystalline Compound 5A is further characterized by a peak temperature of about 149° C. in a DSC curve taken under nitrogen at a heating rate of 10° C./minute in a closed aluminum pan.

A twenty-first embodiment of the present invention (Embodiment E21) is a second crystalline form of Compound 5A wherein the crystalline form is characterized by the XRPD, DSC and TGA analysis set forth in Example 5-1 below. In an aspect of this embodiment, the Form II crystalline Compound 5A is characterized by an X-ray powder diffraction pattern obtained using copper $K_\alpha$ radiation which comprises 2Θ values in degrees of about 8.4, 8.6, 18.0, 20.4, 20.8, 25.9, 26.2 and 27.1. In another aspect of this embodiment, the Form II crystalline Compound 5A is characterized by an X-ray powder diffraction pattern obtained using copper $K_\alpha$ radiation which comprises 2Θ values in degrees of about 8.4, 8.6, 10.3, 14.8, 16.0, 16.7, 18.0, 19.4, 20.4, 20.8, 23.0, 24.4, 25.1, 25.9, 26.2 and 27.1. In another aspect of this embodiment, Form II crystalline Compound 5A is further characterized by a peak temperature of about 155° C. in a DSC curve taken under nitrogen at a heating rate of 10° C./minute in a closed aluminum pan.

A twenty-second embodiment of the present invention (Embodiment E22) is a crystalline form of Compound 6A wherein the crystalline form is characterized by the XRPD, DSC and TGA analysis set forth in Example 6-1 below. In an aspect of this embodiment, the crystalline Compound 6A is characterized by an X-ray powder diffraction pattern obtained using copper $K_\alpha$ radiation which comprises 2Θ values in degrees of about 10.6, 14.2, 17.4, 18.8 and 20.4. In another aspect of this embodiment, the crystalline Compound 6A is characterized by an X-ray powder diffraction pattern obtained using copper $K_\alpha$ radiation which comprises 2Θ values in degrees of about 5.6, 7.0, 9.9, 10.6, 12.8, 14.2, 15.0, 16.0, 16.2, 16.6, 17.4, 18.0, 18.4, 18.8, 19.8, 20.0, 20.4, 20.6, 21.2, 21.7, 22.1, 22.7, 23.1, 23.2, 24.1, 24.8, 25.1, 25.5, 26.1, 26.2, 26.6, 27.9, 28.5, 29.2, 29.3, 30.1, 30.6, 31.0, 31.5, 32.0, 32.3, 32.6, 33.1, 33.9, 34.5, and 35.5.

Embodiments E23 to E26 of the present invention respectively correspond to crystalline Compound 4A, Form I crystalline 5A, Form II crystalline 5A, and crystalline Compound 6A as set forth in Embodiments E19 to E22, wherein the crystalline form is characterized by the PDF trace derived from its X-ray diffraction pattern shown in FIGS. 2, 3, 4 and 5.

The term "about", when modifying the value of a physical property or the like refers to variation in the numerical quantity that can occur, for example, through typical measuring, handling and sampling procedures involved in the characterization of the substance or composition; through inadvertent error in these procedures; through differences in the manufacture, source, or purity of the ingredients employed to prepare the substance or carry out the procedures; and the like. In the particular case of the 2Θ values in degrees in an XRPD described herein, the term "about" typically means the value±0.1.

Another embodiment of the present invention is Compound I, or a pharmaceutically acceptable salt thereof, as defined in any of the foregoing embodiments (e.g., Compound II in Embodiment E2 or Compound III in Embodiment E3) or aspects, wherein the compound or its salt is in a substantially pure form. As used herein "substantially pure" means suitably at least about 75 wt. %, typically at least about 80 wt. %, preferably at least about 90 wt. % (e.g., from about 90 wt. % to about 99 wt. %), more preferably at least about 95 wt. % (e.g., from about 95 wt. % to about 99 wt. %, or from about 98 wt. % to 100 wt. %), and most preferably at least about 97 wt. % (e.g., from about 99 wt. % to 100 wt. %) of a product containing a compound Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined in a given sample, then the method providing the highest purity level governs. A compound or salt of 100% purity is one which is free of detectable impurities as determined by a standard method of analysis. The compounds of the invention have one or two asymmetric centers and thus can occur as mixtures of stereoisomers. It is to be understood that a substantially pure compound can be either a substantially pure mixture of the stereoisomers or a substantially pure individual diastereomer or enantiomer. A substantially pure individual diastereomer or enantiomer is also stereomerically pure.

Other embodiments of the present invention include the following:

(a) A pharmaceutical composition comprising an effective amount of Compound I, or a pharmaceutically acceptable salt thereof, and a pharmaceutically acceptable carrier.

(b) A pharmaceutical composition which comprises the product prepared by combining (e.g., mixing) an effective amount of Compound I, or a pharmaceutically acceptable salt thereof, and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, non-nucleoside HIV reverse transcriptase inhibitors, nucleoside HIV reverse transcriptase inhibitors, HIV integrase inhibitors, HIV fusion inhibitors, and HIV entry inhibitors.

(e) A combination which is (i) Compound I, or a pharmaceutically acceptable salt thereof, and (ii) an anti-HIV agent selected from the group consisting of HIV antiviral agents, immunomodulators, and anti-infective agents; wherein the compound of Formula I and the anti-HIV agent are each employed in an amount that renders the combination effective for the inhibition of HIV integrase, for the treatment or prophylaxis of infection by HIV, or for the treatment, prophylaxis or delay in the onset or progression of AIDS.

(f) The combination of (e), wherein the anti-HIV agent is an antiviral selected from the group consisting of HIV protease inhibitors, non-nucleoside HIV reverse transcriptase inhibitors, nucleoside HIV reverse transcriptase inhibitors, HIV integrase inhibitors, HIV fusion inhibitors, and HIV entry inhibitors.

(g) A method of inhibiting HIV integrase in a subject in need thereof which comprises administering to the subject an effective amount of Compound I, or a pharmaceutically acceptable salt thereof.

(h) A method for the treatment or prophylaxis of infection by HIV in a subject in need thereof which comprises administering to the subject an effective amount of Compound I, or a pharmaceutically acceptable salt thereof.

(i) The method of (h), wherein the compound of Formula I is administered in combination with an effective amount of at least one antiviral selected from the group consisting of HIV protease inhibitors, non-nucleoside HIV reverse transcriptase inhibitors, nucleoside HIV reverse transcriptase inhibitors, HIV integrase inhibitors, HIV fusion inhibitors, and HIV entry inhibitors.

(j) A method for the treatment, prophylaxis, or delay in the onset or progression of AIDS in a subject in need thereof which comprises administering to the subject an effective amount of Compound I, or a pharmaceutically acceptable salt thereof.

(k) The method of (j), wherein the compound is administered in combination with an effective amount of at least one antiviral selected from the group consisting of HIV protease inhibitors, non-nucleoside HIV reverse transcriptase inhibitors, nucleoside HIV reverse transcriptase inhibitors, HIV integrase inhibitors, HIV fusion inhibitors, and HIV entry inhibitors.

(l) A method of inhibiting HIV integrase (e.g., HIV-1 integrase) in a subject in need thereof which comprises administering to the subject the pharmaceutical composition of (a), (b), (c) or (d) or the combination of (e) or (f).

(m) A method for the treatment or prophylaxis of infection by HIV (e.g., HIV-1) in a subject in need thereof which comprises administering to the subject the pharmaceutical composition of (a), (b), (c) or (d) or the combination of (e) or (f).

(n) A method for the treatment, prophylaxis, or delay in the onset or progression of AIDS (e.g., AIDS due to HIV-1) in a subject in need thereof which comprises administering to the subject the pharmaceutical composition of (a), (b), (c) or (d) or the combination of (e) or (f).

The present invention also includes a compound of the present invention or pharmaceutically acceptable salt thereof, (i) for use in, (ii) for use as a medicament for, or (iii) for use in the preparation or manufacture of a medicament for: (a) therapy (e.g., of the human body), (b) medicine, (c) inhibition of HIV integrase, (d) treatment or prophylaxis of infection by HIV, or (e) treatment, prophylaxis of, or delay in the onset or progression of AIDS. In these uses, the compounds of the present invention can optionally be employed in combination with one or more anti-HIV agents selected from HIV antiviral agents, anti-infective agents, and immunomodulators.

Additional embodiments of the invention include the pharmaceutical compositions, combinations and methods set forth in (a)-(n) above and the uses (i)(a)-(e) through (iii)(a)-(e) set forth in the preceding paragraph, wherein the compound of the present invention employed therein is a compound of one of the embodiments (e.g., Compound II in Embodiment E2 or Compound II in Embodiment E3) or an aspect thereof, as described above. In all of these embodiments etc., the compound may optionally be used in the form of a pharmaceutically acceptable salt.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising Compound I or its salt and a pharmaceutically acceptable carrier and optionally one or more excipients, it is understood that the term "substantially pure" is in reference to a compound of Formula I or its salt per se.

Still additional embodiments of the present invention include the pharmaceutical compositions, combinations and methods set forth in (a)-(n) above and the uses (i)(a)-(e) through (iii)(a)-(e) set forth above, wherein the HIV of interest is HIV-1. Thus, for example, in the pharmaceutical composition (d), the compound of Formula I is employed in an amount effective against HIV-1 and the anti-HIV agent is an HIV-1 antiviral selected from the group consisting of HIV-1 protease inhibitors, HIV-1 reverse transcriptase inhibitors, HIV-1 integrase inhibitors, HIV-1 entry inhibitors and HIV-1 fusion inhibitors.

As would be recognized by one of ordinary skill in the art, compounds of the present invention can exist as tautomers, such as the following:

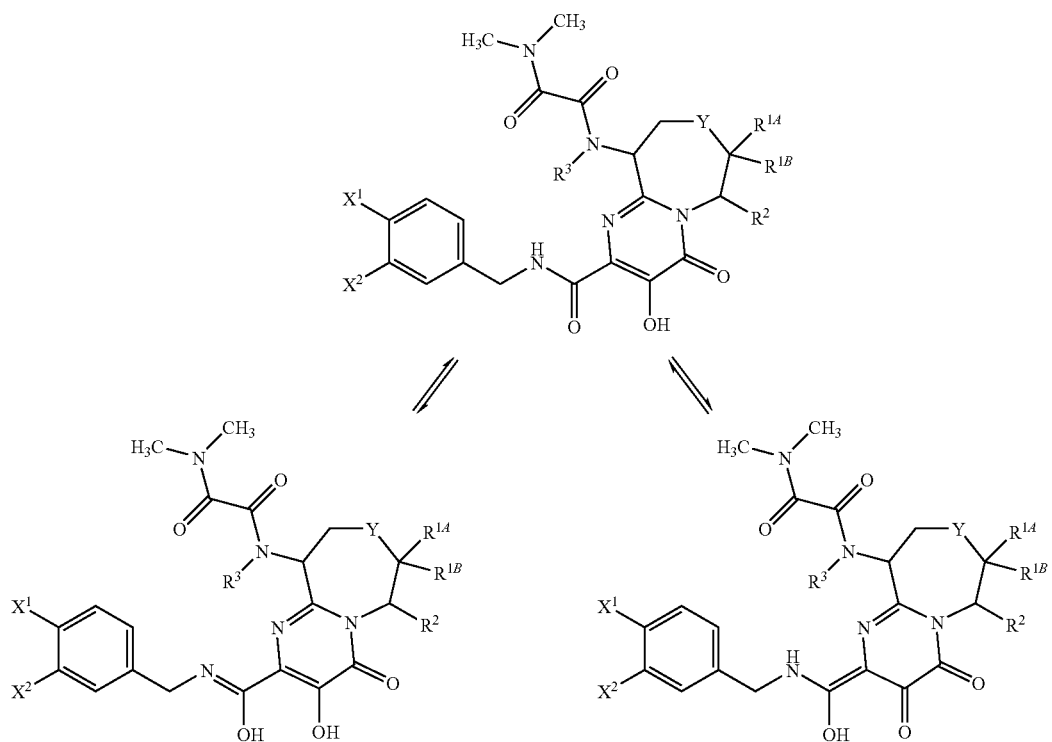

All tautomeric forms of the compounds, whether isolated or in mixtures, are within the scope of the present invention.

The person of ordinary skill in the art would also understand that compounds of the invention can form hydrates and/or solvates. Chemically stable hydrates and solvates of compounds encompassed by Formula I and their pharmaceutically acceptable salts are within the scope of the present invention.

A "stable" compound is a compound which can be prepared and isolated and whose structure and properties remain or can be caused to remain essentially unchanged for a period of time sufficient to allow use of the compound for the purposes described herein.

The compounds of the present inventions are useful in the inhibition of HIV integrase (e.g., HIV-1 integrase), the prophylaxis or treatment of infection by HIV and the prophylaxis, treatment or the delay in the onset or progression of consequent pathological conditions such as AIDS. The prophylaxis of AIDS, treating AIDS, delaying the onset or progression of AIDS, the prophylaxis of infection by HIV, or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention can be commercial products to be sold for these purposes.

The compounds of the present invention can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, or benzoic acid. Compounds of the invention carry an acidic moiety and thus suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administered" or "administering") in reference to a compound of the invention mean providing the compound or its salt (or a hydrate or solvate) to the individual in need of treatment or prophylaxis. When a compound of the invention is provided in combination with one or more other active agents (e.g., antiviral agents useful for the prophylaxis or treatment of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (or, alternatively, "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV integrase and thereby elicit the response being sought (i.e., an "inhibition effective amount"). When the active compound (i.e., active ingredient) is administered as the salt, references to the amount of active ingredient are to the free acid or free base form of the compound.

For the purpose of the inhibition of HIV integrase, the prophylaxis or treatment of HIV infection, or the prophylaxis or treatment or delay in the onset or progression of AIDS, the compounds of the present invention, optionally in the form of a salt (or hydrate or solvate), can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in Remington's Pharmaceutical Sciences, 18$^{th}$ edition, edited by A. R. Gennaro, Mack Publishing Co., 1990 and in Remington—The Science and Practice of Pharmacy, 21$^{st}$ edition, Lippincott Williams & Wilkins, 2005.

The compounds of this invention can be administered orally in a dosage range of about 0.001 to about 1000 mg/kg of mammal (e.g., human) body weight per day in a single dose or in divided doses. One preferred dosage range is about 0.01 to about 500 mg/kg body weight per day orally in a single dose or in divided doses. Another preferred dosage range is about 0.1 to about 100 mg/kg body weight per day orally in single or divided doses. For oral administration, the compositions can be provided in the form of tablets or capsules containing about 1.0 to about 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. In one embodiment, a compound of the present invention is administered orally to adult humans in a convenient form (e.g., as a solution in aqueous methocel, or in the form of capsules or tablets) in an amount of from about 200 mg to about 800 mg once per day or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of the HIV integrase inhibitor compounds of the present invention with one or more anti-HIV agents useful in the treatment of HIV infection or AIDS. An "anti-HIV agent" is any agent which is directly or indirectly effective in the inhibition of HIV integrase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more HIV antivirals, immunomodulators, antiinfectives, or vaccines useful for treating HIV infection or AIDS, such as those disclosed in Table 1 of WO 01/38332 or in the Table in WO 02/30930. Suitable HIV antivirals for use in combination with the compounds of the present invention include, for example, those listed in Table A as follows:

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| efavirenz, EFV, Sustiva ®, Stocrin ® | nnRTI |
| efavirenz + emtricitabine + tenofovir DF, Atripla ® | nnRTI + nRTI |

TABLE A-continued

| Name | Type |
|---|---|
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125, Intelence ® | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ® | InI |
| rilpivirine, TMC-278 | nnRTI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor;
FI = fusion inhibitor;
InI = integrase inhibitor;
PI = protease inhibitor;
nRTI = nucleoside reverse transcriptase inhibitor;
nnRTI = non-nucleoside reverse transcriptase inhibitor.
Some of the drugs listed in the table are used in a salt form; e.g., abacavir sulfate, indinavir sulfate, atazanavir sulfate, nelfinavir mesylate.

It is understood that the scope of combinations of the compounds of this invention with anti-HIV agents is not limited to the HIV antivirals listed in Table A and/or listed in the above-referenced Tables in WO 01/38332 and WO 02/30930, but includes in principle any combination with any pharmaceutical composition useful for the treatment or prophylaxis of HIV infection or AIDS. The HIV antiviral agents and other agents will typically be employed in these combinations in their conventional dosage ranges and regimens as reported in the art, including, for example, the dosages described in the *Physicians' Desk Reference, Thomson PDR*, Thomson PDR, 57$^{th}$ edition (2003), the 58$^{th}$ edition (2004), the 59$^{th}$ edition (2005), and subsequent editions thereof. The dosage ranges for a compound of the invention in these combinations are the same as those set forth above.

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and isopropyl, ethyl and methyl. As still another example, "$C_{1-3}$ alkyl" refers to n- and isopropyl, ethyl and methyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.). A fluoroalkyl of particular interest is $CF_3$.

The term "cycloalkyl" refers to any monovalent monocyclic ring of an alkane having a number of carbon atoms in the specified range. Thus, for example, "$C_{3-6}$ cycloalkyl" (or "$C_3$-$C_6$ cycloalkyl") refers to cyclopropyl, cyclobutyl, cyclopentyl, and cyclohexyl.

The term "C(O)" refers to carbonyl.

An asterisk ("*") at the end of an open bond in a chemical group denotes the point of attachment of the group to the rest of the compound.

The present invention also includes a process (alternatively referred to as Process P) for preparing an alkylamino-substituted tetrahydropyrimidooxazepine carboxamide of Formula IV:

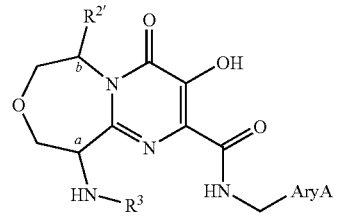

(P-IV)

which comprises:
(C) contacting a compound of Formula P-III:

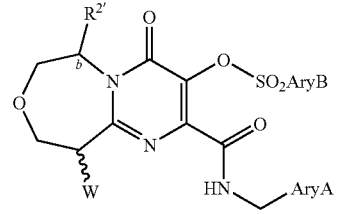

(P-III)

with $R^3NH_2$ to obtain Compound P-IV; wherein:
"a" denotes a stereocenter in the oxazepine ring which is in the R or S configuration;
"b" denotes a stereocenter in the oxazepine ring which is in the R or S configuration;
W is halogen or $O-SO_2R^P$;
$R^P$ is:
(1) $C_{1-6}$ alkyl,
(2) $C_{1-6}$ haloalkyl,
(3) $C_{1-6}$ alkyl substituted with AryC, or
(4) AryC;
AryC is an aryl selected from the group consisting of phenyl and naphthyl, wherein the aryl is optionally substituted with from 1 to 4 substituents each of which is independently halogen, $C_{1-4}$ alkyl, $O-C_{1-4}$ alkyl, $CF_3$, $OCF_3$, $CN$, or nitro;
$R^{2'}$ is $C_{1-3}$ alkyl;
$R^3$ is $C_{1-3}$ alkyl;
AryA is phenyl, wherein the phenyl is optionally substituted with from 1 to 3 substituents each of which is independently: (1) $C_{1-4}$ alkyl, (2) $C_{3-6}$ cycloalkyl, (3) $C_{1-4}$ fluoroalkyl, (4) $O-C_{1-4}$ alkyl, (5) $O-C_{1-4}$ fluoroalkyl, (6) $O-C_{3-6}$ cycloalkyl, (7) halo, (8) CN, (9) N(H)-isopropyl, (10) N(H)-t-butyl, (11) N($-C_{1-4}$ alkyl)$_2$, (12) CH(O), (13)

C(O)—C$_{1-4}$ alkyl, (14) C(O)O—C$_{1-4}$ alkyl, (15) C(O)NH$_2$, (16) C(O)N(H)—C$_{1-4}$ alkyl, (17) C(O)N(—C$_{1-4}$ alkyl)$_2$, (18) C$_{1-4}$ alkyl substituted with: (a) O—C$_{1-4}$ alkyl, (b) O—C$_{1-4}$ fluoroalkyl, (c) O—C$_{3-6}$ cycloalkyl, (d) CN, (e) NO$_2$, (f) N(H)-isopropyl, (g) N(H)-t-butyl, (h) N(—C$_{1-4}$ alkyl)$_2$, (i) CH(O), (j) C(O)—C$_{1-4}$ alkyl, (k) C(O)O—C$_{1-4}$ alkyl, (l) C(O)NH$_2$, (m) C(O)N(H)—C$_{1-6}$ alkyl, or (n) C(O)N(—C$_{1-6}$ alkyl)$_2$, or (19) phenyl, with the proviso that no more than one of the optional substituents is phenyl; and AryB is phenyl wherein the phenyl is optionally substituted with from 1 to 4 substituents each of which is independently halogen, C$_{1-4}$ alkyl, O—C$_{1-4}$ alkyl, CF$_3$, OCF$_3$, CN, or nitro.

The stereocenters a and b in the above process are each independently either wholly or substantially in the R or the S configuration. The term "substantially" means that the compound suitably has at least about a 20% enantiomeric excess (ee) of the one configuration over the other, typically has at least about a 40% ee, and more typically has at least an 80% ee of one configuration over the other at the stereocenter. The compound can have a 90% to 99% ee, or even 100% ee, of one configuration over the other in each of the two stereocenters a and b. In one embodiment of the process, the stereocenters a and b in Compound P-IV are both wholly or substantially in the S configuration.

The squiggly bond " ~~~ " in Compound P-III denotes a mixture of diastereomers.

Features of Compound P-IV and Process P include the following:
(1a) R$^{2'}$ is methyl or ethyl;
(1b) R$^{2'}$ is methyl;
(1c) R$^{2'}$ is ethyl;
(2a) R$^3$ is methyl or ethyl;
(2b) R$^3$ is methyl;
(3a) W is O—SO$_2$R$^P$, wherein R$^P$ is C$_{1-3}$ alkyl, CF$_3$, CF$_2$CF$_3$, CH$_2$CF$_3$, CH$_2$-AryC or AryC; wherein AryC is phenyl which is optionally substituted with from 1 to 3 substituents each of which is independently F, Cl, Br, C$_{1-4}$ alkyl, O—C$_{1-4}$ alkyl, CF$_3$, OCF$_3$, or nitro;
(3b) W is O—SO$_2$R$^P$, wherein R$^P$ is p-toluoyl, phenyl, methyl, trifluoromethyl, or p-nitrophenyl (i.e., SO$_2$R$^P$ is p-toluenesulfonyl, benzenesulfonyl, methanesulfonyl, trifluoromethanesulfonyl, or p-nitrobenzenesulfonyl);
(3c) W is O—SO$_2$R$^P$, wherein R$^P$ is methyl (i.e., SO$_2$R$^P$ is methanesulfonyl);
(3d) W is halogen;
(3e) W is Cl, Br, or I;
(3f) W is Cl or Br;
(3g) W is Br;
(4a) AryA is

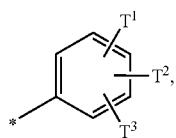

wherein T$^1$, T$^2$ and T$^3$ are each independently H, Cl, Br, F, CN, C$_{1-4}$ alkyl, C$_{1-4}$ fluoroalkyl, O—C$_{1-4}$ alkyl, O—C$_{1-4}$ fluoroalkyl, N(CH$_3$)$_2$, C(O)CH$_3$, or CO$_2$CH$_3$;
(4b) AryA is phenyl which is optionally substituted with from 1 to 3 substituents each of which is independently Cl, Br, F, CN, CH$_3$, CF$_3$, OCH$_3$, OCF$_3$, N(CH$_3$)$_2$, C(O)CH$_3$, or CO$_2$CH$_3$;
(4c) AryA is phenyl which is optionally substituted with from 1 to 3 substituents each of which is independently Cl, Br, F, CH$_3$, or CF$_3$;
(5a) AryA is phenyl which is optionally substituted with 1 or 2 substituents each of which is independently Cl, Br, F, or CH$_3$;
(5c) AryA is

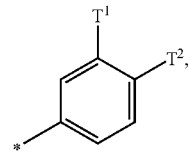

wherein T$^1$ and T$^2$ are each independently selected from the group consisting of H, Cl, Br, F and CH$_3$, with the proviso that no more than one of T$^1$ and T$^2$ is H.
(6a) AryB is phenyl which is optionally substituted with from 1 to 3 substituents each of which is independently F, Cl, Br, C$_{1-4}$ alkyl, O—C$_{1-4}$ alkyl, CF$_3$, OCF$_3$, or nitro;
(6b) AryB is p-methylphenyl, p-nitrophenyl, or phenyl;
(6c) AryB is phenyl.

One or more of these features (1) to (6) can be combined with each other and/or with other relevant features herein, wherein each such combination is an aspect of Compound P-IV and Process P.

Step C involves the displacement of leaving group W on Compound P-m with an amine to provide Compound P-IV. Compound P-IV can be employed as the penultimate intermediate in the preparation of pharmacologically active compounds including certain of the compounds (useful as HIV integrase inhibitors) embraced by Formula I. Step C can provide a amine product with a high diastereomeric excess in high yield. Reference is made to Step 15 in Example 11 and Step 13 in Example 12 below which provide a high diastereomeric excess of the cis-stereoisomer.

Step C is conducted in an organic solvent. When the leaving group W is O—SO$_2$R$^P$, suitable solvents include alcohols such as C$_{1-4}$ alkyl alcohols. The solvent can also be a mixture of an alcohol with a co-solvent. Mixtures suitable for use as solvent include alcohols with ethers and alcohols with halohydrocarbons. Representative solvents include MeOH, EtOH, IPA, n-propanol, an MeOH-THF mixture, an MeOH-MeTHF mixture, and an MeOH-DCM mixture.

When the leaving group W is halogen, suitable solvents include alcohols, ethers, halogenated hydrocarbons, nitriles, and esters. Representative solvents include methanol, ethanol, IPA, n-propanol, THF, MeTHF, DCE, DCM, ACN, EtOAc, and IPAc.

When the leaving group W is O—SO$_2$R$^P$, the reaction in Step C can suitably be conducted at a temperature in a range of from about −20° C. to about 50° C., and is typically conducted at a temperature in a range of from about −20° C. to about 25° C.

When the leaving group W is halogen, the reaction in Step C can suitably be conducted at a temperature in a range of from about −10° C. to about 50° C., is typically conducted at a temperature in a range of from about −5° C. to about 30° C., and is more typically conducted at a temperature in a range of from about 0° C. to about 25° C.

When the leaving group W is O—SO$_2$R$^P$, the amine R$^3$NH$_2$ is typically employed in an amount in a range of from about 2 to about 50 equivalents per equivalent of Compound P-III, is typically employed in an amount in a range of from about 2 to about 20 equivalents per equivalent of Compound P-III, and is more typically employed in an amount in a range of from about 5 to about 15 equivalents.

When the leaving group W is halogen, the amine $R^3NH_2$ can suitably be employed in an amount in a range of from about 3 to about 50 equivalents per equivalent of Compound P-III, is typically employed in an amount in a range of from about 3 to about 10 equivalents, and is more typically employed in an amount in a range of from about 3 to about 7 (e.g., about 5) equivalents.

Compound P-IV can be recovered without undue experimentation using conventional techniques such as extracting the desired compound with a suitable solvent, concentrating and/or adding an anti-solvent to the extracted layer containing the desired compound in solution in order to precipitate the compound (e.g., as a crystalline slurry), and then isolating the desired compound by filtration. In certain cases, a purer form of the desired compound (i.e., improved stereochemical and/or chemical purity) can be recovered by crystallizing the compound in the form of a salt, as described below (see Sub-embodiment SE3 of Process P).

An embodiment of Process P comprises Step C as just described and further comprises:

(B1) treating a compound of Formula P-IIa:

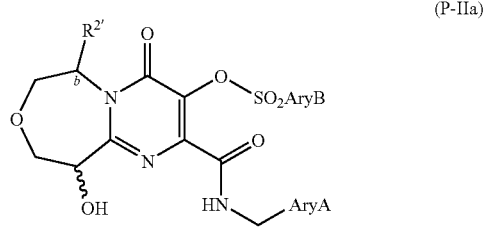

with $R^PSO_2$-G in the presence of a base to obtain Compound P-IIIa:

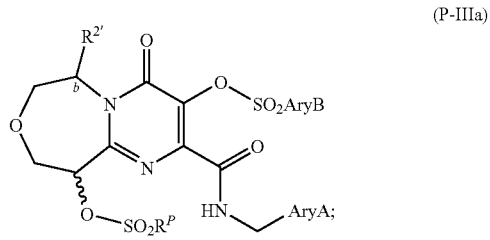

wherein G is halogen or $OS(O)_2R^P$ (i.e., the reagent $R^PSO_2$-G is either a sulfonyl halide or a sulfonyl anhydride).

Step B1 is conducted in an organic solvent. Suitable solvents include non-nucleophilic solvents such as halogenated hydrocarbons, ethers and esters. Representative solvents includes DCM, THF, MeTHF, EtOAc and IPAc. In one aspect of Step B1, the solvent is dichloromethane or MeTHF.

The sulfonating agent $R^PSO_2$-G (e.g., methanesulfonyl chloride or methanesulfonyl anhydride) is typically employed in an amount in a range of from about 1 to about 3 equivalents per equivalent of Compound P-IIa, and is more typically employed in an amount in a range of from about 1 to about 1.5 equivalents.

The base is suitably a tertiary amine. Suitable amines include tri-$C_{1-4}$ alkylamines. A class of suitable amines consists of TEA, DIPEA, and diethylisopropylamine. In one aspect of the process, the base is TEA. The base is typically employed in an amount in a range of from about 1 to about 10 equivalents per equivalent of Compound P-IIa, and is more typically employed in an amount in a range of from about 1 to about 2 equivalents.

The reaction in Step B1 can suitably be conducted at a temperature in a range of from about −40° C. to about 50° C. (e.g., from about −5° C. to about 25° C.) and is typically conducted at a temperature in a range of from about 0° C. to about 20° C.

Another embodiment of Process P comprises Steps C and B1 as just described and further comprises:

(A1) hydrogenating a compound of Formula P-Ia:

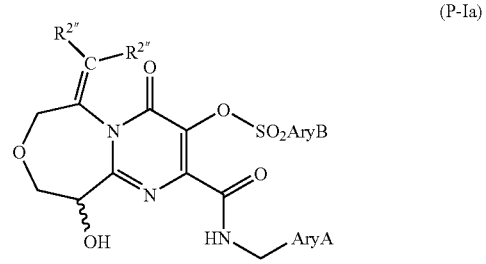

in the presence of a catalytic amount of a cationic rhodium or ruthenium complex having a chiral bidentate or monodentate phosphine ligand to obtain Compound P-IIa; wherein (i) both $R^{2''}$ are $CH_3$ or (ii) one $R^{2''}$ is H and the other $R^{2''}$ is H, $CH_3$, or $CH_2CH_3$.

Step A1 can provide a hydrogenated product with a high enantiomeric excess and with high purity and yield. Reference is made to Step 13 in Example 11 in which the product has high ee.

Step A1 is conducted in an organic solvent. Suitable solvents include alcohols, ethers, esters, ketones, and halogenated hydrocarbons. A class of suitable solvents consists of methanol, ethanol, IPA, MeTHF, cyclopentyl methyl ether, ethyl acetate, acetone, and dichloromethane. Two or more individual substances can be employed as the solvent. A suitable solvent can be, for example, a binary mixture of an alcohol with an ether or a halohydrocarbon, such as a mixture (e.g., a 1:1 mixture) of methanol and dichloromethane.

The catalyst can be a bis(cyclooctadiene)rhodium (I) tetrafluoroborate or bis(norbornadiene)rhodium (I) tetrafluoroborate [(NBD)$_2$RhBF$_4$] complex with ligands such as 1,2-bis(2,5-di-1-propylpholano)benzene; [di(3,5-dimethylphenyl)phosphino]-2-(4-diphenylphosphino-2,5-dimethylthien-3-yl)-1,7,7-trimethylbicyclo[2.2.1]hept-2-ene; 1,2-dimethyl-2,3-bis(diphenylphosphinomethyl)cyclopentyl]methanol; 4,4'-di-t-butyl-4,4',5,5'-tetrahydro-3,3'-bi-3H-dinaphtho[2,1-c:1',2'-e]phosphepine; 1-[2-(bis(3,5-bis(trifluoromethyl)phenyl)phosphino)ferrocenyl]ethyldicyclohexylphosphine; 1-[2-(di-2-furylphosphino)ferrocenyl]ethyldi-tert-butylphosphine; 1-{2-[2-(diphenylphosphino)phenyl]-ferrocenyl}ethylbis[3,5-bis-(trifluoromethyl)phenyl]phosphine; 4,4'-bis(diphenylphosphino)-2,2',5,5'-tetramethylbi-3-thienyl; 2,2'-di-tert-butyl-2,3,2',3'-tetrahydro-1H,1'H(1,1')biisophosphinoindolyl; and (6,6'-dimethoxybiphenyl-2,2'-diyl)bis[bis(3,5-di-tert-butyl-4-methoxyphenyl)phosphine].

A class of suitable catalysts consists of (NBD)$_2$RhBF$_4$ complexes of 1,2-bis(2,5-di-1-propylpholano)benzene; di(3,5-dimethylphenyl)phosphino]-2-(4-diphenylphosphino-2,5-dimethylthien-3-yl)-1,7,7-trimethylbicyclo[2.2.1]

hept-2-ene; 1,2-dimethyl-2,3-bis(diphenylphosphinomethyl)cyclopentyl]methanol; and 4,4'-di-t-butyl-4,4',5,5'-tetrahydro-3,3'-bi-3H-dinaphtho[2,1-c:1',2'-e]phosphepine. The catalyst is suitably employed in an amount of from about 0.1 to about 20 mole percent based on the amount of Compound P-Ia (i.e., moles of catalyst per mole of P-Ia), is typically employed in an amount in a range of from about 0.5 to about 2 mole percent, and is more typically employed in an amount of from about 0.5 to about 1 mole percent.

The hydrogenation in Step A1 can suitably be conducted at a temperature in a range of from about 5° C. to about 60° C., is typically conducted at a temperature in a range of from about 10° C. to about 30° C., and is more typically conducted at a temperature in a range of from about 20° C. to about 25° C.

The source of hydrogen in Step A1 is hydrogen gas, optionally in admixture with a carrier gas that is chemically inert under the reaction conditions employed in Step A1 (e.g., nitrogen or a noble gas such as helium or argon). The pressure is not a critical aspect in Step A1. The pressure can suitably be in a range of from about ambient pressure to about 500 psig, and is typically in a range of from about 50 psig to about 150 psig (e.g., about 100 psig). The uptake of hydrogen is not a critical process parameter, although at least a stoichiometric amount of hydrogen gas is typically employed.

A sub-embodiment of Process P (hereinafter "Sub-embodiment P-SE1") is a process for preparing a compound of Formula P-4:

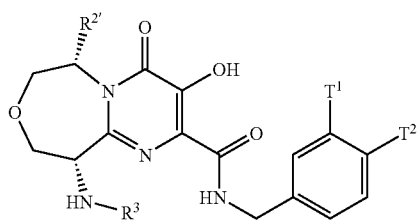

(P-4)

which comprises:
(C) contacting a compound of Formula P-3a:

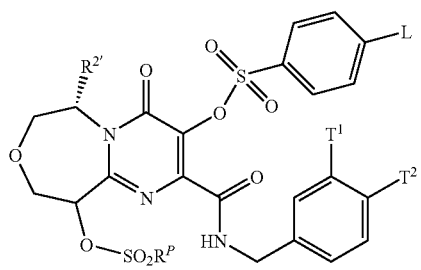

(P-3a)

with $R^3NH_2$ to obtain Compound P-4; wherein:
$R^P$ is $C_{1-3}$ alkyl;
$R^{2'}$ is $CH_3$ or $CH_2CH_3$;
$R^3$ is $C_{1-3}$ alkyl;
L is H, $CH_3$, or $NO_2$; and
$T^1$ and $T^2$ are each independently selected from the group consisting of H, Cl, Br, F and $CH_3$,
with the proviso that no more than one of $T^1$ and $T^2$ is H; and which optionally comprises:

(B1) treating a compound of Formula P-2a:

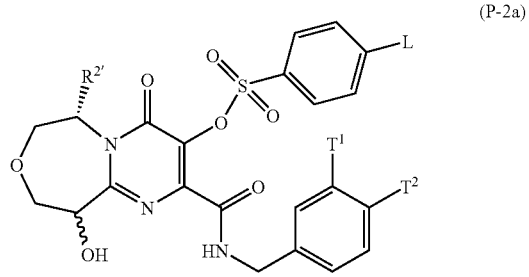

(P-2a)

with $R^PSO_2$-G in the presence of a base to obtain Compound P-IIIa; wherein G is halogen or $OS(O)_2R^P$; and which optionally further comprises:

(A1) hydrogenating a compound of Formula P-1a:

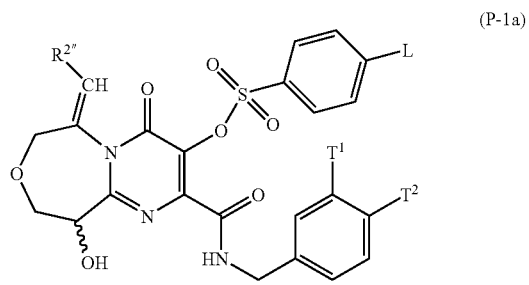

(P-1a)

in the presence of a catalytic amount of a cationic rhodium or ruthenium complex having a chiral bidentate or monodentate phosphine ligand to obtain Compound P-2a; wherein $R^{2''}$ is H or $CH_3$.

Features of the Sub-embodiment P-SE1 include the process as originally described in the sub-embodiment incorporating one or more of features (c1) to (c8), (b1) to (b5) and (a1) to (a4) as follows:
(c1) $R^{2'}$ is $CH_3$;
(c2) $R^P$ is $CH_3$;
(c3) $R^3$ is $CH_3$;
(c4) L is H;
(c5) $T^1$ is $CH_3$ and $T^2$ is F;
(c6) Step C is conducted in a solvent selected from the group consisting of MeOH, EtOH, IPA, n-propanol, MeOH-THF mixture, MeOH-MeTHF mixture, and MeOH-DCM mixture;
(c7) Step C is conducted at a temperature in a range of from about −20° C. to about 25° C.;
(c8) the amine $R^3NH_2$ is employed in an amount in a range of from about 2 to about 20 equivalents per equivalent of Compound P-3a;
(b1-a) G is Cl, Br, or $OS(O)_2R^P$;
(b1-b) G is Cl;
(b2-a) Step B1 is conducted in a solvent selected from the group consisting of DCM, THF, MeTHF, EtOAc and IPAc;
(b2-b) Step B1 is conducted in a solvent selected from the group consisting of DCM and MeTHF;
(b3) Step B1 is conducted at a temperature in a range of from about −5° C. to about 25° C.;
(b4) the base in Step B1 is a tri $C_{1-4}$ alkylamine (e.g., TEA, DIPEA or diethylisopropylamine);
(b5) the base in Step B1 is employed in an amount in a range of from about 1 to about 2 equivalents per equivalent of Compound P-2a;

(a1-a) the catalyst in Step A1 is an (NBD)$_2$RhBF$_4$ complex of 1,2-bis(2,5-di-isopropylphospholano)benzene; di(3,5-dimethylphenyl)phosphino]-2-(4-diphenylphosphino-2,5-dimethylthien-3-yl)-1,7,7-trimethylbicyclo[2.2.1]hept-2-ene; 1,2-dimethyl-2,3-bis(diphenylphosphinomethyl)cyclopentyl]methanol; or 4,4'-di-t-butyl-4,4',5,5'-tetrahydro-3,3'-bi-3H-dinaphtho[2,1-c: 1',2'-e]phosphepine;

(a1-b) the catalyst in Step A1 is a complex of (NBD)$_2$RhBF$_4$ and (+)-1,2-bis((2R,5R)-2,5-di-isopropylphospholano)benzene;

(a2) the catalyst in Step A1 is employed in an amount in a range of from about 0.5 to about 2 mole percent;

(a3) Step A1 is conducted in a solvent selected from the group consisting of MeOH, EtOH, IPA, MeTHF, cyclopentyl methyl ether, ethyl acetate, acetone, DCM., and a mixture of MeOH and DCM;

(a4) the hydrogenation in Step A1 is conducted at a temperature in a range of from about 10° C. to about 30° C.

It is understood that each of the features (c1) to (c8), (b1) to (b5) and (a1) to (a4) can be incorporated singly or multiply in any combination into Sub-embodiment P-SE1 described above and that the process resulting from each such incorporation is an aspect of the sub-embodiment.

Another embodiment of Process P comprises Step C as just described and further comprises:

(B2) contacting a carboxylate of Formula P-IIb:

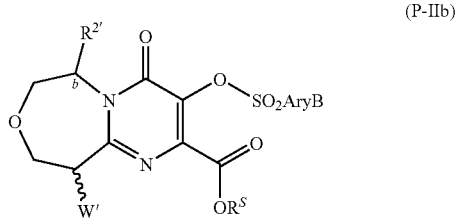

(P-IIb)

with an amine of formula AryA-NH$_2$ to obtain Compound P-IIIb:

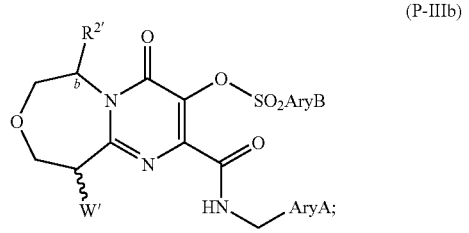

(P-IIIb)

wherein W' is halogen and R$^S$ is C$_{1-4}$ alkyl.

The reaction of Step B2 can be conducted by contacting Compound P-IIIb with the arylamine AryA-NH$_2$ in the presence of an alkylaluminum such as triethylaluminum, trimethyl aluminum or chlorodimethylaluminum. In one aspect, the alkylaluminum and the arylamine are brought together to form an amine-Al complex which is then brought into contact with Compound P-IIb. The coupling reaction is conducted in an organic solvent. Suitable solvents include aromatic hydrocarbons and halogenated hydrocarbons. Representative solvents include DCM and toluene. The reaction can suitably be conducted at a temperature in a range of from about −10° C. to about 30° C. and is typically conducted at a temperature in a range of from about 0° C. to about 25° C.

The arylamine is suitably employed in an amount from about 1 to about 10 equivalents (e.g., from about 1 to about 5 equivalents) per equivalent of Compound P-IIb and is typically employed in an amount of from about 1.4 to about 2 equivalents (e.g., about 1.5 equivalents) per equivalent of Compound P-IIb. The alkylaluminum and the arylamine are typically employed in equimolar amounts. The reaction can be quenched by treatment of the reaction mixture with acid.

The reaction of Step B2 can alternatively be conducted by first hydrolyzing the ester moiety —C(O)OR$^S$ to —COOH and then contacting the acid (or the acid halide such as the acid chloride which can be obtained by treating the acid with, for example, thionyl chloride (SOCl$_2$), phosphorus trichloride (PCl$_3$) or phosphorus pentachloride (PCl$_5$)) with the arylamine. The reaction is conducted in an organic solvent. Suitable organic solvents are aprotic solvents such as halohydrocarbons (note—the terms "halogenated hydrocarbon" and "halohydrocarbon" are used interchangeably herein), ethers, nitriles, and tertiary amides. Representative solvents include DCM, diethyl ether, MTBE, DME, dimethoxymethane, bis(2-methoxyethyl)ether, THF, MeTHF, dioxolane, dioxane, acetonitrile, propionitrile, DMF, DMAC, and NMP. The arylamine is suitably employed in an amount of from about 1 to about 10 equivalents per equivalent of Compound P-IIb and is typically employed in an amount of from about 1.4 to about 2 equivalents (e.g., about 1.5 equivalents) per equivalent of Compound P-IIb. An activating agent (e.g., EDC, DCC or BOP-Cl) can be employed in combination with the arylamine. When used in Step B2, the activating agent is suitably employed in an amount of at least one equivalent per equivalent of Compound P-IIb, and is typically employed in an amount in a range of from about 1 to 1.5 equivalents per equivalent of Compound P-IIb. When the acid halide is employed, the coupling with arylamine is typically conducted in the presence of a base which will neutralize the resulting acid by-products. Suitable bases include alkali metal hydroxides and tertiary amines. Representative bases include LiOH, KOH, NaOH, Na carbonate, K carbonate, NMM, NEM, TEA, DIPEA and DABCO. The base is suitably employed in an amount in a range of from about 1 to about 1.5 equivalents per equivalent of Compound P-IIb. The reaction in Step B2 can suitably be conducted at a temperature in a range of from about −10° C. to about 40° C. and is typically conducted at a temperature in a range of from about 0° C. to about 25° C.

Another embodiment of Process P comprises Steps C and B2 as just described and further comprises:

(A2) treating a halid-dihalide mixture of compounds of Formula P-Ib1 and Formula P-Ib2:

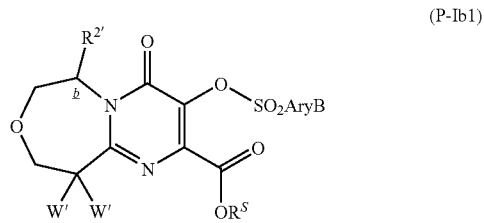

(P-Ib1)

-continued

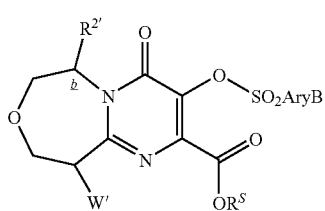
(P-Ib2)

with a reducing agent in the presence of a base to obtain Compound P-IIb.

Step A2 is conducted in an organic solvent. Suitable solvents include hydrocarbons, halohydrocarbons, alcohols, ethers, nitriles, cyclic sulfones, dialkylsulfoxides, N,N'-dialkyl-N,N'-alkylene ureas, and tertiary amides. Representative solvents includes hexane, heptane, toluene, DCM, chlorobenzene, MeOH, EtOH, IPA, MTBE, THF, ACN, sulfolane, DMSO, DMPU, DMF, DMAC and NMP. In one aspect, the solvent is dichloromethane or THF.

Suitable reducing agents include reducing metals, borohydrides, trialkylphosphines, triarylphosphines, dialkyl phosphites, and hydrogen halides. Representative reducing agents include Zn, samarium, Na borohydride, tributylphosphine, triphenylphosphine, dimethyl phosphite, diethylphosphite and HBr. In an aspect of Step A2, the reducing agent is a dialkylphosphite. The reducing agent can suitably be employed in an amount in a range of from about 1 to about 10 equivalents (e.g., from about 1 to about 5 equivalents) per equivalent of Compound P-Ib1 and Compound P-Ib2, and is typically employed in an amount in a range of from about 1 to about 1.5 equivalents.

The base is suitably a tertiary amine. Suitable amines include trialkylamines, pyridines, and N-alkylated cyclic amines. A class of suitable amines consists of TEA, DIPEA, diethylisopropylamine, NMM, pyridine and lutidine. In an aspect of Step A2, the base is NMM. The base can suitably be employed in an amount in a range of from about 0 to about 10 equivalents (e.g., from about 0.5 to about 5 equivalents) per equivalent of Compound P-Ib 1+Compound P-Ib2, and is typically employed in an amount in a range of from about 0.5 to about 1.5 equivalents.

The reaction in Step A2 can suitably be conducted at a temperature in a range of from about −40° C. to about 150° C. and is typically conducted at a temperature in a range of from about 10° C. to about 50° C.

Step A2 can provide the mono-halide in high yield without over-reduction to the non-brominated compound (i.e., where W' is replaced by H). Reference is made to Step 11 in Example 12.

Another sub-embodiment of Process P (Sub-embodiment P-SE2) is a process for preparing a compound of Formula P-4:

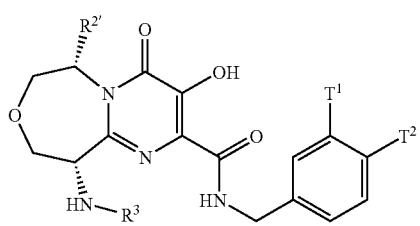
(P-4)

which comprises:

(C) contacting a compound of Formula P-3b:

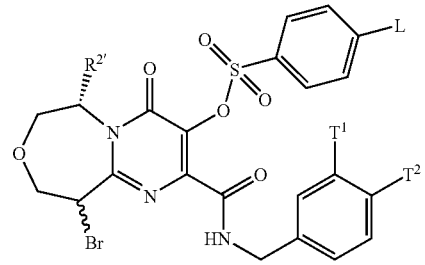
(P-3b)

with $R^3NH_2$ to obtain Compound P-4; wherein:

$R^{2'}$ is $CH_3$ or $CH_2CH_3$;

$R^3$ is $CH_3$ alkyl;

L is H, $CH_3$, or $NO_2$; and $T^1$ and $T^2$ are each independently selected from the group consisting of H, Cl, Br, F and $CH_3$, with the proviso that no more than one of $T^1$ and $T^2$ is H;

and which optionally further comprises:

(B2) contacting a carboxylate of Formula P-2b:

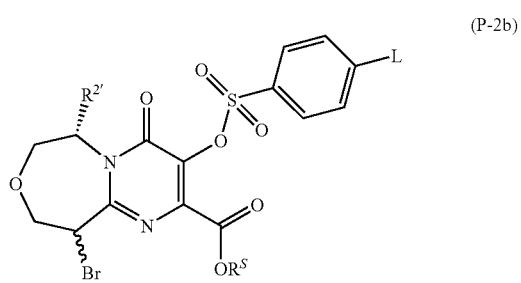
(P-2b)

with an arylamine of formula

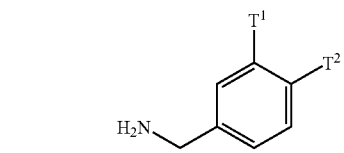

in the presence of an alkylaluminum to obtain Compound P-3b; and which optionally further comprises:

(A2) treating a halid-dibromide mixture of compounds of Formula P-1b1 and Formula P-1b2:

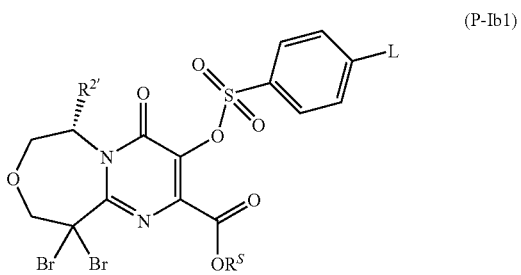
(P-Ib1)

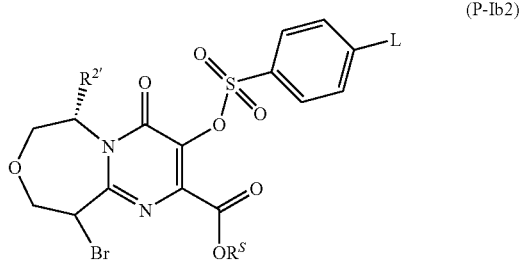

(P-Ib2)

with a dialkyl phosphite in the presence of a base to obtain Compound P-2b.

Features of the Sub-embodiment P-SE2 include the process as originally described in the sub-embodiment incorporating one or more of features (c1) to (c8), (b1) to (b5) and (a1) to (a6) as follows:

(c1) $R^{2'}$ is $CH_2CH_3$;
(c2) $R^3$ is $CH_3$;
(c3) $R^S$ is $CH_3$;
(c4) L is H;
(c5) $T^1$ is H and $T^2$ is F;
(c6) Step C is conducted in a solvent selected from the group consisting of methanol, ethanol, IPA, n-propanol, THF, MeTHF, DCE, DCM. ACN, EtOAc, and TIPAc;
(c7) Step C is conducted at a temperature in a range of from about −5° C. to about 30° C.;
(c8) the amine $R^3NH_2$ is employed in an amount in a range of from about 3 to about 10 equivalents per equivalent of Compound P-3b;
(b1-a) the alkylaluminum is trimethylaluminum or triethylaluminum;
(b1-b) the alkylaluminum is trimethylaluminum;
(b2) the arylamine in Step B2 is employed in an amount in a range of from about 1 to about 5 equivalents per equivalent of Compound P-2b;
(b3) the alkylaluminum and the arylamine are employed in equimolar amounts in Step B2;
(b4) Step B2 is conducted in a solvent selected from the group consisting of DCM and toluene;
(b5) Step B2 is conducted at a temperature in a range of from about −10° C. to about 30° C.;
(a1-a) the dialkylphosphite is dimethylphosphite or diethylphosphite;
(a1-b) the dialkylphosphite is diethylphosphite;
(a2) the dialkylphosphite in Step A2 is employed in an amount in a range of from about 1 to about 5 equivalents per equivalent of Compounds P-1b1 and P-1b2;
(a3-a) Step A2 is conducted in a solvent selected from the group consisting of hexane, heptane, toluene, DCM, chlorobenzene, MeOH, EtOH, IPA, MTBE, THF, ACN, sulfolane, DMSO, DMPU, DMF, DMAC and NMP;
(a3-b) Step A2 is conducted in a solvent selected from the group consisting of DCM and THF;
(a4) Step A2 is conducted at a temperature in a range of from about 10° C. to about 50° C.;
(a5-a) the base in Step A2 is a tertiary amine;
(a5-b) the base in Step A2 is selected from the group consisting of TEA, DIPEA, diethylisopropylamine, NMM, pyridine and lutidine;
(a6) the base in Step A2 is employed in an amount in a range of from about 0.5 to about 5 equivalents per equivalent of Compounds P-1b1 and P-1b2.

It is understood that each of the features (c1) to (c8), (b1) to (b5) and (a1) to (a6) can be incorporated singly or multiply in any combination into Sub-embodiment P-SE2 described above and that the process resulting from each such incorporation is an aspect of the sub-embodiment.

Another sub-embodiment of Process P (Sub-embodiment P-SE3) is the process of Sub-embodiment P-SE1 or P-SE2, which further comprises contacting Compound P-4 with an organic acid (selected, e.g., from alkylsulfonic acids, an arylsulfonic acids, alkylcarboxylic acids, dicarboxylic acids, and the like) in an amount and under conditions sufficient to form an organic acid salt of Compound P-4. In a feature of this sub-embodiment, Compound P-4 is Compound PN-4A:

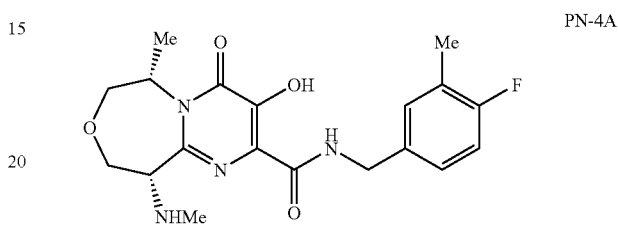

PN-4A and the organic acid is camphoric acid, wherein a solution of camphoric acid in alcohol (e.g., MeOH) can be added to a solution of Compound PN-4A in alcohol (e.g., MeOH), the combined solution can optionally be seeded with the camphoric acid salt, the solution can then be aged at a temperature in a range of from about 15° C. to about 25° C. to obtain a slurry of the desired salt, which can be filtered, washed, and dried to provide the isolated salt. In an aspect of this feature, the camphoric acid salt of Compound PN-4A is a crystalline 2:1 camphoric acid salt of Compound PN-4A.

In another feature of Sub-embodiment P-SE3, Compound P-4 is Compound PN-5A:

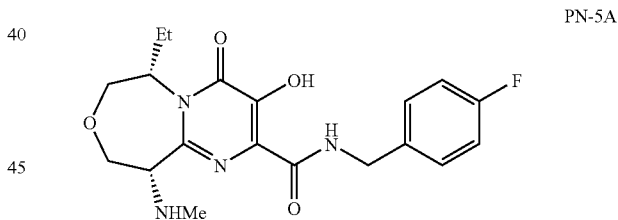

PN-5A and the organic acid is p-toluenesulfonic acid (PTSA), wherein an aqueous solution of the acid can be added to a solution of Compound PN-5A in alcohol (e.g., MeOH), the combined solution can optionally be seeded with the PTSA salt, the solution can then be aged at a temperature in a range of from about 15° C. to about 25° C. to obtain a slurry of the desired salt, which can be filtered, washed, and dried to provide an isolated salt which can be re-slurried in a suitable solvent (e.g., EtOAc) and then filtered, washed and dried to provide a salt of improved purity. In an aspect of this feature, the PTSA salt of Compound PN-5A is a crystalline PTSA salt of Compound PN-5A.

The salt formation step set forth in Sub-embodiment P-SE3 can improve the diastereomeric and chemical purity of Compound P-4.

The present invention also includes a process (Process Q) for preparing a pyrimidooxazepine compound of Formula Q-II:

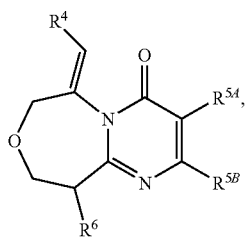

(Q-II)

which comprises contacting a compound of Formula Q-I:

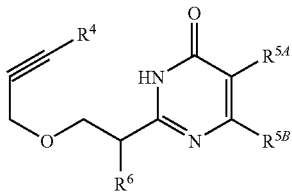

(Q-I)

with (i) a catalytic amount of an Au(I) salt or an Au(II) salt in combination with a bulky monodentate phosphine ligand and (ii) an Ag salt; wherein:

$R^4$ is H or $C_{1-4}$ alkyl;
$R^{5A}$ is OH or OC(O)$R^Q$;
$R^{5B}$ is C(O)O$R^Q$ or C(O)N($R^K$)$R^L$;
$R^Q$ is $C_{1-4}$ alkyl;
$R^K$ and $R^L$ are each independently H or $C_{1-4}$ alkyl;
$R^6$ is H, O—$P^{G1}$, or N(CH$_3$)—$P^{G2}$;
$P^{G1}$ is a hydroxy protective group; and
$P^{G2}$ is an amine protective group.

The hydroxy protective group $P^{G1}$ in the definition of $R^6$ can be any hydroxy protective group that is stable with respect to the reaction conditions employed in preparing Compound Q-II and is sufficiently labile to be removed (cleaved) via contact with a suitable hydroxy deprotecting agent (e.g., by treatment with acid) to give the free OH with little or no degradation of any other functional groups present in the compound. Hydroxy protective groups are known in the art and they and their formation and cleavage are described, for example, in *Protective Groups in Organic Chemistry*, edited by J. F. W. McOmie, Plenum Press, New York, 1973, pp. 95-143; and in T. W. Greene and P. G. M. Wuts, *Protective Groups in Organic Synthesis*, 3$^{rd}$ edition, John Wiley, New York, 1999, pp. 17-245, the disclosures of which are herein incorporated by reference.

The amine protective group $P^{G2}$ in the definition of $R^6$ can be any amine protective group that is stable with respect to the reaction conditions employed in preparing Compound Q-II and is sufficiently labile to be removed (cleaved) via contact with a suitable amine deprotecting agent (e.g., by treatment with an acid or by hydrogenolysis) to give the free amine with little or no degradation of any other functional groups present in the compound. Amine protective groups are known in the art and they and their formation and cleavage are described, for example, in *Protective Groups in Organic Chemistry*, edited by J. F. W. McOmie, Plenum Press, New York, 1973, pp. 43-75; and in T. W. Greene and P. G. M. Wuts, *Protective Groups in Organic Synthesis*, 3$^{rd}$ edition, John Wiley, New York, 1999, pp. 494-653, the disclosures of which are herein incorporated by reference.

Features of Compound Q-II and Process Q include the following:

(1a) $R^4$ is H or methyl;
(1b) $R^4$ is H;
(2a) $R^{5A}$ is OH, OC(O)—CH$_3$ (=acetate) or OC(O)C(CH$_3$)$_3$ (=pivalate);
(2b) $R^{5A}$ is OH;
(3a) $R^{5B}$ is C(O)OCH$_3$, C(O)OCH$_2$CH$_3$, C(O)NH$_2$, C(O)N-HCH$_3$, or C(O)N(CH$_3$)$_2$;
(3b) $R^{5B}$ is C(O)OCH$_3$;
(4a) $R^6$ is H;
(4b) $R^6$ is O—$P^{G1}$, wherein $P^{G1}$ is a silyl group or a sulfonyl group;
(4c) $R^6$ is O—$P^{G1}$, wherein $P^{G1}$ is (1) Si(C$_{1-6}$ alkyl)$_n$(phenyl)$_{3-n}$, wherein n is an integer equal to zero, 1, 2, or 3, (2) SO$_2$—C$_{1-6}$ alkyl, (3) SO$_2$—C$_{1-6}$ haloalkyl, or (4) SO$_2$-phenyl, wherein the phenyl in (1) or (4) is optionally substituted with from 1 to 3 substituents each of which is independently halogen, —C$_{1-4}$ alkyl, —O—C$_{1-4}$ alkyl, or nitro;
(4d) $R^6$ is O—$P^{G1}$, wherein $P^{G1}$ is trimethylsilyl (TMS), t-butyldiphenylsilyl (TBDPS), t-butyldimethylsilyl (TBS), or tri-isopropylsilyl (TIPS);
(4e) $R^6$ is O-TBS;
(4f) $R^6$ is N(CH$_3$)—PG$^2$, wherein $P^{G2}$ is (1) C(=O)—O—(CH$_2$)$_{0-1}$—CH=CH$_2$, (2) C(=O)—O—CH$_2$-phenyl in which the phenyl is optionally substituted with from 1 to 3 substituents each of which is independently halo, —NO$_2$, —C$_{1-4}$ alkyl, or —O—C$_{1-4}$ alkyl, (3) C(=O)—O—C$_{1-4}$ alkyl;
(4g) $R^6$ is N(CH$_3$)—$P^{G2}$, wherein $P^{G2}$ is t-butyloxycarbonyl (Boc), allyloxycarbonyl (Alloc), benzyloxycarbonyl (Cbz), p-methoxybenzyloxycarbonyl, p-nitrobenzyloxycarbonyl, p-bromobenzyloxycarbonyl, p-chlorobenzyloxycarbonyl, or 2,4-dichlorobenzyloxycarbonyl;
(4h) $R^6$ is N(CH$_3$)-Boc.

One or more of these features (1) to (4) can be combined with each other, wherein each such combination is a separate aspect of Compound Q-II and Process Q.

Process Q involves a cyclization via a hydroamination reaction to provide Compound Q-II, which can be employed as an intermediate in the preparation of pharmacologically active compounds including compounds embraced by Formula I. Step 9 of Example 11 illustrates Process Q.

Process Q is conducted in an organic solvent. Suitable solvents include hydrocarbons, halohydrocarbons, ethers, and nitriles. Representative solvents include hexane, toluene, DCM, DCE, trifluorotoluene, acetonitrile, and THF.

Process Q can suitably be conducted at a temperature in a range of from about 0° C. to about 80° C., and is typically conducted at a temperature in a range of from about 30° C. to about 50° C.

Suitable Au salts include AuCl, Me$_2$SAuCl and AuCl$_3$. The Au salt can suitably be employed in Process Q in an amount in a range of from about 0.01 to about 0.40 equivalents per equivalent of Compound Q-I, and is typically employed in an amount in a range of from about 0.02 to about 0.10 equivalents per equivalent of Compound Q-I.

The bulky monodentate phosphine ligand can suitably be a mondentate phosphine ligand substituted with three large hydrocarbyl groups selected from (i) branched $C_{3+}$ alkyl groups (where "$C_{3+}$" means 3 or more carbons in the group), (ii) $C_{5+}$ cycloalkyl groups optionally substituted with one or more branched $C_{3+}$ alkyls, (iii) $C_{7+}$ bicyclic and tricyclic saturated hydrocarbocyclyl groups optionally substituted with one or more branched $C_{3+}$ alkyls wherein the rings in the hydrocarbocyclyl are fused, bridged and/or linked by a single bond, and (iv) $C_{6+}$ aryl groups substituted with one or more branched $C_{3+}$ alkyls; wherein at least two of the three hydrocarbyl groups are typically selected from (i) and (ii).

Suitable bulky mondentate phosphine ligands includes ligands selected from those embraced by formulas $P(AkZ)_3$, $P(AkZ)_2((AryZ)_1$ and $P(AkZ)_2(HcyZ)_1$, wherein AkZ is a branched (i.e., secondary or tertiary) $C_{4-8}$ alkyl or a $C_{5-8}$ cycloalkyl optionally substituted with one or more (e.g., from 1 to 4) branched $C_{3-6}$ alkyl groups; AryZ is phenyl or biphenyl, wherein the phenyl or biphenyl is optionally substituted with one or more (e.g., from 1 to 4) branched $C_{3-6}$ alkyl groups; and HcyZ is bicyclohexyl or a $C_{7-12}$ fused or bridged, bicyclic or tricyclic saturated hydrocarbocyclyl, wherein the bicyclohexyl or the hydrocarbocyclyl is optionally substituted with one or more (e.g., from 1 to 6) branched $C_{3-6}$ alkyl groups. Representative AkZ groups include isopropyl, sec-butyl, isobutyl, t-butyl, cyclohexyl, and cycloheptyl. Representative AryZ groups include 2,4,6-tri-t-butylphenyl and 2', 4',6'-triisopropylbiphenyl Representative HcyZ groups include bicyclohexyl, decalyl, and adamantyl. Exemplary bulky monodentate phosphine ligands include t-butyl-Xphos, Xphos, and tri-t-butylphosphine.

Suitable Ag salts include $AgSbF_6$, $AgBF_4$, and AgOTf. The Ag salt can suitably be employed in Process Q in an amount in a range of from about 0.01 to about 1.2 equivalents per equivalent of Compound Q-I, and is typically employed in an amount in a range of from about 0.02 to about 0.30 equivalents per equivalent of Compound Q-I.

A Lewis acid additive can optionally be employed to enhance selectivity. Suitable optional Lewis acids include LiOTf, $Mg(OTf)_2$, and $Zn(OTf)_2$. The Lewis acid can suitably be employed in Process Q in an amount in a range of from about 0.1 to about 2 equivalents per equivalent of Compound Q-I, and is typically employed in an amount in a range of from about 0.5 to about 1 equivalents per equivalent of Compound Q-I.

Process Q can produce the 7-membered oxazine ring in Compound Q-II with high selectivity with respect to the corresponding 8-membered ring.

The present invention also includes a process (Process R) for preparing a pyrimidooxazepine compound of Formula R-II:

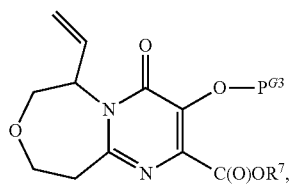

(R-II)

which comprises contacting a compound of Formula R-I:

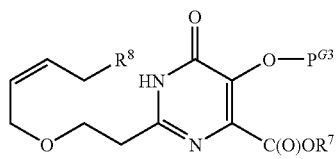

(R-I)

with a catalytic amount of a Pd catalyst in combination with a $C_{1-4}$ alkylphosphine or a phenylphosphine ligand; wherein: $R^7$ is $C_{1-4}$ alkyl;

$R^8$ is halogen or $OC(O)$—$C_{1-6}$ alkyl; and
$P^{G3}$ is a hydroxy protective group.

The description and definition of hydroxy protective group $P^{G1}$ set forth above with respect to Process Q applies equally to $P^{G3}$ in Process R.

Features of Compound R-II and Process R include the following:
(1a) $R^7$ is methyl or ethyl;
(1b) $R^7$ is methyl;
(2a) $R^8$ is halogen;
(2b) $R^8$ is Br, Cl, or F;
(2c) $R^8$ is Cl;
(2d) $R^8$ is $OC(O)$—$CH_3$ (=acetate) or $OC(O)C(CH_3)_3$ (=pivalate);
(2e) $R^8$ is $OC(O)$—$CH_3$;
(3a) $P^{G3}$ is a silyl group or a sulfonyl group;
(3b) $P^{G3}$ is (1) $Si(C_{1-6}$ alkyl$)_n$(phenyl$)_{3-n}$, wherein n is an integer equal to zero, 1, 2, or 3, (2) $SO_2$—$C_{1-6}$ alkyl, (3) $SO_2$—$C_{1-6}$ haloalkyl, or (4) $SO_2$-phenyl, wherein the phenyl in (1) or (4) is optionally substituted with from 1 to 3 substituents each of which is independently halogen, $C_{1-4}$ alkyl, O—$C_{1-4}$ alkyl, or nitro;
(3c) $P^{G3}$ is benzenesulfonyl, p-toluenesulfonyl, methanesulfonyl, p-nitrobenzenesulfonyl, or trifluoromethanesulfonyl;
(3d) $P^{G3}$ is benzenesulfonyl.

One or more of these features (1) to (3) can be combined with each other, wherein each such combination is a separate aspect of Compound R-II and Process R.

Process R involves a cyclization via an intramolecular allylation reaction to provide Compound R-II, which can be employed as an intermediate in the preparation of pharmacologically active compounds including compounds embraced by Formula I. Step 8 of Example 12 illustrates Process R.

Process R is conducted in an organic solvent. Suitable solvents include hydrocarbons, halohydrocarbons, ethers, nitrile, and tertiary amides. Representative solvents include hexane, toluene, DCM, DCE, chloroform, chlorobenzene, o-dichlorobenzene, ACN, DMF, DMAC, NMP, sulfolane and DMPU. In one aspect, the solvent is DCM.

Process R can suitably be conducted at a temperature in a range of from about −20° C. to about 100° C., and is typically conducted at a temperature in a range of from about 10° C. to about 40° C.

The catalyst is a Pd catalyst such as a unsupported Pd metal; Pd metal on a support such as carbon, alumina or calcium carbonate; Pd salts such as $Pd(OAc)_2$, Pd(trifluoroacetate)$_2$, PdC12; or Pd complexes with Pd at an oxidation state 0, 1 or 2. Suitable complexed Pd catalysts include Pd2(dba)$_3$, Pd(dba)$_2$, PdCl(allyl) dimer, $PdCl_2(PPh_3)_2$. The ligand in the complex can be added as a separate entity or it can be complexed to the palladium to form a descrete compound containing both the Pd and the ligand.

Ligands suitable for complexing with Pd include the alkylphosphines and arylphosphines; e.g., $C_{1-4}$ alkylphosphines and phenylphosphines. In one aspect, the ligand is a Monophos ligand or a Trost ligand. Representative ligands include 1,2-diaminocyclohexane-N,N'-bis(2-diphenylphosphino-1-benzoyl and 1,2-diaminocyclohexane-N,N'-bis(2-diphenylphosphino-1-naphthoyl, wherein the ligand is optionally but preferably employed in the presence of a tetraalkyl or tetraaryl ammonium halide or a mixed alkyl+aryl ammonium halide, or a mixed alkylaryl+alkyl ammonium halide. Suitable halides include tetramethyl-, tetraethyl-, tetrabutyl-, tetraphenyl-, and benzyltrimethyl-ammonium bromides and chlorides. In one aspect, the ammonium halide is tetrabutylammonium bromide.

The Pd catalyst can suitably be employed in Process R in an amount in a range of from about 0.001 to about 0.1 equivalents per equivalent of Compound R-I, and is typically employed in an amount in a range of from about 0.01 to about 0.03 equivalents per equivalent of Compound R-I. The Pd catalyst and the ligand are typically employed in a 1:2 ratio of Pd:ligand.

Process R can provide a clean, selective reaction leading to 7-membered ring products with minimal side reactions.

The present invention also includes a process (Process S) for preparing a hexahydropyrimidoazepine compound of Formula S-III:

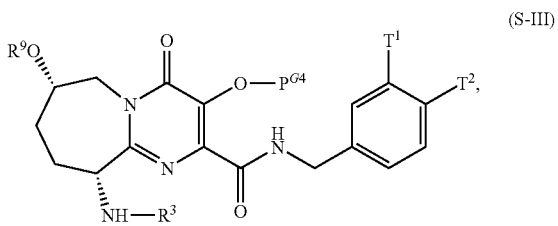

(S-III)

which comprises:
(S-B) hydrogenating a compound of Formula S-II

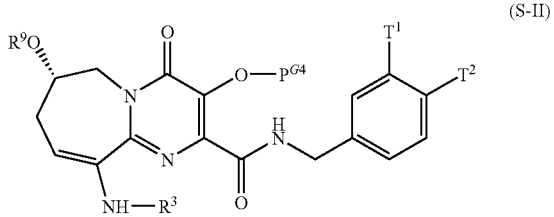

(S-II)

in the presence of a catalytic amount of a cationic rhodium complex having a chiral bidentate or monodentate phosphine ligand; and which optionally further comprises either:
(S-Aa) contacting a compound of Formula S-Ia:

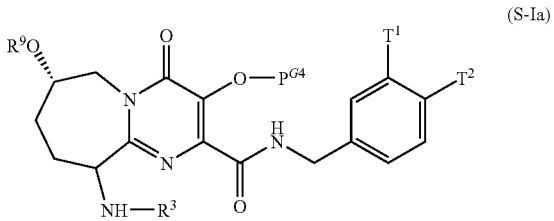

(S-Ia)

first with an oxidizing agent and then with tertiary amine base to obtain Compound S-II; or
(S-Ab) contacting a compound of Formula S-Ib:

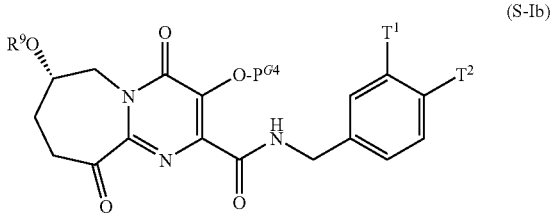

(S-Ib)

with an amine of Formula $R^3$—$NH_2$ in the presence of an acid;

wherein:
$R^3$ is $CH_3$ or $CH_2CH_3$;
$R^9$ is $CH_3$ or $CH_2CH_3$;
$P^{G4}$ is a hydroxy protective group; and
$T^1$ and $T^2$ are each independently selected from the group consisting of H, Cl, Br, F and $CH_3$, with the proviso that no more than one of $T^1$ and $T^2$ is H.

The description and definition of hydroxy protective group $P^{G1}$ set forth above with respect to Process Q applies equally to $P^{G4}$ in Process S.

Features of Compound S-1 and Process S include the following:
(1a) $R^3$ is methyl;
(1b) $R^3$ is ethyl;
(2a) $R^9$ is methyl;
(2b) $R^9$ is ethyl;
(3a) $P^{G4}$ is a silyl group or a sulfonyl group;
(3b) $P^{G4}$ is (1) $Si(C_{1-6}$ alkyl$)_n$(phenyl$)_{3-n}$, wherein n is an integer equal to zero, 1, 2, or 3, (2) $SO_2$—$C_{1-6}$ alkyl, (3) $SO_2$—$C_{1-6}$ haloalkyl, or (4) $SO_2$-phenyl, wherein the phenyl in (1) or (4) is optionally substituted with from 1 to 3 substituents each of which is independently halogen, —$C_{1-4}$ alkyl, —O—$C_{1-4}$ alkyl, or nitro;
(3c) $P^{G4}$ is benzenesulfonyl, p-toluenesulfonyl, methanesulfonyl, p-nitrobenzenesulfonyl, or trifluoromethanesulfonyl;
(3d) $P^{G4}$ is benzenesulfonyl;
(4a) $T^1$ is $CH_3$ and $T^2$ is F;
(4b) $T^1$ is H and $T^2$ is F.

One or more of these features (1) to (4) can be combined with each other, wherein each such combination is a separate aspect of Compound S-III and Process S.

Process S involves the asymmetric hydrogenation of an enamine to provide Compound S-III, which can be employed as an intermediate in the preparation of pharmacologically active compounds including compounds embraced by Formula I. Steps 15 and 16 of Example 13 illustrate the steps of Process S.

Step S-B is conducted in an organic solvent. Suitable solvents for Step S-B include alcohols and fluoroalcohols. Representative solvents for Step S-B include TFE, MeOH and EtOH.

Step S-B can suitably be conducted at a temperature in a range of from about 5° C. to about 60° C., and is typically conducted at a temperature in a range of from about 20° C. to about 25° C.

The hydrogenation catalyst in Step S-B can suitably be a bis(cyclooctadiene)rhodium(I) tetrafluoroborate or a bis(norbornadiene)rhodium(I) tetrafluoroborate complex with ligands such as 1-{2-[2-(diphenylphosphino)phenyl]-ferrocenyl}ethylbis(2-norbornyl)phosphine; 1-{2-[2-(bis(3,5-dimethyl-4-methoxyphenyl)phosphino)phenyl]-ferrocenyl}ethylbis(2-norbornyl)phosphine; 1-[2-(di-2-furylphosphino)ferrocenyl]ethyldi-tert-butylphosphine; 1-[2-(di-2-furylphosphino)ferrocenyl]ethyldicyclohexylphosphine; 1-[2-(di-1-naphthylphosphino)ferrocenyl]ethyldi-tert-butylphosphine; 1-[2-(di-p-tolylphosphino)ferrocenyl]ethyldi-tert-butylphosphine; or 1-{2-[2-(diphenylphosphino)phenyl]-ferrocenyl}ethyldicyclohexylphosphine.

In one aspect, the catalyst is a bis(norbornadiene)rhodium (1) tetrafluoroborate complex of 1-[2-(di-2-furylphosphino)ferrocenyl]ethyldi-tert-butylphosphine or 1-{2-[2-(diphenylphosphino)phenyl]-ferrocenyl}ethylbis(2-norbornyl) phosphine.

The catalyst can suitably be employed in Step S-B in an amount in a range of from about 0.1 to about 20 mole %, and is typically employed in an amount in a range of from about 0.5 to about 1 mole % (i.e., moles catalyst per mole of Compound S-II).

The source of hydrogen in Step S-B is hydrogen gas, optionally in admixture with a carrier gas that is chemically inert under the reaction conditions employed in Step A1 (e.g., nitrogen or a noble gas such as helium or argon). The pressure is not a critical aspect in Step S-B. The pressure can suitably be in a range of from about ambient pressure to about 500 psig, and is typically in a range of from about 50 psig to about 150 psig (e.g., about 100 psig). The uptake of hydrogen is not a critical process parameter, although at least a stoichiometric amount of hydrogen gas is typically employed.

Step S-B can optionally be conducted in the presence of a Bronsted acid such as tetrafluoroboric acid, TFA, dichloroacetic acid, chloroacetic acid, or beznenesulfonic acid. In one aspect the acid is TFA or dichloroacetic acid. In another aspect, the acid is dichloroacetic acid. The acid can suitably be employed in an amount in a range of from about 0.25 to about 1 equivalent per equivalent of Compound S-II, and is typically employed in an amount of from about 0.5 to about 0.8 equivalent.

Step S-B can also optionally be conducted in the presence of a metal or non-metal orthoester such as an additive such as titanium (IV) isopropoxide, aluminum isopropoxide, tetramethyl orthosilicate, trimethyl borate, and ethyl orthoacetate. In one aspect the orthoester is titanium(IV) isopropoxide or aluminum isopropoxide. The orthoester can suitably be employed in an amount in a range of from about 0.25 to about 2 equivalent per equivalent of Compound S-II, and is typically employed in an amount of from about 1 equivalent.

Step S-Aa is conducted in an organic solvent. Suitable solvents for Step S-Aa include esters. Representative solvents for Step S-Aa include EtOAc and IPAc.

Step S-Aa can suitably be conducted at a temperature in a range of from about −5° C. to about 25° C., and is typically conducted at a temperature in a range of from about 0° C. to about 10° C.

The oxidizing agent in Step S-Aa consists of a hypochlorite, an alcohol, and a alkylcarboxylic acid. In one aspect, the oxidizing agent is NaOCl+t-butyl alcohol+acetic acid.

The oxidizing agent can suitably be employed in Step S-Aa in an amount in a range of from about 0.5 to about 2 equivalents per equivalent of Compound S-Ia, and is typically employed in an amount in a range of from about 0.5 to about 1.5 equivalents per equivalent of Compound S-Ia.

The tertiary amine base in Step S-Aa can suitably be DBU, TEA, DABCO or DIPEA. In one aspect, the base is DBU. The tertiary amine base can suitably be employed in Step S-Aa in an amount in a range of from about 1 to about 2 equivalents per equivalent of Compound S-Ia, and is typically employed in an amount in a range of from about 1 to about 1.5 equivalents (e.g., from about 1 to about 1.2 equivalents) per equivalent of Compound S-Ia.

Step S-Ab is conducted in an organic solvent. Suitable solvents for Step S-Ab include halohydrocarbons, ethers, nitriles and amides. Representative solvents for Step S-Ab include DCM, ACN, THF and DMF.

Step S-Ab can suitably be conducted at a temperature in a range of from about 10° C. to about 50° C., and is typically conducted at a temperature in a range of from about 20° C. to about 40° C.

The acid in Step S-Ab can suitably be an organic carboxylic acid or an organic sulfonic acid. Representative acids include acetic acid and methanesulfonic acid. The acid can suitably be employed in Step S-Ab in an amount in a range of from about 4 to about 10 equivalents per equivalent of Compound S-Iba, and is typically employed in an amount in a range of from about 5 to about 7 equivalents per equivalent of Compound S-Ib.

It is to be understood that the solvents, agents, catalysts, reaction amounts, reaction temperatures, etc. described above with respect to Processes P, Q, R and S and embodiments and sub-embodiments thereof are intended only to illustrate, not limit, the scope of the processes. For example, the solvent employed in a particular reaction step (e.g., any of Steps A1, B1, A2, B2 and C of Process R) can be any organic substance which under the reaction conditions employed in the step of interest is in the liquid phase, is chemically inert, and will dissolve, suspend, and/or disperse the reactants and any reagents so as to bring the reactants and reagents into contact and to permit the reaction to proceed. Similar considerations apply to the choice of bases, catalysts, and other reagents employed in the process steps. Furthermore, each of the steps can be conducted at any temperature at which the reaction forming the desired product can detectably proceed. The reactants, catalysts and reagents in a given step can be employed in any amounts which result in the formation of at least some of the desired product. Of course, a high conversion (e.g., at least about 60% and preferably higher) of starting materials in combination with a high yield (e.g., at least about 50% and preferably higher) of desired products is typically the objective in each step, and the choice of solvents, agents, catalysts, reaction amounts, temperatures, etc. that can provide relatively good conversions of reactants and yields of products are preferred, and the choices that can provide optimal conversions and yields are more preferred. The particular solvents, agents, catalysts, reaction amounts, reaction temperatures, etc. described above with respect to Processes P, Q, R and S and embodiments and sub-embodiments thereof can provide good to optimum conversions and yields.

The reaction times for the process steps described above depend upon such factors as (i) the choice and relative proportions of the starting substrate and other reagents, (ii) the choice of solvent, (iii) the choice of reaction temperature, and (iv) the level of conversion desired. The reactions are typically conducted for a time sufficient to achieve 100% conversion.

The progress of any reaction step set forth herein can be followed by monitoring the disappearance of a reactant (e.g., Compound P-III in Step C of Process R) and/or the appearance of the desired product (e.g., Compound P-IV in Step C of Process R) using such analytical techniques as TLC, HPLC, IR, NMR or GC.

To the extent not already described above, the recovery and isolation of products of any of the foregoing reaction steps can typically be achieved using conventional technqiues such as solvent extraction, washing, filtration, crystallization, drying and the like. A reaction product which is for use as a starting material in a subsequent step can alternatively be used directly (i.e., without recovery and isolation from the reaction mixture) in the next step, after (as necessary) suitable work-up using conventional procedures such as removal of by-products and contaminants from the reaction solution containing the desired material (e.g., by washing, filtration or the like), solvent switching, or the like.

The present invention also includes a camphoric acid salt (e.g., a crystalline camphoric acid salt) of Compound PN-4A, a PTSA salt (e.g., a crystalline PTSA salt) of Compound PN-5A, Compound Q-II and embodiments thereof, Compound R-II and embodiments thereof, Compound S-II and embodiments thereof.

Abbreviations employed herein include the following: ACN=acetonitrile; AcOH=acetic acid; Barg=bar-gauge; Bn=benzyl; Boc=t-butyloxycarbonyl; (Boc)₂O=di-t-butyl carbonate; BOP=benzotriazol-1-yloxytris-(dimethylamino) phosphonium; DABCO=1,4-diazabicyclo[2.2.2]octane; DBA (or dba)=dibenzylideneacetone; DBU=1,8-diazabicyclo[5.4.0]undec-7-ene; DCC=dicyclohexyl carbodiimide; DCE=1,2-dichloroethane; DCM=dichloromethane; DMAC=N,N-dimethylacetamide; DMAD=dimethylacetylenedicarboxylate; DMAP=4-dimethylaminopyridine; DMF=N,N-dimethylformamide; DMPU=N,N'-dimethylpropyleneurea; DMSO=dimethylsulfoxide; EDC=1-ethyl-3-(3-dimethylaminopropyl) carbodiimide; ES MS=electrospray mass spectroscopy; Et=ethyl; EtNH₂=ethylamine; EtOAc=ethyl acetate; EtOH=ethanol; FBS=fetal bovine serum; GC=gas chromatography; HDPE=high-density polyethylene; HMPA=hexamethylphosphoramide; HOAT=1-hydroxy-7-azabenzotriazole; HPLC=high performance liquid chromatography; HRMS=high resolution mass spectroscopy; IPA=isopropyl alcohol; IPAc=isopropyl acetate; LAH=lithium aluminum hydride; LC-MS=liquid chromatography-mass spectroscopy; LDA=lithium diisopropylamide; Me=methyl; MeOH=methanol; MeTHF=2-methyltetrahydrofuran; MsCl=methanesulfonyl (or mesyl) chloride; MTBE=methyl tert-butyl ether; NBD=norbornadine; NBS=N-bromosuccinimide; NMM=N-methylmorpholine; NMP=N-methylpyrrolidone; NMR=nuclear magnetic resonance; NOE=nuclear Overhauser effect; OBD=optimum bed density (chromatography column); PTSA=p-toluenesulfonic acid; RB=round bottom(ed) (flask); TBAF=tetrabutylammonium fluoride; TBS-Cl=tert-butyldimethylsilyl chloride; t-BuOK=potassium tert-butoxide; TEA=triethylamine; TEMPO=2,2,6,6-tetramethyl-1-piperidine-1-oxyl; Tf=triflate (=trifluoromethanesulfonate); TFA=trifluoroacetic acid; TFE=2,2,2-trifluoroethanol; THF=tetrahydrofuran; TLC=thin layer chromatography; UV=ultraviolet; XRPD=X-ray powder diffraction.

The following examples serve only to illustrate the invention and its practice. The examples are not to be construed as limitations on the scope or spirit of the invention. In these examples, "room temperature" or "ambient temperature" refers to a temperature in a range of from about 20° C. to about 25° C. The relative stereochemistry of each of the title products in Examples 2-5 was determined by comparative NOE studies of the isomers.

EXAMPLE 1

N-((10R)-2-{[(4-fluoro-3-methylbenzyl)amino]carbonyl}-3-hydroxy-7,7-dimethyl-4-oxo-4,6,7,8,9,10-hexahydropyrimido[1,2-a]azepin-10-yl)-N',N',N'-trimethylethanediamide (Compound 1A).

(1A)

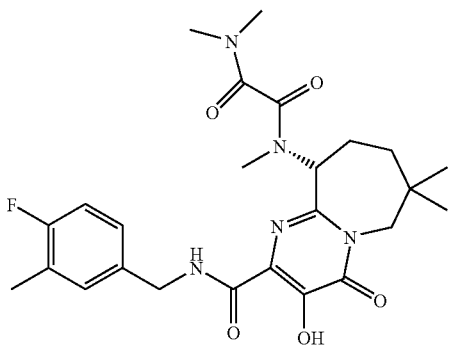

N-((10S)-2-{[(4-fluoro-3-methylbenzyl)amino]carbonyl}-3-hydroxy-7,7-dimethyl-4-oxo-4,6,7,8,9,10-hexahydropyrimido[1,2-a]azepin-10-yl)-N,N',N'-trimethylethanediamide (Compound 1B).

(1B)

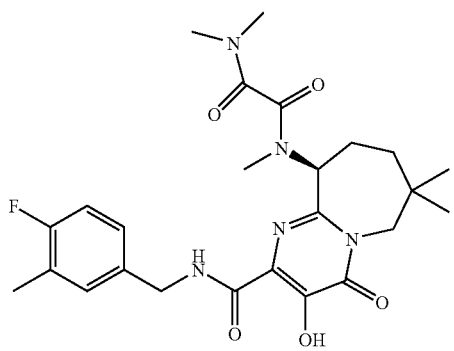

Step 1: Methyl 2,2-dimethyl-3-(tetrahydro-2H-pyran-2-yloxy)propanoate

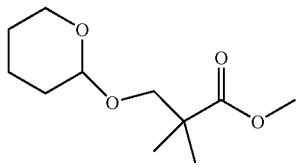

To a stirred mixture of hydroxypivalic acid methyl ester (50.0 g, 378 mmol) and p-toluenesulfonic acid monohydrate (1.439 g, 7.57 mmol) in 250 mL of methyl-tert-butylether was added dihydropyran (48.1 mL, 568 mmol) slowly with cooling. The mixture was stirred at room temperature overnight, 50 mL of saturated NaHCO₃ added and the mixture shaken and separated. The organic layer dried over MgSO₄ and concentrated. Purification of the residue by flash chromatography using 330 g column, 0%-5% ethyl acetate in hexane gave methyl 2,2-dimethyl-3-(tetrahydro-2H-pyran-2-yloxy)propanoate as a clear oil: ¹H NMR (400 MHz, CDCl₃) δ 4.5 (s, 1H), 3.8-3.6 (m, 2H), 3.6 (m, 3H), 3.4 (s, 1H), 3.25 (m, 1H), 1.7 (m, 1H), 1.6-1.18 (m, 5H), 1.05 (m, 6H).

Step 2: 2,2-dimethyl-3-(tetrahydro-2H-pyran-2-yloxy)propan-1-ol

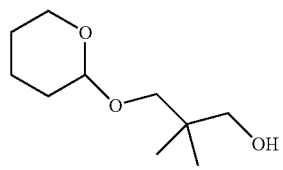

To solution of LiAlH₄ (397 mL, 397 mmol) in THF (250 mL) cooled in an ice bath to 0° C. was added methyl 2,2-dimethyl-3-(tetrahydro-2H-pyran-2-yloxy)propanoate (82 g, 378 mmol) in THF (250 mL) via addition funnel keeping the internal temperature below 6° C. When addition was complete the reaction was allowed to warm to room temperature and stir overnight. The mixture was cooled in an ice bath and quenched with H₂O (16 mL, 888 mmol), then after 5 minutes, 10 N NaOH (16 mL, 160 mmol), and after another 15 minutes, H₂O (48 mL, 2664 mmol). The mixture was allowed to stir for 30 minutes, then filtered with a THF rinse. The filtrate was concentrated and azeotropically dried with toluene. Further drying under vacuum gave 2,2-dimethyl-3-(tetrahydro-2H-pyran-2-yloxy)propan-1-ol as a colorless liquid: ¹H NMR (400 MHz, CDCl₃) δ 4.58 (m, 1H), 3.85 (m, 1H), 3.6 (d, 1H), 3.5 (m, 2H), 3.4 (m, 1H), 3.2 (d, 1H), 2.8 (t, 1H), 1.8 (m, 2H), 1.6 (m, 4H), 0.85 (s, 6H).

Step 3: 2,2-dimethyl-3-(tetrahydro-2H-pyran-2-yloxy)propanal

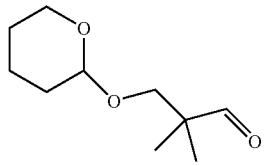

To a stirred solution of 2,2-dimethyl-3-(tetrahydro-2H-pyran-2-yloxy)propan-1-ol (20 g, 106 mmol) an TEA (44.4 mL, 319 mmol) in dry dichloromethane (300 mL) cooled in an ice bath to 0° C.±5° C. was added a solution of sulfur trioxide pyridine complex (50.7 g, 319 mmol) in anhydrous DMSO (300 mL) in one portion. There was an exotherm to 27° C. The bath was removed and the mixture allowed to stir for 20 minutes at room temperature after which time conversion was complete by TLC. The reaction was quenched with 225 mL of saturated NaHCO₃, concentrated on the rotovap to remove dichloromethane and extracted with 3×200 mL of ethyl acetate. The combined extracts were washed once with 250 mL of 10% citric acid, dried over MgSO₄ and concentrated. Drying under vacuum gave 2,2-dimethyl-3-(tetrahydro-2H-pyran-2-yloxy)propanal as an oil. Contains ~40% DMSO by NMR: ¹H NMR (400 MHz, CDCl₃) δ 9.6 (s, 1H), 4.6 (m, 1H), 3.8 (d, 1H), 3.5 (m, 1H), 3.38 (d, 1H), 1.8-1.4 (min, 6H), 1.06 (s, 3H), 1.04 (s, 3H).

Step 4: Ethyl (2E)-4,4-dimethyl-5-(tetrahydro-2H-pyran-2-yloxy)pent-2-enoate

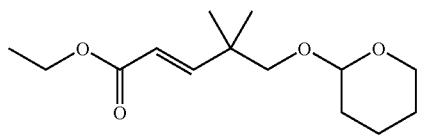 [SMILES: CCOC(=O)/C=C/C(C)(C)COC1CCCCO1]

To a slurry of mixture of acetonitrile (200 mL) and lithium chloride (13.66 g, 322 mmol), under nitrogen at 25° C. was added triethyl phosphonoacetate (64.5 mL, 322 mmol) and then DBU (32.4 mL, 215 mmol). During the addition the reaction temperature rose to 33° C. then cooled back to 25° C. over 30 minutes. The mixture was stirred and cooled to 0° C. and Reactant 1 (20 g, 107 mmol) was added with a 5 mL CH₃CN rinse in. After stirring for 1 hour at 0° C. the mixture was allowed to warm and stir at 25° C. for 2 hours, then diluted with 250 mL of MTBE and 250 mL of water, separated and the organic layer washed with 100 mL of water. The combined aqueous layers extracted 100 mL of MTBE and the combined organic extracts washed 200 mL of brine and dried over MgSO₄, then concentrated. Purification by flash chromatography eluting with 0% to 10% EtOAc in hexane gave ethyl (2E)-4,4-dimethyl-5-(tetrahydro-2H-pyran-2-yloxy)pent-2-enoate as a colorless oil: ¹H NMR (400 MHz, CDCl₃) δ 7.0 (d, 1H), 5.8 (d, 1H), 4.58 (t, 1H), 4.2 (q, 2H), 3.8 (m, 1H), 3.6 (d, 1H), 3.5 (m, 1H), 3.16, (d, 1H), 1.8-1.5 (m, 6H), 1.3 (t, 3H), 1.06 (s, 3H), 1.05 (s, 3H).

Step 4: Ethyl 4,4-dimethyl-5-(tetrahydro-2H-pyran-2-yloxy)pentanoate

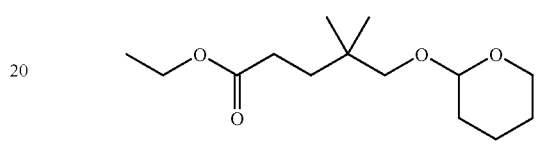

A mixture of ethyl (2E)-4,4-dimethyl-5-(tetrahydro-2H-pyran-2-yloxy)pent-2-enoate (23 g, 90 mmol) and 5% Pt on carbon (3 g, 14.65 mmol) in ethanol (200 mL) was shaken on the Parr under 45 psi of hydrogen for 5 days (complete conversion by TLC: 10% EtOAc/hexane-no UV active spots). The catalyst was filtered off catalyst and the filtrate concentrated. Drying under vacuum gave ethyl 4,4-dimethyl-5-(tetrahydro-2H-pyran-2-yloxy)pentanoate as a colorless oil: ¹H NMR (400 MHz, CDCl₃) δ 4.7 (t, 1H), 4.12 (q, 2H), 3.8 (m, 1H), 3.5 (m, 1H), 3.4 (d, 1H), 3.0, (d, 1H), 2.3 (m, 2H), 1.8 (m, 1H), 1.7-1.5 (m, 6H), 1.9 (s, 3H), 1.88 (s, 3H).

Step 5: 4,4-dimethyl-5-(tetrahydro-2H-pyran-2-yloxy)pentanal

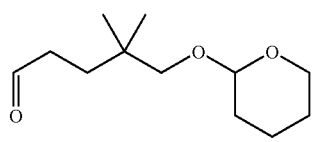

To a solution of ethyl 4,4-dimethyl-5-(tetrahydro-2H-pyran-2-yloxy)pentanoate (11.3 g, 43.7 mmol) in toluene (300 mL) cooled to −78° C. under nitrogen was added diisobutylaluminum hydride 1.0M in heptane (53 mL, 52.5 mmol) slowly, keeping the internal temperature below −70° C. The mixture was allowed to stir in the cold for 15 minutes (TLC: 20% EtOAc in hexane). The reaction was quenched with MeOH (3.00 mL, 161 mmol) allowed to warm to −10 C, diluted with 500 mL of ethyl acetate and 500 mL of saturated NaCl. The mixture was allowed to warm and stir for 60 minutes forming a gel. The gelatinous mixture was filtered through diatomaceous earth and washed with 750 mL of ethyl acetate. The organic layer was separated, dried over MgSO₄ and concentrated. Drying under vacuum gave 4,4-dimethyl-5-(tetrahydro-2H-pyran-2-yloxy)pentanal as a clear oil: ¹H NMR (400 MHz, CDCl₃) δ 9.8 (s, 1H), 4.6 (t, 1H), 3.8 (m, 1H), 3.6 (m, 1H), 3.5 (d, 1H), 3.0, (d, 1H), 2.4 (m, 2H), 1.8 (m, 1H), 1.7-1.5 (m, 6H), 0.93 (s, 3H), 0.92 (s, 3H).

Step 6: tert-Butyl[1-cyano-4,4-dimethyl-5-(tetrahydro-2H-pyran-2-yloxy)pentyl]methylcarbamate

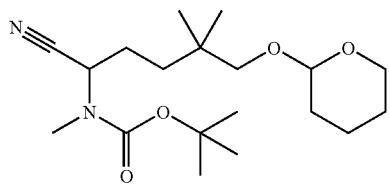 [SMILES: CN(C(=O)OC(C)(C)C)C(C#N)CCC(C)(C)COC1CCCCO1]

A mixture of crude 4,4-dimethyl-5-(tetrahydro-2H-pyran-2-yloxy)pentanal, MTBE (15 mL), methylamine hydrochloride (3.08 g, 45.7 mmol), sodium cyanide (1.399 mL, 45.7 mmol) and water (15.0 mL) was stirred in a stoppered flask for 24 hours. TLC (10% EA/hexanes) indicates complete consumption of starting material. The mixture was extracted with 25 mL of ethyl acetate, concentrated on rotovap. Drying under vacuum gave of a clear oil. The crude aminonitrile was taken up in 25 mL of ethyl acetate and di-tert-butyl dicarbonate (10.49 mL, 45.7 mmol) was added. After stirring at room temperature over the weekend, the mixture was concentrated. Purification by flash chromatography eluting with 10% EtOAc/hexane afforded tert-butyl [1-cyano-4,4-dimethyl-5-(tetrahydro-2H-pyran-2-yloxy)pentyl]methylcarbamate: $^1$H NMR (400 MHz, CDCl$_3$) δ 4.7 (dd, 1H), 3.8 (t, 1H), 3.6 (m, 1H), 3.5 (dd, 1H), 3.0, (dd, 1H), 2.89, 2.88 (2s, 3H), 1.8 (m, 2H), 1.5 (m, 6H), 1.47 (s, 9H), 1.3 (m, 2H), 0.92 (s, 3H), 0.915 (s, 3H).

Step 7: tert-Butyl[1-[amino(hydroxyimino)methyl]-4,4-dimethyl-5-(tetrahydro-2H-pyran-2-yloxy)pentyl]methylcarbamate

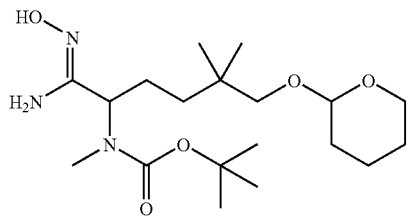 [SMILES: CN(C(=O)OC(C)(C)C)C(CCC(C)(C)COC1CCCCO1)/C(N)=N/O]

To a stirred solution of tert-butyl [1-cyano-4,4-dimethyl-5-(tetrahydro-2H-pyran-2-yloxy)pentyl]methylcarbamate (8.5 g, 23.98 mmol), in methanol (5 mL) was added 50% hydroxylamine (1.543 mL, 25.2 mmol). The mixture was heated to 60° C. for 3 hours (LC-MS indicates complete conversion) cooled and concentrated. Removal of excess hydroxylamine azeotropically with methanol gave tert-butyl [1-[(Z)-amino(hydroxyimino)methyl]-4,4-dimethyl-5-(tetrahydro-2H-pyran-2-yloxy)pentyl]methylcarbamate: MS (ES+): 388.26 (M+H).

Step 8: Dimethyl (2-({[(1-amino-2-[(tert-butoxycarbonyl)(methyl)amino]-5,5-dimethyl-6-(tetrahydro-2H-pyran-2-yloxy)hexylidene]amino}oxy)but-2-enedioate

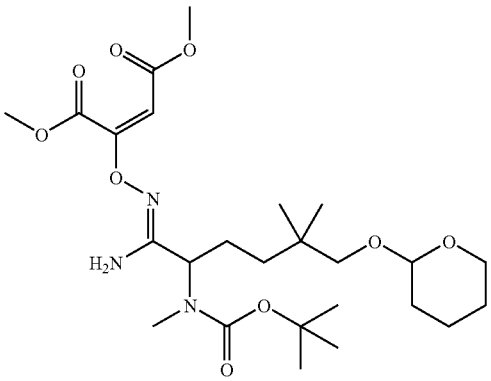 [SMILES: COC(=O)/C=C(/O/N=C(\N)C(CCC(C)(C)COC1CCCCO1)N(C)C(=O)OC(C)(C)C)C(=O)OC]

To a stirred solution of crude tert-butyl [1-[amino(hydroxyimino)methyl]-4,4-dimethyl-5-(tetrahydro-2H-pyran-2-yloxy)pentyl]methylcarbamate (98 mmol) in MeOH (800 mL) cooled to −10° C. under nitrogen was added slowly dimethyl acetylenedicarboxylate (12.09 mL, 98 mmol) keeping the internal temperature at −10° C. The resulting solution was aged at or below −10° C. (in freezer) overnight, then allowed to warm to 25° C. and stir for 30 hours. The mixture was diluted with 200 mL of toluene and concentrated. Drying under vacuum overnight gave a thick brown oil which contained toluene by NMR and was a mixture of isomers. The crude product was used in the next step without further purification: MS (ES+): 530.2 (M+H).

Step 9: Methyl 2-[1-[(tert-butoxycarbonyl)(methyl)amino]-4,4-dimethyl-5-(tetrahydro-2H-pyran-2-yloxy)pentyl]-5-hydroxy-6-oxo-1,6-dihydropyrimidine-4-carboxylate

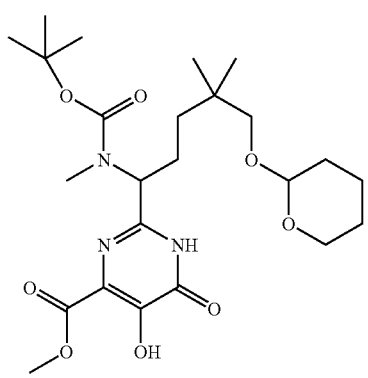 [SMILES: COC(=O)c1nc(C(CCC(C)(C)COC2CCCCO2)N(C)C(=O)OC(C)(C)C)[nH]c(=O)c1O]

The crude dimethyl (2-({[1-amino-2-[(tert-butoxycarbonyl)(methyl)amino]-5,5-dimethyl-6-(tetrahydro-2H-pyran-2-yloxy)hexylidene]amino}oxy)but-2-enedioate (40.6 g) was dissolved in o-xylene (100 mL), and heated at 115° C.±5°

C. (oil bath at 120° C.) for 12 hours. The reaction mixture turned dark soon after reaching 115° C. TLC and LC-MS assay after 48 hours indicated one isomer was consumed, but about 10% of the other (minor) isomer remained. Heating was continued for an additional 48 hours at which time complete conversion was observed as determined by LC-MS. The mixture was cooled to room temperature, diluted with 100 mL of EtOAc filtered through a 4-inch pad of silica gel eluting wth EtOAc. The filtrate was concentrated under reduced pressure. Drying under vacuum gave the title product as a brown foam: MS (ES+): 498.1 (M+H).

Step 10: Methyl 2-{1-[(tert-butoxycarbonyl)(methyl) amino]-5-hydroxy-4,4-dimethylpentyl}-5-hydroxy-6-oxo-1,6-dihydropyrimidine-4-carboxylate

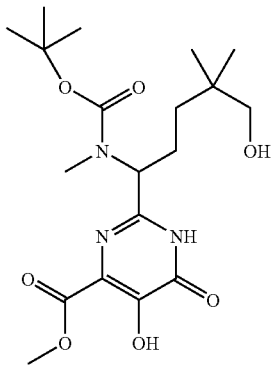 [SMILES: COC(=O)c1nc(C(CCC(C)(C)CO)N(C)C(=O)OC(C)(C)C)[nH]c(=O)c1O]

A mixture of the crude methyl 2-[1-[(tert-butoxycarbonyl)(methyl)amino]-4,4-dimethyl-5-(tetrahydro-2H-pyran-2-yloxy)pentyl]-5-hydroxy-6-oxo-1,6-dihydropyrimidine-4-carboxylate (32 g) and 1 g of p-toluenesulfonic acid monohydrate was dissolved in methanol (100 mL) and stirred at room temperature for 2 hours. The reaction was quenched with 3 mL of saturated NaHCO₃ and concentrated. The residue was taken up in 500 mL of EtOAc, washed with saturated NaHCO₃ and dried over Na₂SO₄. Removal of solvents under reduced pressure gave the title product as a brown foam: MS (ES+): 314.1 (M+H).

Step 11: tert-Butyl[1-(4-{[(4-fluoro-3-methylbenzyl) amino]carbonyl})-5-hydroxy-6-oxo-1,6-dihydropyrimidin-2-yl)-5-hydroxy-4,4-dimethylpentyl]methylcarbamate

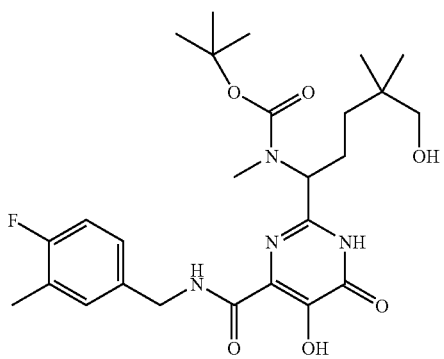 [SMILES: Cc1cc(CNC(=O)c2nc(C(CCC(C)(C)CO)N(C)C(=O)OC(C)(C)C)[nH]c(=O)c2O)ccc1F]

A mixture of methyl 2-{1-[(tert-butoxycarbonyl)(methyl)amino]-5-hydroxy-4,4-dimethylpentyl}-5-hydroxy-6-oxo-1,6-dihydropyrimidine-4-carboxylate (5.11 g, 12.36 mmol), 1-(4-fluoro-3-methylphenyl)methanamine (2.064 g, 14.83 mmol), and TEA (3.45 mL, 24.72 mmol) in 2-propanol (80 mL) under nitrogen was heated to 80° C.±2° C. (oil bath at 82° C.) overnight. The mixture was concentrated and the residue taken up in 100 mL of iPrOAc, washed with 2×50 mL of 1N HC, 2×25 mL of water, 25 mL of saturated NaHCO₃, and dried over MgSO₄. The solution was diluted with 50 mL of toluene and concentrated. Drying under vacuum gave a tan foam: MS (ES+): 521.19 (M+H). ¹H NMR (400 MHz, CDCl₃) δ 9.3 (br s, 1H), 7.2 (m, 2H), 6.9 (t, 1H), 5.4 (br s, 1H), 4.8 (d, 1H), 4.5 (m, 2H), 3.3 (m, 1H), 3.0, (s, 3H), 2.2 (s, 3H), 2.0 (m, 1H), 1.7 (m, 2H), 1.2 (s, 9H), 0.92 (s, 6H).

Step 12: 5-[(tert-Butoxycarbonyl)(methyl)amino]-5-(4-{[(4-fluoro-3-methylbenzyl)amino]carbonyl}-5-hydroxy-6-oxo-1,6-dihydropyrimidin-2-yl)-2,2-dimethylpentyl methanesulfonate

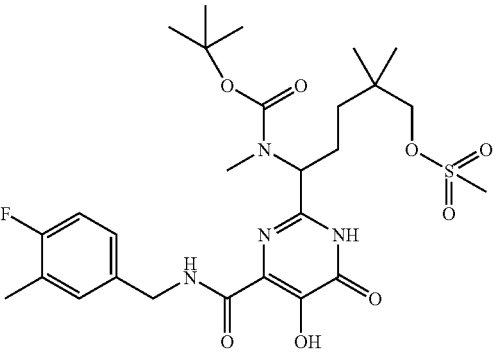

To an ice cold solution (T=2° C.±2° C.) of (5.45 g, 10.47 mmol) was added TEA (8.75 mL, 62.8 mmol), then MsCl (4.89 mL, 62.8 mmol) dropwise keeping the internal temperature below 10° C. The resulting slurry was aged at 2° C.±2° C. for 2.5 hours, then 5N NaOH (14.66 mL, 73.3 mmol) was added slowly to the cold reaction mixture. The reaction mixture was then warmed to 80° C.±2° C. (oil bath at 83° C.) for 20 hours. After cooling to 50° C., 6N HCl (34.0 mL, 68.0 mmol) was added dropwise over 1 hour until the pH was 2.5-3.0 (pH indicator paper and strips). The filtrate was diluted with 100 mL of water, adjusted the pH to 2 (from ~8) with 2N HCl and extracted 3×500 mL of isopropyl acetate. The extracts were combined, dried over Na₂SO₄ and concentrated under reduced pressure. The resulting tan solid product was dried under vacuum: MS (ES+): 599.1 (M+H).

Step 13: tert-Butyl (2-{[(4-fluoro-3-methylbenzyl)amino]carbonyl}-3-hydroxy-7,7-dimethyl-4-oxo-4,6,7,8,9,10-hexahydropyrimido[1,2-a]azepin-10-yl)methylcarbamate

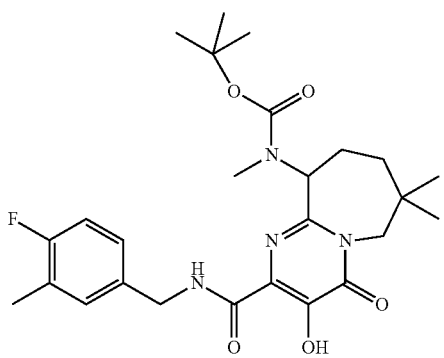

A mixture of 5-[(tert-butoxycarbonyl)(methyl)amino]-5-(4-{[(4-fluoro-3-methylbenzyl)amino]carbonyl}-5-hydroxy-6-oxo-1,6-dihydropyrimidin-2-yl)-2,2-dimethylpentyl methanesulfonate (7.8 g, 13.03 mmol), cesium carbonate (11 g, 33.8 mmol) and 75 mL of dioxane was heated to 80° C. overnight. After cooling to room temperature, the mixture was diluted with 100 mL of EtOAc, washed with water (150 mL), saturated NaCl (50 mL), dried over Na$_2$SO$_4$ and concentrated. The resulting tan solid product was dried under vacuum: MS (ES+): 503.3 (M+H); $^1$H NMR (400 MHz, CDCl$_3$) δ 7.8 (br s, 1H), 7.6 (br s, 1H), 7.17 (m, 2H), 7.0 (m, 1H), 4.9 (m, 1H), 4.5 (m, 2H), 3.3 (dd, 1H), 2.8 (s, 3H), 2.3, (s, 3H), 1.6 (complex m, 6H), 1.3 (s, 9H), 1.1 (s, 3H), 0.83 (s, 3H).

Step 14: N-(4-Fluoro-3-methylbenzyl)-3-hydroxy-7,7-dimethyl-10-(methylamino)-4-oxo-4,6,7,8,9,10-hexahydropyrimido[1,2-a]azepine-2-carboxamide hydrochloride

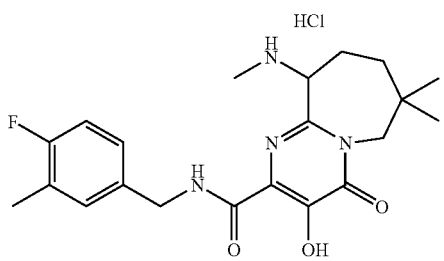

The tert-butyl (2-{[(4-fluoro-3-methylbenzyl)amino]carbonyl}-3-hydroxy-7,7-dimethyl-4-oxo-4,6,7,8,9,10-hexahydropyrimido[1,2-a]azepin-10-yl)methylcarbamate (6.1 g, 12.14 mmol) was treated with 4N HCl in dioxane (15.17 mL, 60.7 mmol). The mixture was allowed to sir at room temperature for 1.5 hours (complete conversion by LC-MS) then concentrated. Drying under vacuum gave N-(4-fluoro-3-methylbenzyl)-3-hydroxy-7,7-dimethyl-10-(methylamino)-4-oxo-4,6,7,8,9,10-hexahydropyrimido[1,2-a]azepine-2-carboxamide hydrochloride as a tan crystalline solid: MS (ES+): 403.2 (M+H).

Step 15: N-(2-{[(4-Fluoro-3-methylbenzyl)amino]carbonyl}-3-hydroxy-7,7-dimethyl-4-oxo-4,6,7,8,9,10-hexahydropyrimido[1,2-a]azepin-10-yl)-N,N',N'-trimethylethanediamide

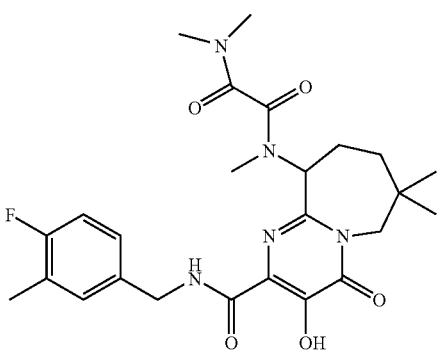

To a mixture of N-(4-fluoro-3-methylbenzyl)-3-hydroxy-7,7-dimethyl-10-(methylamino)-4-oxo-4,6,7,8,9,10-hexahydropyrimido[1,2-a]azepine-2-carboxamide hydrochloride (200 mg, 0.421 mmol), HOAt (68.7 mg, 0.5 mmol), N,N-dimethyloxamic acid (74 mg, 0.631 mmol) and triethylamine (0.235 mL, 1.683 mmol), in dichloromethane (5 mL) was added EDC (224 mg, 1.262 mmol). The mixture was stirred at room temperature under nitrogen overnight, diluted with 25 mL EtOAc, washed with 10 mL each of saturated NaHCO$_3$ solution, H$_2$O, and brine, and dried over Na$_2$SO$_4$. Concentration gave a crude title product which was purified by preparative reverse phase chromatography (gradient elution 0.1% AcOH in water/acetonitrile) to give the title product as a solid: HRMS (ES+): 502.2484 (M+H); $^1$H NMR (400 MHz, CDCl$_3$) δ 9.35 (br s, 3H), 7.2 (m, 2H), 6.9 (t, J=9 Hz, 1H), 5.34 (br s, 1H), 4.8 (d, J=14 Hz, 1H), 4.5 (m, 21H), 4.5 (m, 2H), 3.3 (d, J=14 Hz, 1H), 3.0 (s, 3H), 2.98, (s, 3H), 2.96 (s, 3H), 2.2 (s, 3H), 2.0 (m, 2H), 1.9 (m, 1H), 1.7 (s, 2H), 1.12 (s, 3H), 0.83 (s, 3H).

Resolution on a chiral column gave:

1A. N-((10R)-2-{[(4-fluoro-3-methylbenzyl)amino]carbonyl}-3-hydroxy-7,7-dimethyl-4-oxo-4,6,7,8,9,10-hexahydropyrimido[1,2-a]azepin-10-yl)-N,N',N'-trimethylethanediamide. [α]$_D$23° C.=+67.6° (c=0.5, MeOH); HRMS (ES+): 502.2482 (M+H); $^1$H NMR (400 MHz, CDCl$_3$) δ 9.35 (br s, 3H), 7.2 (m, 2H), 6.9 (t, J=9 Hz, 1H), 5.34 (br s, 1H), 4.8 (d, J=14 Hz, 1H), 4.5 (m, 21H), 4.5 (m, 2H), 3.3 (d, J=14 Hz, 1H), 3.0 (s, 3H), 2.98, (s, 3H), 2.96 (s, 3H), 2.2 (s, 3H), 2.0 (m, 2H), 1.9 (m, 1H), 1.7 (s, 2H), 1.12 (s, 3H), 0.83 (s, 3H).

1B. N-((10S)-2-{[(4-fluoro-3-methylbenzyl)amino]carbonyl}-3-hydroxy-7,7-dimethyl-4-oxo-4,6,7,8,9,10-hexahydropyrimido[1,2-a]azepin-10-yl)-N,N',N'-trimethylethanediamide. [α]$_D$23° C.=−72.4° (c=0.5, MeOH); HRMS (ES+): 502.2481 (M+H); $^1$H NMR (400 MHz, CDCl$_3$) δ 9.35 (br s, 3H), 7.2 (m, 2H), 6.9 (t, J=9 Hz, 1H), 5.34 (br s, 1H), 4.8 (d, J=14 Hz, 1H), 4.5 (m, 2H), 4.5 (m, 2H), 3.3 (d, J=14 Hz, 1H), 3.0 (s, 3H), 2.98, (s, 3H), 2.96 (s, 3H), 2.2 (s, 3H), 2.0 (m, 2H), 1.9 (m, 1H), 1.7 (s, 2H), 1.12 (s, 3H), 0.83 (s, 3H).

EXAMPLE 2

Isolated stereoisomers of N-(2-{[(4-fluoro-3-methyl-benzyl)amino]carbonyl}-3-hydroxy-7-methoxy-7-methyl-4-oxo-4,6,7,8,9,10-hexahydropyrimido[1,2-a]azepin-10-yl)-N,N',N'-trimethylethanediamide

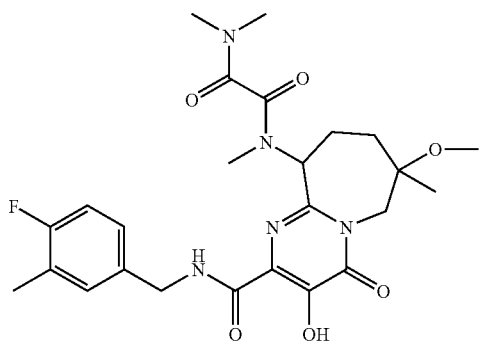

Step 1: Methyl 2-methoxy-2-methylpent-4-enoate

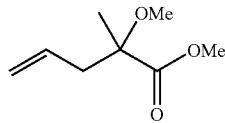

To a solution of diisopropylamine (2.34 L, 16.4 mol) in THF (6 L) at −48° C. was added n-butyllithium (5.78 L, 14.5 mol) via additional funnel over 35 minutes, and the resulting mixture was warmed to −15° C. over 20 minutes, held at −15° C. for 10 minutes, then cooled down to −40° C. To this solution was added methyl 2-methoxypropionate (1.85 kg, 12.4 mol) via additional funnel over 1.75 hours. After stirring for 30 minutes, allyl bromide (1.4 L, 16.4 mol) was added via additional funnel. The resulting solution was stirred for 30 minutes, warmed to 0° C. over 1 hour, then quenched with 3NHCl (7 L), and extracted with MTBE (2×4 L). The combined organic layers were washed with brine, dried over MgSO$_4$, filtered, and concentrated in vacuo. The crude residue was used in the next reaction without further purification.

Step 2: tert-Butyl[(2-methoxy-2-methylpent-4-en-1-yl)oxy]dimethylsilane

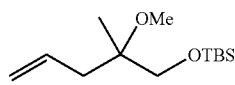 [SMILES: C=CCC(C)(CO[Si](C)(C)C(C)(C)C)OC]

To a suspension of LAH (pellets, 251.4 g, 6.29 mol) in THF (6 L) at <10° C. was added methyl 2-methoxy-2-methylpent-4-enoate (1.9 kg crude) via additional funnel while maintaining the reaction temperature below 23° C. The resulting mixture was stirred at −5° C. for 1 hour; then quenched with water (250 mL, 13.9 mol), 15% NaOH (250 mL, 12.4 mol), and water (750 mL, 41.6 mol); then diluted with 8 L of MTBE; dried over 500 g of MgSO$_4$ overnight; and filtered via vacuum filtration. The resulting filter cake was washed with THF and MTBE. The filtrates were combined and concentrated in vacuo to provide a crude alcohol.

To a solution of TBS-Cl (4.06 kg, 26.1 mol) in DCM (23 L) was added DMAP (74 g, 0.606 mol) and the crude alcohol (2.6 kg, 20.08 mol) and TEA (3.94 L, 28.1 mol). The resulting mixture was stirred overnight at ambient temperature and quenched with water (6 L). The organic layer was collected, washed with 1M HCl (6 L) and with brine (4 L), then dried over MgSO$_4$, filtered and concentrated in vacuo. Flash column chromatography (Biotage 150 L, 5 kg silica) eluted with DCM provided the TBS ether derivative. The material was carried forward to next step without further purification.

Step 3: 5-{[tert-Butyl(dimethyl)silyl]oxy}-4-methoxy-4-methylpentan-1-ol

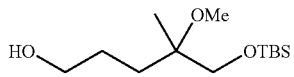

To a solution of tert-butyl [(2-methoxy-2-methylpent-4-en-1-yl)oxy]dimethylsilane (2.45 kg, 10.04 mol) in THF (3.5 L) at <5° C. was added BH3 in THF (1M solution, 11.05 L, 11.05 mol) via a funnel while maintaining the reaction temperature at <15° C. The reaction mixture was stirred for 30 minutes and quenched with water (11.75 L, 652 mol). To the stirred mixture was added sodium perborate tetrahydrate (4.64 kg, 30.2 mol) and the mixture was stirred overnight at ambient temperature. The reaction mixture was then filtered, and the filter cake washed with 14 L MTBE. The combined organic layers were washed with brine/water (7 L/3 L). The aqueous layer was extracted with MTBE (14 L). The combined organic layers were sequentially washed with 18.75 L of 5% aqueous sodium thiosulfate/brine/water (10 L/5 L/3.75 L) and then concentrated in vacuo to provide crude material. Flash column chromatography (multiple runs) eluted with 0% to 100% DCM in heptane, then 1% to 50% EtOAc in DCM provided the desired alcohol. $^1$H NMR (300 MHz, CDCl$_3$): δ 3.65-3.59 (m, 2 H); 3.47 (dd, J=23.9, 10.1 Hz, 2 H); 3.24 (s, 3 H); 2.21-2.07 (m, 1 H); 1.63-1.54 (m, 4 H); 1.05-0.70 (m, 9 H); 0.04 (s, 6H).

Step 4: 5-{[tert-Butyl(dimethyl)silyl]oxy}-4-methoxy-4-methylpentanal

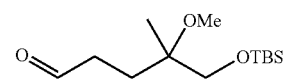

To a solution of sodium bicarbonate (627 g, 74.6 mol) and potassium bromide (672 g, 56.5 mol) in water (20 L) was added 5-{[tert-butyl(dimethyl)silyl]oxy}-4-methoxy-4-methylpentan-1-ol (3.5 kg, 11.2 mol), DCM (10 L), TEMPO (17.6 g, 113 mol). The resulting mixture was cooled to <5° C. and NaOCl (13% solution, total 6.7 L, 14.6 mol) was added in portions via a funnel while maintaining the reaction temperature <5° C. The mixture was stirred 6 hours warming to ambient temperature. The organic layer was collected. The aqueous layer was extracted with 4 L DCM. The combined organic layers were dried over MgSO$_4$, filtered, and concentrated in vacuo. The crude material, 4.2 kg, was used in the next step without further purification. $^1$H NMR (300 MHz, CDCl$_3$): δ 9.75 (t, J=1.8 Hz, 1 H); 3.43 (q, J=10.4 Hz, 2H); 3.17 (s, 3H); 2.43 (t, J=1.8 Hz, 2H); 2.02-1.65 (m, 2 H); 0.99-0.71 (s, 9H); 0.14 (s, 6H).

Step 5: tert-Butyl(5-{[tert-butyl(dimethyl)silyl]oxy}-1-cyano-4-methoxy-4-methylpentyl)methylcarbamate

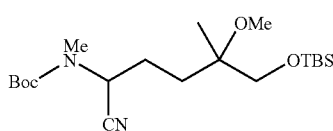

To a solution of methylamine hydrochloride (0.83 kg, 12.34 mol) in water (14.66 L) was added dioxane (24.43 L) and 5-{[tert-butyl(dimethyl)silyl]oxy}-4-methoxy-4-methylpentanal (crude, 2.9 kg, 11.22 mol) and NaCN (0.605 kg, 12.34 mol) over 10 minutes while maintaining the reaction temperature at 15° C. The reaction mixture was stirred overnight, then NaCl (1.7 kg) was added and the layers separated. The aqueous layer was extracted with EtOAc (2×4 L). The combined organic layers were dried over Na$_2$SO$_4$, filtered and concentrated to provide 5.63 kg (>100%) of crude material. To a solution of the crude residue in EtOAc (20 L) at 6° C. was added di-tert-butyldicarbonate (2.57 kg, 11.78 mol) in 1.5 L of EtOAc via additional funnel over 5 minutes. The reaction mixture was stirred at 15° C. overnight and concentrated in vacuo. Flash column chromatography eluted with 0 to 30% EtOAc in heptane provided the desired product.

Step 6: tert-Butyl {5-{[tert-butyl(dimethyl)silyl]oxy}-1-[(hydroxyamino)(imino)methyl]-4-methoxy-4-methylpentyl}methylcarbamate

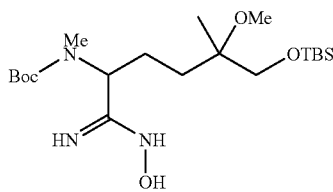 [SMILES: COC(C)(CCC(C(=N)NO)N(C)C(=O)OC(C)(C)C)CO[Si](C)(C)C(C)(C)C]

To a solution of tert-butyl(5-{[tert-butyl(dimethyl)silyl]oxy}-1-cyano-4-methoxy-4-methylpentyl)methylcarbamate (4.37 kg, 10.91 mol) in MeOH (28 L) at 30° C. was added aqueous hydroxylamine (50% in water, 1.2 L, 19.63 mol). The resulting mixture was heated to 40° C. overnight, then cooled and concentrated in vacuo. The crude residue was dissolved in 1.5 L of toluene, concentrated under reduced pressure, and dried in vacuo. The crude material was used in the next step without further purification. LC-MS: 434.3.

Step 7: Methyl 2-(1-[(tert-butoxycarbonyl)(methyl)amino]-5-{[tert-butyl(dimethyl)silyl]oxy})-4-methoxy-4-methylpentyl)-5-hydroxy-6-oxo-1,6-dihydropyrimidine-4-carboxylate

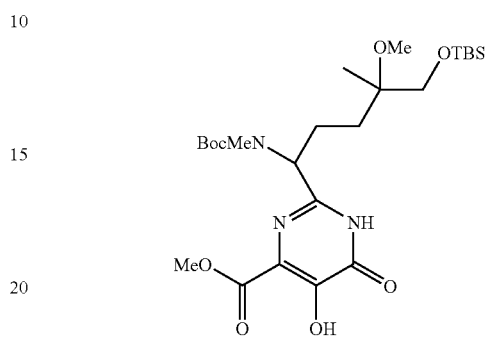

To a solution of tert-butyl {5-{[tert-butyl(dimethyl)silyl]oxy}-1-[(hydroxyamino)(imino)methyl]-4-methoxy-4-methylpentyl}methylcarbamate (4.17 kg, 96.18 mol) in MeOH (26 L) at 0° C. was added dimethyl acetylene dicarboxylate (1.3 L, 10.7 mol) over minutes while maintaining the reaction temperature below 8° C. The reaction mixture was heated to 30° C. overnight. Additional dimethyl acetylene dicarboxylate (total 0.454 L, 3.7 mol) was added. The reaction mixture was stirred at 30° C. overnight, cooled, concentrated in vacuo, and concentrated from xylene to provide the desired diester derivative. LC-MS: 576.2.

A solution of the diester derivative (4.15 kg, 7.21 mol) in xylene (24 L) was heated at 140° C. for 20 hours, then cooled, diluted the reaction mixture with 4 L of heptane, and filtered through a pad of Celite 545. Flash chromatography (Biotage Flash Si 150 L, 5.0 kg silica) of the filtrate eluting first with heptane, then 100% EtOAc over 60 minutes, and finally EtOAc with 1% acetic acid to provide the title product. LC-MS: 544.1.

Step 8: tert-Butyl[1-(4-{[(4-fluoro-3-methylbenzyl)amino]carbonyl}-5-hydroxy-6-oxo-1,6-dihydropyrimidin-2-yl)-5-hydroxy-4-methoxy-4-methylpentyl]methylcarbamate

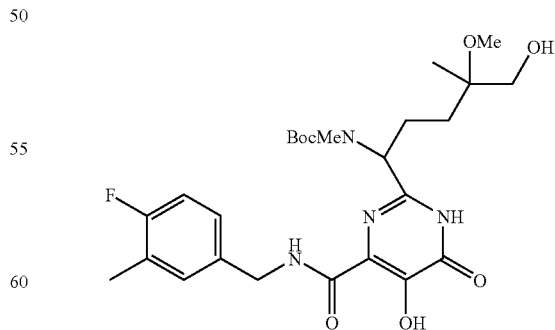

To a solution of methyl 2-(1-[(tert-butoxycarbonyl)(methyl)amino]-5-{[tert-butyl(dimethyl)silyl]oxy})-4-methoxy-4-methylpentyl)-5-hydroxy-6-oxo-1,6-dihydropyrimidine-4-carboxylate (1.73 kg, 5.11 mol) in 2-propanol (10.23 L)

was added 4-fluoro-3-methylbenzylamine (0.854 kg, 6.14 mol). The resulting mixture was heated to 75° C. overnight, then cooled and concentrated in vacuo. The residue was diluted with EtOAc (8 L) and washed with 10% aqueous citric acid (5 L). The white solid was removed by filtration. The aqueous layer was extracted with EtOAc (2×2 L). The combined organic layers were washed with 50% saturated sodium bicarbonate (1×5 L), and brine (1×5 L), dried over sodium sulfate, filtered, and concentrated in vacuo to provide the crude amide. LC-MS: 651.1.

To a solution of the crude amide (1.75 kg, 2.69 mol) in THF (0.75 L) at 25° C. was added TBAF (1M in THF, 7.26 L, 7.26 mol) and powdered activated 3 Å molecular sieves (500 g). The reaction mixture was rotated at 25° C. overnight, concentrated in vacuo, and then additional TBAF (1M in THF, 1.076 L, 1.076 mol) and powdered activated 3 Å molecular sieves (300 g) were added. The reaction mixture was rotated at 30° C. overnight and then filtered to remove the molecular sieves. The filter cake was washed with MeOH (3 L) and the filtrate was concentrated in vacuo. The residue was dissolved in 6 L of DCM, washed with 30% sat NaHCO$_3$ (4×4 L), dried over sodium sulfate, filtered, and concentrated in vacuo to afford crude title product, which was used in the next step without further purification. LC-MS: 537.1.

Step 9: tert-Butyl (2-{[(4-fluoro-3-methylbenzyl)amino]carbonyl}-3-hydroxy-7-methoxy-7-methyl-4-oxo-4,6,7,8,9,10-hexahydropyrimido[1,2-a]azepin-10-yl)methylcarbamate

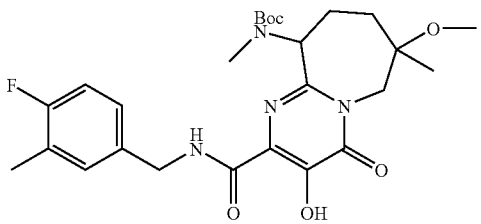

To a solution of tert-butyl [1-(4-{[(4-fluoro-3-methylbenzyl)amino]carbonyl}-5-hydroxy-6-oxo-1,6-dihydropyrimidin-2-yl)-5-hydroxy-4-methoxy-4-methylpentyl]methylcarbamate (1.44 kg, 2.68 mol) in anhydrous acetonitrile (5.37 L) at 0° C. was added TEA (1.87 L, 13.42 mol) and methanesulfonyl chloride (0.836 L, 10.73 mol) dropwise over 45 minutes while maintaining the reaction temperature below 5° C. The resulting mixture was stirred at 0° C. for 14 hours, diluted with 30% saturated NaHCO$_3$ (10 L), and extracted with MTBE (4×2 L). The combined organic layers were washed with 5% citric acid and brine, dried over Na$_2$SO$_4$, filtered, and concentrated in vacuo to provide a crude mesylate. LC-MS: 670.1 (M+1-Boc).

To a solution of the crude mesylate from the previous step (1.53 kg, 1.985 mol) in DMF (7.94 L) was added Cs$_2$CO$_3$ (2.59 kg, 7.94 mol). The reaction mixture was heated to 100° C. for 15 hours, then cooled and concentrated in vacuo. The residue was diluted with EtOAc (4 L) and acidified to pH 4 with 10% critic acid. The layers were separated. The aqueous layer was extracted with EtOAc (3×2 L). The combined organic layers were washed with 50% brine (10 L), and brine (5 L), dried over Na$_2$SO$_4$, filtered, and concentrated in vacuo. The crude title product was used in the next reaction without further purification. LC-MS: 519.1.

Step 10: 10-[(tert-Butoxycarbonyl)(methyl)amino]-2-{[(4-fluoro-3-methylbenzyl)amino]carbonyl}-7-methoxy-7-methyl-4-oxo-4,6,7,8,9,10-hexahydropyrimido[1,2-a]azepin-3-yl methanesulfonate

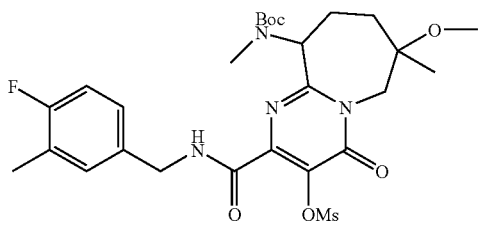

To a solution of tert-butyl (2-{[(4-fluoro-3-methylbenzyl)amino]carbonyl}-3-hydroxy-7-methoxy-7-methyl-4-oxo-4,6,7,8,9,10-hexahydropyrimido[1,2-a]azepin-10-yl)methylcarbamate (1.029 kg, 1.98 mol) in dry acetonitrile (8 L) at 15° C. was added MsCl (0.27 L, 3.47 mol). The reaction mixture was stirred at −60° C. for 1 hour, diluted with EtOAc (4 L), potassium hydrogen sulfate (1.08 kg, 7.94 mol, in 8 L H$_2$O), 4 L of brine, and 6 L of EtOAc. The organic layer was collected and washed with brine (2×5 L), dried over Na$_2$SO$_4$, filtered, and concentrated in vacuo. The crude residue was dissolved in DCM (1.5 L) and heptane (1 L) and solids were removed by filtration. The filtrate was concentrated and purified by flash column chromatography (Biotage 150 L, 5 kg silica) eluting with 50% heptane in DCM, then 100% DCM, and finally to 12% acetone in DCM and gave the desired mesylate. LC-MS: 597.2.

Step 11: N-(2-{[(4-Fluoro-3-methylbenzyl)amino]carbonyl}-3-hydroxy-7-methoxy-7-methyl-4-oxo-4,6,7,8,9,10-hexahydropyrimido[1,2-a]azepin-10-yl)-N,N',N'-trimethylethanediamide

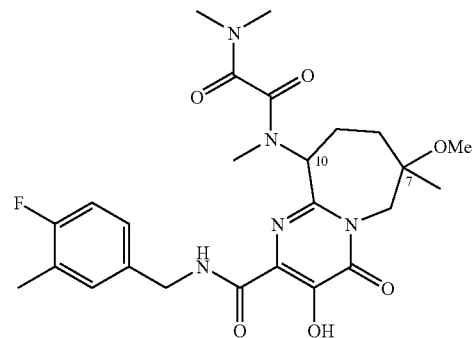 [SMILES: COC1(C)CCC(N(C)C(=O)C(=O)N(C)C)c2nc(C(=O)NCc3ccc(F)c(C)c3)c(O)c(=O)n2C1]

To a suspension of 10-[(tert-butoxycarbonyl)(methyl)amino]-2-{[(4-fluoro-3-methylbenzyl)amino]carbonyl}-7-methoxy-7-methyl-4-oxo-4,6,7,8,9,10-hexahydropyrimido[1,2-a]azepin-3-yl methanesulfonate (0.291 kg, 0.488 mol) in EtOAc (3.2 L) at 0° C. was bubbled HCl (g) until saturation. The reaction mixture was stirred at 0° C. for 1 hour, warmed to 15° C. for 15 minutes, then cooled to 0° C. and stirred at 0° C. for 2 hours. The reaction mixture was purged with N2 gas for 20 minutes and concentrated in vacuo. The residue was concentrated twice from EtOAc (1.5 L) to remove HCl and was crystallized with 1 L of EtOAc and 500 mL of MTBE. Filtration provided a light tan solid which was rinsed with 500 mL of 1:1 EtOAc/MTBE following by 1 L of MTBE. The solid was dried in vacuo at 50° C. for 30 minutes to afford an HCl salt. LC-MS: 497.1.

To a solution of the HCl salt (197.9 g, 371 mol) in DCM (2 L) at ambient temperature was added N,N-dimethyloxamic acid (87 g, 743 mol), EDC (157 g, 817 mol), and HOAt (50.5 g, 371 mol). The reaction mixture was cooled to 9° C. To the cooled solution was added N-methylmorpholine (0.204 L, 18.56 mol) over 2 minutes. Additional N,N-dimethyloxamic acid (21.74 g, 186 mol), EDC (36.6 g, 189 mol), and HOAT (25.3 g, 186 mol) were added. The resulting mixture was diluted with $H_2O$ (2 L) and brine (1 L). The layers were separated. The aqueous layer was extracted with DCM (1 L). The combined organic layers were washed with 50% brine (2×2 L), dried over $Na_2SO_4$, filtered, and concentrated in vacuo. The product was crystallized from DCM. The crystallization mixture was diluted with iso-propyl acetate. Filtration provided a white solid which was dried in a vacuum oven at 30° C. LC-MS: 596.2.

To a solution of mesylate product (148.9 g, 250 mmol) in 2-propanol (1.5 L) was added 1M NaOH (375 mL, 375 mmol). The resulting mixture was sonicated without heating. After 3 hours, additional 1M NaOH (125 mL, 125 mmol) was added and the mixture was sonicated without heating for 1 hour. The reaction mixture was filtered and concentrated in vacuo. The crude material was crystallized by addition of 1M HCl (500 mL, 500 mmol) and filtered. The filter cake was washed with 50% $EtOH/H_2O$ and EtOH, then dried in vacuo at 50° C. for 18 hours. The mixture was purified by chiral SFC (AD-H column, 40% IPA, sample dissolved at 60 mg/mL in 1:1 chloroform:IPA, 1 mL injection, 50 mL/minute, cycle time: 3.5 minutes):

Compound 2A—The second eluting peak: 7-OMe is trans to 10-amide side chain, determination of absolute stereochemistry described below, LC-MS: M+1=518.2. HR MS ESI: M+1 theoretical 518.2409, observed 518.2436. $^1$H NMR (399 MHz, $CDCl_3$): δ 12.20 (s, 1 H); 9.45-9.31 (m, 1 H); 7.23 (dd, J=7.5, 2.1 Hz, 1 H); 6.95-6.88 (m, 1 H); 5.17 (d, J=14.1 Hz, 1 H); 4.56 (dd, J=14.5, 6.6 Hz, 1 H); 4.46 (dd, J=14.5, 6.3 Hz, 1 H); 3.39-3.29 (m, 4 H); 3.03 (s, 3 H); 3.00 (s, 3 H); 2.98 (s, 3 H); 2.24 (d, J=1.9 Hz, 3 H); 2.22-2.16 (m, 1 H); 2.00-1.90 (m, 3 H); 1.12 (s, 3 H).

Compound 2B—The third eluting peak: 7-OMe is trans to 10-amide side chain, absolute stereochemistry described below, LC-MS: M=1=518.2. HR MS ESI: M+1 theoretical 518.2409, observed 518.2435. $^1$H NMR is same as the second eluting peak.

Compound 2C—The fourth eluting peak: 7-OMe is cis to 10-amide side chain, absolute stereochemistry not determined, LC-MS: M+1=518.2. HR MS ESI: M+1 theoretical 518.2409, observed 518.2436. $^1$H NMR is the same as the first eluting peak.

Compound 2D—The first eluting peak: 7-OMe is cis to 10-amide side chain, absolute stereochemistry not determined, LC-MS: M+1=518.2, HR MS ESI: M+1 theoretical 518.2409, observed 518.2437. $^1$H NMR (399 MHz, $CDCl_3$): δ 12.10 (s, 1 H); 9.28 (s, 1 H); 7.22 (d, J=7.5 Hz, 1 H); 6.97-6.87 (m, 1 H); 5.35 (s, 1 H); 5.27 (dd, J=14.9, 2.0 Hz, 1 H); 4.58 (dd, J=14.5, 6.6 Hz, 1 H); 4.49-4.40 (m, 1 H); 3.36 (d, J=14.8 Hz, 1 H); 3.20 (s, 3 H); 3.04-2.97 (m, 10 H); 2.24 (s, 3 H); 2.16 (d, J=15.0 Hz, 2 H); 1.88 (d, J=13.2 Hz, 1 H); 1.81-1.70 (m, 1 H); 1.46-1.24 (m, 3 H).

Crystalline Compound 2A
Preparation

Amorphous Compound 2A material obtained from the chromatographic separation described above was dissolved in boiling absolute ethanol, the minimum amount required for complete dissolution, and filtered through a fluted filter paper. The hot solution was allowed to slowly cool to ambient temperature during which time fine needles crystallized from solution. The cooled crystallization mixture was aged for 3 hours and the crystalline compound was isolated by filtration, washed with 10 mL of ice cold absolute ethanol, and dried under vacuum.

Characterization

An X-ray powder diffraction (XRPD) pattern of the crystalline Compound 2A was generated on a Philips Analytical X'Pert PRO X-ray Diffraction System with PW3050/60 console using a continuous scan from 4 to 40 degrees 2θ (2 theta). Copper K-Alpha 1 ($K_{α1}$) and K-Alpha 2 ($K_{α2}$) radiation was used as the source. The experiment was run under ambient conditions. The diffraction peak positions were referenced by silicon which has a 2θ value of 28.443 degree. The XRPD pattern is shown in FIG. 1. 2θ values and the corresponding d-spacings in the XRPD pattern include the following:

TABLE 2A

| 2θ (degrees) | d-spacing (Å) |
|---|---|
| 5.7 | 15.4 |
| 8.5 | 10.5 |
| 8.9 | 9.9 |
| 9.3 | 9.5 |
| 11.6 | 7.6 |
| 12.6 | 7.0 |
| 13.3 | 6.6 |
| 14.6 | 6.1 |
| 15.9 | 5.6 |
| 16.4 | 5.4 |
| 17.0 | 5.2 |
| 17.5 | 5.1 |
| 18.4 | 4.8 |
| 18.8 | 4.7 |
| 19.7 | 4.5 |
| 20.4 | 4.4 |
| 20.8 | 4.3 |
| 21.7 | 4.1 |
| 23.3 | 3.8 |
| 23.7 | 3.8 |
| 24.5 | 3.6 |
| 25.5 | 3.5 |
| 25.7 | 3.5 |
| 26.0 | 3.4 |
| 26.3 | 3.4 |
| 26.9 | 3.3 |
| 27.9 | 3.2 |
| 28.4 | 3.1 |
| 29.3 | 3.0 |
| 30.4 | 2.9 |
| 30.6 | 2.9 |
| 31.2 | 2.9 |
| 32.3 | 2.8 |
| 32.7 | 2.7 |
| 34.2 | 2.6 |
| 34.5 | 2.6 |
| 34.8 | 2.6 |
| 35.5 | 2.5 |
| 36.4 | 2.5 |
| 36.6 | 2.5 |
| 38.6 | 2.3 |
| 39.3 | 2.3 |

The crystalline Compound 2A was also analyzed with a TA Instruments DSC Q 1000 differential scanning calorimeter (DSC) at a heating rate of 10° C./minute from 25° C. to 350°

C. in an open aluminum pan in a nitrogen atmosphere. The DSC curve showed an endotherm with an onset temperature of 197° C. and a peak temperature of 198° C. The enthalpy change was 84 J/g. The endotherm is believed to be due to melting.

A thermogravimetric analysis (TGA) of the crystalline compound was performed with a TA Instruments TGA Q 500 under nitrogen at a heating rate of 10° C./minute from 25° C. to 350° C. The TG curve showed a weight loss of 0.21 wt. % up to 100° C. indicating the absence of water of hydration and solvent of solvation.

An X-ray crystallographic study of Compound 2A was performed on crystalline Compound 2A prepared as described above. The study was done using a CCD-based diffractometer from Oxford Diffraction (radiation source: Enhance-Ultra Cu, detector model: Ruby) controlled by Oxford Diffraction CrysAlis Pro software. Data collection, using Cu radiation, was performed at 100 K to limit thermal motion and dynamic disorder as well as to improve the diffraction measurements. The crystal selected was representative of the bulk sample. Crystal data at 100 K:

| | | |
|---|---|---|
| a = 5.49010(12) Å | α = 90.00° | V = 2467.40(11) Å$^3$ |
| b = 20.4635(6) | β = 90.00 | Space group = P2$_1$2$_1$2$_1$, #19 |
| c = 21.9624(6) | γ = 90.00 | Z = 4 |

A total of 20038 reflections were measured to a resolution of 0.84 Å$^{-1}$ which yielded 4297 unique reflections. The refinement, using SHELXL software, was complete with $R_1$=5.04% and $wR_2$=13.6% using all 4297 reflections. The absolute configurations at C7 and C10 (see structure below) are both R as determined by the anomalous dispersion arising from the six oxygen atoms in the molecule. Analysis of the anomalous dispersion effect was performed using the refined Flack parameter, −0.1(2), and the Hooft parameter −0.05(4), both of which confirm the choice of absolute configuration. Accordingly, Compound 2A is N-((7R,10R)-2-{[(4-fluoro-3-methylbenzyl)amino]carbonyl}-3-hydroxy-7-methoxy-7-methyl-4-oxo-4,6,7,8,9,10-hexahydropyrimido[1,2-a]azepin-10-yl)-N',N'-trimethylethanediamide.

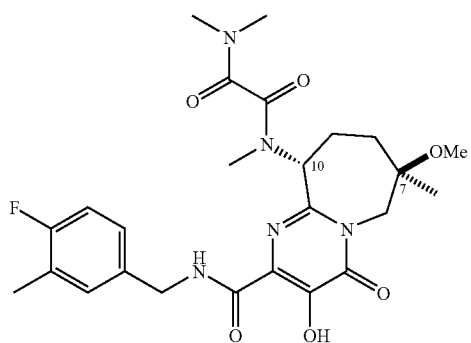 [SMILES: CO[C@]1(C)CC[C@@H](N(C)C(=O)C(=O)N(C)C)c2nc(C(=O)NCc3ccc(F)c(C)c3)c(O)c(=O)n2C1]

In view of the stereochemistry assigned to Compound 2A, by process of elimination, Compound 2B is N-((7S,10S)-2-{[(4-fluoro-3-methylbenzyl)amino]carbonyl}-3-hydroxy-7-methoxy-7-methyl-4-oxo-4,6,7,8,9,10-hexahydropyrimido[1,2-a]azepin-10-yl)-N,N',N'-trimethylethanediamide.

EXAMPLE 3-1

Racemic-trans-N-(2-{[(3-fluoro-4-methylbenzyl)amino]carbonyl}-3-hydroxy-6-methyl-4-oxo-4,6,7,8,9,10-hexahydropyrimido[1,2-a]azepin-10-yl)-N,N',N'-trimethylethanediamide (Compound 3A)

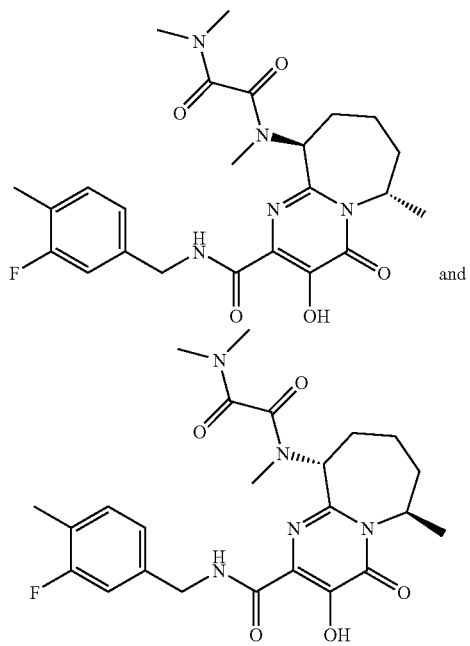

Step 1: 6-Methyltetrahydro-2H-pyran-2-ol

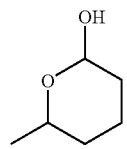

A solution of diisobutylaluminum hydride in methylene chloride (1M, 420 mL) was added slowly to a −78° C. solution of 6-hexanolactone (40 g, 350 mmol) in methylene chloride (1000 mL) over 1 hour. The resulting thin white suspension was allowed to warm up gradually over 2 hours whereupon at −40° C. a clear solution was attained. The reaction mixture was cautiously quenched via slow proportion-wise addition of methanol (105 mL) over 30 minutes. It was then stirred for 15 minutes, after which saturated aqueous sodium potassium tartrate (350 mL) was added. The reaction mixture was then allowed to warm to room temperature overnight. The organic phase was removed and washed with brine and then dried over magnesium sulfate. The aqueous phase was extracted with ethyl acetate, the extract then washed with brine and also similarly dried. Filtration and concentration gave a mixture of diastereomeric lactols as a colorless oil: $^1$H NMR (400 MHz, CDCl$_3$) Diastereomer A, δ 5.28 (s, 1H), 4.07 (m, 1H), 2.42 (br m, 1H), 1.13-1.87 (m, 6H), 1.11 (d, J=6.2 Hz, 3H). Diastereomer B, δ 4.70 (m, 1H), 3.56 (m, 1H), 2.86 (br m, 1H), 1.13-1.87 (m, 6H), 1.21 (d, J=6.2 Hz, 3H).

Step 2: 6-Hydroxy-2-(methylamino)heptanenitrile

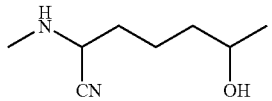

The 6-methyltetrahydro-2H-pyran-2-ol (42 g, 350 mmol) was dissolved in dioxane (300 mL) and treated with methylamine (40% in water, 32 mL, 350 mmol) followed by methylamine.HCl (19 g, 280 mmol) and then sodium cyanide (17 g, 350 mmol) followed by water (50 mL). After stirring at room temperature overnight, the organic phase was decanted off and concentrated. The residue was dissolved in ethyl acetate. Water was added to the initial aqueous suspension (which had been left behind) until dissolution was complete, after which both phases were combined and extracted. The organic phase thus obtained was concentrated. The aqueous phase was extracted twice more with fresh ethyl acetate and the extracts concentrated. The combined residue was dissolved in ether and filtered to remove the remaining solids. Concentration gave the product as a colorless oil: $^1$H NMR (400 MHz, CDCl$_3$) δ 3.81 (m, 1H), 3.46 (t, J=7 Hz, 1H), 2.53 (s, 3H), 1.76 (m, 2H), 1.34-1.65 (m, 4H), 1.19 (d, J=6.2 Hz, 3H).

Step 3: tert-Butyl (1-cyano-5-hydroxyhexyl)methylcarbamate

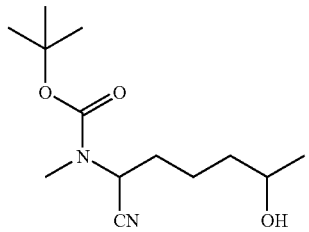 [SMILES: CC(O)CCCC(C#N)N(C)C(=O)OC(C)(C)C]

A solution of 6-hydroxy-2-(methylamino)heptanenitrile (76 g) in isopropyl acetate (350 mL) was warmed to 30° C. and then a solution of di-tert-butyl dicarbonate in isopropyl acetate (150 mL) was added dropwise. Whenever the internal temperature of the reaction rose above 35° C., heating was discontinued or the rate of addition was slowed to keep the internal temperature within a few degrees of this set point. The total required addition time was about 1 hour. Heating was then resumed and the temperature was maintained at 35° C. overnight. The reaction mixture was then cooled to room temperature and treated with ammonium chloride (7 g), water (50 mL) and concentrated aqueous ammonia (13 g) and the resulting mixture allowed to stir at room temperature overnight. The reaction mixture was then cooled to 0° C. and the organic phase separated and washed with cold (0° C.) 1M NaOH, then 10% ammonium chloride, then 20% NaCl, then dried over sodium sulfate. Filtration and concentration gave the product as a very thick opaque oil which contained an undetermined amount of t-butanol: $^1$H NMR (400 MHz, CDCl$_3$) δ 5.20 (m, 1H), 3.78 (br s, 1H), 2.87 (s, 3H), 1.81 (m, 2H), 1.25-1.63 (m, 4H), 1.45 (s, 9H), 1.18 (d, J=6.2 Hz, 3H).

Step 4: tert-Butyl {1-[(Z)-amino(hydroxyimino)methyl]-5-hydroxyhexyl}methylcarbamate

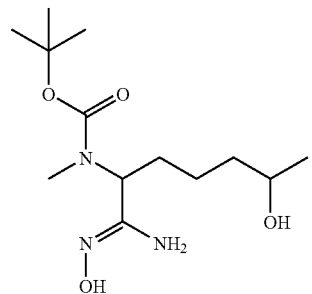 [SMILES: CC(O)CCCC(/C(N)=N/O)N(C)C(=O)OC(C)(C)C]

The tert-butyl (1-cyano-5-hydroxyhexyl)methylcarbamate (129 g) which contained an undetermined amount of t-butanol was dissolved in methanol (250 mL) and treated with 50% aqueous hydroxylamine (33 mL). The mixture was then heated to 60° C. for 3 hours. The reaction mixture was then cooled and the solvents removed in vacuo. The residue was azeotropically dried twice with toluene (200 mL each time) and dried in vacuo at 50° C. to give the product as a very thick clear oil which was contaminated by t-butanol: ES MS M+1=290.0.

Step 5: Dimethyl (2E)-2-[({(1Z)-1-amino-2-[(tert-butoxycarbonyl)(methyl)amino]-6-hydroxyheptylidene}amino)oxy]but-2-enedioate

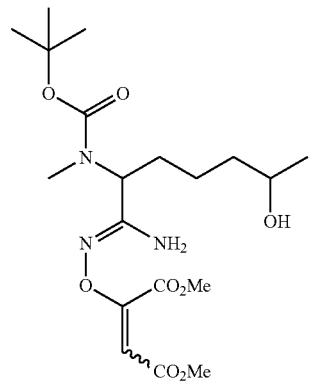 [SMILES: COC(=O)C=C(O/N=C(\N)C(CCCC(C)O)N(C)C(=O)OC(C)(C)C)C(=O)OC]

The tert-butyl {1-[(Z)-amino(hydroxyimino)methyl]-5-hydroxyhexyl}methylcarbamate (161 g, overweight) was dissolved in methanol (250 mL) and cooled to −10° C. DMAD (65 mL) was added dropwise without allowing the reaction temperature to rise above −5° C. then the reaction mixture was stored in a freezer at −10° C. for 2 days. The reaction mixture was then concentrated to dryness. It was azeotropically dried twice with toluene and dried in vacuo at 30° C. to constant weight to afford the title product: ES MS M+1=431.9.

Step 6: Methyl 2-{1-[(tert-butoxycarbonyl)(methyl)amino]-5-hydroxyhexyl}-5-hydroxy-6-oxo-1,6-dihydropyrimidine-4-carboxylate

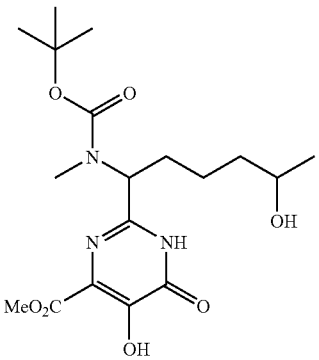 [SMILES: COC(=O)c1nc(C(CCCC(C)O)N(C)C(=O)OC(C)(C)C)[nH]c(=O)c1O]

The dimethyl (2E)-2-[({(1Z)-1-amino-2-[(tert-butoxycarbonyl)(methyl)amino]-6-hydroxyheptylidene}amino)oxy]but-2-enedioate (239 g, overweight) was dissolved in o-xylene (1000 mL) and the resulting solution heated at 120° C. for 48 hours. The resulting deep wine red solution was cooled to room temperature and the solvent concentrated in vacuo. The thick dark residue was dissolved in ethyl acetate (400 mL) and dichloromethane (100 mL), cooled in an ice bath and treated with 1M sodium hydroxide (400 mL). The mixture was transferred to a separataory funnel but it was difficult to see any separation due to the dark brown nature of the two layers. Therefore, 400 mL of the aqueous phase was drawn off. The remaining mixture was washed once with 1M sodium hydroxide (100 mL), then 300 mL of liquid was run off. The 400 mL and 300 mL draws were combined and extracted with ether (300 mL). The separation between the phases was now visible. The aqueous phase was separated off and cooled in an ice bath and while stirring rapidly, it was acidified with 6M HCl (85 mL). The resulting mixture was then extracted with methylene chloride and dried over sodium sulfate. Concentration and drying under vacuum gave the title product as a tacky brown sponge (140 g): ES MS M+1=399.8.

Step 7: Methyl 2-{1-[(tert-butoxycarbonyl)(methyl)amino]-5-[(methylsulfonyl)oxy]hexyl}-5,6-bis[(methylsulfonyl)oxy]pyrimidine-4-carboxylate

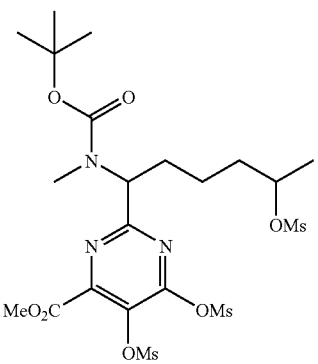 [SMILES: COC(=O)c1nc(C(CCCC(C)OS(C)(=O)=O)N(C)C(=O)OC(C)(C)C)nc(OS(C)(=O)=O)c1OS(C)(=O)=O]

The methyl 2-{1-[(tert-butoxycarbonyl)(methyl)amino]-5-hydroxyhexyl}-5-hydroxy-6-oxo-1,6-dihydropyrimidine-4-carboxylate from Step 6 was azeotroped dry with acetonitrile (500 mL). The resulting thick wine red gummy sponge (39 g) was redissolved in acetonitrile (500 mL) and cooled to 15-20° C. Triethylamine (54 mL) was added followed dropwise over 30 minutes by mesyl chloride (27 mL). After stirring at the same temperature for an additional 30 minutes, there had been complete conversion to a 2:1 mixture of tri-mesylate and di-mesylate as determined by LC-MS. The reaction mixture was filtered to remove triethylamine hydrogen chloride and the filter cake washed well with methylene chloride. The filtrate was concentrated and then partitioned between methylene chloride and half-saturated brine. The organic phase was removed and dried over sodium sulfate. Filtration and concentration gave a dark red foam which was azeotropically dried with acetonitrile (500 mL) and gave a wine red gum which was the tri-mesylate.

Step 8: Methyl trans-rac-10-[(tert-butoxycarbonyl)(methyl)amino]-6-methyl-3-[(methylsulfonyl)oxy]-4-oxo-4,6,7,8,9,10-hexahydropyrimido[1,2-a]azepine-2-carboxylate

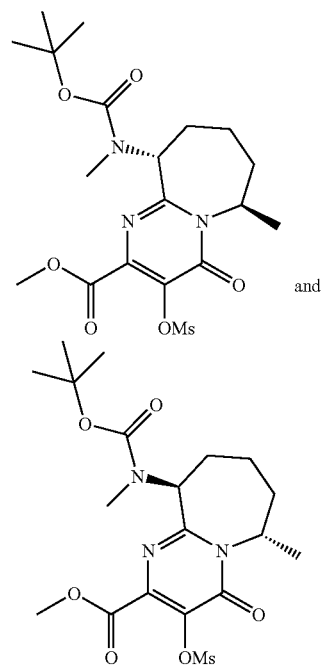

A mixture of the methyl 2-{1-[(tert-butoxycarbonyl)(methyl)amino]-5-[(methylsulfonyl)oxy]hexyl}-5,6-bis[(methylsulfonyl)oxy]pyrimidine-4-carboxylate (62 g, 98 mmol) and cesium carbonate (64 g, 196 mmol) in DMF (400 mL) was heated at 100° C. overnight. The reaction mixture was cooled to room temperature and then cooled further to 0° C. More cesium carbonate (60 g) was added followed by MsCl (10 mL) and stirring continued for 1 hour. The reaction mixture was filtered to remove solids and the solids were then washed with methylene chloride until the filtrate ran clear. The filtrate was then stripped and finally under high vacuum at 35° C. to remove the DMF. The thick dark red residual sludge was diluted with ether and filtered. The filter cake was washed with ether. The resulting cream colored solid was dissolved in methylene chloride and washed once with cold half-saturated brine and the solution dried over sodium sulfate. Filtration and concentration gave the racemic trans diastereomer as determined by NMR and LC-MS: ¹H NMR (400 MHz, CDCl₃) δ 5.74 (m, 1H), 5.41 (dd, J=1.6, 13.5 Hz, 1H), 3.92 (s, 3H), 3.50 (s, 3H), 2.95 (s, 3H), 1.60-2.94 (m, 6H), 1.57 (d, J=7.3 Hz, 3H), 1.44 (s, 9H). ES MS M+1=460.12.

Step 9: Methyl trans-rac-6-methyl-10-(methylamino)-3-[(methylsulfonyl)oxy]-4-oxo-4,6,7,8,9,10-hexahydropyrimido [1,2-a]azepine-2-carboxylate

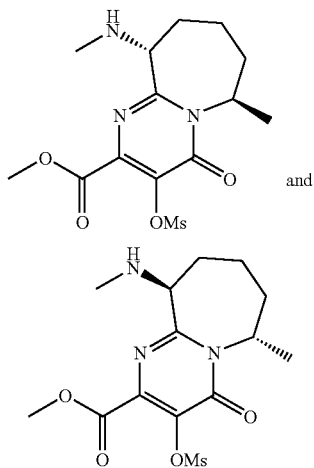

and

To a solution of the methyl trans-rac-10-[(tert-butoxycarbonyl)(methyl)amino]-6-methyl-3-[(methylsulfonyl)oxy]-4-oxo-4,6,7,8,9,10-hexahydropyrimido [1,2-a]azepine-2-carboxylate (3.5 g) in dioxane (25 mL) at 0° C. was added 4M HCl in dioxane (25 mL). After stirring for 30 minutes the reaction mixture was allowed to warm to room temperature and stirred there for 4 hours. The solvent was stripped and the residue dissolved in water and treated with excess sodium carbonate. The resulting mixture was extracted with methylene chloride, then chloroform and dried over sodium sulfate. Filtration and concentration gave the amine as dark brown viscous oil.

Step 10: Trans-rac-methyl 10-[[(dimethylamino)(oxo)acetyl](methyl)amino]-6-methyl-3-[(methylsulfonyl)oxy]-4-oxo-4,6,7,8,9,10-hexahydropyrimido[1,2-a]azepine-2-carboxylate

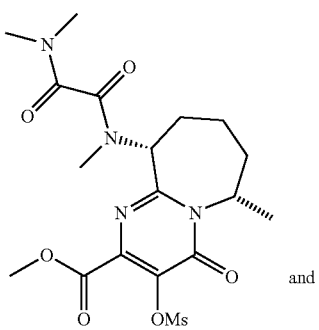

and

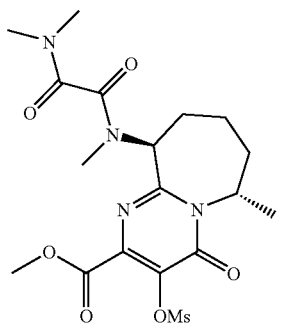

Ethyl chloroformate (0.4 mL) was added to a solution of dimethyloxamic acid (0.49 g) in tetrahydrofuran (15 mL) at −15° C. N-methylmorpholine (0.52 mL) was added slowly in portions while maintaining the temperature below −5° C. As the addition proceeded the amine salt crashed out as a white solid. Stirring was continued for 90 minutes then the salts were filtered off and the resulting cold solution used directly. The methyl trans-rac-6-methyl-10-(methylamino)-[(methylsulfonyl)oxy]-4-oxo-4,6,7,8,9,10-hexahydropyrimido [1,2-a]azepine-2-carboxylate from Step 9 was dissolved in THF (5 mL) and added to the mixed anhydride as prepared above while cooling in a cold water bath. When the addition was complete, the reaction mixture was allowed to warm up gradually to room temperature whereupon a cream solid precipitated. The solid precipitate was filtered off and washed well with ether then dried under vacuum. The resulting white solid was the desired title compound: ¹H NMR (400 MHz, CDCl₃) δ 5.69-5.79 (m, 2H), 3.91 (s, 3H), 3.51 (s, 3H), 3.12 (s, 3H), 3.03 (s, 3H), 3.00 (s, 3H), 1.82-2.14 (m, 6H), 1.61 (d, J=7.3 Hz, 3H).

Step 11: Racemic-trans-N-(2-{[(3-fluoro-4-methylbenzyl)amino]carbonyl}-3-hydroxy-6-methyl-4-oxo-4,6,7,8,9,10-hexahydropyrimido[1,2-a]azepin-10-yl)-N,N',N'-trimethylethanediamide The trans-rac-methyl 10-[[(dimethylamino)(oxo)acetyl](methyl)amino]-6-methyl-3-[(methylsulfonyl)oxy]-4-oxo-4,6,7,8,9,10-hexahydropyrimido[1,2-a]azepine-2-carboxylate from Step 10 (50 mg) was dissolved in DMSO (2 mL) and 4-methyl-3-fluorobenzylamine (0.1 mL) added. The resulting mixture was heated at 100° C. for 30 minutes. As determined by LC-MS, there was complete conversion to product which was purified by reverse phase Gilson chromatography: ¹H NMR (400 MHz, CDCl₃) δ 9.46 (br s, 1H), 7.05 (m, 3H), 5.96 (m, 1H), 5.56 (br s, 1H), 4.47 (qd, J=6.8, 14.5 Hz, 2H), 3.02 (s, 3H), 2.99 (s, 3H), 2.94 (s, 3H), 2.21 (s, 3H), 1.61-2.24 (m, 6H), 1.47 (d, J=7.5 Hz, 3H). ES MS M+1=487.8.

EXAMPLE 3-2

Isolated cis enantiomer of N-(2-{[(3-fluoro-4-methylbenzyl)amino]carbonyl}-3-hydroxy-6-methyl-4-oxo-4,6,7,8,9,10-hexahydropyrimido[1,2-a]azepin-10-yl)-N,N',N'-trimethylethanediamide (Compound 3B)

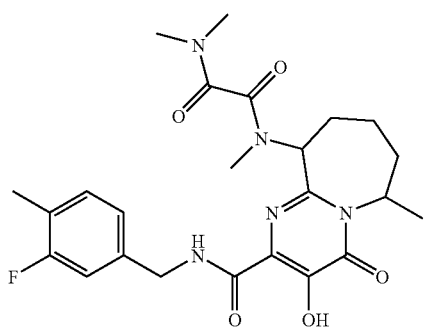

Step 1: Methyl cis-10-[(tert-butoxycarbonyl)(methyl)amino]-6-methyl-3-[(methylsulfonyl)oxy]-4-oxo-4,6,7,8,9,10-hexahydropyrimido[1,2-a]azepine-2-carboxylate

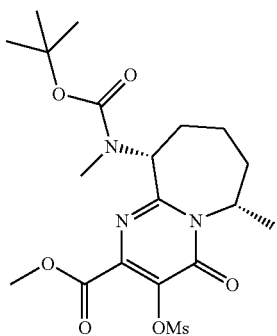 [SMILES: COC(=O)c1nc2n(c(=O)c1OS(C)(=O)=O)[C@@H](C)CCC[C@H]2N(C)C(=O)OC(C)(C)C]

This compound was prepared according to the procedure described for Example 3-1, Step 8, except that here the reaction mixture was heated at 100° C. for 4 hours instead of overnight. As a result of the reduced reaction time, the product was isolated as a racemic cis-trans mixture of diastereomers. This mixture was separated into its 4 diastereomerically pure components by chiral supercritical fluid chromatography: $^1$H NMR (400 MHz, CDCl$_3$) C is diastereomer of unknown absolute configuration. δ 5.45 (m, 1H), 4.77 (m, 1H), 3.90 (s, 3H), 3.49 (s, 3H), 2.81 (s, 3H), 1.58-2.07 (m, 6H), 1.55 (d, J=6.8 Hz, 3H), 1.45 (s, 9H). ES MS M+1=460.10.

Step 2: Cis-N-(2-{[(3-fluoro-4-methylbenzyl)amino]carbonyl}-3-hydroxy-6-methyl-4-oxo-4,6,7,8,9,10-hexahydropyrimido[1,2-a]azepin-10-yl)-N,N',N'-trimethylethanediamide The methyl cis-10-[(tert-butoxycarbonyl)(methyl)amino]-6-methyl-3-[(methylsulfonyl)oxy]-4-oxo-4,6,7,8,9,10-hexahydropyrimido[1,2-a]azepine-2-carboxylate from Step 1 was converted to the title compound according to the procedures described for Example 3-1, Steps 8-11. Absolute stereochemistry—either (6R,10S) or 6S,10R)—was not determined. $^1$H NMR (400 MHz, CDCl$_3$) δ 9.66 (br s, 1H), 7.05 (m, 3H), 5.67 (br s, 1H), 5.00 (br s, 1H), 4.54 (qd, J=6.6, 14.5 Hz, 2H), 3.06 (s, 3H), 3.01 (s, 3H), 2.83 (s, 3H), 2.21 (s, 3H), 1.92-2.23 (m, 6H), 1.49 (d, J=6.3 Hz, 3H). ES MS M+1=488.11.

EXAMPLE 4-1

N-((6S,10S)-2-{[(4-fluoro-3-methylbenzyl)amino]carbonyl}-3-hydroxy-6-methyl-4-oxo-6,7,9,10-tetrahydro-4H-pyrimido[1,2-d][1,4]oxazepin-10-yl)-N,N',N'-trimethylethanediamide (Compound 4A)

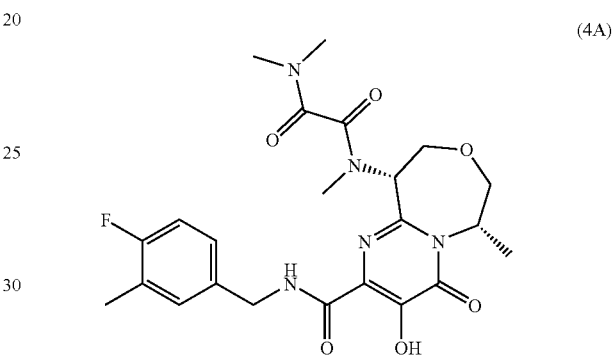
(4A)

N-((6S,10R)-2-{[(4-fluoro-3-methylbenzyl)amino]carbonyl}-3-hydroxy-6-methyl-4-oxo-6,7,9,10-tetrahydro-4H-pyrimido[1,2-d][1,4]oxazepin-10-yl)-N,N',N'-trimethylethanediamide. (Compound 4B)

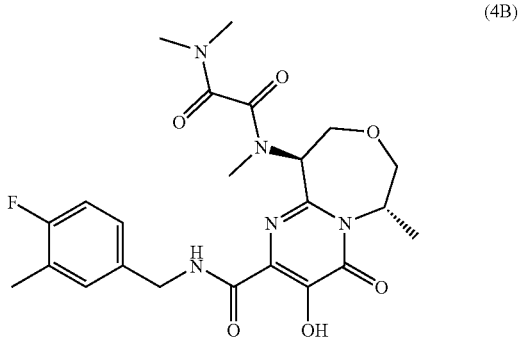 [SMILES: Cc1cc(CNC(=O)c2nc3n(c(=O)c2O)[C@@H](C)COC[C@@H]3N(C)C(=O)C(=O)N(C)C)ccc1F]
(4B)

Step 1: 2(R)-1-(Allyloxy)propan-2-ol

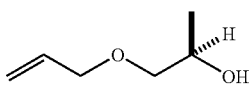

To a stirred solution of allyl alcohol (55.0 g, 947 mmol) in 300 mL of anhydrous N,N-dimethylformamide cooled in an ice bath was added 60% oil dispersion of sodium hydride (37.9 g, 947 mmol) in 4 portions over 30 minutes. The mixture was allowed to warm to ambient temperature and after 30 minutes the mixture was cooled in an ice bath and (R)-1,2-epoxypropane (50 g, 861 mmol) was added slowly over 30 minutes. The reaction mixture was allowed to warm to room temperature and stirred for 72 hours. The reaction mixture was cooled in an ice bath, diluted with water, and extracted with ethyl acetate (4×). The combined organic extracts were washed with water (3×), brine (1×) and dried over anhydrous magnesium sulfate. Concentration under reduced vacuum gave the crude product as an oil which was used in the next step without purification: $^1$H NMR (400 MHz, CDCl$_3$): δ 5.92 (ddt, J=17.2, 10.4, 5.6 Hz, 1H); 5.26 (dq, J=17.2, 1.6 Hz, 1 H); 5.20 (dq, J=10.3, 1.3 Hz, 1 H); 4.03 (dt, J=5.6, 1.4 Hz, 2 H); 3.95 (m, 1 H); 3.4-3.5 (m, 1 H); 3.24 (dd, J=9.4, 8.2 Hz, 1 H); 2.4 (br s, 1 H); 1.15 (d, J=6.4 Hz, 3 H).

Step 2: 6(R)-6-Methyl-1,4-dioxan-2-ol

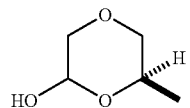

A stream of ozone was dispersed into a cold (initial T=−78° C.) stirred solution of 2(R)-1-(allyloxy)propan-2-ol (84 g, 723 mmol) in dichloromethane (400 mL) until a blue color persisted (required 4 hours). The solution was purged with nitrogen until a clear, colorless solution was obtained. Dimethyl sulfide (134 mL, 1.8 mol) and triethylamine (302 mL, 2.17 mol) were added. The stirred mixture was allowed to warm to room temperature over 60 minutes. A test for peroxide with wet starch-iodide paper was negative. The mixture was concentrated under reduced pressure at ambient temperature to provide the crude title product which was used directly in the next step without purification.

Step 3: tert-Butyl (1-cyano-2-{[(2)-2-hydroxypropyl]oxy}ethyl)methylcarbamate

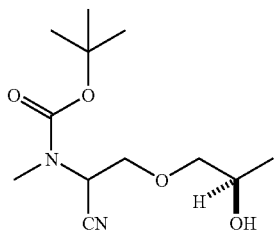 [SMILES: C[C@@H](O)COCC(C#N)N(C)C(=O)OC(C)(C)C]

To a stirred solution of 6(R)-6-methyl-1,4-dioxan-2-ol (100 g, 847 mmol) in dioxane and water (3:1, 400 mL) was added methylamine hydrochloride (114 g, 1.69 mol) and sodium cyanide (83 g, 1.69 mol). The solution was stirred for 72 hours. The product was extracted into ethyl acetate (3×) and the combined organic layers were dried over anhydrous sodium sulfate, filtered, and the solvent was removed under reduced pressure. The residue was dissolved in ethyl acetate (100 mL) and to the solution was added di-tert-butyl dicarbonate (369 g, 1.69 mol). The solution was stirred at room temperature for 18 hours, diluted with ethyl acetate and washed with water (1×), and brine (1×). After drying over sodium sulfate the crude product solution was filtered and concentrated under reduced pressure. Purification by medium pressure chromatography on silica gel with a 30-50% ethyl acetate in hexane gradient gave the title product.

$^1$H NMR (399 MHz, CDCl$_3$): δ 5.5-5.1 (br m, 1 H); 3.9 (m, 1 H); 3.8 (m, 2 H); 3.53 (td, J=9.5, 3.0 Hz, 1 H); 3.34 (ddd, J=14.1, 9.5, 7.4 Hz, 1 H); 2.96 (s, 1.5 H); 2.96 (s, 1.5 H); 1.48 (s, 9 H); 1.16 (d, J=6.4 Hz, 3 H).

Step 4: tert-Butyl[(2)-2-amino-1-({[(2R)-2-hydroxypropyl]oxy}methyl)-2-(hydroxyimino)ethyl]-methyl carbamate

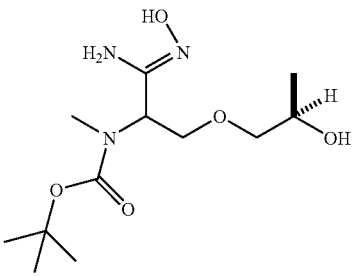 [SMILES: C[C@@H](O)COCC(/C(N)=N/O)N(C)C(=O)OC(C)(C)C]

To a solution of tert-butyl (1-cyano-2-{[(2)-2-hydroxypropyl]oxy}ethyl)methyl-carbamate (20 g, 77 mmol) in methanol (100 mL) was added a 50% aqueous solution of hydroxylamine (5.63 g, 85 mmol) and the mixture was stirred at 40° C. for 18 hours. The solution was concentrated under reduced pressure and the residue was purified by medium pressure chromatography on silica gel with a 10-90% ethyl acetate in hexane gradient gave the title product as a yellow oil. ES MS=292.2 (M+1).

Step 5: Dimethyl (2)-2-{[((1)-1-amino-2-[(tert-butoxycarbonyl)(methyl)amino]-3-{[(2R)-2-hydroxypropyl]oxy}propylidene)amino]oxy}but-2-enedioate

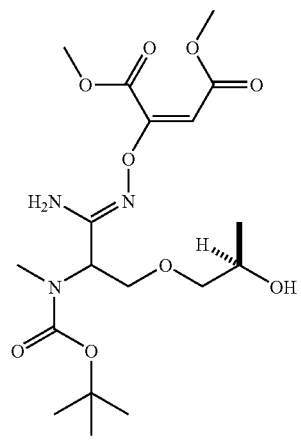

To a stirred solution of tert-butyl[(2)-2-amino-1-({[(2R)-2-hydroxypropyl]oxy}methyl)-2-(hydroxyimino)ethyl]-methylcarbamate (123.5 g, 424 mmol) in methanol at 0° C. was added dimethyl acetylenedicarboxylate (52.4 mL, 424 mmol). After the addition, the reaction mixture was allowed to warm to room temperature. Stirring was continued for 18 hours. The solvent was removed under reduced pressure. The crude product was purified by medium pressure chromatography on silica gel with a 10-85% ethyl acetate in hexane gradient providing the title product. ES MS=435.4 (M+1).

Step 6: Methyl 2-(1-[(tert-butoxycarbonyl)(methyl)amino]-2-{[(2R-)-2-hydroxypropyl]oxy}ethyl)-5,6-dihydroxypyrimidine-4-carboxylate

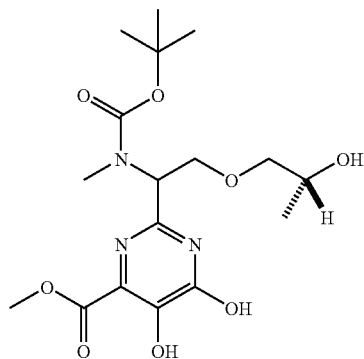

A solution of dimethyl (2)-2-{[((1)-1-amino-2-[(tert-butoxycarbonyl)(methyl)amino]-3-{[(2R)-2-hydroxypropyl]oxy}propylidene)amino]oxy}but-2-enedioate (140 g, 323 mol) in o-xylene (1000 mL) was heated at 120° C. for 18 hours. The temperature of the solution was then increased to 140° C. for 6 hours to convert the last of the substrate. The mixture was allowed to cool to ambient temperature and concentrated under reduced pressure. The crude residue was purified by medium pressure liquid chromatography on silica gel with 40% ethyl acetate in hexane to remove low polarity components and then the product was eluted with 10% ethanol in dichloromethane providing the title product. ES MS=402.4 (M+1).

Step 7: tert-Butyl (1-(4-{[(4-fluoro-3-methylbenzyl)amino]carbonyl}-5,6-dihydroxypyrimidin-2-yl)-2-{[(2)-2-hydroxypropyl]oxy}ethyl)methylcarbamate

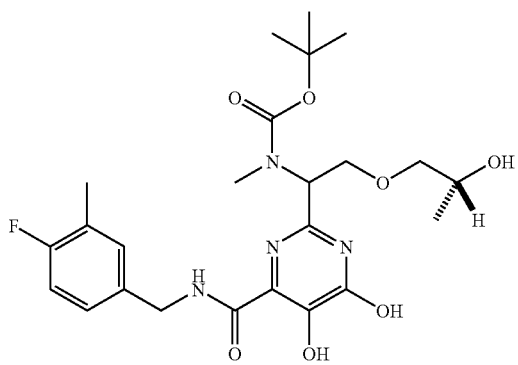 [SMILES: Cc1cc(CNC(=O)c2nc(C(COC[C@@H](C)O)N(C)C(=O)OC(C)(C)C)nc(O)c2O)ccc1F]

To a stirred solution of methyl 2-(1-[(tert-butoxycarbonyl)(methyl)amino]-2-{[(2R-)-2-hydroxypropyl]oxy}ethyl)-5,6-dihydroxypyrimidine-4-carboxylate (40 g, 100 mmol) 2-propanol (400 mL) was added 4-fluoro-3-methylbenzylamine (20.8 g, 149 mmol) in two parallel runs. The mixtures were heated to 60° C. for 16 hours. With some substrate ester remaining as determined by LC-MS, the temperatures of the heating baths were increased to 80° C. for 3 hours. The solutions were cooled and combined and the solvent was removed under reduced pressure. The crude product was dissolved in ethyl acetate and washed with aqueous 10% citric acid (2×), saturated sodium bicarbonate (1×) and brine (1×). The organic layer was separated, dried over anhydrous sodium sulfate, filtered, and the solvent was removed under reduced pressure. The crude product was used without further purification in the next step: ES MS=509.5 (M+1).

Step 8: (6S,10S) and (6S,10R) tert-Butyl((6,10)-2-{[(4-fluoro-3-methylbenzyl)amino]carbonyl}-3-hydroxy-6-methyl-4-oxo-6,7,9,10-tetrahydro-4-pyrimido[1,2-][1,4]oxazepin-10-yl)methylcarbamate

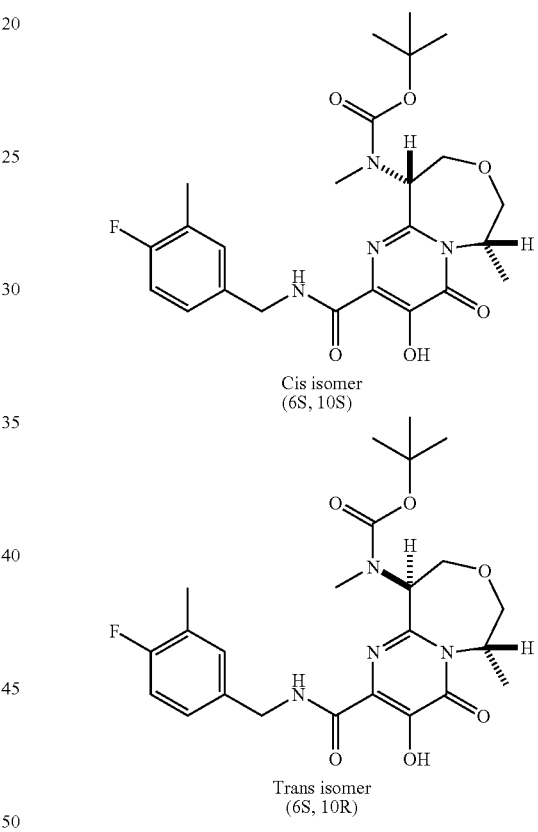

Tert-butyl (1-(4-{[(4-fluorobenzyl)amino]carbonyl}-5,6-dihydroxypyrimidin-2-yl)-2-{[(2)-2-hydroxybutyl]oxy}ethyl)methylcarbamate (40 g, 79 mmol) in two parallel runs was dissolved in dry acetonitrile (200 mL) and cooled in ice bath under nitrogen. To the stirred solution was added triethylamine (99 mL, 472 mmol) followed by the dropwise addition of methanesulfonyl chloride (36.8 mL, 472 mmol) in 73 mL anhydrous methylene chloride. The mixtures were stirred for 30 minutes and then treated with deionized water. The mixtures were combined and extracted with chloroform. The organic layer was separated and dried over anhydrous sodium sulfate, filtered, and concentrated under reduced pressure. The residue was chromatographed in 2 runs on a 340 g Biotage SNAP cartridge with a 10% to 90% ethyl acetate in hexane gradient to afford the crude trimesylate: ES MS: m/z=743.5 (M+1).

A stirred solution of the trimesylate (25 g, 33.7 mmol) in dimethylacetamide (500 mL) was purged with nitrogen gas for 10 minutes, treated with cesium carbonate (43.9 g, 135 mmol) and stirred vigorously in a 100° C. oil bath for 15 hours. The reaction mixture was allowed to cool to ambient temperature and filtered. The filtrate was diluted with water and extracted with ethyl acetate. The organic layer was washed with water (3×), brine (1×), dried over anhydrous sodium sulfate, filtered, and concentrated under reduced pressure. The crude product was suspended in ether (200 mL), stirred for 30 minutes, and the insoluble dark material was removed by filtration. This material was suspended in ether again (600 mL), stirred for 48 hours, and filtered. The combined filtrates were concentrated under reduced pressure to provide the crude product. $^1$H NMR analysis indicated a 1:2 mixture of cis: trans diastereomers. ES MS=491.2 (M+1)

Step 9: (6S,10S) and (6S,10R)—N-(4-fluoro-3-methylbenzyl)-3-hydroxy-6-methyl-10-(methylamino)-4-oxo-6,7,9,10-tetrahydro-4-pyrimido[1,2-][1,4]oxazepine-2-carboxamide hydrochloride

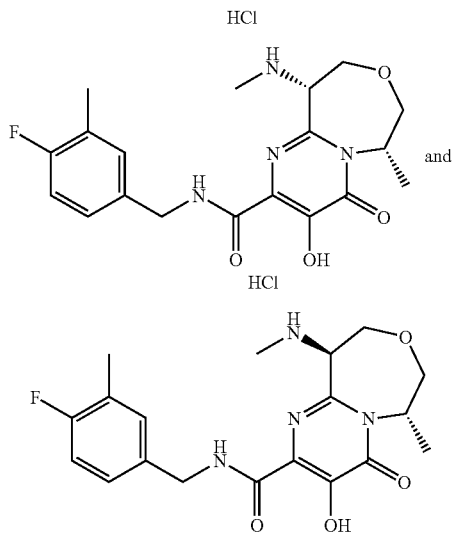

The mixture of cis and trans diastereomers from the previous step, (6S,10S) and (6S,10R) tert-butyl(((6,10)-2-{[(4-fluoro-3-methylbenzyl)amino]carbonyl}-3-hydroxy-6-methyl-4-oxo-6,7,9,10-tetrahydro-4-pyrimido[1,2-][1,4]oxazepin-10-yl)methylcarbamate (13.5 g, 27.5 mmol), was dissolved in 4M HCl in dioxane (206 mL). After 30 minutes the precipitated solid was collected by filtration and dried under vacuum. $^1$H NMR analysis of this solid found a 3:2 mixture of trans:cis diastereomers of the titled product. The filtrate was found to contain predominantly the trans diastereomer. ES MS: m/z=391.2 (M+1)

Step 10: N-((6S,10S)-2-{[(4-fluoro-3-methylbenzyl)amino]carbonyl}-3-hydroxy-6-methyl-4-oxo-6,7,9,10-tetrahydro-4H-pyrimido[1,2-d][1,4]oxazepin-10-yl)-N,N',N'-trimethylethanediamide (Compound 4A) and N-((6S,10R)-2-{[(4-fluoro-3-methylbenzyl)amino]carbonyl}-3-hydroxy-6-methyl-4-oxo-6,7,9,10-tetrahydro-4H-pyrimido[1,2-d][1,4]oxazepin-10-yl)-N,N',N'-trimethylethanediamide (Compound 4B)

A solution of the mixture of diastereomers form the previous step, (6S,10S) and (6S,10R)—N-(4-fluoro-3-methylbenzyl)-3-hydroxy-6-methyl-10-(methylamino)-4-oxo-6,7,9,10-tetrahydro-4-pyrimido[1,2-][1,4]oxazepine-2-carboxamide hydrochloride (3.5 g, 9.0 mmol), ethyl-(dimethylaminopropyl)carbodiimide hydrochloride (5.16 g, 26.9 mmol), 1-hydroxy-7-azabenzotriazole (3.66 g, 26.9 mmol), N,N-dimethyloxalamic acid (1.58 g, 13.5 mmol) and triethylamine (2.56 mL, 44.8 mmol), in dry dichloromethane (10 mL), was stirred at room temperature for 18 hours. The mixture was washed with water (6×) and with brine (1×). The aqueous washes were back extracted with chloroform (3×) and the combined organic layers were dried over sodium sulfate, filtered, and concentrated under reduced pressure. The crude product was first purified by reverse phase preparative HPLC on an Xterra (Waters) Prep MS C18 OBD 50×250 mmn column using a 10-75% CH$_3$CN/H$_2$O (0.1% TFA) 45 minute gradient with a flow rate of 85 mL/minute. Concentration under reduced pressure gave a 3:2 mixture of trans:cis diastereomers as a amorphous white solid. This material was separated to give the cis-(6S,10S) and trans-(6S,10R) title diastereomers using supercritical fluid chromatography on a OJ-H column (Chiralcel) with 15% ethanol in carbon dioxide as the mobile phase. The first eluting peak was the trans diastereomer and the second eluting peak was the cis diastereomer:

Compound 4A—Cis diastereomer (title compound, (6S, 10S)): $^1$H NMR (400 MHz, CDCl$_3$): δ 9.59 (t, J=6.4 Hz, 1 H); 7.21 (dd, J=7.5, 2.1 Hz, 1 H); 7.20-7.13 (m, 1 H); 6.91 (t, J=9.0 Hz, 1 H); 5.81 (s, 1 H); 4.99-4.90 (m, 1 H); 4.51 (d, J=6.5 Hz, 2 H); 4.46 (t, J=10.6 Hz, 1 H); 4.31 (d, J=14.1 Hz, 1 H); 4.15 (dd, J=11.8, 2.5 Hz, 1 H); 4.05 (dd, J=14.1, 5.3 Hz, 1 H); 3.07 (s, 3 H); 3.02 (s, 3 H); 2.87-2.84 (m, 3 H); 2.28-2.21 (m, 3 H); 1.62 (d, J=6.9 Hz, 3H). HR MS: ESI=490.2086 (M+1); calculated 490.2096 (M+1).

Compound 4B—Trans diastereomer (6S,10R): $^1$H NMR (appears as a 2:1 mixture of rotational isomers) (400 MHz, CDCl$_3$): δ 12.6-12.2 (br m, 1H); 9.7-9.5 (m, 1 H); 7.2 (m, 2 H); 6.9 (t, J=9.0 Hz, 1 H); 5.8-5.7 (m, 2 H); 4.5-4.1 (m, 5 H); 3.8-3.6 (m, 2 H); 3.1 (s, 3 H); 3.1 (s, 3 H); 3.0-2.8 (m, 3 H); 2.2 (d, J=1.8 Hz, 3 H); 1.6-1.5 (m, 2 H) HR MS: ESI=490.2086 (M+1); calculated 490.2096 (M+1).

Alternative Procedure

Step 1: The mixture of diastereomers in Step 8 was separated utilizing reverse phase liquid chromatography on an Xterra (Waters) Prep MS C18 OBD 50×250 mm column eluted with a 10-75% CH$_3$CN/H$_2$O (0.1% TFA) 45 minute gradient at a flow rate of 85 mL/minute. Lyophilization of the fractions containing the first and second eluting products gave the cis and trans diastereomers, respectively, as tan amorphous solids:

Cis diastereomer (6S,10S): $^1$H NMR (400 MHz, CDCl$_3$): δ 12.2-11.8 (br.s, 1 H), 7.77 (br s, 1H); 7.12 (m, 2 H); 6.97 (t, J=8.9 Hz, 1 H); 5.3-.5.0 (br m, 1 H); 4.90 (t, J=6.5 Hz, 1 H); 4.51 (d, J=6.4 Hz, 2 H); 4.36 (t, J=9.5 Hz, 1 H); 4.12 (m, 2 H); 4.01 (dd, J=13.9, 5.5 Hz, 1H); 2.80 (br s, 3 H); 2.23 (d, J=1.8 Hz, 3 H); 1.62 (d, J=6.9 Hz, 3 H); 1.27 (s, 9 H): ES MS: m/z=491.1 (M+1).

Trans diastereomer (6S,10R): 111 NMR (appears as a 2:1 mixture of rotational isomers) (400 MHz, CDCl$_3$): δ 12.2-11.8 (br.s, 1 H), 7.83 (br s, 2/3 H); 7.59 (br s, 1/3 H); 7.14 (m, 2 H); 6.98 (m, 1 H); 5.65 (m, 4/3H); 5.38 (m, 2/3H); 4.47 (m, approximately. 2 H); 4.29-4.10 (m, approximately. 2 H); 3.59 (d, J=13.4 Hz, approximately. 2H); 2.79 (s) 2.76 (s) (3H); 2.26 (s, 3 H); 1.56 (d, J=7.3 Hz, 1 H); 1.50 (d, J=7.1 Hz, 2 H); 1.29 (s, 3H); 1.25 (s, 6H): ES MS=491.2 (M+1).

Step 2: The cis isomer from the previous step, (6S,10S) tert-butyl((6,10)-2-{[(4-fluoro-3-methylbenzyl)amino]carbonyl}-3-hydroxy-6-methyl-4-oxo-6,7,9,10-tetrahydro-4-pyrimido[1,2-][1,4]oxazepin-10-yl)methylcarbamate (1.7 g, 3.5 mmol), was dissolved in ethyl acetate (69 mL), cooled in an ice bath with stirring, and the solution was saturated with anhydrous HCl gas over 5 minutes. The mixture was stirred in an ice bath for 1 hour and then concentrated under reduced pressure. The residue was dissolved in and concentrated from ethyl acetate twice more and then dried under vacuum to give the hydrochloride salt of (6S,10S)—N-(4-fluoro-3-methylbenzyl)-3-hydroxy-6-methyl-10-(methylamino)-4-oxo-6,7,9,10-tetrahydro-4-pyrimido[1,2-][1,4]oxazepine-2-carboxamide hydrochloride as a solid.

$^1$H NMR (399 MHz, d6DMSO): δ 12.45 (s, 1 H); 9.95 (t, J=6.5 Hz, 1 H); 9.54 (br d, J=24.7 Hz, 2 H); 7.21 (m, 2 H); 7.10 (t, J=9.0 Hz, 1 H); 5.03 (s, 1 H); 4.75 (td, J=6.8, 2.7 Hz, 1 H); 4.47 (d, J=6.4 Hzm, 2 H); 4.1 (m, 2 H); 3.88 (m, 2 H); 2.65 (s, 3 H); 2.21 (d, J=1.6 Hz, 3 H); 1.53 (d, J=6.8 Hz, 3 H): ES MS: m/z=391.1 (M+1).

Step 3: A solution of (6S,10S)—N-(4-fluoro-3-methylbenzyl)-3-hydroxy-6-methyl-10-(methylamino)-4-oxo-6,7,9,10-tetrahydro-4-pyrimido[1,2-][1,4]oxazepine-2-carboxamide hydrochloride (1.38 g, 3.2 mmol), ethyl-(dimethylaminopropyl)carbodiimide hydrochloride (1.24 g, 6.5 mmol), 1-hydroxy-7-azabenzotriazole (0.44 g, 3.2 mmol), N,N-dimethyloxalamic acid (0.57 g, 4.9 mmol) and N-methylmorpholine (1.42 mL, 12.9 mmol), in anhydrous N,N-dimethylformamide (32 mL) was stirred at room temperature for 18 hours. The mixture was diluted with ethyl acetate and 5% aqueous potassium hydrogen sulfate. The layers were separated and the aqueous layer was extracted with ethyl acetate (4×). The combined organic extracts were washed with brine, dried over magnesium sulfate, filtered, and concentrated under reduced pressure. The crude product was purified by reverse phase preparative HPLC on an Xterra (Waters) Prep MS C18 OBD 50×250 mm column eluted with 10-75% CH$_3$CN/H$_2$O (0.1% TFA) 45 minute gradient at a flow rate of 85 mL/minute. Product fractions were combined and lyophilized overnight to give Compound 4A (cis-(6S,10S) diastereomer).

Crystallization of Compound 4A

Amorphous Compound 4A prepared using the chromatographic separation procedure described above was redissolved in methylene chloride and partitioned with water adjusted to pH 3 with NaHCO$_3$. The aqueous layer was extracted 3 times with methylene chloride. The combined organics were dried over Na$_2$SO$_4$, filtered, and concentrated under reduced pressure. The resulting solid was dissolved in warm MeOH, filtered through a nylon syringe filter into a glass vial. The vial of solution was allowed to stand open in a beaker containing EtOAc. Large crystals formed on the bottom of the MeOH vial overnight. The solid was washed with ice cold MeOH, and then Et$_{20}$ to afford Compound 4A as crystalline solid.

Figure 2:
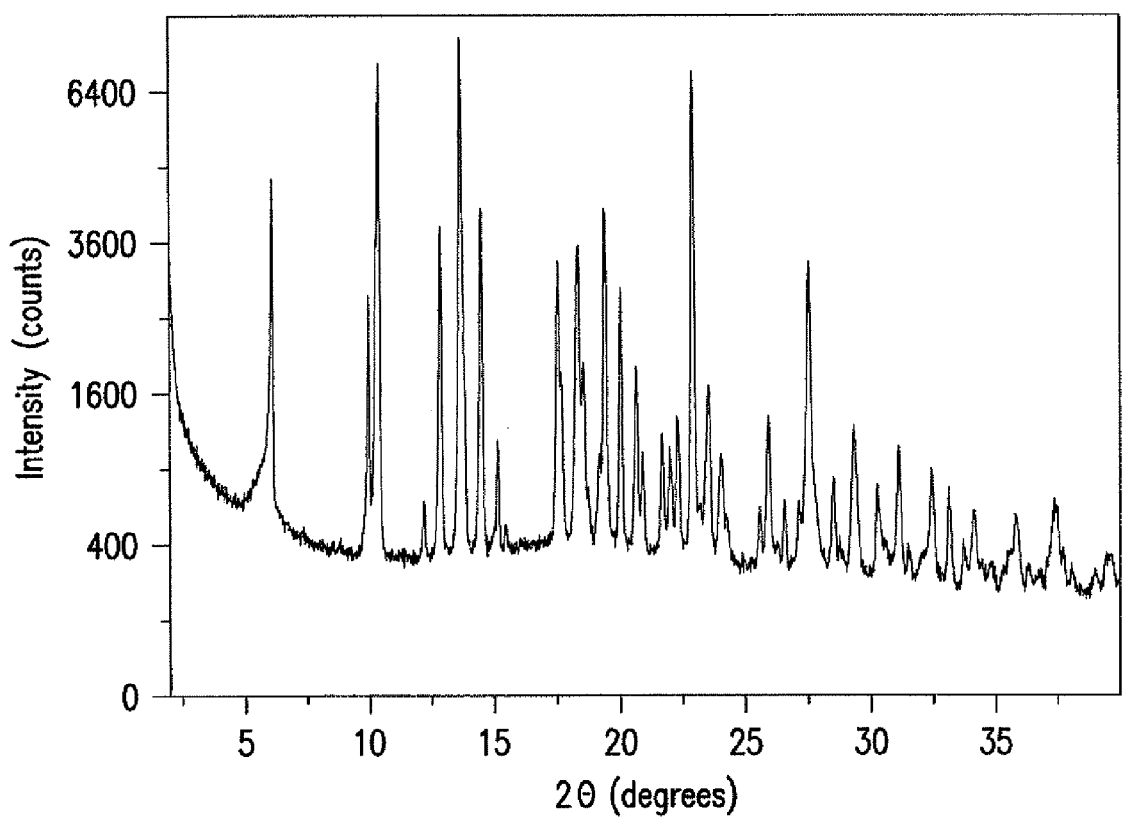
FIG. 2 is the X-ray powder diffraction pattern for the crystalline form of Compound 4A described in Example 4-1.

Characterization. An XRPD pattern of the crystalline Compound 4A was generated on a Philips Analytical X'Pert PRO X-ray Diffraction System with PW3050/60 console using a continuous scan from 4 to 40 degrees 2θ. Copper K$_{α1}$ and K$_{α2}$ radiation was used as the source. The experiment was run under ambient conditions. The diffraction peak positions were referenced by silicon which has a 2Θ value of 28.443 degree. The XRPD pattern is shown in FIG. 2. 2θ values and the corresponding d-spacings in the XRPD pattern include the following:

TABLE 4A

| 2θ (degrees) | d-spacing (Å) |
|---|---|
| 6.1 | 14.5 |
| 10.0 | 8.9 |
| 10.3 | 8.6 |
| 10.4 | 8.5 |
| 12.2 | 7.2 |
| 12.9 | 6.9 |
| 13.7 | 6.5 |
| 14.5 | 6.1 |
| 15.1 | 5.8 |
| 15.5 | 5.7 |
| 17.5 | 5.1 |
| 17.7 | 5.0 |
| 18.3 | 4.8 |
| 18.6 | 4.8 |
| 19.2 | 4.6 |
| 19.4 | 4.6 |
| 20.0 | 4.4 |
| 20.6 | 4.3 |
| 20.9 | 4.2 |
| 21.7 | 4.1 |
| 22.0 | 4.0 |
| 22.3 | 4.0 |
| 22.9 | 3.9 |
| 23.5 | 3.8 |
| 24.0 | 3.7 |
| 25.6 | 3.5 |
| 25.9 | 3.4 |
| 26.5 | 3.4 |
| 27.1 | 3.3 |
| 27.5 | 3.2 |
| 28.5 | 3.1 |
| 29.3 | 3.0 |
| 30.2 | 2.9 |
| 31.1 | 2.9 |
| 31.5 | 2.8 |
| 32.4 | 2.8 |
| 33.1 | 2.7 |
| 33.7 | 2.7 |
| 34.1 | 2.6 |
| 35.8 | 2.5 |
| 37.4 | 2.4 |

The crystalline Compound 4A was also analyzed with a TA Instruments DSC Q 1000 differential scanning calorimeter at a heating rate of 10° C./minute from 25° C. to 350° C. in an open aluminum pan in a nitrogen atmosphere. The DSC curve showed an endotherm with an onset temperature of 139° C. and a peak temperature of 144° C. The enthalpy change was 67 J/g. The endotherm is believed to be due to melting.

TGA of the crystalline compound was performed with a TA Instruments TGA Q 500 under nitrogen at a heating rate of 10° C./minute from 25° C. to 350° C. The TG curve showed a weight loss of 0.03 wt. % up to 100° C. indicating the absence of water of hydration and solvent of solvation.

EXAMPLE 4-2

N-((6R,10R)-2-{[(4-fluoro-3-methylbenzyl)amino]carbonyl}-3-hydroxy-6-methyl-4-oxo-6,7,9,10-tetrahydro-4H-pyrimido[1,2-d][1,4]oxazepin-10-yl)-N,N',N'-trimethylethanediamide (Compound 4C)

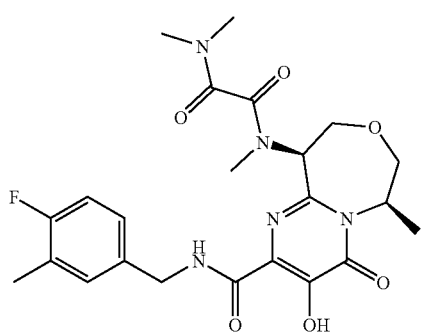

(4C)

N-((6R,10S)-2-{[(4-fluoro-3-methylbenzyl)amino]carbonyl}-3-hydroxy-6-methyl-4-oxo-6,7,9,10-tetrahydro-4H-pyrimido[1,2-d][1,4]oxazepin-10-yl)-N,N',N'-trimethylethanediamide (Compound 4D)

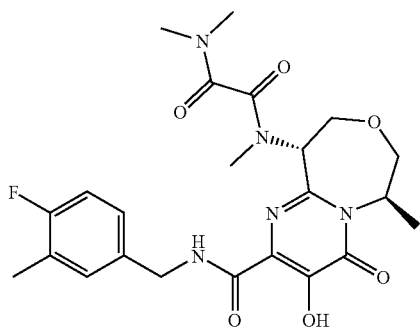

(4D)

The title compounds were prepared using the procedures set forth in Example 4-1 except that (S)-1,2-epoxypropane was used in place of (R)-1,2-epoxypropane in Step 1.

Cis diastereomer (6R,10R): $^1$H NMR (399 MHz, CDCl$_3$): δ 12.6-12.1 (br s, 1H) 9.60 (t, J=5.9 Hz, 1 H); 7.21 (d, J=7.5, Hz, 1 H); 7.20-7.16 (m, 1 H); 6.91 (t, J=9.0 Hz, 1 H); 5.81 (s, 1 H); 4.94 (m, 1 H); 4.51 (d, J=6.4 Hz, 2 H); 4.45 (t, J=10.7 Hz, 1 H); 4.31 (d, J=14.1 Hz, 1 H); 4.15 (dd, J=11.7, 2.4 Hz, 1 H); 4.04 (dd, J=14.1, 5.3 Hz, 1 H); 3.07 (s, 3 H); 3.02 (s, 3 H); 2.85 (s, 3 H); 2.24 (d, J=1.5 Hz, 3 H); 1.62 (d, J=6.8 Hz, 3 H). HR MS: ESI=490.2088 (M+1); calculated 490.2096 (M+1).

Trans diastereomer (6R,10S): $^1$H NMR (appears as a 2:1 mixture of rotational isomers) (399 MHz, CDCl$_3$): δ 9.7 (br s, 1/3 H); 9.54 (br s, 2/3 H); 7.21 (d, J=7.3 Hz, 1 H); 7.19-7.15 (m, 1H); 6.91 (t, J=8.9 Hz, 1 H); 5.80 (br d, J=6.4 Hz 2/3 H) 5.69 (br s, 4/3 H); 4.58-4.36 (m, approximately. 3 H); 4.27 (d, J=11.7 Hz, approximately. 1 H); 4.15 (m, approximately. 1H); 3.78-3.60 (m, 2 H); 3.07 (s, 3 H); 3.02 (s, 3 H); 3.97-2.82 (m, 3 H); 2.24 (d, J=1.8 Hz, 3 H); 1.56 (m, 2 H)

HR MS: ESI=490.2098 (M+1); calculated 490.2096 (M+1).

EXAMPLE 5-1

N-((6S,10S)-6-ethyl-2-{[(4-fluorobenzyl)amino]carbonyl}-3-hydroxy-4-oxo-6,7,9,10-tetrahydro-4-pyrimido[1,2-][1,4]oxazepin-10-yl)-N N'N'-trimethylethanediamide (Compound 5A)

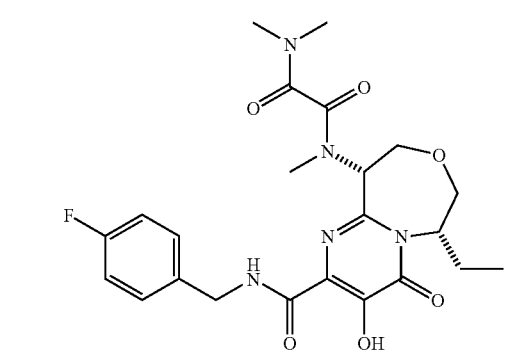

(5A)

Step 1: 2(R)-1-(Allyloxy)butan-2-ol

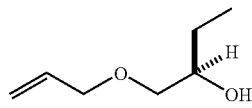

To an oven dried one liter round bottom flask was added sodium hydride (30.5 g, 763 mmol) and DMF (433 mL). The mixture was cooled in an ice bath and allyl alcohol (51.9 mL, 763 mmol) was added in dropwise, keeping the temperature below 6° C. After the addition was completed, the reaction mixture was stirred while being maintained in the ice bath for 15 minutes, and then at room temperature for 45 minutes. The mixture was then cooled again in an ice bath and (R)-1,2-epoxybutane (50 g, 760 mmol) was added slowly over 30 minutes as a DMF (30 mL) solution. The reaction mixture was allowed to warm to room temperature and stirred for 72 hours. The reaction mixture was then cooled and diluted with water (500 mL) and ether (200 mL). The layers were separated and the product was extracted from the aqueous layer twice more with diethyl ether (200 mL). The combined organic extracts were dried over anhydrous sodium sulfate. Concentration gave a yellow oil. The crude product was used in the next step without purification: $^1$H NMR (400 MHz, CDCl$_3$): δ 5.92 (ddt, J=17.2, 10.4, 5.6 Hz, 1 H); 5.28 (dq, J=17.2, 1.6 Hz, 1 H); 5.20 (dq, J=10.4, 1.3 Hz, 1 H); 4.03 (dt, J=5.6, 1.3 Hz, 2 H); 3.76-3.68 (m, 1 H); 3.48 (dd, J=9.5, 3.0

Hz, 1 H); 3.29 (dd, J=9.5, 8.0 Hz, 1 H); 2.34 (d, J=3.3 Hz, 1 H); 1.56-1.41 (m, 2 H); 0.97 (t, J=7.5 Hz, 3 H).

Step 2: 6(R)-6-Ethyl-1,4-dioxan-2-ol

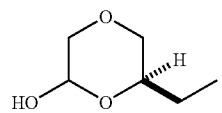

A stream of ozone was dispersed into a cold (initial T=−78° C.) stirred solution of 2(R)-1-(allyloxy)butan-2-ol (50 g, 384 mmol) in methanol (200 mL) until blue color persisted (required 2 hours). The solution was purged for 10 minutes with nitrogen until a clear, colorless solution was obtained. Dimethyl sulfide (45.5 mL, 615 mmol) and triethylamine (30 mL) were added. The stirred mixture was allowed to warm to room temperature over 60 minutes. (A test for peroxide with wet starch-iodide paper was negative.) The mixture was concentrated under reduced pressure at ambient temperature to provide crude title product which was used directly in the next step without purification.

Step 3: tert-Butyl (1-cyano-2-{[(2)-2-hydroxybutyl]oxy}ethyl)methylcarbamate

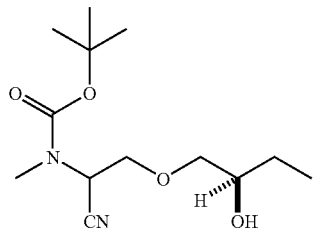 [SMILES: CC[C@@H](O)COCC(C#N)N(C)C(=O)OC(C)(C)C]

To a stirred solution of 6(R)-6-ethyl-1,4-dioxan-2-ol (50 g, 378 mmol) in methanol and water (1:1, 300 mL) was added methylamine hydrochloride (51 g, 757 mmol) and sodium cyanide (28 g, 568 mmol). The solution was stirred for 24 hours. The solution was made basic (pH=9) with saturated sodium carbonate solution (50 mL). The product was extracted into ethyl acetate (3×200 mL). The ethyl acetate layers were combined, washed with brine (100 mL), and dried over anhydrous magnesium sulfate. The solvent was removed under reduced pressure. The residue was dissolved in dichloromethane (300 mL) and to the stirred solution was added di-tert-butyl dicarbonate (83 g, 378 mmol). The solution was stirred at room temperature for 18 hours, then acidified with hydrochloric acid (50 mL, 1M). The organic layer was separated, washed with water (50 mL) and brine solution (50 mL). The organic layer was dried over magnesium sulfate, filtered, and the solvent was removed under reduced pressure. Purification by flash chromatography on silica gel (750 g cartridge) with a 5-50% ethyl acetate in hexane gradient gave the desired product (Rf=0.5, 40% EtOAc/hexane).

$^1$H NMR (400 MHz, CDCl$_3$): δ 5.44-5.37 (m, 1 H); 3.77 (dd, J=10.6, 10.5 Hz, 1 H); 3.76 (dd, J=13.4, 6.6 Hz, 2 H); 3.61-3.53 (m, 1 H); 3.39 (ddd, J=14.1, 9.5, 7.4 Hz, 1 H); 2.96 (s, 3 H); 1.51-1.47 (m, 2 H), 1.48 (s, 9 H); 0.97 (t, J=7.5 Hz, 3H). ES MS=273.3 (M+1).

Step 4: tert-Butyl[(2)-2-amino-1-({[(2R)-2-hydroxybutyl]oxy}methyl)-2-(hydroxyimino)ethyl]-methylcarbamate

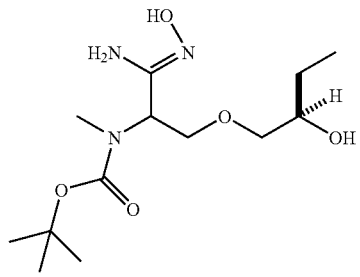 [SMILES: CC[C@@H](O)COCC(/C(N)=N/O)N(C)C(=O)OC(C)(C)C]

To a solution of tert-butyl (1-cyano-2-{[(2)-2-hydroxybutyl]oxy}ethyl)methyl-carbamate (5.1 g, 18.7 mmol) in methanol (80 mL) was added a 50% aqueous solution of hydroxylamine (1.62 mL, 26.4 mmol) and the mixture was stirred at 60° C. for 18 hours. The solution was concentrated under reduced pressure and azeotropically dried with methanol (2×50 mL) to remove traces of hydroxylamine and water. The crude product was used without purification in the next step: ES MS=306.2 (M+1).

Step 5: Dimethyl (2)-2-{[((1)-1-amino-2-[(tert-butoxycarbonyl)(methyl)amino]-3-{[(2R)-2-hydroxybutyl]oxy}propylidene)amino]oxy}but-2-enedioate

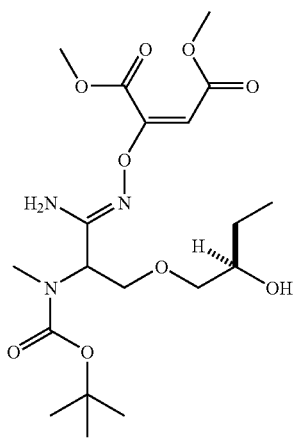 [SMILES: CC[C@@H](O)COCC(/C(N)=N/O/C(=C/C(=O)OC)C(=O)OC)N(C)C(=O)OC(C)(C)C]

To a stirred solution of tert-butyl[(2)-2-amino-1-({[(2R)-2-hydroxybutyl]oxy}methyl)-2-(hydroxyimino)ethyl]-methylcarbamate (5.7 g, 18.7 mmol) in methanol (100 mL) under nitrogen at −20° C. was added dimethyl acetylenedicarboxylate (2.5 mL, 20.6 mmol). The reaction mixture was stirred at −20° C. for 2 hours and then allowed to warm to room temperature with stirring for 18 hours. The solvent was removed under reduced pressure. The crude product was azeotropically dried with toluene (50 mL) and used without purification in the next step: ES MS=448.2 (M+1).

Step 6: Methyl 2-(1-[(tert-butoxycarbonyl)(methyl)amino]-2-{[(2R-)-2-hydroxybutyl]oxy}ethyl)-5,6-dihydroxypyrimidine-4-carboxylate

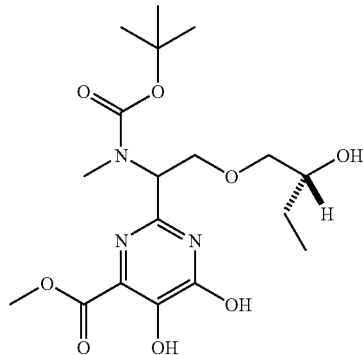 [SMILES: CC[C@@H](O)COCC(c1nc(O)c(O)c(C(=O)OC)n1)N(C)C(=O)OC(C)(C)C]

To a stirred solution of dimethyl (2)-2-{[((1)-1-amino-2-[(tert-butoxycarbonyl)(methyl)amino]-3-{[(2R)-2-hydroxybutyl]oxy}propylidene)amino]oxy}but-2-enedioate (8.4 g, 18.7 mol) in o-xylene (700 mL) under nitrogen was added diisopropylethyl amine (4.9 mL, 28 mmol). The mixture was heated at 120° C. for 24 hours. The solution was cooled and diluted with EtOAc (500 mL), water (100 mL) and hydrochloric acid (30 mL, 1 M). The aqueous layer was separated and extracted with ethyl acetate (2×100 mL.) The organic layers were combined, diluted with 50 mL acetonitrile to dissolve particulate matter, dried over anhydrous sodium sulfate, filtered, and the solvents were removed under reduced pressure. The crude product was dissolved in ether and the product precipitated by addition of hexane. Filtration and drying under reduced pressure gave a red solid (7.4 gm, 95%): ES MS=416.2 (M+1).

Step 7: tert-Butyl (1-(4-{[(4-fluorobenzyl)amino]carbonyl}-5,6-dihydroxypyrimidin-2-yl)-2-{[(2)-2-hydroxybutyl]oxy}ethyl)methylcarbamate

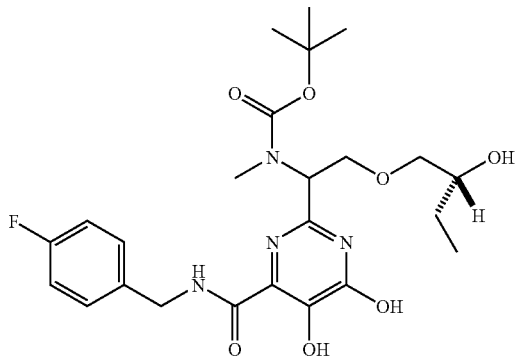 [SMILES: CC[C@@H](O)COCC(c1nc(O)c(O)c(C(=O)NCc2ccc(F)cc2)n1)N(C)C(=O)OC(C)(C)C]

To a stirred solution of methyl 2-(1-[(tert-butoxycarbonyl)(methyl)amino]-2-{[(2R-)-2-hydroxybutyl]oxy}ethyl)-5,6-dihydroxypyrimidine-4-carboxylate (7.4 g, 18 mmol) 2-propanol (160 mL) was added 4-fluorobenzylamine (8.1 mL, 71 mmol). The mixture was heated to 60° C. for 24 hours. The solution was cooled and the solvent was removed under reduced pressure. The crude product was taken up in ethyl acetate (150 mL) and washed with aqueous hydrochloric acid (2×50 mL, 0.5 M) and brine (50 mL). The organic layer was separated, dried with anhydrous sodium sulfate, filtered, and the solvent was removed under reduced pressure. The crude product was used without purification in the next step: ES MS=509.1 (M+1).

Step 8: (6S,10S) and (6S,10R) tert-Butyl((6,10)-6-ethyl-2-{[(4-fluorobenzyl)amino]carbonyl}-3-hydroxy-4-oxo-6,7,9,10-tetrahydro-4-pyrimido[1,2]-[1,4]oxazepin-10-yl)methylcarbamate

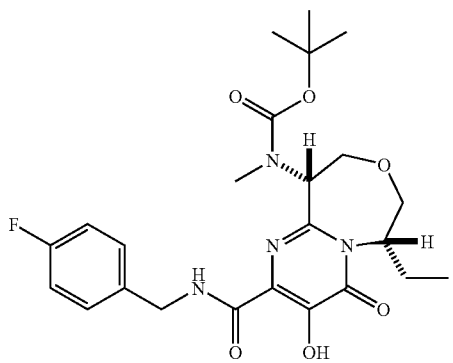

Cis isomer
(6S, 10S)

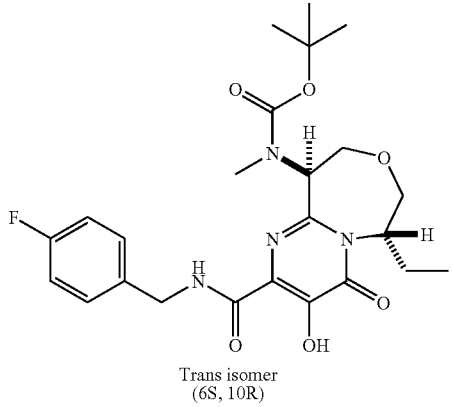

Trans isomer
(6S, 10R)

The tert-butyl (1-(4-{[(4-fluorobenzyl)amino]carbonyl}-5,6-dihydroxypyrimidin-2-yl)-2-{[(2)-2-hydroxybutyl]oxy}ethyl)methylcarbamate (7.7 g, 15 mmol) was dissolved in dry acetonitrile (150 mL) and cooled in ice bath under nitrogen. To the stirred solution was added triethylamine (8.4 mL, 60 mmol) followed by methanesulfonyl chloride (3.9 mL, 50 mmol). The mixture was stirred for 1 hour and then the solvent was removed under reduced pressure. The crude product was dissolved in ethyl acetate (200 mL) and washed with aqueous hydrochloric acid (50 mL, 0.5M), aqueous sodium bicarbonate (50 mL), and brine (50 mL). The organic layer was dried over anhydrous sodium sulfate, filtered, and concentrated. The residue was stirred in toluene (500 mL) which dissolved most of this material. The undissolved solid was filtered, rinsing with toluene (2×100 mL). The toluene solution was concentrated to give the crude trimesylate: ES MS: m/z=743.1 (M+1).

A stirred solution of the trimesylate (9.4 g, 12.6 mmol) in dimethylacetamide (190 mL) was purged with nitrogen gas.

This solution was divided between 10 microwave reaction vessels, each containing potassium carbonate (615 mg, 4.5 mmol). Each reaction vessel was stirred and heated to 140° C. for 7 minutes in a microwave oven. The reaction mixtures of all 10 reaction vessels were combined and diluted with ethyl acetate (400 mL) and water. The organic layer was washed with aqueous hydrochloric acid (2×100 mL, 0.5 M), brine (50 mL), dried over anhydrous sodium sulfate, filtered, and concentrated under reduced pressure. The crude product was suspended in ether (700 mL) and stirred for 18 hours. The black precipitate was removed by filtration. The filtrate solvent was concentrated under reduced pressure and the residue was purified by reverse phase HPLC (C18, Xterra) with a water:acetonitrile containing 0.1% TFA mobile phase gradient (30-75% acetonitrile over 40 minutes, 85 mL/minute). Lyophilization of the fractions containing the first and second eluting products gave the cis and trans diastereomers, respectively, as white amorphous solids: Cis diastereomer (6S,10S) $^1$H NMR (399 MHz, CDCl$_3$): δ 11.80 (br.s, 1 H), 7.80 (s, 1 H); 7.31 (dd, J=8.4, 5.3 Hz, 2 H); 7.04 (t, J=8.4 Hz, 2 H); 5.25 (br. s, 1 H); 4.62-4.54 (m, 3 H); 4.33 (m, 1 H); 4.16 (dd, J=14.1, 5.9 Hz, 1 H); 4.08 (dd, J=12.2, 3.1 Hz, 1 H); 4.02 (d, J=14.8 Hz, 1 H); 2.82-2.75 (m, 3 H); 2.17-1.80 (m, 2 H); 1.27 (m, 9 H); 1.12 (t, J=7.4 Hz, 3 H): ES MS: m/z=491.2 (M+1). Trans diastereomer (6S,10R) $^1$H NMR (400 MHz, CDCl$_3$): δ 11.90 (br.s, 1 H), 7.90-7.60 (m, 1H); 7.33 (m, 2 H); 7.04 (m, 2 H); 5.50-5.30 (m, 2H); 4.55 (m, 2 H); 4.25 (m, 2 H); 3.55 (d, J=13.3 Hz, 2 H); 2.75 (m, 3 H); 2.10-1.85 (m, 2 H); 1.28 (m, 9 H); 0.98 (m, 3 H). ES MS=491.2 (M+1)

Step 9: (6S,10S)-6-Ethyl-(4-fluorobenzyl)-3-hydroxy-10-(methylamino)-4-oxo-6,7,9,10-tetrahydro-4-pyrimido[1,2-][1,4]oxazepine-2-carboxamide hydrochloride

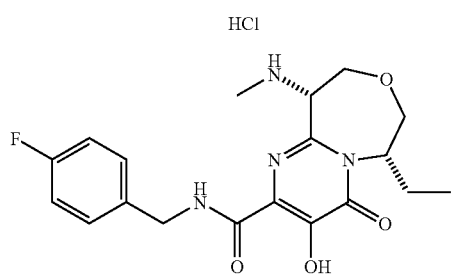 [SMILES: Cl ; CC[C@H]1COC[C@@H](NC)c2nc(C(=O)NCc3ccc(F)cc3)c(O)c(=O)n21]

The (6S,10S) tert-butyl((6,10)-6-ethyl-2-{[(4-fluorobenzyl)amino]carbonyl}-3-hydroxy-4-oxo-6,7,9,10-tetrahydro-4-pyrimido [1,2-][1,4]oxazepin-O-yl)methylcarbamate (1.8 g, 3.67 mmol) was dissolved in HCl-dioxane (50 mL, 4 M). After 3 hours, the solution was concentrated under reduced pressure and then azeotropically dried with methanol and toluene. The crude product was dried under high vacuum and used without purification in the next step: ES MS: m/z=391.2 (M+1)

Step 10: N-((6S,10S)-6-Ethyl-2-{[(4-fluorobenzyl)amino]carbonyl}-3-hydroxy-4-oxo-6,7,9,10-tetrahydro-4-pyrimido[1,2-][1,4]oxazepin-10-yl)-N N' N'-trimethylethanediamide

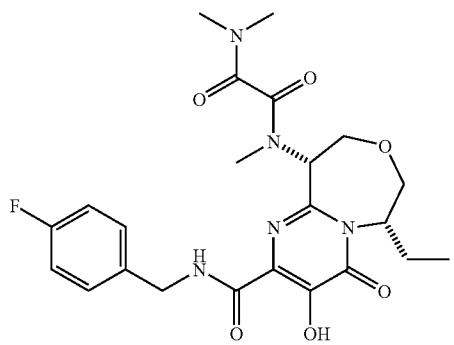 [SMILES: CC[C@H]1COC[C@@H](N(C)C(=O)C(=O)N(C)C)c2nc(C(=O)NCc3ccc(F)cc3)c(O)c(=O)n21]

To a stirred solution of (6S,10S)-6-ethyl-(4-fluorobenzyl)-3-hydroxy-10-(methylamino)-4-oxo-6,7,9,10-tetrahydro-4-pyrimido[1,2-][1,4]oxazepine-2-carboxamide hydrochloride (200 mg, 0.46 mmol), EDC (99 mg, 0.51 mmol) in dry dichloromethane (5 mL) under nitrogen was added HOAT (70 mg, 0.51 mmol), N,N-dimethyloxalamic acid (82 mg, 0.71 mmol) and N-methylmorpholine (155 uL, 1.4 mmol). The reaction was stirred at room temperature for 1 hour, then quenched with 1M HCl (5 mL). The aqueous layer was extracted with dichloromethane (3×20 mL). The organic layers were combined, dried over sodium sulfate, filtered, and concentrated under reduced pressure. The crude product was purified by reverse phase HPLC (C18, Xterra) using a water:acetonitrile containing 0.1% TFA mobile phase gradient (20-70% acetonitrile over 30 minutes, 50 mL/minute). Concentration gave the desired product as an amorphous white solid: $^1$H NMR (399 MHz, CDCl$_3$): δ 11.90 (br.s, 1 H); 9.62 (t, J=6.2 Hz, 1 H); 7.37 (dd, J=8.4, 5.5 Hz, 2 H); 6.98 (d, J=8.6 Hz, 2 H); 5.83 (m, 1 H); 4.63 (m, 1 H); 4.54 (d, J=6.4 Hz, 2 H); 4.43 (t, J=10.4 Hz, 1 H); 4.21 (d, J=3.3 Hz, 2 H); 4.13 (dd, J=11.8, 2.8 Hz, 1 H); 3.07 (s, 3 H); 3.02 (s, 3 H); 2.84 (s, 3 H); 2.07 (m, 1 H); 1.83 (m, 1H); 1.14 (t, J=7.3 Hz, 3 H). HR MS: ESI=490.2119 (M+1); calculated 490.2096 (M+1).

Crystallization of Form I of Compound 5A

Amorphous Compound 5A, which can be obtained as described above, dissolved in dichloromethane was solvent switched to isopropanol to provide a mixture containing about 150-200 mg of Compound 5A per mL of isopropanol. The mixture was then heated to 60° C. to form a brown homogeneous solution. The hot solution was then allowed to cool to room temperature during which time the solution forms a slurry. The slurry was filtered, the resulting crystals were washed first with a mixture of isopropanol and n-heptane (1:1), then with n-heptane, and dried under vacuum to provide Form I crystals of Compound 5A.

Figure 3:
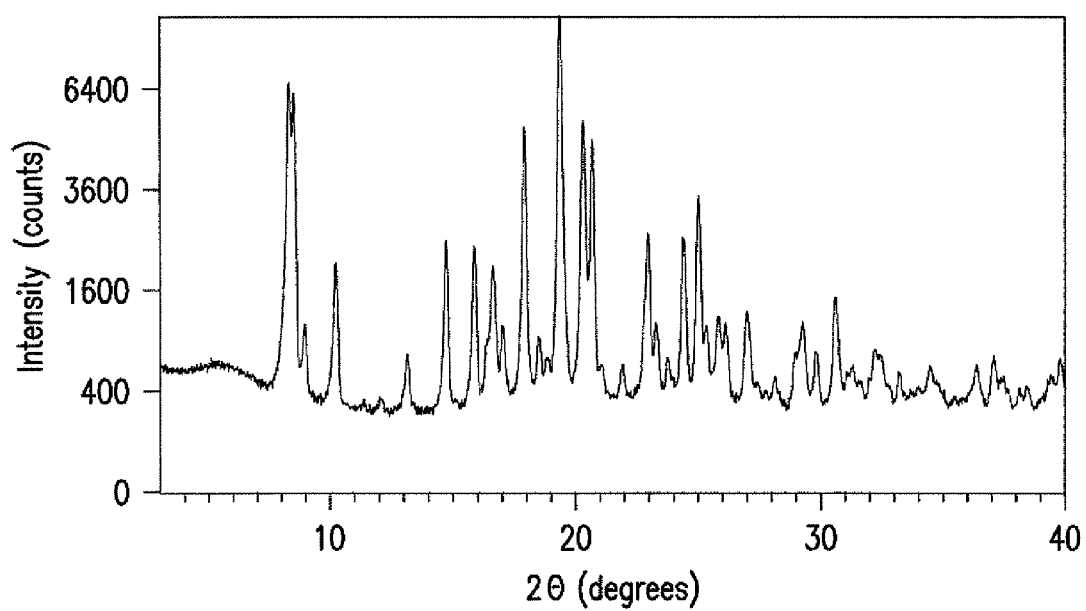
FIG. 3 is the X-ray powder diffraction pattern for crystalline Form I of Compound 5A described in Example 5-1.

Characterization. An XRPD pattern of Form I crystalline Compound 5A was generated on a Philips Analytical X'Pert PRO X-ray Diffraction System with PW3050/60 console using a continuous scan from 2 to 40 degrees 2θ. Copper K$_{α1}$ and K$_{α2}$ radiation was used as the source. The experiment was run under ambient conditions. The diffraction peak positions were referenced by silicon which has a 2Θ value of 28.443 degree. The XRPD pattern is shown in FIG. 3. 2θ values and the corresponding d-spacings in the XRPD pattern include the following:

TABLE 5A-1

| 2θ (degrees) | d-spacing (Å) |
|---|---|
| 8.4 | 10.5 |
| 8.6 | 10.3 |
| 10.4 | 8.5 |
| 14.8 | 6.0 |
| 16.0 | 5.5 |
| 16.8 | 5.3 |
| 18.0 | 4.9 |
| 19.5 | 4.5 |
| 20.5 | 4.3 |
| 20.8 | 4.3 |
| 23.0 | 3.9 |
| 24.5 | 3.6 |
| 25.2 | 3.5 |
| 26.1 | 3.4 |
| 27.2 | 3.3 |

The crystalline Form I of Compound 5A was analyzed with a TA Instruments DSC 2920 differential scanning calorimeter at a heating rate of 10° C./minute from 25° C. to 350° C. in a closed aluminum pan in a nitrogen atmosphere. The DSC curve showed an endotherm with an onset temperature of 142° C. and a peak temperature of 149° C. The enthalpy change was 52 J/g. The endotherm is believed to be due to melting.

TGA of the crystalline compound was performed with a Perkin Elmer TGA 7 under nitrogen at a heating rate of 10° C./minute from 25° C. to 300° C. The TG curve showed a weight loss of 0.3 wt. % up to 80° C. and a second weight loss of 0.4 wt. % up to 174° C. due to isopropanol loss at melt.

The DSC and TGA results indicated that crystalline Form I is anhydrous.

Crystallization of Form II of Compound 5A

Amorphous Compound 5A obtained as described above was redissolved in methylene chloride and partitioned with water adjusted to pH 3 with NaHCO₃. The aqueous layer was extracted 3 times with methylene chloride. The combined organics were dried over Na₂SO₄, filtered, and concentrated under reduced pressure. The solid obtained was dissolved in hot isopropanol at a concentration of 70 mg/mL. The hot solution was allowed to slowly cool to ambient temperature during which time fine needles crystallized from solution. The cooled crystallization mixture was aged overnight and the crystalline compound was isolated by filtration, washed with isopropanol, and dried under vacuum.

Figure 4:
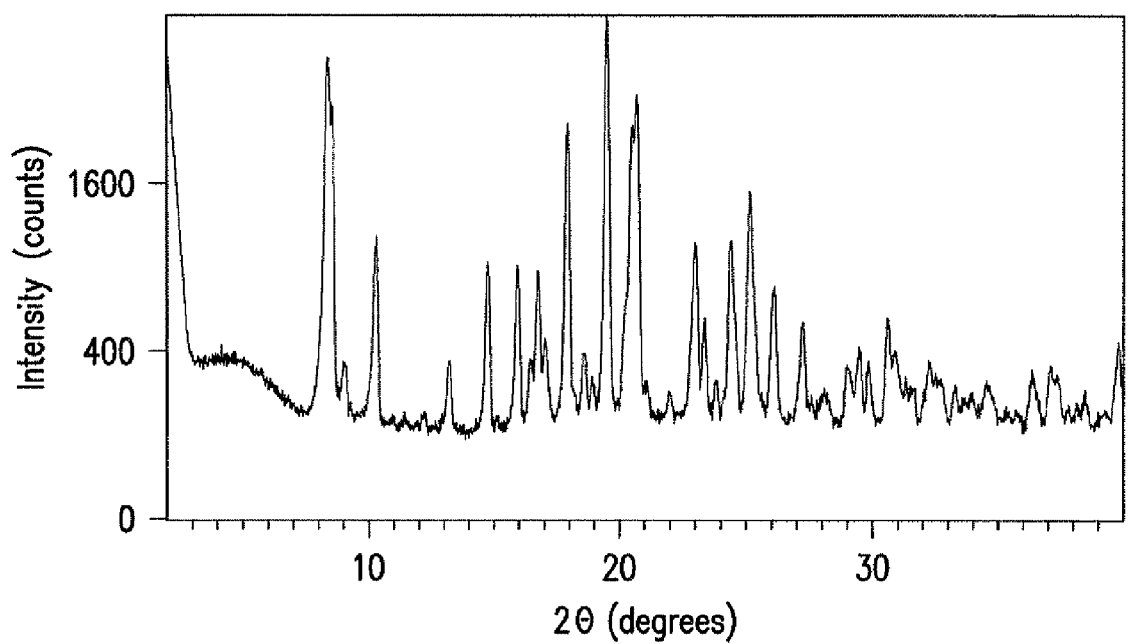
FIG. 4 is the X-ray powder diffraction pattern for crystalline Form II of Compound 5A described in Example 5-1.

Characterization. An XRPD pattern of Form II crystalline Compound SA was generated on a Philips Analytical X'Pert PRO X-ray Diffraction System with PW3050/60 console using a continuous scan from 2 to 40 degrees 2θ. Copper $K_{\alpha 1}$ and $K_{\alpha 2}$ radiation was used as the source. The experiment was run under ambient conditions. The diffraction peak positions were referenced by silicon which has a 2θ value of 28.443 degree. The XRPD pattern is shown in FIG. 4. 2θ values and the corresponding d-spacings in the XRPD pattern include the following:

TABLE 5A-2

| 2θ (degrees) | d-spacing (Å) |
|---|---|
| 8.4 | 10.5 |
| 8.6 | 10.3 |
| 10.3 | 8.6 |

TABLE 5A-2-continued

| 2θ (degrees) | d-spacing (Å) |
|---|---|
| 14.8 | 6.0 |
| 16.0 | 5.6 |
| 16.7 | 5.3 |
| 18.0 | 4.9 |
| 19.4 | 4.6 |
| 20.4 | 4.3 |
| 20.8 | 4.3 |
| 23.0 | 3.9 |
| 24.4 | 3.6 |
| 25.1 | 3.5 |
| 25.9 | 3.4 |
| 26.2 | 3.4 |
| 27.1 | 3.3 |

The crystalline Form II was analyzed with a TA Instruments DSC 2920 differential scanning calorimeter at a heating rate of 10° C./minute from 25° C. to 250° C. in a closed aluminum pan in a nitrogen atmosphere. The DSC curve showed an endotherm with an onset temperature of 149° C. and a peak temperature of 155° C. The enthalpy change was 73 J/g. The endotherm is believed to be due to melting.

TGA of the crystalline compound was performed with a Perkin Elmer TGA 7 under nitrogen at a heating rate of 10° C./minute from 25° C. to 300° C. The TG curve showed a weight loss of 0.1 wt. % up to 126° C. and a second weight loss of 0.1 wt. % up to 171° C. due to isopropanol loss at melt.

The DSC and TGA results indicated that crystalline Form II is anhydrous.

EXAMPLE 5-2

N-((6S,10R)-6-ethyl-2-{[(4-fluorobenzyl)amino]carbonyl)}-3-hydroxy-4-oxo-6,7,9,10-tetrahydro-4H-pyrimido[1,2-d][1,4]oxazepin-10-yl)-N N' N'-trimethylethanediamide (Compound 5B)

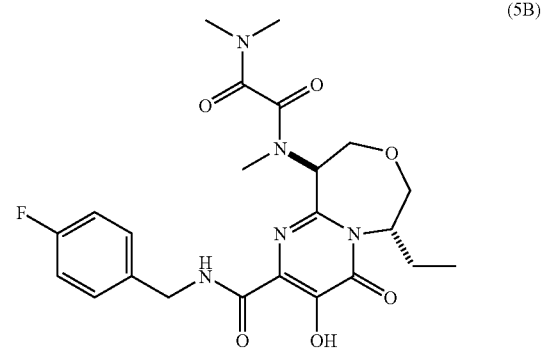 [SMILES: CC[C@H]1COC[C@H](N(C)C(=O)C(=O)N(C)C)c2nc(C(=O)NCc3ccc(F)cc3)c(O)c(=O)n21]

(5B)

Following the procedure as described in Example 5-1, Steps 9 and 10 using the (6S,10R) tert-butyl((6,10)-6-ethyl-2-{[(4-fluorobenzyl)amino]carbonyl}-3-hydroxy-4-oxo-6,7,9,10-tetrahydro-4-pyrimido[1,2-][1,4]oxazepin-10-yl)methylcarbamate isomer from Example 5-1, Step 8 gave N-((6S,10R)-6-ethyl-2-{[(4-fluorobenzyl)amino]carbonyl}-3-hydroxy-4-oxo-6,7,9,10-tetrahydro-4H-pyrimido[1,2-d][1,4]oxazepin-10-yl)-N N'N'-trimethylethanediamide: ¹H NMR (399 MHz, CDCl₃): δ 11.90 (br. s, 1 H); 9.82-9.55 (m, 1 H); 7.38 (dd, J=8.4, 5.5 Hz, 2 H); 6.98 (t, J=8.7 Hz, 2 H); 5.82-5.43 (m, 2 H); 4.62-4.20 (m, 4 H); 3.78-3.52 (m, 2 H);

3.06 (s, 3 H); 3.01 (s, 3 H); 2.87 (m, 3 H); 2.13-1.80 (m, 2 H); 0.99 (t, J=7.5 Hz, 3 H). HR MS: ESI=490.2119 (M+1); calculated 490.2096 (M+1).

EXAMPLE 5-2A

Alternative Procedure for the Preparation of Compounds 5A and 5B

Crude product obtained in Step 8 of Example 5-1 was not separated into individual cis and trans diastereomers, but was instead carried through Steps 9 and 10 as described in Example 5-1 as a mixture of diastereomers. In Step 9, the mixture was treated with 4N HCl in dioxane as previously described. Upon completion of the reaction as assessed by LC-MS, ether was added which caused precipitation of a brown solid. This solid was collected by filtration and stirred in 2:1 MeOH-water. The undissolved tan solid was collected by filtration and dried under vacuum to provide a 3:2 mixture of the trans:cis diastereomers. This solid was then coupled with N,N-dimethyloxamic acid using the procedure in Step 10. The product mixture was separated on a ChiralPak AD column using ethanol with 0.1% TFA as the mobile phase. The first eluting peak was the trans diastereomer (Compound 5B) and the second eluting peak was the cis diastereomer (Compound 5A).

EXAMPLE 5-3

N-((6R,10R)-6-ethyl-2-{[(4-fluorobenzyl)amino]carbonyl}-3-hydroxy-4-oxo-6,7,9,10-tetrahydro-4H-pyrimido[1,2-d][1,4]oxazepin-10-yl)-N N'N'-trimethylethanediamide (Compound 5C)

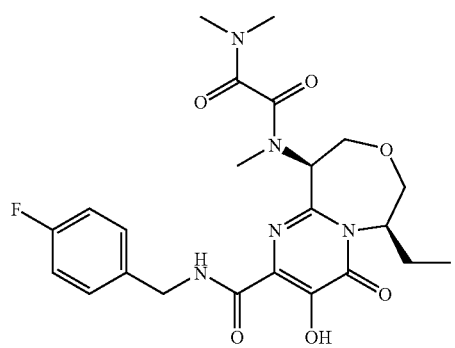

(5C)

The (6R,10R) isomer was synthesized by starting with (S)-1,2-epoxybutane utilizing the procedures as described for Example 5-1. The corresponding cis intermediate (6R,10R) from Step 8 of Example 5-1 was further elaborated as in Steps 9 and 10 and gave the desired product. HR MS: ESI=490.2107 (M+1); calculated 490.2096 (M+1).

EXAMPLE 5-4

N-((6R,10S)-6-ethyl-2-{[(4-fluorobenzyl)amino]carbonyl}-3-hydroxy-4-oxo-6,7,9,10-tetrahydro-4H-pyrimido[1,2-d][1,4]oxazepin-10-yl)-N N' N'-trimethylethanediamide (Compound 5D)

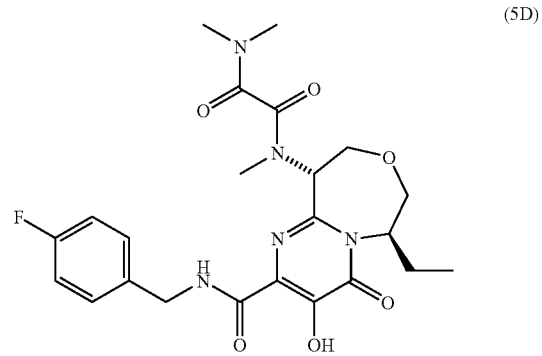 [SMILES: CC[C@@H]1COC[C@@H](N(C)C(=O)C(=O)N(C)C)c2nc(C(=O)NCc3ccc(F)cc3)c(O)c(=O)n21]

(5D)

The (6R,10S) isomer was synthesized by starting with (S)-1,2-epoxybutane utilizing the procedure as described for Example 5-1. The corresponding trans intermediate (6R,10S) from Step 8 of Example 5-1 was further elaborated as in Steps 9 and 10 and gave the desired product. HR MS: ESI=490.2112 (M+1); calculated 490.2096 (M+1).

EXAMPLE 6-1

N-ethyl-N-((7S,10R)-2-{[(4-fluorobenzyl)amino]carbonyl}-3-hydroxy-7-methoxy-4-oxo-4,6,7,8,9,10-hexahydropyrimido[1,2-a]azepin-10-yl)-N',N'-dimethylethanediamide (Compound 6A)

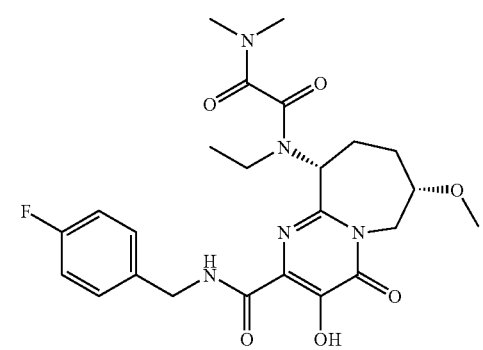 [SMILES: CCN(C(=O)C(=O)N(C)C)[C@@H]1CC[C@H](OC)Cn2c1nc(C(=O)NCc1ccc(F)cc1)c(O)c2=O]

Step 1: (2S)-1-(benzyloxy)hex-5-en-2-ol

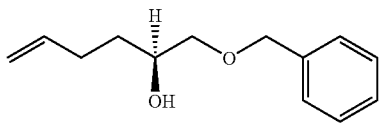

To a solution of (2S)-2-[(benzyloxy)methyl]oxirane (50 g, 305 mmol) in THF (1500 mL) at 0° C. was added copper bromide (4.37 g, 30.5 mmol). The resulting solution was stirred at 0° C. for 10 minutes and allylmagnesium bromide (1M in THF, 335 mL, 335 mmol) was added. The reaction was stirred for 2 hours at 0° C. and then quenched at 0° C. with saturated aqueous $NH_4Cl$ and diluted with DCM. The mixture was stirred at ambient temperature for 20 minutes and filtered to remove insoluble material. The filtrate was extracted with DCM (3×) and the combined organic phases were dried over $MgSO_4$, filtered, and concentrated in vacuo. Flash column chromatography eluted with 10 to 40% EtOAc/hexanes provided (2S)-1-(benzyloxy)hex-5-en-2-ol. $^1$H NMR (400 MHz, $CDCl_2$): δ 7.37-7.26 (m, 5 H); 5.88-5.74 (m, 1 H); 5.08-4.93 (m, 2 H); 4.54 (s, 2 H); 3.83 (s, 2 H); 3.53-3.44 (m, 1 H); 3.33 (dd, J=9.1, 8.2 Hz, 1 H); 2.49 (s, 1 H); 2.30-2.00 (m, 2 H); 1.64-1.39 (m, 2 H).

Step 2: ({[(2S)-2-methoxyhex-5-en-1-yl]oxy}methyl)benzene

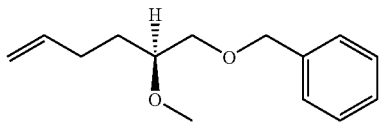

To a stirred solution of (2S)-1-(benzyloxy)hex-5-en-2-ol (71 g, 344 mmol) in DMF (500 mL) at 0° C. was added sodium hydride (16.52 g, 413 mmol) in portions over 30 minutes. The resulting suspension was stirred at 0° C. for 15 minutes and then at ambient temperature for 15 minutes. The mixture was cooled to 0° C. and methyl iodide (43 mL, 688 mmol) was added. The reaction mixture was stirred at ambient temperature overnight. The mixture was cooled to 0° C. and quenched with water. The mixture was extracted with DCM (3×). The organic layers were combined and washed with water (2×), dried over $MgSO_4$, filtered, and concentrated in vacuo. The crude residue was used in the next reaction without further purification. $^1$H NMR (400 MHz, $CDCl_2$): δ 7.34 (s, 5 H); 5.85-5.74 (m, 1 H); 5.06-4.89 (m, 2 H); 4.55 (s, 2 H); 3.49 (d, J=4.7 Hz, 2 H); 3.41 (s, 3 H); 3.37 (m, 1 H); 2.16-2.04 (m, 2 H).

Step 3: (4S)-5-(benzyloxy)-4-methoxypentanal

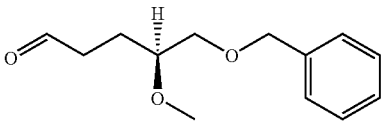

A stream of ozone was dispersed into a cold (initial T=−78° C.) stirred solution of ({[(2S)-2-methoxyhex-5-en-1-yl]oxy}methyl)benzene (40 g, 182 mmol) in dichloromethane (1800 mL) until a blue color persisted. The solution was purged with nitrogen until a clear, colorless solution was obtained. Dimethyl sulfide (67.2 mL, 908 mmol) and triethylamine (76 mL, 545 mmol) were added. The stirred mixture was allowed to warm to room temperature over 60 minutes. (A test for peroxide with wet starch-iodide paper was negative.) The mixture was concentrated under reduced pressure to provide the crude title product which was used in the next step without purification.

Step 4: tert-butyl[(4S)-5-(benzyloxy)-1-cyano-4-methoxypentyl]ethylcarbamate

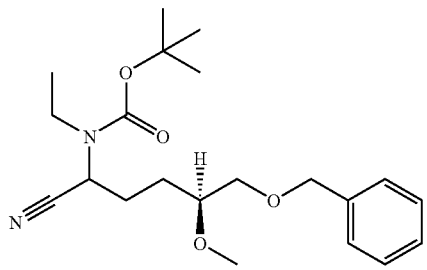

To a solution of (4S)-5-(benzyloxy)-4-methoxypentanal (109 g, 490 mmol) in dioxane (500 mL) at room temperature was added $EtNH_2.HCl$ (60 g, 736 mmol), NaCN (36 g, 736 mmol), and $H_2O$ (500 mL). The reaction mixture was stirred for 2 days, then diluted with saturated aqueous $NaHCO_3$ and extracted with EtOAc (3×). The combined organic layers were dried over $Na_2SO_4$, filtered, and concentrated in vacuo. To a solution of the crude residue in EtOAc (500 mL) was added $(Boc)_2O$ (107 g, 492 mmol). The resulting mixture was stirred at 40° C. for 2 days. The reaction mixture was cooled to ambient temperature, diluted water, and extracted with EtOAc (3×). The combined organic layers were dried over $Na_2SO_4$, filtered, and concentrated in vacuo. Flash column chromatography eluted with 10 to 40% EtOAc in hexanes provided tert-butyl[(4S)-5-(benzyloxy)-1-cyano-4-methoxypentyl]ethylcarbamate. LC-MS: 377.4 (M+1).

Step 5: tert-butyl{(4S)-5-(benzyloxy)-1-[(hydroxyamino)(imino)methyl]-4-methoxypentyl}ethylcarbamate

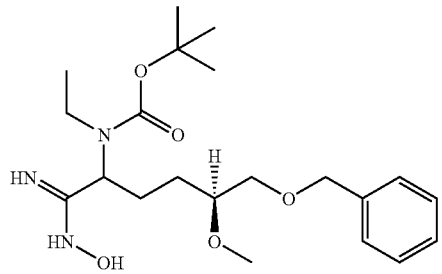

To a solution of tert-butyl[(4S)-5-(benzyloxy)-1-cyano-4-methoxypentyl]ethylcarbamate (74 g, 197 mmol) in EtOH (1000 mL) was added TEA (54.8 mL, 393 mmol) and NH₂OH (50% in water, 14.45 mL, 236 mmol). The resulting solution was stirred at 40° C. overnight and then concentrated in vacuo. The residue was dissolved in MeOH and the solvent was removed under reduced pressure (3×) to remove water. The crude residue was used in the next reaction without further purification. LC-MS: 410.5 (M+1).

Step 6: methyl 2-{(4S)-5-(benzyloxy)-1-[(tert-butoxycarbonyl)(ethyl)amino]-4-methoxypentyl}-5-hydroxy-6-oxo-1,6-dihydropyrimidine-4-carboxylate

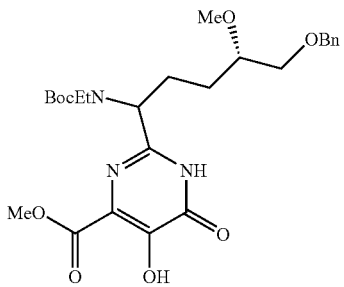

To a solution of tert-butyl{(4S)-5-(benzyloxy)-1-[(hydroxyamino)(imino)methyl]-4-methoxypentyl}ethylcarbamate (72.6 g, 177 mmol) in MeOH (1773 ml) at 0° C. was added dimethyl acetylene dicarboxylate (26.3 mL, 213 mmol). The reaction mixture was stirred at ambient temperature overnight and then concentrated in vacuo. The residue was dissolved in toluene and concentrated in vacuo (3×) to remove MeOH. The crude product was used in the next reaction without purification. LC-MS: 553.5 (M+1).

A solution of the crude material from the previous step (104 g, 189 mmol) in o-xylene (500 mL) was heated to reflux for 11 hours, then cooled and concentrated in vacuo. The crude residue was used in the next step without further purification. LC-MS: 520.5 (M+1).

Step 7: methyl 2-{(4S)-1-[(tert-butoxycarbonyl)(ethyl)amino]-5-hydroxy-4-methoxypentyl}-5-hydroxy-6-oxo-1,6-dihydropyrimidine-4-carboxylate

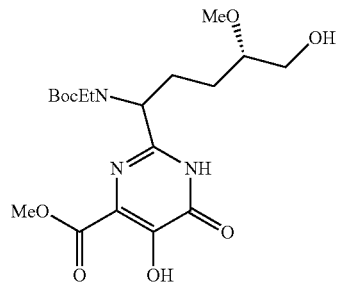

To a solution of methyl 2-{(4S)-5-(benzyloxy)-1-[(tert-butoxycarbonyl)(ethyl)amino]-4-methoxypentyl}-5-hydroxy-6-oxo-1,6-dihydropyrimidine-4-carboxylate (13 g, 25.02 mmol) in EtOAc (30 mL) and MeOH (30 mL) was added acetic acid (20 mL) and palladium on carbon (Degussa, 10% by mass, 13 g, 122 mmol). The reaction mixture was shaken on a Parr apparatus under hydrogen gas (50 psi) for 4 days and then filtrated through a pad of celite. The filter cake was washed with MeOH. The filtrate was concentrated in vacuo. The crude residue was used in the next reaction without further purification. LC-MS: 429.89 (M+1).

Step 8: tert-butyl ethyl[(4S)-1-(4-{[(4-fluorobenzyl)amino]carbonyl}-5-hydroxy-6-oxo-1,6-dihydropyrimidin-2-yl)-5-hydroxy-4-methoxypentyl]carbamate

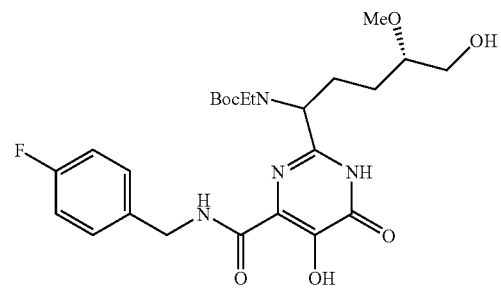

To a solution of methyl 2-{(4S)-1-[(tert-butoxycarbonyl)(ethyl)amino]-5-hydroxy-4-methoxypentyl}-5-hydroxy-6-oxo-1,6-dihydropyrimidine-4-carboxylate (48 g, 112 mmol) in MeOH (1118 mL) was added 4-fluoro-benzylamine (28 g, 224 mmol) and triethylamine (31.2 mL, 224 mmol). The resulting mixture was sealed and heated at 80° C. overnight. The reaction mixture was cooled to ambient temperature, diluted with 10% citric acid (~100 mL), and extracted with DCM (3×). The combined organic layers were dried over Na₂SO₄, filtered, and concentrated in vacuo. The crude residue was dissolved in acetonitrile and concentrated under reduced pressure (3×) to remove MeOH. The residue was dried under high vacuum for 2 days and used in the next reaction without purification. LC-MS: 523.5 (M+1).

Step 9: 2-{(4S)-1-[(tert-butoxycarbonyl)(ethyl)amino]-4-methoxy-5-[(methylsulfonyl)oxy]pentyl}-6-{[(4-fluorobenzyl)amino]carbonyl}pyrimidine-4,5-diyl dimethanesulfonate

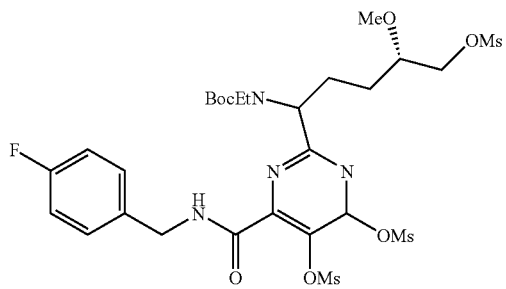

To a stirred solution of tert-butyl ethyl[(4S)-1-(4-{[(4-fluorobenzyl)amino]carbonyl}-5-hydroxy-6-oxo-1,6-dihydropyrimidin-2-yl)-5-hydroxy-4-methoxypentyl]carbamate (30 g, 57.4 mmol) in AcCN (500 mL) at 0° C. was added TEA (48 mL, 344 mmol) followed by a dropwise addition of a solution of MsCl (22.37 mL, 287 mmol) in DCM (15 mL). The resulting mixture was stirred at 0° C. for 30 minutes, then diluted with H₂O (~100 mL) and extracted with EtOAc (3×). The combined organic layers were dried over Na₂SO₄, filtered, and concentrated in vacuo. The crude residue was used in the next step without further purification. LC-MS: 757.5 (M+1).

Step 10: (7S)-10-[(tert-butoxycarbonyl)(ethyl)amino]-2-{[(4-fluorobenzyl)amino]carbonyl}-7-methoxy-4-oxo-4,6,7,8,9,10-hexahydropyrimido[1,2-a]azepin-3-yl methanesulfonate

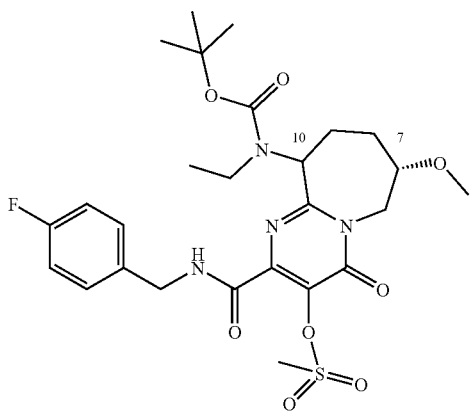 [SMILES: CCN(C(=O)OC(C)(C)C)C1CC[C@H](OC)Cn2c1nc(C(=O)NCc1ccc(F)cc1)c(OS(C)(=O)=O)c2=O]

To a solution of the trismesylate from the previous step (21.8 g, 28.8 mmol) in DMF (288 mL) was added Cs₂CO₃ (28.2 g, 86 mmol). The stirred reaction mixture was heated to 100° C. for 1 hour, then cooled to 0° C., and MsCl (6.73 mL, 86 mmol) was added and the mixture was stirred at 0° C. for 20 minutes. The mixture was diluted with DCM and insoluble material was removed by filtration. The filtrate was concentrated in vacuo. The residue was diluted with water and extracted with DCM (3×). The organic layers were combined, dried over Na₂SO₄, filtered, and concentrated in vacuo. Flash column chromatography eluted with 30 to 70% EtOAc in hexanes.

First eluting peak: was the 7,10-trans isomer: (7S,10S)-10-[(tert-butoxycarbonyl)(ethyl)amino]-2-{[(4-fluorobenzyl)amino]carbonyl}-7-methoxy-4-oxo-4,6,7,8,9,10-hexahydropyrimido[1,2-a]azepin-3-yl methanesulfonate (1.5 g), ¹H NMR (599 MHz, DMSO, 50° C.): a 8.34 (t, J=6.1 Hz, 1 H); 7.35 (dd, J=8.3, 5.5 Hz, 2 H); 7.13 (t, J=8.7 Hz, 2 H); 5.17 (d, J=10.0 Hz, 1 H); 4.96 (d, J=14.0 Hz, 1 H); 4.50-4.35 (m, 2 H); 3.72-3.61 (m, 1 H); 3.49 (s, 3 H); 3.60-3.10 (m, 1 H); 3.22 (s, 3 H); 3.19-3.07 (m, 2 H); 2.09 (d, J=11.3 Hz, 2 H); 2.02-1.93 (m, 1 H); 1.91-1.82 (m, 1 H); 1.27 (s, 9 H); 1.13-1.04 (m, 3 H).

Second eluting peak was the 7,10-cis isomer: (7S,10R)-10-[(tert-butoxycarbonyl)(ethyl)amino]-2-{[(4-fluorobenzyl)amino]carbonyl}-7-methoxy-4-oxo-4,6,7,8,9,10-hexahydropyrimido[1,2-a]azepin-3-yl methanesulfonate (935 mg). ¹H NMR (599 MHz, DMSO, 50° C.): δ 8.44 (t, J=6.1 Hz, 1 H); 7.35-7.29 (m, 2 H); 7.13-7.04 (m, 2 H); 5.23 (dd, J=15.0, 5.7 Hz, 1 H); 4.46-4.39 (m, 1 H); 4.35 (dd, J=15.1, 5.9 Hz, 1 H); 3.79 (d, J=14.9 Hz, 1 H); 3.70-3.63 (m, 1 H); 3.43 (s, 3 H); 3.33-3.28 (m, 1 H); 3.18 (s, 3 H); 3.13-3.08 (m, 1 H); 1.98-1.85 (m, 3 H); 1.23 (s, 9 H); 1.10-1.04 (m, 3 H).

Step 11: (7S,10R)-10-(ethylamino)-2-{[(4-fluorobenzyl)amino]carbonyl}-7-methoxy-4-oxo-4,6,7,8,9,10-hexahydropyrimido[1,2-a]azepin-3-yl methanesulfonate

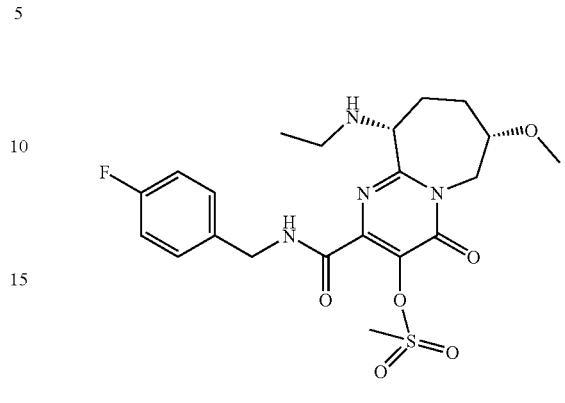

Into a stirred solution of the second eluting component from the previous step, (7S,10R)-10-[(tert-butoxycarbonyl)(ethyl)amino]-2-{[(4-fluorobenzyl)amino]carbonyl}-7-methoxy-4-oxo-4,6,7,8,9,10-hexahydropyrimido [1,2-a]azepin-3-yl methanesulfonate, (9 g, 15.45 mmol) in EtOAc (154 mL) at 0° C. was bubbled HCl (g) for 5 minutes. The reaction mixture was stirred at room temperature for 10 minutes and concentrated in vacuo. The residue was diluted with saturated aqueous NaHCO₃ and extracted with DCM (3×). The combined organic layers were dried over Na₂SO₄, filtered, and concentrated in vacuo. Flash column chromatography eluted with 0 to 7% MeOH in DCM provided (7S,1R)-10-(ethylamino)-2-{[(4-fluorobenzyl)amino]carbonyl}-7-methoxy-4-oxo-4,6,7,8,9,10-hexahydropyrimido [1,2-a]azepin-3-yl methanesulfonate. LC-MS: 483.4 (M+1). ¹H NMR (599 MHz, CDCl₃): δ 7.84 (s, 1 H); 7.32 (dd, J=13.0, 6.9 Hz, 2 H); 7.03 (t, J=8.6 Hz, 2 H); 5.26 (dd, J=14.3, 6.9 Hz, 1 H); 4.62 (dd, J=14.9, 6.3 Hz, 1 H); 4.52 (dd, J=14.9, 5.6 Hz, 1 H); 4.00 (d, J=14.3 Hz, 1 H); 3.81 (d, J=8.1 Hz, 1 H); 3.54 (s, 3H); 3.46 (d, J=7.8 Hz, 1 H); 3.35 (s, 3 H); 2.59 (q, J=7.1 Hz, 2 H); 2.11-2.03 (m, 1 H); 1.95-1.83 (m, 3H); 1.04 (t, J=7.1 Hz, 3 H).

Step 12: (7S,10R)-10-[[(dimethylamino)(oxo)acetyl](ethyl)amino]-2-{[(4-fluorobenzyl)amino]carbonyl}-7-methoxy-4-oxo-4,6,7,8,9,10-hexahydropyrimido[1,2-a]azepin-3-yl methanesulfonate

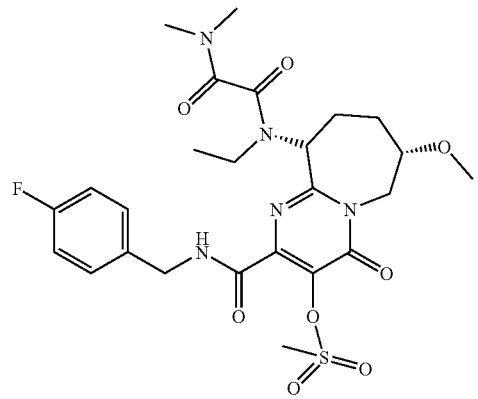

To a solution of the (7S,10R)-10-(ethylamino)-2-{[(4-fluorobenzyl)amino]carbonyl}-7-methoxy-4-oxo-4,6,7,8,9, 10-hexahydropyrimido[1,2-a]azepin-3-yl methanesulfonate (4.8 g, 9.99 mmol) in DCM (100 mL) at room temperature was added TEA (8.35 mL, 59.9 mmol), N,N-dimethyloxamic acid (2.34 g, 19.98 mmol), EDC (5.74 g, 30 mmol), and HOAt (4.62 g, 30 mmol). The resulting mixture was stirred at room temperature overnight, then diluted with $H_2O$ and extracted with DCM (3×). The combined organic layers were dried over $Na_2SO_4$, filtered, and concentrated in vacuo. To a solution of crude material (8 g, 15.89 mmol) in ACN (159 mL) at 0° C. was added TEA (6.64 mL, 47.7 mmol) and MsCl (3.64 g, 31.8 mmol) dropwise. The reaction mixture was stirred at 0° C. for 20 min, then diluted with water and extracted with EtOAc (3×). The combined organic extracts were concentrated in vacuo and the residue was purified by flash column chromatography eluted with 0 to 7% MeOH in DCM to provide (7S,10R)-10-[[(dimethylamino)(oxo)acetyl](ethyl)amino]-2-{([(4-fluorobenzyl)amino]carbonyl}-7-methoxy-4-oxo-4, 6,7,8,9,10-hexahydropyrimido [1,2-a]azepin-3-yl methanesulfonate, LC-MS: 582.5 (M+1).

Step 13: N-ethyl-N-((7S,10R)-2-{[(4-fluorobenzyl)amino]carbonyl}-3-hydroxy-7-methoxy-4-oxo-4,6,7,8,9,10-hexahydropyrimido[1,2-a]azepin-10-yl)-N', N'-dimethylethanediamide (Compound 6A)

To a stirred solution of (7S,10R)-10-[[(dimethylamino)(oxo)acetyl](ethyl)amino]-2-{[(4-fluorobenzyl)amino]carbonyl}-7-methoxy-4-oxo-4,6,7,8,9,10-hexahydropyrimido [1,2-a]azepin-3-yl methanesulfonate (1 g, 1.72 mmol) in 2-propanol (17 mL) was added 2M NaOH (2.58 mL, 5.16 mmol). The resulting mixture was stirred at ambient temperature for 30 minutes, quenched with HCl (1M, 5.16 mL, 5.16 mmol), and extracted with EtOAc (3×). Three additional reactions on the same scale were performed in parallel. The combined organic layers from all four reactions were dried over $Na_2SO_4$, filtered, and concentrated in vacuo. The residue was purified by reverse phase HPLC (C18 Sunfire column) using a water/acetonitrile mobile phase gradient containing 0.5% TFA or by precipitation from water to provide N-ethyl-N-((7S,10R)-2-{[(4-fluorobenzyl)amino]carbonyl}-3-hydroxy-7-methoxy-4-oxo-4,6,7,8,9,10-hexahydropyrimido [1,2-a]azepin-10-yl)-N',N'-dimethylethanediamide. LC-MS: 504.5 (M+1).
$^1$H NMR (599 MHz, DMSO, 50° C.): δ 11.89 (s, 1 H); 9.45 (s, 1 H); 7.37-7.30 (m, 2 H); 7.14-7.08 (m, 2 H); 5.22 (dd, J=15.0, 5.4 Hz, 1 H); 4.93 (bs, 1 H); 4.50-4.42 (m, 2 H); 3.71-3.66 (m, 2 H); 2.92 (s, 3 H); 2.88 (s, 3 H); 2.05-1.99 (m, 1 H); 1.97-1.86 (m, 2 H); 1.08 (t, J=7.1 Hz, 3 H). LC-MS: HRMS: calculated: 504.2253, found: 504.2273.

Recrystallization of Compound 6A

Residual oily material obtained by concentrating the organic layers in the manner described in Step 13 just above (i.e., prior to purification via reverse phase HPLC) was dissolved in the minimal amount of warm anhydrous methanol. The resultant solution was placed in the freezer held at −10° C. for several days, and then allowed to warm slowly to ambient temperature. The fine crystalline needles obtained thereby were isolated by filtration, washed with anhydrous methanol, and dried under vacuum.

Figure 5:
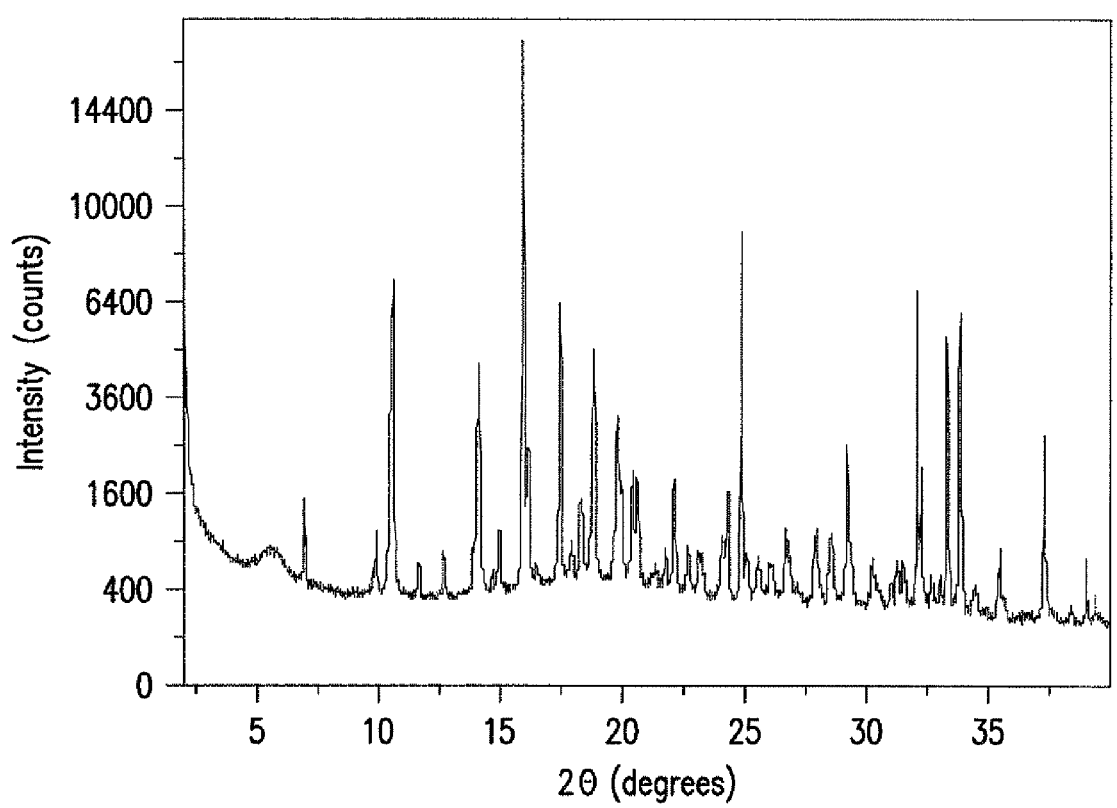
FIG. 5 is the X-ray powder diffraction pattern for the crystalline form of Compound 6A described in Example 6-1.

Characterization. An XRPD pattern of the crystalline Compound 6A was generated on a Philips Analytical X'Pert PRO X-ray Diffraction System with PW3050/60 console using a continuous scan from 4 to 40 degrees 2θ. Copper $K_{\alpha 1}$ and $K_{\alpha 2}$ radiation was used as the source. The experiment was run under ambient conditions. The diffraction peak positions were referenced by silicon which has a 2θ value of 28.443 degree. The XRPD pattern is shown in FIG. 5. 2θ values and the corresponding d-spacings in the XRPD pattern include the following:

TABLE 6A

| 2θ (degrees) | d-spacing (Å) |
|---|---|
| 5.6 | 15.7 |
| 7.0 | 12.6 |
| 9.9 | 8.9 |
| 10.6 | 8.3 |
| 12.8 | 6.9 |
| 14.2 | 6.2 |
| 15.0 | 5.9 |
| 16.0 | 5.5 |
| 16.2 | 5.5 |
| 16.6 | 5.3 |
| 17.4 | 5.1 |
| 18.0 | 4.9 |
| 18.4 | 4.8 |
| 18.8 | 4.7 |
| 19.8 | 4.5 |
| 20.0 | 4.4 |
| 20.4 | 4.3 |
| 20.6 | 4.3 |
| 21.2 | 4.2 |
| 21.7 | 4.1 |
| 22.1 | 4.0 |
| 22.7 | 3.9 |
| 23.1 | 3.8 |
| 23.2 | 3.8 |
| 24.1 | 3.7 |
| 24.8 | 3.6 |
| 25.1 | 3.5 |
| 25.5 | 3.5 |
| 26.1 | 3.4 |
| 26.2 | 3.4 |
| 26.6 | 3.3 |
| 27.9 | 3.2 |
| 28.5 | 3.1 |
| 29.2 | 3.1 |
| 29.3 | 3.0 |
| 30.1 | 3.0 |
| 30.6 | 2.9 |
| 31.0 | 2.9 |
| 31.5 | 2.8 |
| 32.0 | 2.8 |
| 32.3 | 2.8 |
| 32.6 | 2.7 |
| 33.1 | 2.7 |
| 33.9 | 2.6 |
| 34.5 | 2.6 |
| 35.5 | 2.5 |

The crystalline Compound 6A was also analyzed with a TA Instruments DSC Q 1000 differential scanning calorimeter at a heating rate of 10° C./minute from 25° C. to 350° C. in an open aluminum pan in a nitrogen atmosphere. The DSC curve showed an endotherm with an onset temperature of 170° C. and a peak temperature of 173° C. The enthalpy change was 84 J/g. The endotherm is believed to be due to melting.

TGA of the crystalline compound was performed with a TA Instruments TGA Q 500 under nitrogen at a heating rate of 10° C./minute from 25° C. to 350° C. The TG curve showed a weight loss of 0.05 wt. % up to 100° C. indicating the absence of water of hydration and solvent of solvation.

EXAMPLE 6-2

N-ethyl-N-((7S,10S)-2-{[(4-fluorobenzyl)amino]carbonyl}-3-hydroxy-7-methoxy-4-oxo-4,6,7,8,9,10-hexahydropyrimido[1,2-a]azepin-10-yl)-N,N-dimethylethanediamide (Compound 6B)

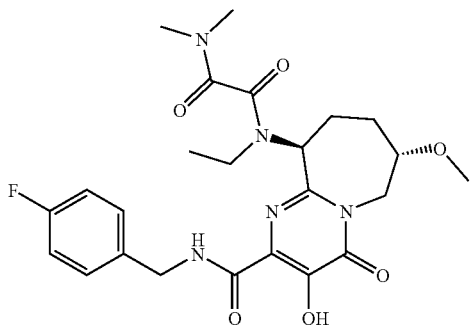 [SMILES: CCN(C(=O)C(=O)N(C)C)[C@H]1CC[C@H](OC)Cn2c1nc(C(=O)NCc1ccc(F)cc1)c(O)c2=O]

The title compound was prepared from the first eluting peak in Step 10 in Example 6-1 using the procedures given in Steps 11-13 in Example 6-1. $^1$H NMR (599 MHz, DMSO, 50° C.): δ 12.45-11.65 (m, 1 H); 9.47 (s, 1 H); 7.39-7.31 (m, 2 H); 7.18-7.09 (m, 2 H); 5.05 (bs, 1 H); 4.94 (d, J=13.9 Hz, 1 H); 4.51-4.42 (m, 2 H); 3.58 (dd, J=16.6, 11.1 Hz, 1 H); 3.44-3.26 (s, 3 H); 3.34-3.26 (m, 3 H); 3.19 (t, J=9.7 Hz, 1 H); 2.95 (s, 3 H); 2.91 (s, 3 H); 2.30 (d, J=13.7 Hz, 1 H); 2.23-2.18 (m, 1 H); 2.11 (d, J=13.3 Hz, 1 H); 1.85-1.77 (m, 1 H); 1.10 (t, J=7.1 Hz, 3H). LC-MS: HRMS: calculated: 504.2253. found: 504.2271.

EXAMPLE 7

HIV-1 Integrase Assay: Strand Transfer Catalyzed by Recombinant Integrase

Assays for the strand transfer activity of integrase were conducted in accordance with WO 02/30930 for recombinant integrase. Representative compounds of the present invention exhibit inhibition of strand transfer activity in this assay. For example, the compounds prepared in Examples 1 to 5 were tested in the integrase assay and found to have the IC$_{50}$ values in Table B. (Compounds 6A and 6B were not tested in this assay.)

TABLE B

| Compound | IC$_{50}$ (nM) |
| --- | --- |
| 1A - 10R isomer | 42 |
| 1B - 10S isomer | 38 |
| 2A - trans isomer | 37 |
| 2B - trans isomer | 41 |
| 2C - cis isomer | 73 |
| 2D - cis isomer | 46 |
| 3A - racemic trans isomer | 40 |
| 3B - (6R,10S) or (6S,10R) cis isomer | 44 |
| 4A - 6S,10S cis isomer | 38 |
| 4B - 6S,10R trans isomer | 39 |
| 4C - 6R,10R cis isomer | 48 |
| 4D - 6R,10S trans isomer | 36 |
| 5A - 6S,10S cis isomer | 46 |

TABLE B-continued

| Compound | IC$_{50}$ (nM) |
| --- | --- |
| 5B - 6S,10R trans isomer | 40 |
| 5C - 6R,10R cis isomer | 41 |
| 5D - 6R,10S trans isomer | 42 |
| 6A - 7S,10R cis isomer | — |
| 6B - 7S,10S trans isomer | — |

Further description on conducting the assay using preassembled complexes is found in Wolfe, A. L. et al., *J. Virol.* 1996, 70: 1424-1432, Hazuda et al., *J. Virol.* 1997, 71: 7005-7011; Hazuda et al., *Drug Design and Discovery* 1997, 15: 17-24; and Hazuda et al., *Science* 2000, 287: 646-650.

EXAMPLE 8

Assay for Inhibition of HIV-1 Replication

Assays for the inhibition of acute HIV-1 infection of T-lymphoid cells were conducted in accordance with Vacca, J. P. et al, *Proc. Natl. Acad. Sci. USA* 1994, 91: 4096. Representative compounds of the present invention exhibit inhibition of HIV replication in this assay (also referred to herein as the "spread assay"). For example, the compounds of Examples 1 to 6 were tested in this assay and found to have the IC$_{95}$ values in Table C.

TABLE C

| Compound | IC$_{95}$ (nM) in the presence of 10% FBS |
| --- | --- |
| 1A - 10R isomer | 12 |
| 1B - 10S isomer | 10 |
| 2A - trans isomer | 14 |
| 2B - trans isomer | 9 |
| 2C - cis isomer | 9 |
| 2D - cis isomer | 14 |
| 3A - racemic trans isomer | 18 |
| 3B - cis isomer | 41 |
| 4A - 6S,10S cis isomer | 10 |
| 4B - 6S,10R trans isomer | 7 |
| 4C - 6R,10R cis isomer | 10 |
| 4D - 6R,10S trans isomer | 6 |
| 5A - 6S,10S cis isomer | 12 |
| 5B - 6S,10R trans isomer | 10 |
| 5C - 6R,10R cis isomer | 14 |
| 5D - 6R,10S trans isomer | 20 |
| 6A - 7S,10R cis isomer | 12 |
| 6B - 7S,10S trans isomer | 14 |

EXAMPLE 9

Assay for Inhibition of Hiv Integrase Mutant Virus Replication

An assay for measuring the inhibition of acute HIV infection with HeLa P4-2 cells in a single cycle infectivity assay was conducted using methods described in Joyce et al., *J. Biol. Chem.* 2002, 277: 45811, Hazuda et al., *Science* 2000, 287: 646, and Kimpton et al, *J. Virol.* 1992, 66: 2232. Proviral plasmids encoding viruses containing specific mutations in the integrase gene (N155H, Q148R, Y143R, E92Q, or G140S/Q148H) were generated by site-directed mutagenesis, and viruses were produced by transfecting 293T cells with the appropriate proviral plasmids. Representative compounds of the present invention exhibit inhibition of HIV replication in the mutant assays For example, the compounds of Examples 1 to 6 were found to have the IC$_{50}$ values in these assays shown in Table D.

TABLE D

| Example No. | wild type IIIB IC$_{50}$ (nM) | N155H | Q148R | Y143R | E92Q | G140S/Q148H |
|---|---|---|---|---|---|---|
| 1A - 10R isomer | 41 | 1 | 2 | 1 | | 9 |
| 1B - 10S isomer | 13 | 14 | 12 | 1 | | 34 |
| 2A - trans isomer | 17 | 2 | 1 | 2 | 1 | 10 |
| 2B - trans isomer | 8 | 24 | 24 | 3 | | 190 |
| 2C - cis isomer | 8 | 19 | 22 | 3 | | 68 |
| 2D - cis isomer | 23 | 2 | 1 | 2 | | 4 |
| 3A - racemic trans isomer | 31 | 1 | 1 | | | 4 |
| 3B - cis isomer | 48 | 1 | 1 | 1 | | 2 |
| 4A - 6S,10S cis isomer | 19 | 2 | 2 | 2 | 1 | 12 |
| 4B - 6S,10R trans isomer | 32 | 2 | 3 | 2 | | 20 |
| 4C - 6R,10R cis isomer | 26 | 3 | 3 | 1 | | 11 |
| 4D - 6R,10S trans isomer | 20 | 8 | 9 | 2 | | 72 |
| 5A - 6S,10S cis isomer | 28 | 1 | 1 | 1 | 2 | 4 |
| 5B - 6S,10R trans isomer | 42 | 3 | 1 | 2 | 1 | 11 |
| 5C - 6R,10R cis isomer | 21 | 7 | 7 | 2 | | 116 |
| 5D - 6R,10S trans isomer | 26 | 13 | 14 | 1 | | 18 |
| 6A - 7S,10R cis isomer | 16 | 2 | 1 | 3 | 3 | 2 |
| 6B - 7S,10S trans isomer | 13 | 13 | >100 | >100 | | >100 |
| Compound V[2] | 37 | 10 | 13 | 1 | | >32 |
| Compound W[3] | 26 | 29 | 67 | 3 | | >73 |
| Compound X[4] | 52 | 13 | 22 | 15 | 3 | 397 |
| Compound Y[5] | 16 | 15 | 26 | 1 | 4 | 406 |
| Compound Z[6] | 34 | 32 | >34 | 1 | 26 | >34 |

[1] A number "k" in columns 3-7 in the table where k > 1 means the compound is k-fold less potent against the mutant compared to its potency against the wild type, i.e., k = IC$_{50}$(mutant)/IC$_{50}$(wild type).
[2] Compound V is (+)-N-(2-{[(4-fluorobenzyl)amino]carbonyl}-3-hydroxy-4-oxo-6,7,9,10-tetrahydro-4h-pyrimido[1,2-d][1,4]oxazepin-10-yl)-N,N',N'-trimethylethanediamide (Compound 180 in WO 2006/103399).
[3] Compound W is (−)-N-(2-{[(4-fluorobenzyl)amino]carbonyl}-3-hydroxy-4-oxo-6,7,9,10-tetrahydro-4h-pyrimido[1,2-d][1,4]oxazepin-10-yl)-N,N',N'-trimethylethanediamide (Compound 181 in WO 2006/103399).
[4] Compound X is raltegravir (Example 19 in U.S. Pat. No. 7,169,780).
[5] Compound Y is (−)-N-(2-{[(4-fluorobenzyl)amino]carbonyl}-3-hydroxy-4-oxo-4,6,7,8,9,10-hexahydropyrimido[1,2-a]azepin-10-yl)-N,N',N'-trimethylethanediamide (Example 12 in U.S. Pat. No. 7,414,045).
[6] Compound Z is N-[(4-fluorophenyl)methyl]-3-hydroxy-9,9-dimethyl-4-oxo-4,6,7,9-tetrahydro-6H-pyrimido[2,1-c][1,4]oxazine-2-carboxamide (compound exemplified in WO 2007/064502 A1).

EXAMPLE 10

Cytotoxicity

Cytotoxicity was determined by microscopic examination of the cells in each well in the spread assay, wherein a trained analyst observed each culture for any of the following morphological changes as compared to the control cultures: pH imbalance, cell abnormality, cytostatic, cytopathic, or crystallization (i.e., the compound is not soluble or forms crystals in the well). The toxicity value assigned to a given compound is the lowest concentration of the compound at which one of the above changes is observed. Representative compounds of the present invention that were tested in the spread assay (see Example 8) were examined for cytotoxicity up to a concentration of 0.5 micromolar, and no cytotoxicity was exhibited. In particular, the compounds set forth in Examples 1 to 6 exhibited no cytotoxicity at concentrations up to 0.5 micromolar.

EXAMPLE 11

Preparation of Compound 4A

Step 1: Propagylation Reaction

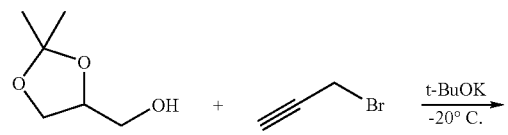

-continued

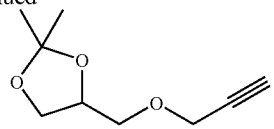

To a 100-L vessel equipped with thermocouple, nitrogen flow, cooling bath and overhead stirrer was charged solid t-BuOK (7.40 kg, 65.9 mol) and THF (44 L). The slurry was stirred at ambient temperature until all the solids dissolved. The solution was cooled to about −20° C. using acetone/dry ice bath. Solketal (9.58 kg, 72.5 mol) was added slowly while maintaining the internal temperature below −10° C. After ageing the reaction mixture for 45 minutes at about −20° C., propagyl bromide (7.31 L, 80% solution in toluene) was added slowly over 190 minutes while maintaining the internal temperature below −10° C. After the addition of the propagyl bromide, the reaction mixture was aged at about −25° C. for 1 hour. The acetone was then drained from the bath and the reaction mixture was slowly allowed to warm to ambient temperature overnight. The reaction was complete after overnight age at ambient temperature as evidenced by TLC and GC. To the reaction mixture was added water (24.5 L) and saturated aqueous NaHCO$_3$ (24.5 L). The solution was transferred to a 170 L extractor and extracted with ethyl acetate (2×24.5 L). The combined organic layer was washed with additional water (2×24.5 L) and brine (1×24.5 L; note: the phase separation was slow with the water washes so additional brine (8.0 L) was used with each wash to help speed up the phase separation). The solution was concentrated under vacuum to provide the desired propagylated product as a crude oil. The material was used in the subsequent step without further purification.

Step 2: Deprotection of the Solketal

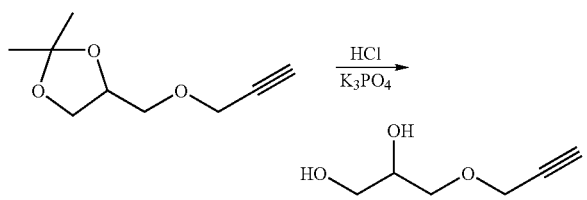

To a 100-L vessel equipped with thermocouple, nitrogen flow, and overhead stirrer was charged the crude propagylated compound of Step 1 (10.7 kg), MTBE (10.7 L), water (32.1 L) and 5.0 N HCl (1.26 L). The reaction was complete after 6 hours age at ambient temperature as evidenced by GC and TLC (30% EtOAc/hexane). After the reaction was complete, additional MTBE (16.1 L) was added for a total of 26.8 L. After a 1 hour age at ambient temperature, the solution was transferred to a 100 L extractor and the layers were separated. The organic layer was extracted with additional water (1×32.1 L). The pH of the combined aqueous layer was adjusted from pH=1.2 to pH=6.9 using solid $K_3PO_4$ (1.0 kg). Assay yield via aGC of the desired diol was 6.96 kg (85%).

Step 3: Aldehyde Formation

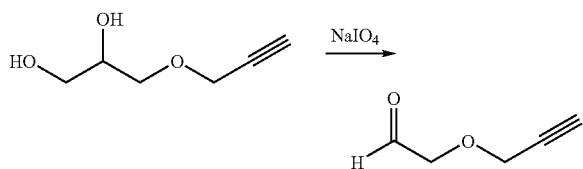

To a 100-L vessel equipped with a thermocouple, nitrogen inlet, cooling bath and overhead stirrer, was charged an aqueous solution (pH ~7) of the diol (3.42 kg, 26.3 mol) prepared in Step 2. The solution was cooled to about 10° C. and to the cold solution was added $NaIO_4$ (8.43 kg, 39.4 mol) in four portions. After the addition of $NaIO_4$, the reaction mixture was slowly warmed to ambient temperature. The reaction was complete after 2 hours at ambient temperature as evidenced by TLC (30% EtOAc/hexane) and GC (<1 A % of starting diol). Prior to filtration, the slurry was cooled to about 5° C. and aged for 1 hour. The slurry was filtered and the cake was rinsed with water (1×3.4 L). The resulting solution of the aldehyde was used directly in the next step.

Step 4: Cyanohydrin Formation

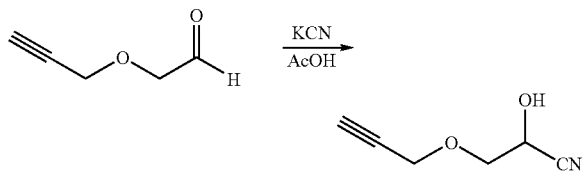

To a 100 L vessel equipped with thermocouple, nitrogen inlet, cooling bath, two addition funnels and overhead stirrer, was charged aqueous solution (pH ~4) of the aldehyde (2.25 kg, 22.94 mol) of Step 3 and the solution was cooled to about 6° C. To the cold solution was added acetic acid (2.76 L, 48.2 mol) and 8.0 L of aqueous solution of KCN (2.99 kg, 45.9 mol) simultaneously while keeping the internal temperature below 15° C. After the addition of acetic acid and aqueous solution of KCN, the reaction mixture was warmed to ambient temperature and aged. The reaction was complete after 1 hour age at ambient temperature as evidenced by TLC (50% EtOAc/hexane) and GC (1 A % of starting aldehyde). The reaction mixture was cooled to about 10° C. and slowly quenched with saturated $NaHCO_3$ (11.5 L). After the addition, the batch was warmed to ambient temperature and aged for 1 hour. The solution was transferred to a 100 L extractor and extracted with ethyl acetate (2×12 L). The combined organic layer was washed with 25% brine (6×12 L). The resulting solution of cyanohydrin was used directly in the next step.

Step 5: Silylation Reaction

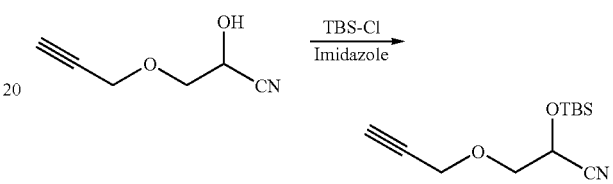

In a 100 L vessel equipped with a thermocouple, steam bath and overhead stirrer, the ethyl acetate solution of the cyanohydrin of Step 4 (2.87 kg theoretical amount of cyanohydrin assuming 100% yield in the previous step) was concentrated under vacuum and flushed with additional ethyl acetate (54 L) to a final volume of 30 L. After the concentration, the steam bath was replaced with a cooling bath and nitrogen inlet was attached. The solution was cooled to about 5° C. and to the cold solution was added TBS-Cl (3.63 kg, 24.08 mol) in one portion. Then imidazole was added in two portions (with about 8° C. exotherm observed). The batch was slowly allowed to warm to ambient temperature overnight. The reaction was complete after overnight age at ambient temperature as evidenced by and GC and TLC (30% EtOAc/hexane). The reaction was slowly quenched with water (6.0 L) and transferred to a 100 L extractor. Additional water (9.0 L) for a total of 15.0 L was added followed by ethyl acetate (6.0 L). The layers were separated and the organic layer was washed with saturated $Na_2CO_3$ (1×15 L) and water (2×15 L). The resulting desired silyloxy nitrile was obtained in 4.74 kg (85.8%) assay yield as determined by GC.

A second batch was done using 2.95 kg of the cyanohydrin to provide the desired silyloxy nitrile in 4.79 kg (86.3%) assay yield.

Step 6: Amidoxime Preparation

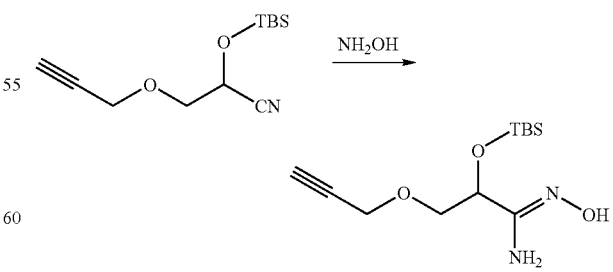

A 100 L flask was equipped with an overhead stirrer, a thermocouple, an inlet line with an in-line filter and a batch concentrator. Silylated hydroxynitrile, as a solution in ethyl acetate from the previous step (37.1 mol; total volume 59.7 liters) was charged in. During concentration, methanol was added (60 L) and the batch was concentrated to approximately 9 L volume (ethyl acetate content ~1.5% by NMR). Methanol (17.8 L) was added. The batch concentrator was removed and replaced with a condenser and nitrogen inlet. A solution of hydroxylamine (50% in water, 2.96 L, 48.3 mol, 1.3 equiv) was added over 1 hour at an initial internal temperature of 18° C. Upon completion of the addition, the reaction temperature increased to 39° C. Stirring was continued for 30 minutes followed by heating for 90 minutes at 50° C. The reaction mixture was transferred into a 170 L extractor containing MTBE (71 L) and water (44 L). Following partition, the organic layer was washed with water twice (44 L each). 1st aqueous loss=0.29% (pH=8), 2nd aqueous loss=0.07% (pH=7), 3rd aqueous loss=0.08% (pH=6). Assay yield of the amidoxime product in the organic layer was 10.05 kg (99%), as determined by HPLC. The solution was used directly in the subsequent reaction.

Step 7: DMAD Adduct Formation

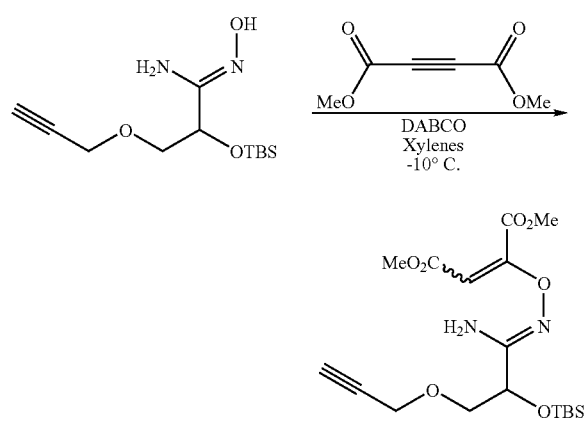

To a 100 L vessel equipped with a thermocouple, steam bath and overhead stirrer was charged the solution of amidoxime in MTBE (9.86 kg assay, 36.2 mol), concentrated under vacuum and flushed with additional MTBE (54.0 L) to provide the neat amidoxime product as a liquid. After the concentration, the steam bath was replaced with a cooling bath and nitrogen inlet was attached. To the neat amidoxime was added xylene (29.6 L) and DABCO (41 g, 0.362 mol, 0.01 equiv) and the solution was cooled to about –20° C. using acetone/dry ice bath. To the cold solution was added DMAD (5.14 kg) as a solution in xylene (19.7 L) slowly while maintaining the batch temperature below –10° C. After 1 hour age at about –10° C., there was 3.6 A % of starting amidoxime remaining so additional DMAD (0.05 eq.=257 g) was added neat (for a total of 5.40 kg DMAD, 38.0 mol, 1.05 equiv). The reaction was complete after another 1 hour age at about –10° C. as evidenced by HPLC. The batch was warmed to about –5° C. and slowly quenched with 1% $H_3PO_4$ (30 L). After 1 hour age, the batch was transferred to a 100 L extractor, the layers were separated and the organic layer was washed with water (2×40 L). The resulting desired DMAD adduct was obtained in 15.0 kg (100%) assay yield with 1:5.2 ratio in favor of the desired isomer. HPLC indicated no detectable product loss in the water washes.

Step 8: Cyclization Reaction

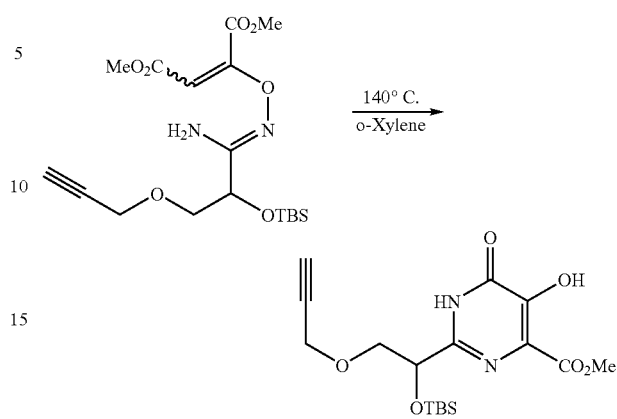

o-Xylene (30 L) was charged to a 100 L vessel equipped with a thermocouple, nitrogen flow, heating mantle, addition funnel, distillation apparatus and overhead stirrer. The o-xylene was heated to 135° C. To the hot o-xylene solution was added the DMAD adduct as a solution in xylene (30 kg solution=7.5 kg of adduct, 18.09 mol) via the addition funnel while maintaining the internal temperature above 125° C. The reaction was complete after 2 hours age at about 137° C. as evidenced by HPLC. The heat was turned off and the batch was allowed to slowly cool to ambient temperature. At about 80° C., Darco KB-G charcoal (2.1 kg, 30 wt %) was added and the cooling continued to ambient temperature overnight. The solution was filtered through Solka Floc and the cake was rinsed with o-xylene (1×15 L). The solution was transferred to a 170 L extractor and to the solution was added water (37.5 L), heptane (37.5 L) and triethylamine (7.6 L, 54.3 mol, 3.0 equiv). The layers were separated and the organic layer was back extracted with water (1×22.5 L). The combined aqueous layer was then washed with MTBE (1×22.5 L). The aqueous layer (pH=10.2) was diluted with MTBE (37.5 L) and acidified with 85% phosphoric acid (2.0 L) to pH=3.9. The layers were separated and the aqueous layer was back extracted with MTBE (1×22.5 L). There was no significant loss in the aqueous layer (<1%). The organic solution was concentrated under vacuum and flushed with additional MTBE (72.0 L) to final volume of about 22.0 L. The solution was heated to about 53° C. to dissolve all the solids and to the hot solution was added heptane (60.0 L) slowly. After the addition of heptane, the slurry was slowly cooled to ambient temperature overnight. Prior to filtration, the slurry was cooled to about 5° C. with ice/water and aged for 1 hour. The slurry was filtered and the cake was slurry washed with 1:3 mixture of MTBE: heptane (1×16.0 L) and heptane (1×16.0 L). The cake was dried in the filter pot under nitrogen sweep and high vacuum at ambient temperature over the weekend. The resulting desired pyrimidinone was obtained in 3.80 kg (54.9%) with 95.6 wt % and 97.3 LCAP. HPLC indicated approximately 4.2% product loss in the mother liquor and washes. A second batch was done using 7.5 kg (30 kg solution) of the DMAD adduct to provide the desired pyrimidinone in 4.06 kg (58.7%) with 94.7 wt % and 97.9 LCAP.

Step 9: Hydroamination

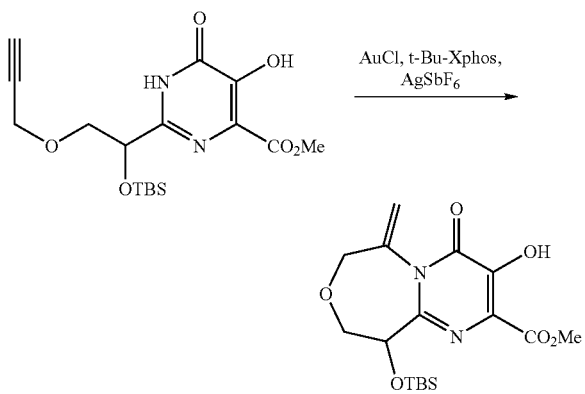

Preparation of the catalyst: In a 5 L 3-necked RB flask with an overhead stirrer were charged AuCl (63.9 g, 0.275 mol) and DCM (2.75 L). To the stirred suspension was added t-Butyl-Xphos (i.e., 2-di-tert-butylphosphino-2',4',6'-triisopropylbiphenyl) (117 g, 0.275 mol) in one portion. The mixture was stirred vigorously for 1 hour to form a catalyst solution.

Preparation of Ag salt solution: In an 8 L glass bottle with a magnetic stir bar were charged $AgSbF_6$ (118 g, 0.343 mol) and DCE (4.3 L). The mixture was stirred for 30 minutes.

Reaction: In a 100 L flask equipped with a thermocouple, an overhead stirrer, a steam bath, a condenser with cold water, and nitrogen sweep were charged DCM (63 L) and pyrimidinone (3.66 kg, 3.5 kg assay, 9.15 mol). To the solution were added the catalyst solution (2.75 L, 0.275 mol) and the $AgSbF_6$ solution (4.3 L, 0.343 mol) subsequently at room temperature. The reaction mixture was heated to 40° C., and aged at 40° C. for 5 hours. The reaction was monitored by HPLC to confirm the starting material was completely consumed. After cooling to room temperature, the flask was attached to a batch concentrator. The mixture was concentrated in vacuo (~11° C., 22 in Hg). After distillation of ~55 L of the solvent mixture, the mixture was solvent-switched to MeOH (total 24 L of MeOH was used, final volume was ~14 L). The MeOH solution of the product (40:1 ratio of 7- vs 8-membered rings) was used in the next reaction step as is.

Step 10: TBS Deprotection

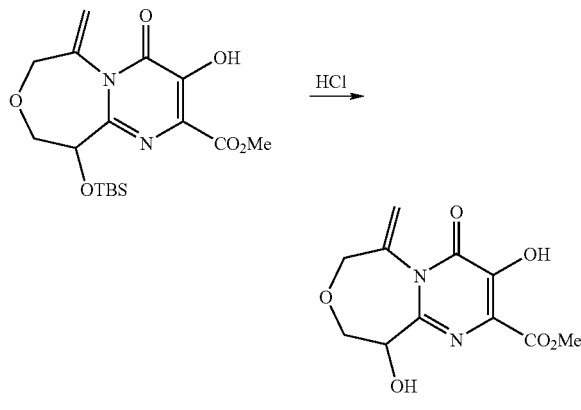

The solution of the starting material (~3.5 kg, ~9.15 mol) in MeOH (~14 L) from the previous reaction was placed in a 50 L RB flask with an overhead stirrer, a thermocouple, a steam bath, and a condenser with cold water. To the mixture was added concentrated HCl (83 mL, 1.01 mol) at room temperature. The mixture was heated to 45° C., and aged at 45° C. for 6 hours. In the course of the reaction, the product precipitated out to form a slurry. After 6 hours, the heating was stopped. The mixture was stirred at ambient temperature overnight. The reaction was monitored by HPLC to confirm the starting material was consumed (99% conversion). To the mixture was then added IPA (6 L) dropwise. The mixture was aged at room temperature for 3 hours. The solid was filtered, rinsed with MeOH—IPA (3:1, 4 L), then dried with $N_2$ stream to afford the product (2.29 kg net, 2.20 kg assay, 8.20 mol, 90% isolated yield over 2 steps) as an off-white solid.

Step 11: Amide Formation

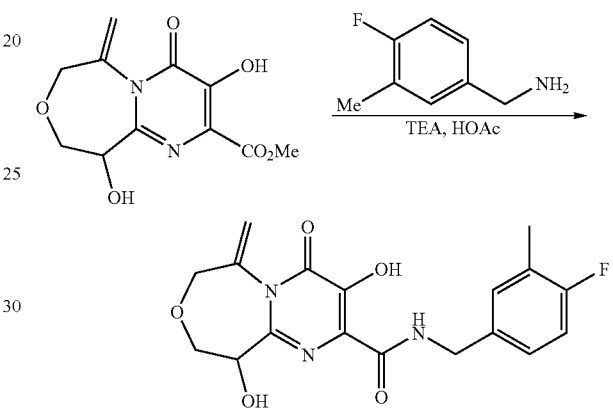

In a 30 L RB jacketed cylindrical vessel with an overhead stirrer, a thermocouple, and a condenser with cold water were charged the starting material ester (2.12 kg assay, 7.89 mol), MeOH (11 L), 3-methyl-4-fluorobenzylamine (1.428 kg, 10.26 mol) and TEA (1.198 kg, 11.84 mol) subsequently. The mixture was heated at 55~57° C. overnight (~21 hours). The reaction was monitored by HPLC to confirm the starting material was consumed (98% conversion). Then the mixture was filtered hot (~55° C.) through in-line filter (pore size 1 μm) to remove precipitates into a 50 L RB flask with an overhead stirrer, a thermocouple and a steam bath. The mixture was heated back to 45° C. from 38° C. Then acetic acid (0.904 L) was added dropwise. The mixture was cooled to room temperature, during which time water (9 L) was added dropwise over 1.5 hours to crystallize the product. The mixture was further cooled to room temperature. The solid was filtered, rinsed with MeOH—$H_2O$ (3:2, 7 L), then dried with $N_2$ stream to afford the amide (2.88 kg net, 2.79 kg assay, 7.43 mol, 94% isolated yield) as an off-white solid.

Step 12: Benzenesulfonyl Protection

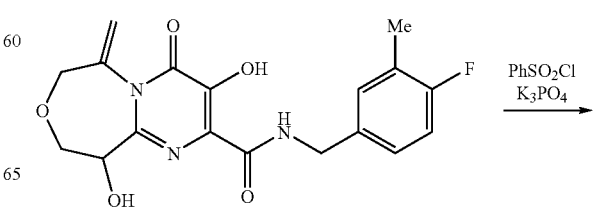

-continued

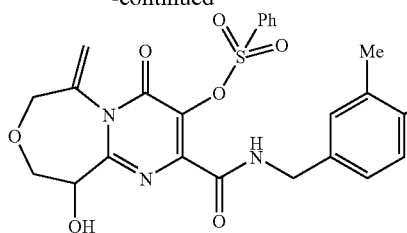

A 50 L four neck flask was equipped with an overhead stirrer, thermocouple, addition funnel and nitrogen inlet followed by charging with the alcohol substrate (2.698 kg, 6.96 mol). DMF (8.1 L) was added. The resulting suspension was stirred at an internal temperature of 21° C. as solid potassium phosphate (4.43 kg, 20.9 mol, 3 equiv) was added over 5 minutes, using a nitrogen tent to maintain the phosphate as an anhydrous solid. The internal temperature rose to 27° C. during the addition. The reaction mixture was cooled to −10° C. using a dry ice/acetone bath. Upon reaching −10° C., benzenesulfonyl chloride (897 mL) was added dropwise over 1 hour, maintaining an internal temperature of −7° C. throughout the addition. After addition was complete, the reaction was stirred for 20 minutes. HPLC analysis shows an LCAP of 92 for the product, 5 for starting material and 1 for bis sulfonylated by product. An additional charge of benzene sulfonyl chloride (44 mL, total of 7.30 mol, 1.05 equiv) was made and stirring continued for 40 minutes. HPLC analysis determined the reaction to be complete. The reaction was transferred into a 100 L extractor containing 48 L of 1 $NH_3$ $PO_4$ and 10 L of dichloromethane. Additional dichloromethane (14.3 L) was used to complete the transfer from the reaction vessel. After partitioning, the pH of the aqueous phase was 7. The organic layer was washed with water (3×48 L). A 50 L flask was equipped with a thermocouple, an inlet with a 0.45 micron in-line filter; an overhead stirrer and a batch concentrator. The dichloromethane solution was fed into the flask via the filter line and batch concentration was performed until approximately 7 L remained. Methanol (10.8 L) was added and batch concentration continued until approximately L methanol remained. As the solution was stirred, seeding was performed. Stirring was continued for 90 minutes, as a gentle exotherm (maximum temperature=27° C.) occurred and crystallization proceeded. An ice water bath was used to cool the batch to 5° C. The batch was stirred overnight (14 hours) with warming to 12° C. HPLC analysis for mother liquor losses showed 3.3%. The batch was cooled to 5° C. with an ice water bath and the batch was filtered. The cake was washed with 3.5 L of cold (5° C.) methanol. The mother liquor and cake wash were analyzed for losses (2.1% in mother liquor and 0.64% in cake wash). The cake was dried under a nitrogen tent with vacuum applied for 72 hours. 3.60 kg (94%) was recovered as an off white solid. NMR analysis indicates that a methanol solvate is formed (approximately 0.9 equivalents of methanol are present).

$^1$H-NMR ($CDCl_3$, 400 MHz) 1.05 (1H; br s); 2.27 (s, 3H); 3.49 (s, 2.9 methanol solvate); 3.63-3.66 (m, 1H); 3.98-4.06 (m, 2H); 4.18 (m, 1H); 4.24-4.27 (d, 1H); 4.55 (m, 2H); 4.87-4.92 (m, 1H); 5.57 (s, 1H); 5.93 (s, 1H); 6.94-6.99 (t, 1H J=8.8 Hz); 7.11-7.15 (m, 1H); 7.18-7.20 (d, 1H J=7.2); 7.42 (m, 1H); 7.55-7.59 (t, 2H J=7.9 Hz); 7.68-7.72 (t, 1H J=7.4 Hz); 8.07-8.09 (d, 2H J=7.9 Hz).

Step 13: Asymmetric Hydrogenation

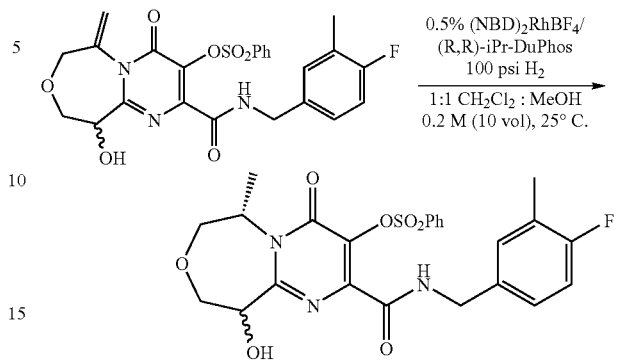

In a nitrogen-purged glovebox with $O_2$<5 ppm, bis(norbornadiene)rhodium (1) tetrafluoroborate (6.24 g, 16.68 mmol), (+)-1,2-bis((2R,5R)-2,5-diisopropylphospholano)-benzene ((R,R)-iPr-DuPhos) (7.33 g, 17.52 mmol), and dichloromethane (85 mL) were added to a 250 mL round-bottom flask. The catalyst mixture was stirred for one hour and transferred via cannula to a 150 mL stainless steel vessel followed by 15 mL of dichloromethane rinse. 100 mL of methanol was added to a second 150 mL stainless steel vessel, and the catalyst charge apparatus was sealed and removed from the glovebox.

A solution of the starting material (1.72 kg, 3.34 mol) was prepared in 8.5 L of dichloromethane and then drawn via vacuum into a 10 gallon stirred autoclave. 8.5 L of methanol was charged to the autoclave in a similar manner and the catalyst charge assembly was attached via flexible tubing. The autoclave was inerted with three nitrogen/vacuum purges and the autoclave was placed under partial vacuum. The catalyst solution was drawn into the autoclave followed by the methanol rinse. The autoclave was subjected to three hydrogen purges, thermostatted to 25° C., and pressurized with hydrogen gas to 100 psig. The reaction mixture was agitated at 600 rpm for 18 hr. HPLC analysis confirms >99% conversion to the desired product with 96% ee and ~1:1 dr. The resulting slurry of the product was used directly in the next step.

$^1$H-NMR of the 1:1 mixture of diastereomers ($CDCl_3$, 400 MHz): 8.02-8.09 (m, 4H), 7.79 (t, J=5.9 Hz, 1H), 7.67-7.74 (m, 2H), 7.53-7.62 (m, 4H), 7.47 (t, J=5.7 Hz, 1H), 7.06-7.19 (m, 4H), 6.94 (td, J=9.2, 4.3 Hz, 2H), 5.32-5.40 (m, 1H), 5.01-5.09 (m, 1H), 4.92 (dd, J=10.3, 3.6 Hz, 1H), 4.84 (d, J=3.1 Hz, 1H), 4.44-4.52 (m, 3H), 4.37 (dd, J=14.7, 5.8 Hz, 1H), 4.18 (dt, J=12.5, 3.8 Hz, 2H), 4.13 (dd, J=14.0, 3.8 Hz, 1H), 4.05 (dd, J=13.8, 3.6 Hz, 1H), 3.65-3.73 (m, 2H), 3.59 (d, J=13.7 Hz, 1H), 3.41 (dd, J=12.1, 8.9 Hz, 1H), 3.15 (br s, 2H), 2.26 (s, 6H), 1.62 (d, J=7.1 Hz, 3H), 1.48 (d, J=7.3 Hz, 3H).

Step 14: Mesylation

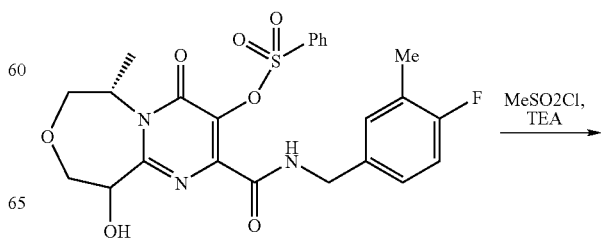

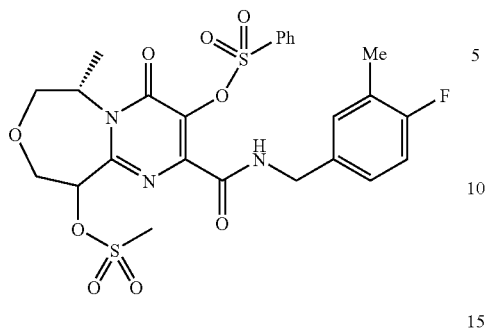

The two batches from the preceding hydrogenation step were combined together with ~50 L of dichloromethane (total assay 3.13 kg, 6.05 mol). The resulting clear solution was concentrated in a 100 L round bottom flask using 115 L of 2-methyltetrahydrofuran to reduce the level of MeOH to 4 mol % with respect to the starting material by HNMR. The final volume of the concentrated solution was ~20 L. The solution was cooled in an ice bath to +3° C. A thin suspension formed. TEA (1.26 L, 9.07 mol) was added over ~5 minutes (exotherm from +2 to +4° C.). MsCl (0.566 L, 7.26 mol) was added over 1 hour at +10° C. After 1 hour, the reaction was complete, and the mixture was quenched with 2 L of water (exotherm from +5 to +7° C.). 1M aqueous $H_3PO_4$ (9.4 L) was added. The mixture was transferred into a 100 L extractor rinsing with 15.5 L of Me-THF. Additional 22 L of water was added, phases were separated. The organic layer was washed with 31 L of water. The organic layer contained 3.57 kg assay (99%) of the product and was used directly in the next step.

1H-NMR of the 1:1 mixture of diastereomers ($CDCl_3$, 400 MHz): 8.49 (t, J=6.2 Hz, 1H), 7.99-8.08 (m, 4H), 7.76 (t, J=6.0 Hz, 1H), 7.65-7.72 (m, 2H), 7.50-7.58 (m, 4H), 7.04-7.17 (m, 4H), 6.89-6.96 (m, 2H), 5.75 (dd, J=10.0, 3.1 Hz, 1H), 5.64 (d, J=3.3 Hz, 1H), 5.37-5.47 (min, 1H), 5.08-5.18 (m, 1H), 4.32-4.49 (m, 5H), 4.21 (dd, J=12.1, 3.1 Hz, 1H), 4.13 (dd, J=14.1, 3.4 Hz, 1H), 4.06 (dd, J=13.9, 3.7 Hz, 1H), 3.16 (s, 3H), 3.11 (s, 3H), 2.24 (s, 6H), 1.56 (d, J=7.1 Hz, 3H), 1.48 (d, J=7.3 Hz, 3H).

Step 15: Mesylate Displacement

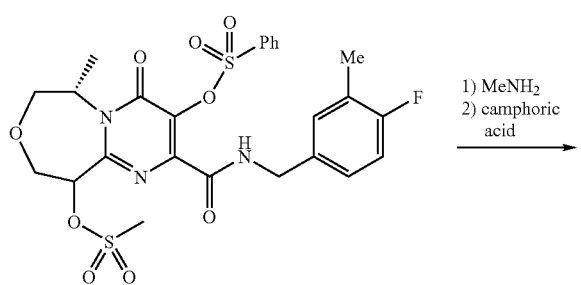

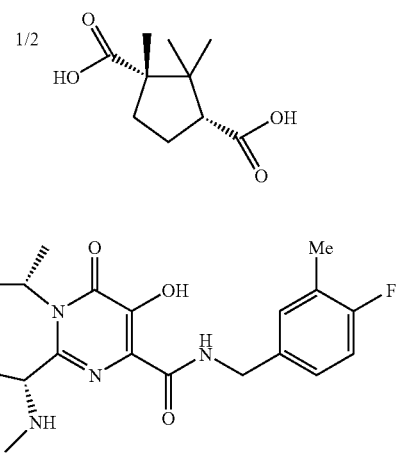

The solution of mesylate from the preceding step (~1:1 dr, 3.45 kg, 5.79 mol) was concentrated in a 75 L RB flask with 35 L of 2-methyltetrahydrofuran to 6.9 L volume. MeOH (24 L) was added (13:1 molar ratio of MeOH/MeTHF by H-NMR). The resulting slurry was cooled to −15° C. A 33% solution of $MeNH_2$ in EtOH (7.2 L, 57.9 mol) was added below −15° C. over 1 hour. The slurry was stirred at −10 to −8° C. for 7 hours, then to +14° C. for 15 hours. The resulting clear solution was concentrated with 17.2 L of MeOH to ~10 L volume, cooled in ice-water bath and treated with 3.5 L water and 6.9 L MTBE. 1 M aqueous $H_3PO_4$ (23.2 L) was added below +22° C. The mixture was transferred into a 100 L cylindrical vessel and combined with 24 L of MTBE and 4 L of water. The layers were separated and the aqueous phase was re-extracted with 31 L of MTBE. The aqueous phase was combined with 31 L of dichloromethane and neutralized with 4.3 L of 5M aqueous KOH to pH 5-6 (2.04 kg assay or 90% yield of free base in the dichloromethane layer, 98:2 dr). The dichloromethane phase was concentrated in a 75 L flask with 20 L of MeOH to ~13.5 L volume. The resulting fine slurry was filtered to remove 125 g of racemic product and the cake was washed with 2.3 L of MeOH. The filtrate was transferred back into the 75 L flask using 2.3 L of MeOH. A solution of 0.638 kg of (−)-camphoric acid (3.19 mol) in 3.4 L of MeOH was added at 18 to 21° C. over 1 hour and the mixture was seeded. Additional 1.1 L of MeOH was added, stirring was continued at +20° C. for 3 hours. The suspension was filtered and the cake was washed with 2×7.0 L of 1:1 MeOH/water and dried under nitrogen to provide 2.16 kg of the product (76% yield) as an off-white powder, a 2:1 salt according to HNMR, 99.6:0.4 dr by HPLC, >99.8% ee by chiral HPLC after derivatization as the API.

1H-NMR ($CDCl_3$, 400 MHz): 7.88 (br t, J=5.2 Hz, 1H), 7.12-7.21 (m, 2H), 7.02 (t, J=9.2 Hz, 1H), 5.22-5.31 (m, 1H), 4.63 (dd, J=14.8, 6.6 Hz, 1H), 4.51 (dd, J=14.8, 5.9 Hz, 1H), 4.13-4.22 (m, 2H), 3.84 (dd, J=3.4, 1.2 Hz, 1H), 3.63-3.73 (m, 2H), 2.87 (t, J=9.2 Hz, 0.5H), 2.52-2.63 (m, 0.5H), 2.38 (s, 3H), 2.30 (s, 3H), 2.14-2.26 (m, 0.5H), 1.82-1.92 (m, 0.5H), 1.69 (d, J=7.2 Hz, 3H), 1.52-1.60 (m, 0.5H), 1.34 (s, 1.5H), 1.38 (s, 1.5H), 0.94 (s, 1.5H).

Step 16: Final Coupling

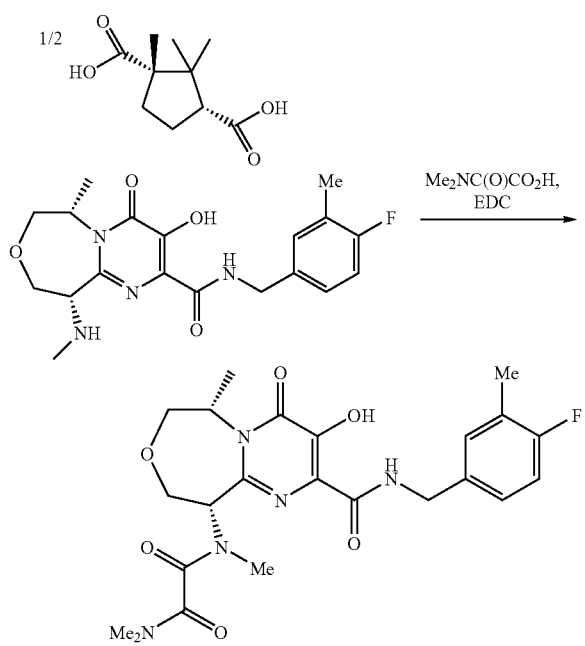

In a visually clean 50 L cylinder vessel, penultimate salt (1.95 kg, 3.98 mol), DCM (20 L), 0.75 M pH 6.8 potassium phosphate buffer (20 L) were placed. The mixture was stirred for 30 minutes for salt break, then allowed to settle. The organic layer was separated, and back-transferred to the vessel, where the same buffer (20 L) was placed. The mixture was stirred for 10 minutes, and then allowed to settle. The organic layer was separated from the aqueous layer and transferred to a visually clean 4-necked 50 L RB flask with an overhead stirrer and a thermocouple. N,N-dimethyloxamic acid (0.745 kg, 6.36 mol) was added, and stirred for 10 minutes. EDC (1.143 kg, 5.96 mol) was added portionwise to the mixture (internal temperature was kept below ~30° C.) over 10 minutes, followed by the addition of another portion of EDC (0.20 kg, 1.29 mol). After 25 minutes, the reaction mixture was monitored by HPLC to confirm the starting material was consumed (>99% conversion). The mixture was transferred into a visually clean 50 L cylinder vessel, where GMP-water (20 L) was placed. Then the flask was rinsed with DCM (1 L) and GMP-water (1 L). The mixture was stirred at room temperature for minutes, and then allowed to settle. The organic layer was separated, back-transferred to the vessel, washed with water (20 L) again for 30 minutes, and collected in polyjugs. The next day the organic layer was sucked into a visually clean 50 L RB flask equipped with an overhead stirrer, a batch concentrator, a thermocouple and a steam bath via an in-line filter for concentration. The mixture was concentrated/solvent-switched in vacuo to EtOH (final volume of EtOH, 10 L, total ~12 L). Seed crystals were added at ~45° C. to the mixture. The mixture was cooled to room temperature, and aged at room temperature overnight. The solid was filtered, then washed with EtOH (5 L), and dried with N$_2$ stream for overnight to afford the desired product (1.796 kg net, 99 wt %, 91% isolated yield) as an off-white solid.

$^1$H NMR (500 MHz, CDCl$_3$, ppm): 12.35 (br s, 1 H), 9.60 (t, J=6.3 Hz, 1 H), 7.22 (dd, J=7.4, 1.9 Hz, 1 H), 7.20-7.16 (m, 1H), 6.91 (dd, J=9.5, 8.6 Hz, 1 H), 5.81 (br s, 1 H), 4.96-4.91 (m, 1H), 4.51 (d, J=6.5 Hz, 2 H), 4.46 (t, J=11.1 Hz), 4.31 (d, J=14.1 Hz, 1 H), 4.15 (dd, J=11.8, 2.5 Hz, 1 H), 4.04 (dd, 14.1, J=5.4 Hz, 1 H), 3.07 (s, 3 H), 3.02 (s, 3 H), 2.86 (s, 3 H), 2.24 (d, J=1.9 Hz, 3 H), 1.61 (d, J=6.9 Hz, 3 H).

The product was wet milled using an IKA mill to a mean particle size of about 18 microns and a particle size range of from about 0.5 to about 100 microns, as determined using a Microtrac particle size analyzer with laser diffraction technology. The milled product can be employed in biological studies such as the determination of the compounds pharmacokinetics in animals or humans.

EXAMPLE 12

Preparation of Compound 5A

Step 1: TBS Ether Formation

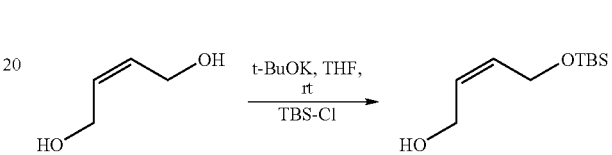

A 75 L 3-necked RB flask was charged with THF (27.5 L) and t-BuOK (95 wt %, 6.10 kg, 51.6 moles) at room temperature to give a thick but easily stirred white slurry. Cis-2-butene-1,4-diol (4.55 kg, 51.6 moles) was added as neat liquid over 0.5 hour maintaining the temperature below 20° C. The resulting loose slurry was aged at room temperature for 30 minutes and TBS-Cl (7.00 kg, 46.5 moles) dissolved in THF (3.5 L) was added over 0.5 hour keeping the temperature below +30° C. The reaction mixture was aged at room temperature for 1-2 hours and reverse quenched into an extractor containing water (25 L) and MTBE (25 L). The layers were separated, the organic layer was washed with 5% NH$_4$Cl (18 L) and 5% brine (2×18 L). The MTBE layer was concentrated to dryness (oil) and flushed with heptane (20 L) to afford the TBS ether as a crude oil (>10 kg, containing about 12 A % (=area percent) bis-OTBS as determined via GC) which was used without further purification in the next step.

Step 2: Acrylonitrile Addition

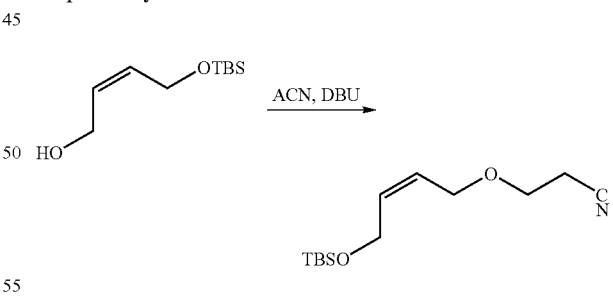

A 50 L 3-necked RB flask was charged with mono-TBS alcohol (9.187 kg, 45.4 moles), acrylonitrile (68.1 moles, 4.46 L) and DBU (0.684 L, 4.54 moles) at room temperature and the reaction mixture heated to +60° C. for 16 hours. The reaction was cooled to room temperature, diluted with MTBE (25 L), transferred into a 100 L extractor and washed with 5% aqueous KH$_2$PO$_4$ (20 L). The layers were separated, the organics washed with water (2×18 L) and concentrated. The solution was solvent switched to MeOH to afford the coupled nitrile (10.5 kg by assay) as a solution in MeOH (30 L total volume), which was used as is in the next step.

Step 3: Amidoxime Formation

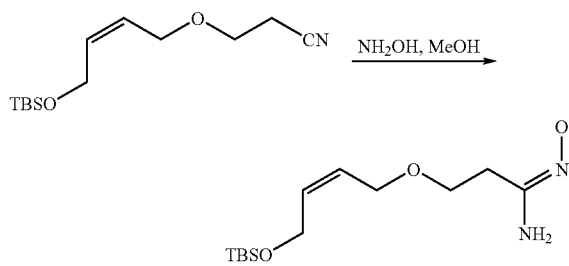

A 75 L 3-necked RB flask was charged with a solution of the coupled nitrile of Step 2 (10.42 kg, 40.8 moles in 30 L of MeOH). Hydroxylamine (50% aqueous, 2.75 L, 44.9 moles) was added at room temperature in one portion and the resulting solution heated to +60° C. for 6 hours (circa 99.8 A % conversion). The reaction mixture was cooled to room temperature, transferred into an extractor containing MTBE (35 L) and water (35 L). The layers were separated (pH ~9) and the organic phase washed with 5% brine (2×18 L). The aqueous portion was back extracted with MTBE (15 L). The combined organic layers were concentrated to an oil and solvent switched to methanol (circa 3 L/kg solution) to afford a solution of the amidoxime which was used as is in the next step.

Steps 4 and 5: Pyrimidinone Formation

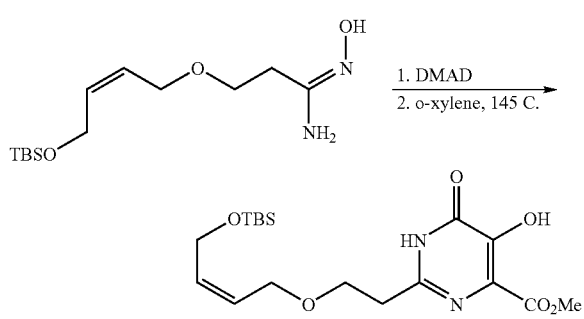

A 75 L 3-necked RB flask was charged with amidoxime solution of Step 3 (10.95 kg, 38 moles in 27 L of MeOH). The reaction mixture was cooled to −20° C. and DMAD (4.67 L, 38 moles) added over 45 minutes keeping the temperature below +5° C. The reaction mixture was concentrated and solvent switched to o-xylene to make a 50 wt % solution. A 100 L 3-necked RB flask was charged with o-xylene (55 L) and heated to 143-145° C. (gentle reflux). DMAD adduct in xylene (7.4 kg assay, circa 50 wt % o-xylene solution) was added over 2 hours to the hot o-xylene solution. The reaction mixture was aged 3 additional hours at the end of the addition, allowed to cool slightly to about +130° C. and o-xylene (15 L) distilled under partial reduced pressure (internal temp circa 120-130° C.). The reaction mixture was allowed to cool to room temperature to give a slurry of crystallized pyrimidinone. The slurry was aged overnight at room temperature. Heptane (circa 45 L) was added over 2 hours and then aged for 2 hours. The slurry was filtered and the cake washed with 1/1 toluene/heptane (15 L) and then with heptane (10 L). The cake was dried under vacuum and a stream of nitrogen for 3 days at room temperature to give the TBS-pyrimidinone (3.75 kg, >97 A %, 85 wt %, 47% yield).

Step 6: Besylation

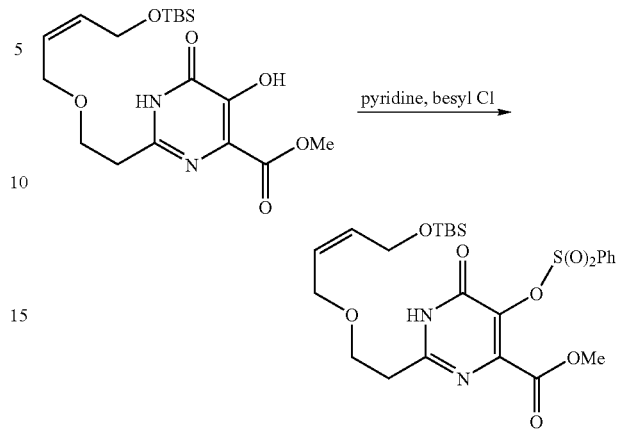

TBS pyrimidinone prepared as described in Steps 4 and 5 (7.2 kg, ~85 wt %) was charged to a 100 L RB flask. Pyridine (10.5 kg) was added at room temperature, followed by the addition of benzenesulfonyl chloride (3.70 kg) over 30 minutes while maintaining the temperature at 25-30° C. The solution was stirred at 25-30° C. for 2 hours. The batch was cooled to 20° C. and methanol (21 L) added followed by water (17.5 L). The slurry was stirred at 28-30° C. for 30 minutes. Water (17.5 L) was added at 20-25° C. The slurry was aged 30 minutes. Slurry was filtered and cake washed with MeOH/water (3:5 v/v, 30 L). The cake was dried in a nitrogen stream on the filter pot overnight to give the TBS besylate (10.3 kg, 71 wt %, 88% yield).

Step 7: De-TBS and Acetate-Besylate Formation

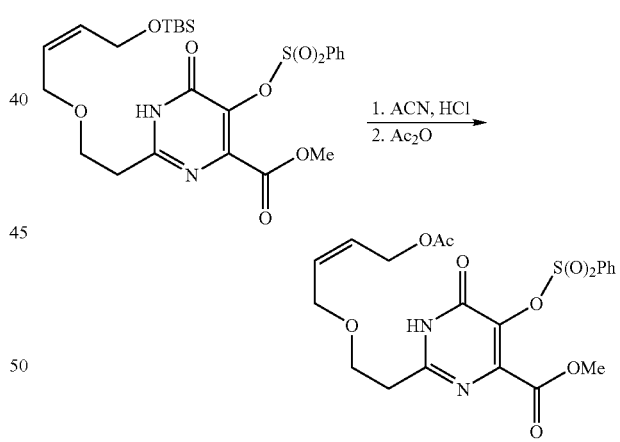

TBS besylate of Step 6 (9.9 kg, 71 wt %) was charged to a 50 L RB and acetonitrile (18 L) added. Conc-HCl (95 mL) was added and the solution stirred at 15-18° C. for 1 hour. The mixture was washed with heptane (2×9 L). The acetonitrile layer was charged to a 72 L RB and pyridine (190 mL) added. The solution was concentrated to approximately 15 L and flushed with acetonitrile (18 L). Acetic anhydride (4.5 kg) was added and the solution warmed to 75° C. for 3 hours. IPA (30 L) was added and the batch concentrated under reduced pressure (50° C.) to remove approximately 20 L solvent. IPA was added to obtain final volume of 55 L at 50° C. The solution was treated with DARCO-G60 (activated carbon, 900 g), stirred at 50° C. for 1 hour and filtered warm through a small solka-floc pad into a 100 L RB. The cake was washed with IPA (10 L) at 50° C. The combined filtrates were stirred, cooled to 30° C. and seeded with product (1 g). The slurry was allowed to cool to 20° C. over 1 hour and then cooled to 2° C. and aged 1 hour. The slurry was filtered and washed with IPA (10 L) and heptane (10 L). The cake was dried to give the acetate-besylate (5.2 kg, >98 wt %, 86% yield)

Step 8: Intramolecular Allylation

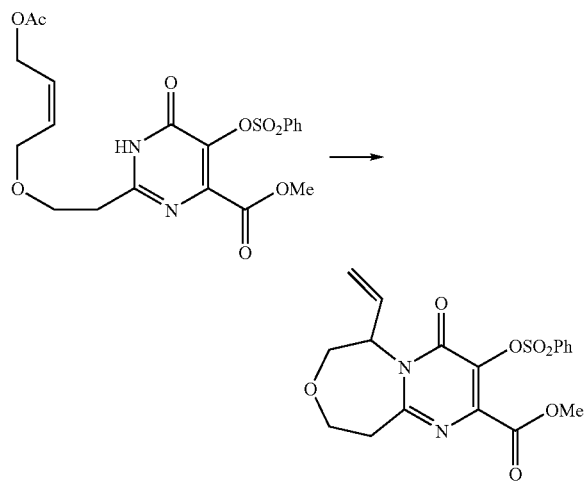

A solution of the acetate besylate of Step 7 (2.50 kg) and tetrabutylammonium bromide (173 g) in DCM (20 L) was degassed with nitrogen. Degassed DCM (6.8 L) was added to a mixture of $Pd_2 dba_3$ (37 g) and (R,R)-Napthyl Trost ligand (1R,2R)-(+)-1,2-Diaminocyclohexane-N,N'bis(2-diphenylphosphino-1-naphthoyl, CAS Registry No. 174810-09-4) (134 g). After stirring for 10 minutes, the catalyst solution was transferred to the stirred reaction vessel. The reaction mixture was aged for about 8 hours with periodic sampling to determine the end of reaction. Solid $Pd(OAc)_2$ (60 g) was added to quench the reaction. The resultant solution of allylated product was carried forward to the next step. Two batches were run at the same scale.

Step 9: Hydrogenation

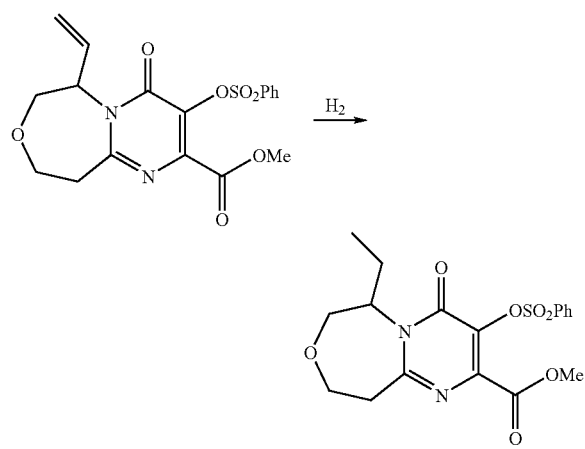

5% Pd (S)/C (828 g) was added to the DCM solution of allylated product of Step 8 (2.03 kg, assuming 100% yield). The slurry was charged to a 10 gallon stirred autoclave. The reaction vessel was pressurized with hydrogen to 45 psi and heated at 30° C. until hydrogen uptake showed complete conversion. This was repeated on a second batch.

The two hydrogenation batches were combined, MTBE (2.5 L) was added and the mixture was then stirred with $MgSO_4$ (0.8 kg) and $K_2HPO_4$ (0.8 kg) for 30 minutes. The mixture was filtered through silica (6 kg). The silica pad was washed with 9:1 DCM/MTBE (25 L). The combined filtrates were concentrated and solvent switched to isopropyl acetate (circa 13 L). The mixture was cooled to 22° C. over 1 hour. The resulting slurry was filtered on a pad of silica (0.25 kg) and the filter cake of racemate was washed with iPrOAc (4 L) to give on drying the racemic ethyl oxepanopyrimidinone (0.17 kg, 10-20% ee). The filtrates were concentrated and solvent switched to IPA (13 L). The mixture was treated with Darco G60 (0.3 kg) at 80° C. for 1 hour. The mixture was filtered hot through a pad of Solkafloc, and washed with hot IPA (4 L) and acetone (1.3 L). The combined filtrates were solvent switched to IPA at 60-80° C. and cooled to 23° C. over 3 hours. The slurry was cooled to 10° C. over 2 hours and filtered. The cake was washed with IPA (3 L) at 10° C. The cake was dried under nitrogen stream to give the ethyl oxepanopyrimidinone (3.186 kg, 95 wt % purity).

Step 10: Bromination

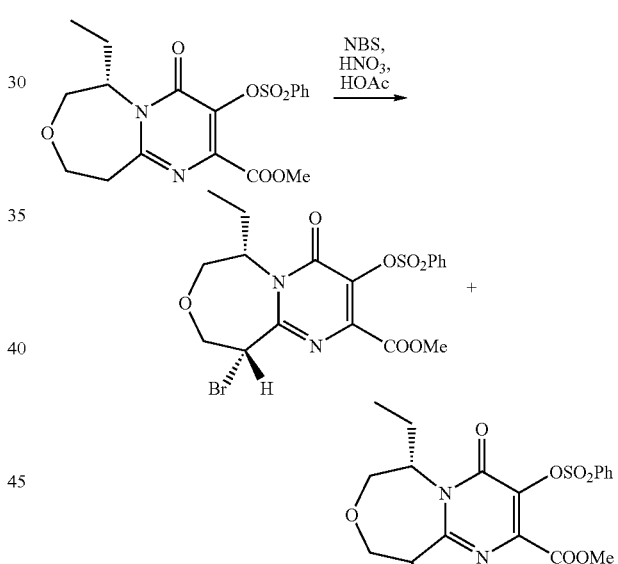

Ethyl oxepanopyrimidinone of Step 10 (4.08 kg, 10 mol) was suspended in acetic acid (30 L) in a 100 L 4-neck RB flask. NBS (5.3 kg, 30 mol) was added followed by concentrated nitric acid (3 L). The mixture was warmed to 75° C. over 30 minutes and the resulting homogenous orange mixture was maintained at 72-80° C. for 3 hours. A small amount of bromine vapor evolved during the reaction. The mixture was concentrated under vacuum (50 Torr at 50° C.) to remove 5 L orange distillate, leaving a pale yellow residual solution. The mixture was cooled to 20° C., DCM (15 L) and water (20 L) were added. The organic layer was separated and the aqueous phase back-extracted with DCM (5 L). The combined organic phases were washed with water (20 L) and 1.67M aqueous $K_2 HPO_4$ (30 L). The combined DCM extracts were dried over $MgSO_4$ (100 g), filtered and concentrated. The residue was solvent switched to circa 10 L THF with a 4:3 mixture of di-bromo/mono-bromo products, which was used directly in the next step.

Step 11: Mono-Bromide Formation

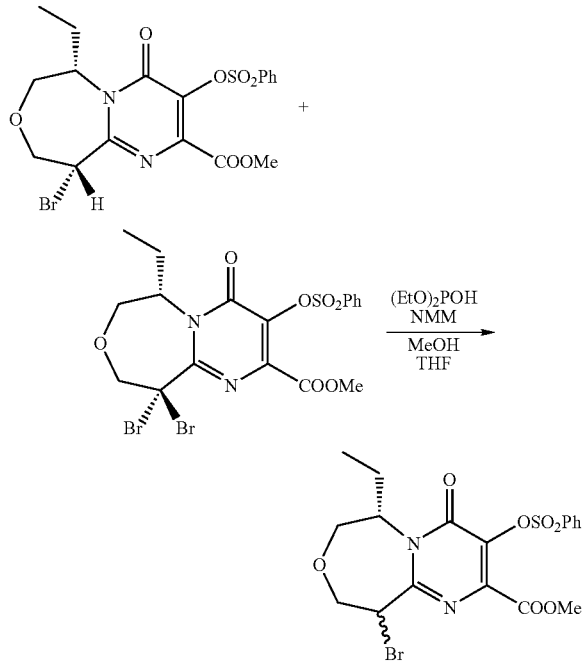

To the circa 4:3 mixture of di-bromo/mono-bromo oxepanopyrimidinones (4.8 kg) from the previous step was added MeOH (20 L), NMM (708 g, 7 mol) and diethyl phosphite (967 g, 7 mol). The mixture was stirred for 1 hour at 25-40° C. Water (20 L) was added drop-wise over 2 hours while the mixture was gradually cooled to 10° C. The resulting slurry was filtered and the filter cake was washed with 1:1 MeOH/water (10 L) and dried to provide the diastereomeric mixture of syn/anti-monobromides. Syn monobromide: $^1$H NMR (CD$_3$CN 400 MHz) 7.94 (m, 2H), 7.78 (m, 1H), 7.63 (m, 2H), 5.33 (dd, 1H, J=2.7, 1.6), 4.88 (m, 1H), 4.25 (dd, 1H, J=14.3, 3.4), 4.14 (dd, 1H, J=14.3, 2.9), 4.07 (dd, 1H, J=14.3, 1.6), 3.73 (s, 3H), 3.70 (m, 1H), 2.39 (m, 1H), 1.99 (m, 1H), 0.87 (t, 2H, J=14.9); Anti monobromide $^1$H NMR (CD$_3$CN 400 MHz) 7.94 (m, 2H), 7.78 (m, 1H), 7.62 (m, 2H), 5.47 (dd, 11H, J=10.0, 2.8), 5.03 (m, 1H), 4.36 (dd, 1H, J=12.4, 2.8), 4.07 (dd, 1H, J=14.0, 4.3), 3.82 (dd, 1H, J=12.4, 10.0), 3.74 (s, 3H), 3.72 (m, 1H), 1.98 (m, 1H), 1.86 (m, 1H), 0.85 (t, 2H, J=14.9).

Step 12: Amidation

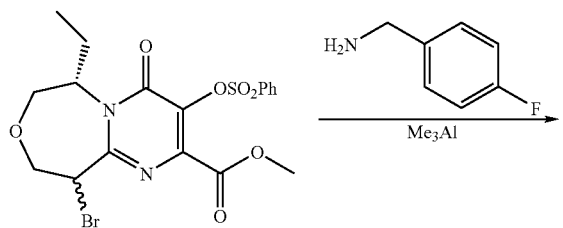

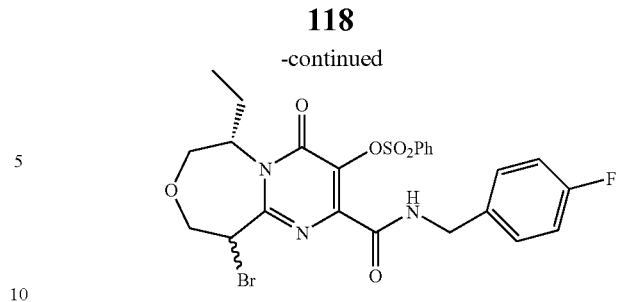

DCM (10.5 L) was charged a 50 L round bottom flask. 4-Fluorobenzylamine (578 g, 4.62 Mol) was added and the slightly yellow solution degassed with N2 for approximately 60 minutes. Me$_3$Al (2M in hexanes, 2.3 L, 4.62 Mol) was added slowly to the benzylamine solution over 60 minutes. The solution was aged at room temperature for 75 minutes. The bromide product of Step 11 (1.5 kg, 3.08 mol) dissolved in DCM (6 L) was added to the amine-Al complex solution over 20 minutes. The slight exotherm was controlled with an ice bath. The reaction mixture was aged at room temperature for 60 minutes. On complete reaction the mixture was pumped into a 50 L cylindrical vessel containing 1N HCl (15 L) at 10° C. The relatively large exotherm and rapid gas evolution was controlled by the slow addition of the mixture to the aqueous HCl. The organics were washed with 1N HCl (2×15 L), saturated NaHCO$_3$ (15 L) and saturated brine (15 L) at room temperature. The organic layer containing the amide product (1.69 kg by HPLC assay, 95%) was concentrated and solvent switched to methanol. The final volume of the MeOH solution was approximately 25 L and the solution of the amide was used in next step without further purification.

LCMS: (M+H)$^+$=582.0.

Two batches were run at the same scale.

Step 13: Methylamine Displacement

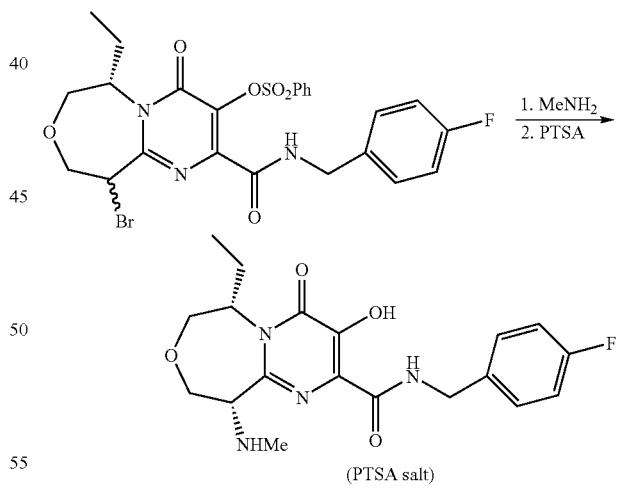

A 100 L cylindrical vessel equipped with cooling jacket, overhead stirrer, temperature probe, was charged with the starting material solution in methanol (2.80 kg by HPLC). The batch volume was 28 L. The batch was cooled to 5° C. Methylamine solution (33% wt, 8 M, 3.15 L) in ethanol was added over 15 minutes. Slight exotherm was observed and the batch temperature went to 11° C. After aging for 30 minutes, the batch was warmed to 20° C. over 1 hr. Separately a 1 M solution of PTSA was prepared by mixing p-TSA monohydrate (3.67 Kg) and 16 L water. This solution was charged into the batch 4 hours after methylamine addition. The batch temperature went to 28° C. due to exotherm. The batch was seeded. After stirring for 3.5 hours, a thick slurry was formed. Water (45 L) was added to the batch over 45 minutes. The batch was aged at 20° C. overnight (9 hours). The solid product was collected by filtration and the wet cake was washed with 2/1 water/MeOH (3×5 L) and water (10 L). The wet cake was dried on the filter pot with nitrogen flow overnight then in 35-40° C. vacuum oven with nitrogen flow for 3 days. The crude product was slurried in ethyl acetate (27 L), agitated for 2 hours and filtered. The wet cake was washed with ethyl acetate (13 L) and then dried on filter pot with nitrogen flow and vacuum suction overnight to give aminep-TSA salt (2.15 kg, 79%). The diastereomeric excess was 97:3 in the displacement reaction and was 98.5/1.5 after isolation as the tosylate. LC-MS M+1 391

NMR data: $^1$H NMR (500.1 MHz, CD$_3$OD) δ 7.63 (d, J=8.2 Hz, 2H), 7.37 (m, 2H), 7.18 (d, J=8.2 Hz, 2H), 7.04 (m, 2H), 4.97 (t, J=5.1 Hz, 1H), 4.60 (m, 1H), 4.54 (s, 2H), 4.13 (d, J=5.1 Hz, 2H), 4.06 (dd, J=12.9, 7.8 Hz, 1H), 3.84 (dd, J=12.8, 3.0 Hz, 1H), 2.85 (s, 3H), 2.36 (s, 3H), 2.19 (m, 1H), 1.96 (m, 1H), 1.07 (t, J=7.4 Hz, 3H).

Step 14: Acylation

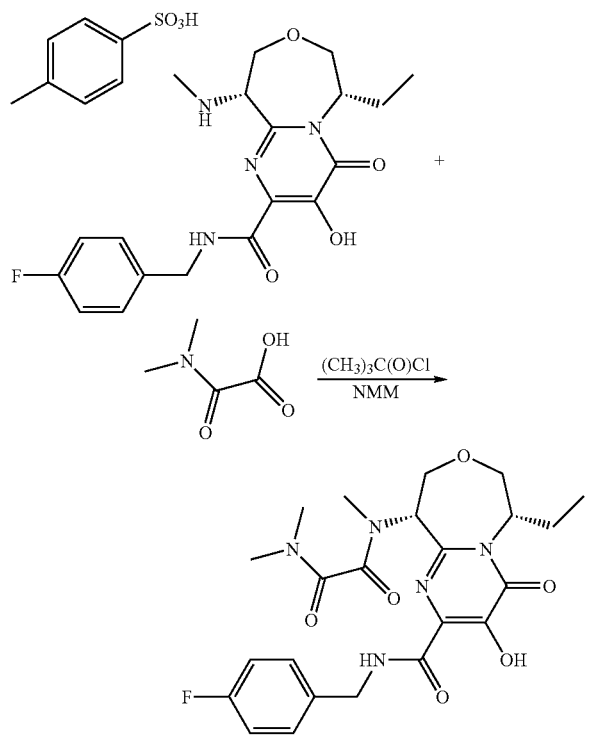

A 50 L flask was charged with dimethyloxamic acid (0.64 kg), DCM (16 L), and NMM (1.12 kg). The mixture was cooled to 15° C. Pivaloyl chloride (0.62 kg) was added and aged 2 hours at room temperature. Amine PTSA salt of Step 13 (2.01 kg) was added in one portion and aged 2 hours. The mixture was quenched with water (12 L) and 5M HCl (0.21 L). The lower organic layer was separated and washed with water (2×12 L). The solution was concentrated to low volume and IPA (8 L) added. The solution was heated to 55-60° C., seeded (24 g Compound 5A, crystalline Form II), solvent switch continued at 55-60° C. by adding IPA to maintain the volume at approximately 10 L. The slurry was aged at 55-60° C. for 4.5 hours, cooled to room temperature and filtered. The cake was washed with IPA/heptane (2×8 L) and heptane (2×4.5 L) and dried in vacuo at room temperature to afford the title compound as a white crystalline solid (1.6 kg, >98 wt % purity, 91% yield). LCMS: (M+H)$^+$ 490.1; $^1$H NMR (500 MHz, CDCl$_3$): δ 12.32 (br.s, 1 H); 9.63 (t, J=6.1 Hz, 1 H); 7.40 (m, 2 H); 6.98 (m, 2 H); 5.85 (br s, 1H); 4.64 (m, 1H); 4.56 (d, J=6.5 Hz, 2 H); 4.45 (t, J=10.4 Hz, 1 H); 4.22 (d, J=3.1 Hz, 2 H); 4.15 (dd, J=11.8, 2.8 Hz, 1 H); 3.09 (s, 3 H); 3.04 (s, 3 H); 2.87 (s, 3 H); 2.08 (m, 1 H); 1.85 (m, 1 H); 1.16 (t, J=7.3 Hz, 3 H).

The title product was dry milled using a pin mill to a mean particle size of about 23 microns and a particle size range of from about 0.9 to about 160 microns, as determined using a Microtrac particle size analyzer with laser diffraction technology. The milled product can be employed in biological studies such as the determination of the compounds pharmacokinetics in animals or humans.

EXAMPLE 13

Preparation of Compound 6A

Step 1: Preparation of the Vinyl Alcohol

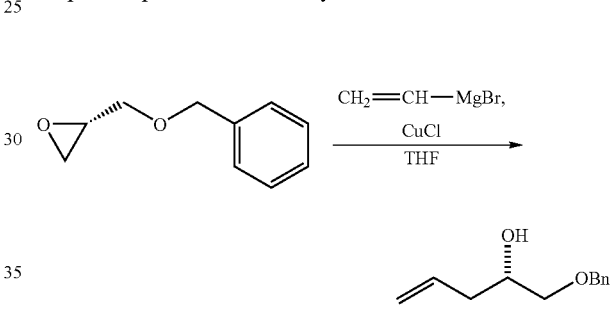

To a 400 L hastalloy vessel was charged vinyl magnesium chloride 1M in THF (372 kg). The vinyl magnesium chloride was transferred through a filter to a glass-lined vessel. The reagent was cooled to −10° C., and then copper(I) chloride was added (4.82 kg) under a nitrogen atmosphere.

(S)-(+)-Benzyl glycidal ether (40 kg) was charged to a glass-lined vessel, followed by THF (177.8 kg), and the solution cooled to 0° C. This solution was added to the vinyl magnesium chloride over a period of 3 hours while maintaining the reaction temperature below 0° C. The mixture was aged for ten minutes at which point HPLC indicated the reaction was complete. The reaction mixture was then quenched by adding methanol (19.5 kg) over a period of 2 hours while maintaining the temperature below 25° C. and concurrently controlling ethylene emissions. After the methanol quench, 2N HCl (412 kg) was added over a period of 45 minutes, and the batch was then stirred at room temperature overnight. The aqueous and organic layers were then separated, the aqueous layer was back-extracted with MTBE (148 kg), and the combined organics were washed sequentially with 1N HCl (98 kg), water (50 kg), Na$_2$S$_2$O$_3$ (10% in 100 kg water), and water (200 kg). The batch was then concentrated to a volume of 80 L, and then DMAC added (83 kg), followed by heptane (800 L), and the solution was distilled to about 170 L to afford a solution of the alcohol (150 L total; 44.86 kg assay; 96% yield).

Step 2: Methylation

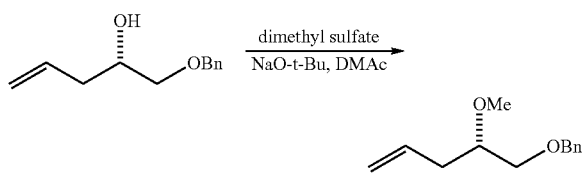

The DMAC solution of the alcohol of Step 1 plus a DMAC rinse (50 kg) were charged to a glass-lined vessel, and the solution was cooled to 0° C. Sodium tert-butoxide (32.3 kg) was charged in six portions, and the mixture was aged for 15 minutes, and then re-cooled to 0° C. Dimethyl sulfate (40.9 kg) was then added over 40 minutes while maintaining an internal temperature of less than 25° C. The reaction mixture was then aged for 30 minutes at 20° C. 2N HCl (145 kg water and 34.2 kg conc. HCl) was then added to the reaction mixture, over 30 minutes, followed by MTBE (133.2 kg). The lower aqueous acidic layer was removed and the organic washed with 5 wt % solution of LiCl twice (200 L followed by 150 L), followed by water (150 kg). The organic was concentrated to 50-60 L while maintaining the internal temperature at less than 35° C. Heptane (200 L) was then charged and concentrated to 50-60 L while maintaining internal temperature at less than 35° C. The concentrated solution was diluted with heptane (140 L) and filtered to a clean, plastic-lined steel drum (227 L total; 47.02 kg assay; 96% assay yield and KF 79 ppm).

Step 3: Hydroboration to Give the Primary Alcohol

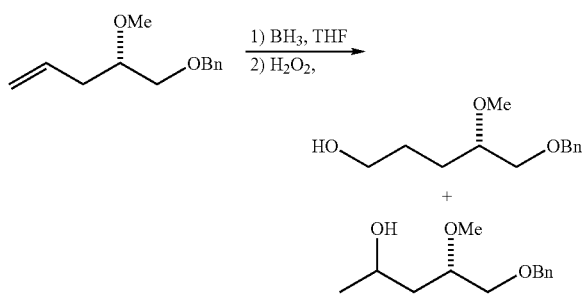

The methyl ether of Step 2 (23.5 kg, in heptane 29.5 wt. %) was charged to a glass-lined steel vessel under insert gas. The solution was cooled to 0° C., and then 1M borane in THF (51.2 kg) was charged over a period of 30 minutes while maintaining the temperature at less than 20° C. The mixture was then aged for 15 minutes, after which HPLC confirmed complete reaction. The reaction was quenched by carefully adding 2M NaOH (61.4 kg) over 20 minutes while maintaining the temperature at less than 20° C. The batch was re-cooled to 0° C., and the reactor headspace purged to remove any residual $H_2$.

Once the quench was complete, $H_2O_2$ (11.63 kg) was charged over 50 minutes while maintaining the temperature at less than 20° C., followed by a 1 hour age. The batch was re-cooled to 0° C., and the reaction quenched by adding 10% $Na_2S_2O_3$ (94 kg) over a period of 1 hour while maintaining the temperature at less than 20° C. The headspace was again purged, to remove any traces of oxygen.

The biphasic mixture was allowed to settle, and the lower organic phase removed. The aqueous phase was back-extracted twice with MTBE (89.4 kg). The combined organics were concentrated to a volume of 50 L. Heptane (100 kg) was added to the concentrated organics and the batch re-distilled to 50 L. DCM was added (67.5 kg), and the batch was dropped to a clean plastic-lined drum. The vessel was rinsed with DCM (67.5 kg), to give a final DCM:heptane solution of the product (169.8 kg; 23.41 kg product, 91%).

Step 4: Oxidation to Aldehyde

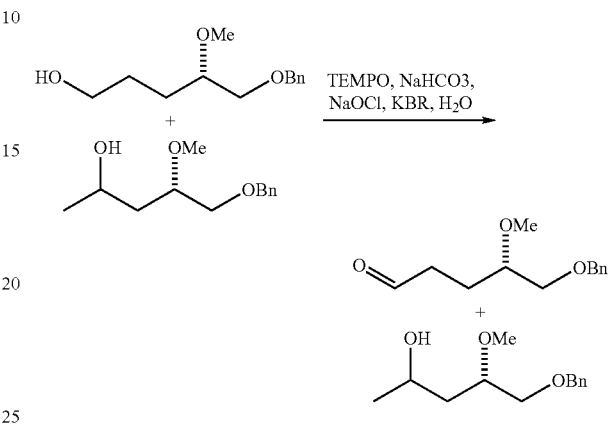

$NaHCO_3$ (3.07 kg) and KBr (1.86 kg) were charged to a glass-lined steel vessel. After purging the vessel with $N_2$, water (70 kg) was added. The alcohol in DCM:heptane of Step 3 (169.8 kg, 13.79 wt %) was charged through a filter into the vessel, the mixture was cooled to 0° C. TEMPO (0.49 kg) was then added, followed by the addition Na hypochlorite (95 kg) over a period of 1 hour while maintaining the temperature at less than 20° C. HPLC indicated that the reaction was not complete after a 10 minute age, and additional Na hypochlorite (20 kg) was added to complete the reaction. The reaction was quenched by the addition of 10% aqueous solution of $Na_2S_2O_3$ (51.5 kg), which was added over a period of 20 minutes while maintaining the temperature at less than 20° C. The lower organic phase containing product was removed and the aqueous layer extracted with MTBE (58.4 kg). The combined organic streams were charged to a clean plastic-lined steel drum (22.04 kg of product, as a solution in MTBE/DCM; 9.87 wt %, 95%).

Step 5: Preparation of the Bisulfite Adduct

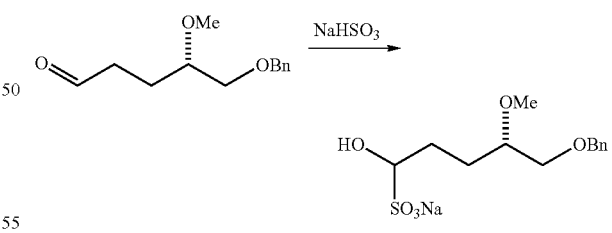

Sodium metabisulfite (11.9 kg) and water (55.1 kg) were charged to a glass-lined steel vessel, followed by the addition of the aldehyde of Step 4 (223.4 kg, 9.87 wt %), and the mixture was then warmed to 28° C. After a ten minute age, HPLC confirmed formation of the bisulfite adduct. The biphasic mixture was allowed to separate, and the aqueous layer containing product was removed. The organic layer was washed with water (55.2 kg), and the two aqueous phases were then combined, and washed with MTBE (55.1 kg). The aqueous layer was placed in a clean plastic-lined steel drum (31.2 kg of bisulfite adduct in water; 21.75 wt %).

Step 6: BOC-Protected Strecker Adduct Prep

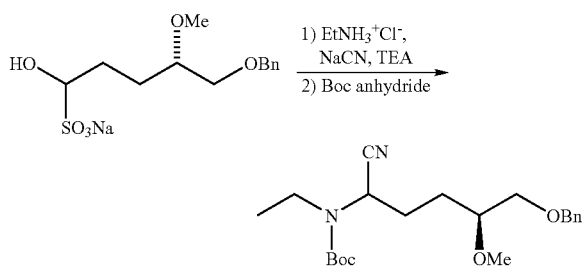

Ethylamine.HCl (11.69 kg) and NaCN (7.03 kg) were charged to a 400 L glass-lined steel vessel equipped with a scrubber containing 1% NaOCl and 1M NaOH (250 L). The vessel was re-inerted using a vacuum/N2 cycle, after which water (106.1 kg) added, followed by methanol (74.04 kg). The solution was stirred for 5 minutes, and then the bisulfite adduct solution in water of Step 5 (143.4 kg, 21.75 wt %) was charged. TEA (29.22 kg) was then charged over a period of 15 minutes while maintaining the temperature at less than 30° C. The mixture was then aged for a total of 3 hours. HPLC indicated incomplete reaction, so additional NaCN (0.703 kg, 0.15 equiv.) and ethylamine.HCl (1.17 kg, 0.15 equiv.) were charged, followed by TEA (2.9 kg, 0.3 equiv.). MTBE (69.4 kg) was then added to the reaction mixture. The aqueous phase containing cyanide residues was cut away, and the organic phase was then washed with 5% NaHCO3 solution (93.6 kg).

Boc anhydride (22.95 kg) was charged to a glass-lined steel vessel pre-warmed to 30° C. After vacuum/N2 cycle on the vessel, the BOC anhydride was dissolved in MTBE (46.24 kg), the resulting solution was cooled to 25° C., and the cooled solution added to the Strecker adduct solution over a period of 10 minutes. The batch was then aged for a total of 48 hours at 25° C. HPLC indicated incomplete reaction, so a further charge of BOC-anhydride (13.72 kg, 1.3 equiv.) was made, the mixture stirred at 25° C. for 16 hours, and then the batch warmed to 50° C. for 5 hours. 10% NaHCO3 solution (93.6 kg) was then added. The aqueous phase was removed, and the organics were concentrated to a volume of 63 L. Methanol (123.4 kg) was added and the batch concentrated to 63 L. Methanol (123.4 kg) was added and the solution was placed in a clean, plastic-lined steel drum (30.6 kg of BOC Strecker adduct formed as a solution in methanol; 27.8 wt %, 90%).

Step 7: Amidoxime Formation

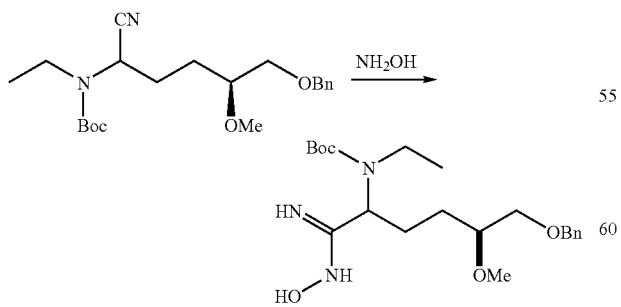

The methanol solution of the nitrile of Step 6 (30.6 kg, 110 kg at 27.7 wt %), MeOH (47 kg) and water (30 kg) were charged to a glass-lined vessel and the mixture was stirred at 25° C. Hydroxylamine (10.7 kg) was added to the reaction mixture over 30 minutes while maintaining the temperature of the batch at 40° C. or less. The resulting stirred solution was heated to 50° C., and aged at this temperature for 14 hours. The reaction mixture was then cooled to 25° C., and MTBE (89 kg) was added. Aqueous AcOH (9.7 kg in 150 kg water) was added, and the reaction mixture stirred for 15 minutes. The aqueous layer was removed, followed by the organic. The aqueous layer was back extracted twice with MTBE (57 kg, then 77 kg). The combined organic extracts were analysed for residual hydroxylamine content. The batch was concentrated, using partial vacuum, to a volume of ~200 L. The MTBE solution of the amidoxime was stored in a plastic lined steel drum under nitrogen at 5° C. for later use.

Step 8: DMAD Adduct Formation

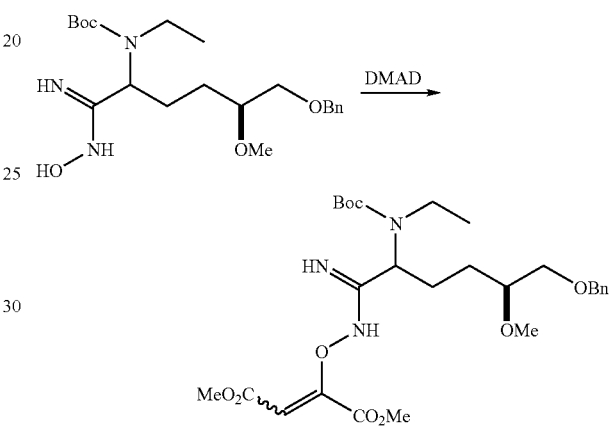

The solution of the amidoxime in MTBE of Step 7 was charged to a glass-lined vessel, followed by the addition of MeOH (26 kg). The resulting solution was cooled to 0° C., then DMAD (12.12 kg) was added over 15 minutes while maintaining the temperature at 10° C. or less. The solution was warmed to 20° C., and aged at this temperature for 16 hours. Aqueous NaHCO3 (6.6 kg in 132 kg water) was added to the batch and stirred for 15 minutes. The aqueous layer was removed, and the organic layer washed with water (60 kg). The batch was concentrated, using partial vacuum, to a volume of approximately 80 L. Toluene (173 kg) was added to the batch, and concentrated using partial vacuum to a volume of approximately 190 L. This afforded a 24.3 wt % solution of the DMAD adduct (159.4 kg total; 38.74 kg assay; 87% yield over 2 steps), which was stored in a plastic lined steel drum under nitrogen at 5° C. for later use.

Step 9: Pyrimidinone Formation

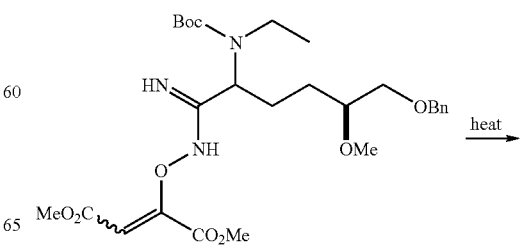

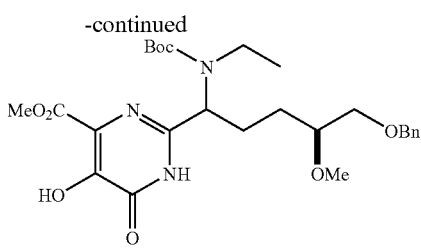

The DMAD adduct solution in toluene of Step 8 (158.6 kg, 24.46 wt %) was transferred over a period of 2 hours to a glass-lined steel vessel containing refluxing xylenes (137.6 kg, 160 L) at approximately 140° C. The toluene and MeOH were allowed to distil-out as during the transfer of the adduct. A second charge of xylenes (86 kg, 100 L) was charged to the vessel, and distillation continued until a final volume of 260 L was achieved. The batch was cooled to 25° C. over a period of seven hours, after which HPLC indicated complete reaction. The reaction stream was filtered, and washed with xylenes (2×17.2 kg) to afford a 15.67 wt % solution of the pyrimidinone (148.7 kg total; 15.7 WT. %, 23.3 kg assay; 66%), which was stored in a plastic lined steel drum under nitrogen at 5° C. for later use.

Step 10: Amide Formation

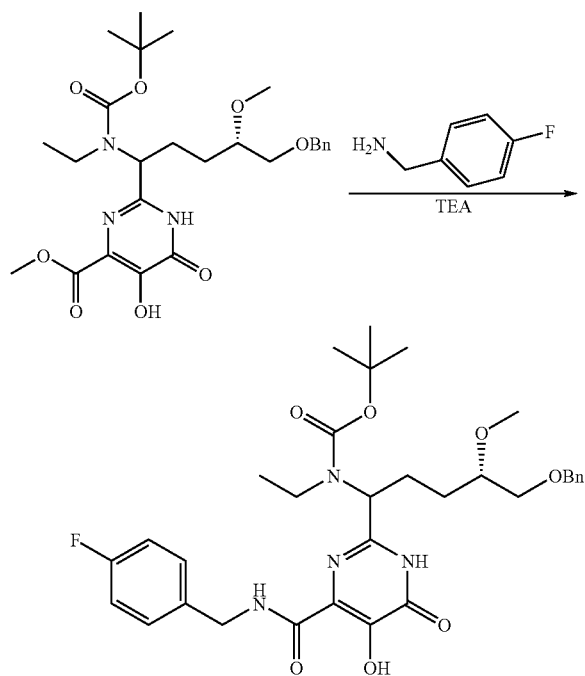

The xylene solution of the pyrimidinone methyl ester of Step 9 (23.3 kg as a 15.7 wt % solution in xylenes; 148.7 kg) was charged to a glass-lined vessel equipped with a scrubber containing 1N HCl (200 L). The xylene solution was then concentrated via distillation to a final volume of 50 L (2.15 vol). Methanol (184.5 kg) was then charged to the vessel, followed by TEA (9.08 kg) and 4-fluorobenzylamine (7.5 kg). The vessel contents were heated to 63° C., and aged at that temperature for a period of 16 hours. The batch was cooled to less than 40° C., and additional 4-fluorobenzylamine (4.88 kg, 0.5 eq) was charged. The batch was left at 62° C. for a further 16 hours, then cooled to ambient temperature and aged for a further 48 hours. The batch was then re-heated to mild reflux for a further 3 hours. The vessel contents were concentrated to a final volume of 80 L, then MTBE (148 kg) was added. The organic stream was washed sequentially with 5% NaHCO₃ solution (100 kg), 10% AcOH solution (100 kg), 1N HCl (50 kg), and water (100 kg). The organics were concentrated to a final volume of 50 L. Ethanol (78.9 kg) was added and the organic stream concentrated to a final volume of 138 L. The contents of the vessel were transferred to a clean, plastic-lined steel drum (18 wt %, 23.23 kg amide, 90%).

Step 11: Debenzylation

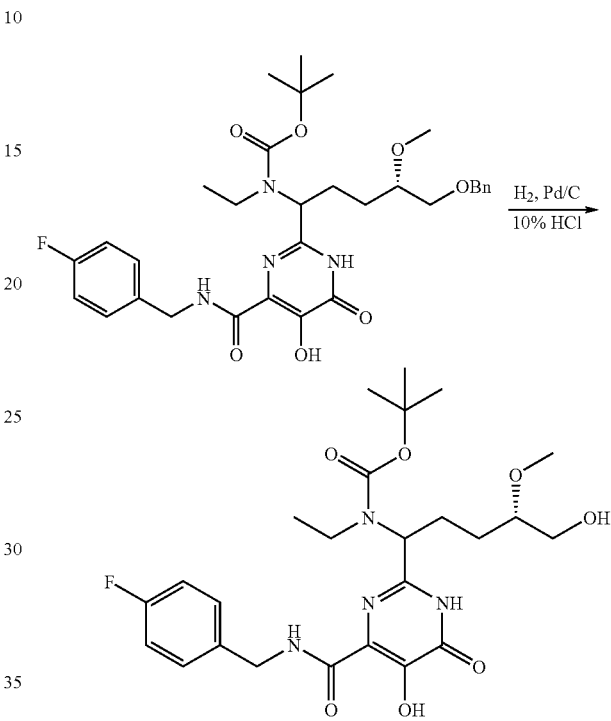

The starting amide solution (15.5 kg) in ethanol (total 93.4 L; 86.2 kg+ethanol rinse (10 L)) was added to a reaction vessel containing 20% Pd/C (3.10 kg), followed by the addition of 1N aqueous HCl (3.1 L). The vessel was evacuated and purged with nitrogen and the mixture adjusted to a temperature of approximately 20° C. The vessel was then evacuated and then set to a hydrogen pressure of 4.1 Barg. The reaction mixture with stirring was warmed to 40° C. until the hydrogen uptake ceased. The reaction mixture was then filtered through solka floc, washed with ethanol (40.4 kg) and collected in a clean, steel, plastic-lined drum (137 L total; 12.56 kg assay; 95% assay yield). A second run was conducted.

The batches of alcohol in ethanol from the two runs were combined (182.8 kg, 10.28 wt %) was charged to a glass-lined vessel and the solution concentrated to a final volume of 50 L. MTBE (111.6 kg, 151 L) was added, followed by TEA (7.35 kg, 2 eq) and water (150.7 kg). The resulting mixture was stirred for 15 minutes. The aqueous layer, containing product, was removed, followed by the organic. The aqueous was washed with MTBE (2×41.8 kg). The combined MTBE cuts were washed with a solution of TEA (0.73 kg, 0.2 eq) in water (56.5 kg). The lower aqueous phase was removed and combined with the previous aqueous phase (both containing product). To the aqueous phase containing product was added MTBE (112 kg), followed by 1N HCl (98 kg). The mixture was stirred for 30 minutes and then the lower aqueous layer was removed. The organic stream, containing product, was concentrated to a volume of 40 L, then flushed with THF (178 kg) and concentrated to 94 L. This afforded a THF solution of the alcohol (18.45 kg assay; 98% recovery), which was stored in a plastic lined steel drum under nitrogen at 5° C. for later use.

Step 12: Mesylation and Cyclization of the Seven-Membered Ring

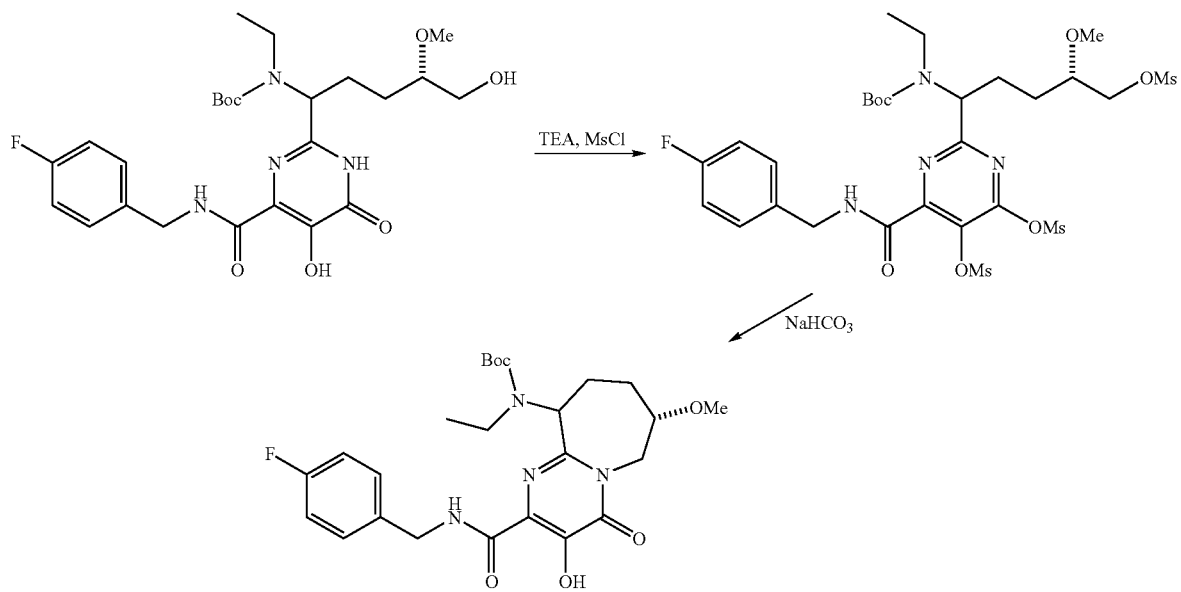

A THF solution of the product of Step 11 was charged to a glass-lined vessel and then cooled to 0° C., after which TEA (19.6 kg) was added over 15 minutes while maintaining the temperature at 10° C. or less. MsCl (16 kg) was added over 35 minutes while maintaining the temperature at 10° C. or less. The solution was aged at 10° C. for 10 minutes. Water (53 kg) was then added, followed by aqueous 2N HCl (3.85 kg in 50 kg water). MTBE (111 kg, 150 L) was added and the batch stirred for 15 minutes. The aqueous layer was removed, followed by the organic layer. The aqueous cut was back extracted with MTBE (37 kg), and the combined organics washed with water (40 kg). The batch was concentrated, using partial vacuum, to a volume of approximately 80 L. Toluene (87 kg) was added to the batch, and concentrated, using partial vacuum, to a volume of approximately 60 L (KF=1437 ppm). The mesylate solution was then diluted with DMSO (58 kg) and transferred to a glass-lined vessel.

NaHCO$_3$ (20.7 kg) was charged to a separate glass-lined vessel, followed by DMSO (117 kg), and the solution was heated to 35° C., after which the mesylate solution transferred thereto over 1 hour. The resulting mixture was heated to 80° C. The reaction mixture was heated at 80° C. for 16 hours, at which point HPLC analysis showed the reaction was complete. The batch was cooled to 25° C. EtOAc (89 kg) was added to the batch, followed by aqueous 2N HCl (14 kg in 95 kg water). The aqueous layer was removed, followed by the organic layer. The aqueous cut was back-extracted with EtOAc (82 kg), and the combined organics washed with water (90 kg). The batch was concentrated, using partial vacuum, to a volume of ~54 L (KF=138 ppm) to afford a 18.67 wt % solution of the cyclized product (83.7 kg total; 15.63 kg assay; 88% yield over 2 steps), which was stored in a plastic lined steel drum under nitrogen at 5° C. for later use.

Step 13: Formation of the Besylate

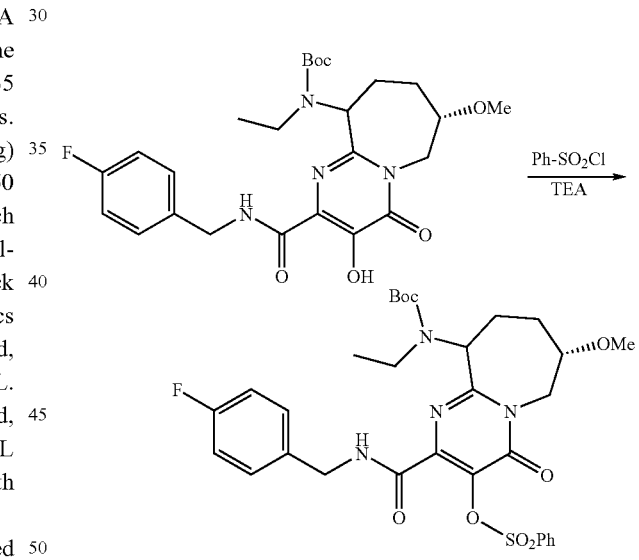

The phenol in ethyl acetate of Step 12 (15.5 kg; 83.6 kg at 18.5 wt %) was charged to a glass-lined steel vessel, and the solution cooled to 5° C. TEA (6.84 kg) was then added, followed by benzenesulfonyl chloride (10.85 kg) over a 10 minute period, while maintaining the batch temperature at less than 10° C. The batch was then aged at a temperature of less than 10° C. for 1 hour and then warmed to 20° C. and then the batch was stirred at this temperature for 16 hours. EtOAc (13.9 kg) was added, followed by water (31 kg) and TEA (300 g, 0.1 equiv). The mixture was warmed to 5° C. and aged for 2 hours, then cooled to 25° C., and DCM (104.6 kg) added. 1N HCl (38.6 kg) was added and the mixture stirred for 15 minutes. The organic phase was removed, and the aqueous layer was extracted with DCM (21 kg). The combined organics were washed with 5% NaHCO$_3$ solution (129 kg), which was then back-extracted with DCM (21 kg). The combined organics were concentrated under partial vacuum to a volume of 120 L. Ethyl acetate (50 kg) was added and the organics concentrated to a final volume of 170 L and used directly in the next step.

Step 14: Boc-Deprotection

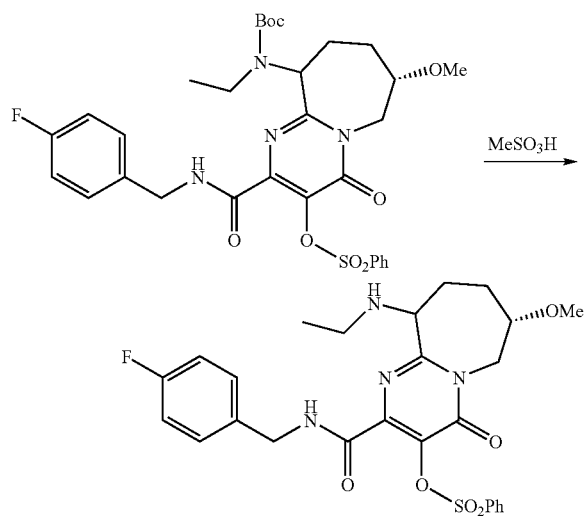

The Boc-amine solution in EtOAc of Step 13 (170 L, 16.8 kg) was charged to a glass-lined vessel, and the solution cooled to 15° C. Methanesulfonic acid (7.51 kg) was added over 20 minutes while maintaining the temperature at less than 30° C. The mixture was carefully heated to an internal temperature of 60° C. and aged for 3 hours. The mixture was then cooled to 10° C. and a 1 M $K_2CO_3$ solution ($K_2CO_3$ [10.8 kg] in water [78 kg]) was added while maintaining the temperature at less than 20° C. The aqueous layer was removed, followed by the organic layer. The aqueous cut was back-extracted with EtOAc (30.2 kg). The combined organics were washed with water (56 kg) and then concentrated to a final volume of 56 L. EtOAc (89 kg) was added to dilute the solution to 140 L to afford a solution of the amine (140 L total; 16.58 kg assay; 99% yield over 2 steps), which was stored in a plastic lined steel drum under nitrogen at 5° C. for later use.

Step 15: Formation of the Enamine

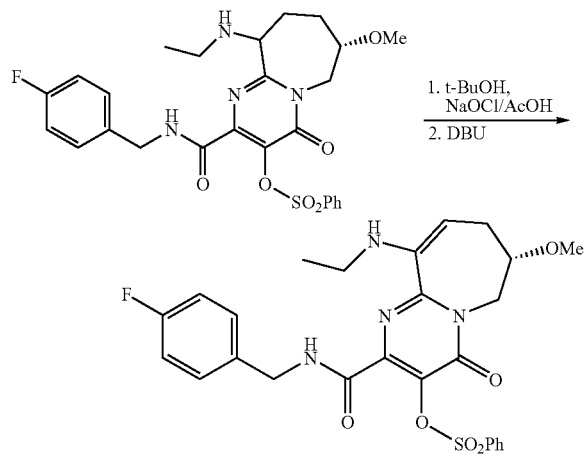

The EtOAc solution of the amine of Step 14 (140 L total; 16.58 kg assay) and t-butanol (1.13 kg) were charged to a glass-lined vessel, follow by the addition of t-butanol (1.13 kg). The resulting solution was cooled to 5° C., then acetic acid (2.01 kg) was added over 10 minutes while maintaining the temperature at 10° C. or less. Sodium hypochlorite (40.9 kg) was added over 40 minutes while maintaining the temperature at 10° C. or less. The solution was aged at 5° C. for 20 minutes. A further charge of sodium hypochlorite (11 kg, 0.3 equivalents) was made, and the batch aged for 10 minutes. The batch was warmed to 20° C. and stirring stopped. The aqueous layer was removed, and the organic layer washed with 5% aqueous NaCl (2.25 kg in 45 kg water). The batch was cooled to 5° C., then DBU (5.1 kg) was added over 20 minutes while maintaining the temperature at 10° C. or less. The batch was aged at 10° C. for 20 minutes, at which point HPLC analysis showed the reaction was >98% conversion to enamine.

Water (85 kg) was added to the batch and the mixture stirred for 15 minutes. The aqueous layer was removed, followed by the organic. The aqueous cut was back-extracted with EtOAc (46 kg), then the combined organics washed with sodium sulfite (1.92 kg in 16 kg water), then aqueous NaCl (1 kg in 51 kg water). The batch was concentrated, using partial vacuum, to a volume of ~50 L. MTBE (89 kg) was added to the batch over 20 minutes, the slurry cooled to 15° C. and aged overnight. The batch was filtered, washing the cake with MTBE (27 kg), then dried on the filter using a positive pressure of nitrogen (assay yield of 74%).

The enamine solid was then charged to a glass-lined vessel, followed by ACN (59 kg), and the resulting slurry was heated to 50° C. until all the solid had dissolved. Water (75 kg) was then added to the batch over 20 minutes. The batch was cooled to 5° C. over 1 hour, filtered, the resulting wetcake washed three times with a 1:1 mixture of ACN (6 kg) and water (8 kg), then dried overnight in the oven, under vacuum, at 50° C. to afford enamine as a yellow solid, 8.8 kg, 75% from the crude amine.

$^1$H NMR: (400 MHz, d6-DMSO): δ 9.15 (1H, t, J=6.0 Hz), 7.94-7.91 (2H, m), 7.80 (1H, t, J=7.6 Hz), 7.65 (2H, t, J=7.6 Hz), 7.35-7.30 (2H, m), 7.18-7.11 (2H, m), 5.15 (1H, t, J=5.4 Hz), 4.80 (1H, t, J=8.0 Hz), 4.35 (1H, dd, J=13.6, 3.6 Hz), 4.31 (2H, d, J=6.0 Hz), 3.92-3.86 (1H, m), 3.77 (1H, dd, J=13.6 Hz, 4.0 Hz), 3.26 (3H, s), 2.93-2.86 (2H, m), 2.32-2.25 (1H, m), 1.90-1.82 (1H, m), 1.15 (3H, t, J=7.0 Hz).

Step 16: Asymmetric Hydrogenation

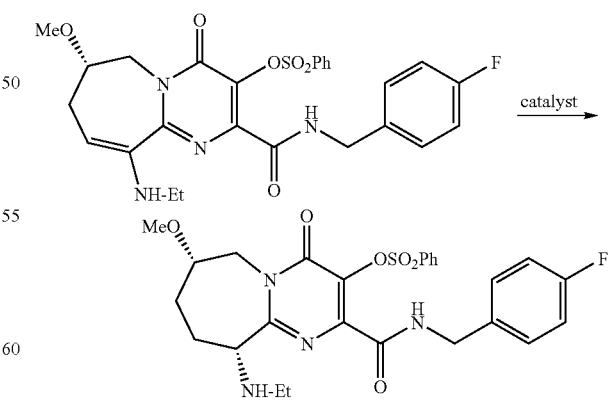

In a nitrogen-purged glovebox with $O_2$<5 ppm, bis(norbornadiene)rhodium (1) tetrafluoroborate (345 mg, 0.922 mmol), (S)-1-[(R)-2-(di-2-furylphosphino)ferrocenyl]ethyldi-tert-butylphosphine (505 mg, 0.968 mmol), and dichloromethane (4.6 mL) were added to a 20 mL vial. The catalyst mixture was stirred for 30 minutes and transferred to a 25 mL stainless steel vessel with the aid of 10 mL of 2,2,2-trifluoroethanol (TFE). 10 mL of TFE was added to a second 25 mL stainless steel vessel, and the catalyst charge apparatus was sealed and removed from the glovebox.

A solution of 12.16 mL (147 mmol) of dichloroacetic acid was prepared in 350 mL TFE. 55 mL (184 mmol) of titanium (IV) isopropoxide was added slowly with vigorous stirring and stirred until the mixture was homogeneous. The starting enamine (100 g, 184 mmol) was added with the aid of 50 mL TFE and stirred to give a dark red-orange solution. The solution was drawn via vacuum into a 1 L stirred autoclave with the aid of an additional 80 mL TFE. The catalyst charge assembly was attached via flexible tubing. The autoclave was inerted with three nitrogen/vacuum purges and placed under partial vacuum. The catalyst solution was drawn into the autoclave followed by the TFE rinse. The autoclave was subjected to three hydrogen purges, thermostatted to 25° C., and pressurized with hydrogen gas to 100 psig. The reaction mixture was agitated at 1000 rpm for 18 hours. LC-MS: $(M+H)^+=545.0$ The crude reaction solution was diluted with 1.5 L IPAC, then potassium glycolate (1 L of 5M solution in water) was added at room temperature, and the mixture was aged for 2 hours. The reaction mixture was then washed with 5 wt,% aqueous $NaHCO_3$ solution, and then with 5 wt. % aqueous NaCl solution. The organic layer was dried over $Na_2SO_4$, filtered, concentrated to 0.5 L, and the concentrated organic was mixed with PTSA monohyrate (30.3 g) p-toluenesulfonic acid monohydrate in 0.9 L IPAc in the presence of 2% seed at 50-60° C. The slurry was aged 12 hours at room temperature, filtered, washed with 0.1 L IPAC and then with 200 mL IPAc/n-heptane (1:1 mixture), and the solid was dried in vacuo at room temperature to afford the amine PTSA salt (105.9 g, 92.2 wt %, 73% yield).

$^1$H NMR (400 MHz, $CDCl_3$): δ 9.31 (br s, 1 H), 9.01 (br s, 1H), 7.98-7.96 (m, 2 H), 7.68-7.65 (m, 1 H), 7.56-7.50 (m, 4H), 7.20 (dd, J=8.3, 5.5 Hz, 2H), 7.07 (d, J=8.0 Hz, 2H), 6.86 (t, J=9.7 Hz, 2H), 5.25 (dd, J=15.0, 5.7 Hz, 1 H), 4.51 (dd, J=14.6, 6.4 Hz, 1 H), 4.37 (br s, 1 H), 4.23 (dd, J=14.6, 5.8 Hz, 1H), 3.55 (br s, 1 H), 3.37-3.26 (m, 2H), 3.18 (s, 3H), 3.14-3.09 (m, 1H), 2.32 (s, 3 H), 2.28-2.20 (m, 1 H), 2.17-2.04 (m, 2H), 1.90 (br s, 1H), 1.83-1.70 (m, 1 H), 1.37 (t, J=7.0 Hz, 3 H).

The amine PTSA salt can then be treated with the appropriate amount of base (e.g., NaOH or methylamine) and the resulting free amine can then be acylated with N,N-dimethyloxamic acid in a manner similar to that described in Step 12 of Example 6-1 to provide Compound 6A which can be recrystallized, e.g., in the manner described at the end of Example 6-1.

EXAMPLE 14

Alternative Preparation of the Enamine in Step 15 of Example 13

Step 1: Formation of the Ketone

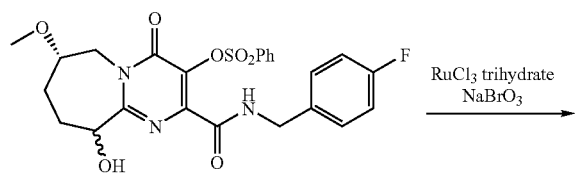

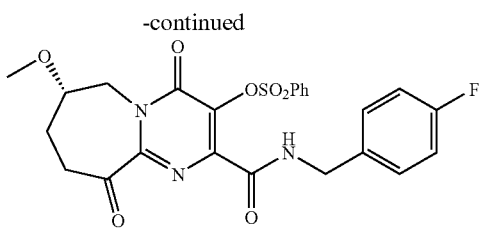

The alcohol starting material (4.1 g, 7.92 mmol) was dissolved in acetonitrile (30 mL) and water (15 mL) in a 150 mL RB with over-head stirrer. Ruthenium trichloride trihydrate (0.041 g, 0.158 mmol) was added, followed by the addition of sodium bromate (0.7 g, 4.64 mmol) in one portion at room temperature, resulting in a mild and gradual exotherm from 18° C. up to 25° C. over 10 minutes. The reaction mixture was aged at room temperature for 1 hour, then water (15 mL) was added and the slurry aged 30 minutes at room temperature. The slurry was then filtered, rinsed with 60/40 water/acetonitrile (25 mL), dried at 45° C. in vacuum oven for 4 hours to afford the desired ketone as white crystalline solid (3.3 g, 83% yield).

Step 2: Formation of the Enamine

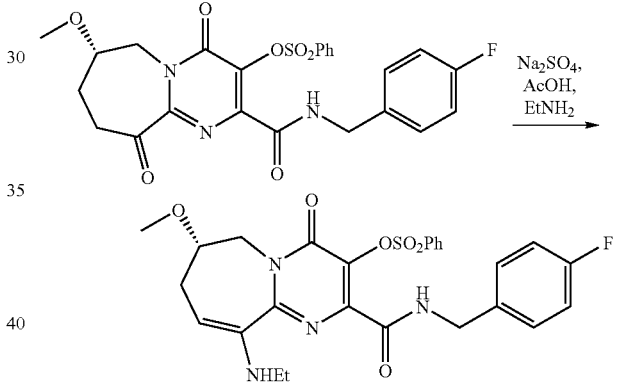

Ethylamine (2.0M in THF, 2.91 mL) was add to a mixture of sodium sulfate (331 mg) and acetic acid (384 mg) in MeCN (6 mL), and the resulting slurry was aged for 5 minutes, after which the starting ketone (600 mg) in MeCN (6 mL) was added. The reaction mixture was then aged at 35° C. for 3 hours, cooled to room temperature, filtered, and concentrated to 6 mL. The resulting mixture was added to aqueous 1M $NaHCO_3$ solution (40 mL) and the solid was filtered, washed with water, and dried in vacuo at 35° C. for 12 hours to afford a yellow solid (530 mg, 82% yield). $^1$H NMR (500 MHz, DMSO-$d_6$): δ 9.16 (t, J=6.1 Hz, 1H), 7.93-7.91 (m, 2H), 7.80 (t, J=7.4 Hz, 1H), 7.65 (t, J=7.5 Hz, 2H), 7.34-7.31 (dd, J=8.6, 5.6 Hz, 2H), 7.18-7.11 (m, 2H), 5.15 (br s, 1H), 4.79 (t, J=7.7 Hz, 1H), 4.36-4.33 (m, 1H), 4.31 (d, J=6.0 Hz, 2H), 3.92-3.86 (m, 1H), 3.77 (dd, J=13.6 Hz, 4.0 Hz, 1H), 3.26 (s, 3H), 2.90 (q, J=7.0 Hz, 2H), 2.32-2.25 (m, 1H), 1.89-1.84 (m, 1H), 1.15 (t, J=7.0 Hz, 3H).

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of Formula I:

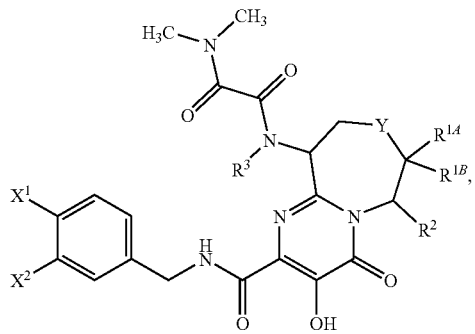

or a pharmaceutically acceptable salt thereof, wherein:
$X^1$ and $X^2$ are each independently H, halogen, or $C_{1-3}$ alkyl, with the proviso that at least one of $X^1$ and $X^2$ is other than H;
Y is $CH_2$;
$R^3$ is $C_{1-3}$ alkyl; and
(i) $R^2$ is H, $R^{1A}$ is $C_{1-3}$ alkyl and $R^{1B}$ is $C_{1-3}$ alkyl or O—$C_{1-4}$ alkyl; or
(ii) $R^2$ is $C_{1-3}$ alkyl, $R^{1A}$ is H, and $R^{1B}$ is H; or
(iii) $R^2$ is H, $R^{1A}$ is H, and $R^{1B}$ is O—$C_{1-4}$ alkyl.

2. A compound according to claim 1, or a pharmaceutically acceptable salt thereof, wherein:
$X^1$ is F or $CH_3$;
$X^2$ is H, F, or $CH_3$, and provided that:
(A) when $X^1$ is F, then $X^2$ is H or $CH_3$, and
(B) when $X^1$ is $CH_3$, then $X^2$ is F;
Y is $CH_2$;
$R^3$ is $CH_3$ or $CH_2CH_3$; and
(i) $R^2$ is H, $R^3$ is $CH_3$, $R^{1A}$ is $CH_3$ and $R^{1B}$ is $CH_3$ or $OCH_3$; or
(ii) $R^2$ is $CH_3$, $R^3$ is $CH_3$, $R^{1A}$ is H, and $R^{1B}$ is H; or
(iii) $R^2$ is H, $R^3$ is $CH_2CH_3$, $R^{1A}$ is H, and $R^{1B}$ is $OCH_3$.

3. A compound according to claim 2, or a pharmaceutically acceptable salt thereof, wherein the compound is a compound of Formula II:

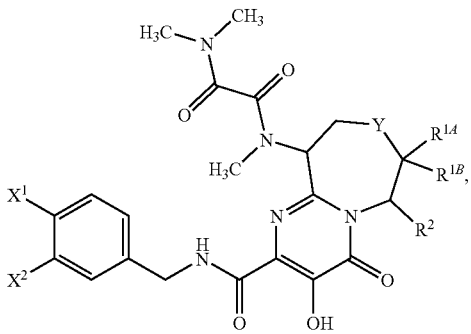

wherein
(i) $R^2$ is H, $R^{1A}$ is $CH_3$ and $R^{1B}$ is $CH_3$ or $OCH_3$, or
(ii) $R^2$ is $CH_3$, and $R^{1A}$ is H, and $R^{1B}$ is H.

4. A compound according to claim 2, or a pharmaceutically acceptable salt thereof, wherein the compound is a compound of Formula III:

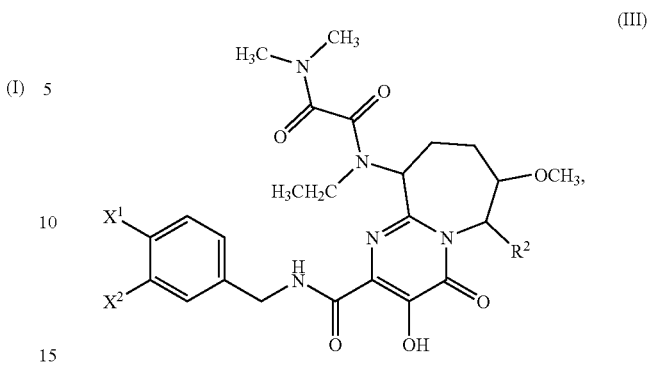

wherein R2 is H.

5. A compound according to claim 1, or a pharmaceutically acceptable salt thereof, wherein the compound is a stereomerically pure compound.

6. A compound according to claim 1, or a pharmaceutically acceptable salt thereof, wherein the compound is

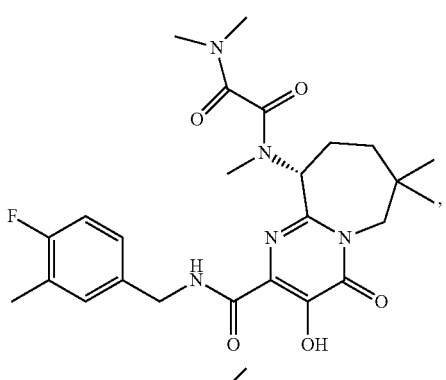

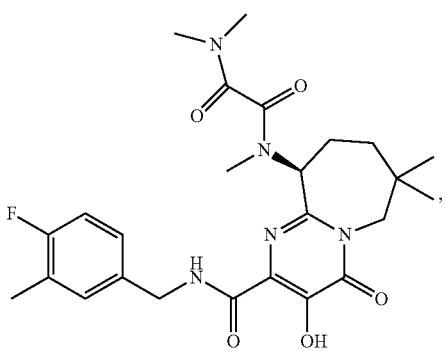 [SMILES: Cc1cc(CNC(=O)c2nc3n(c(=O)c2O)CC(C)(C)CC[C@H]3N(C)C(=O)C(=O)N(C)C)ccc1F]

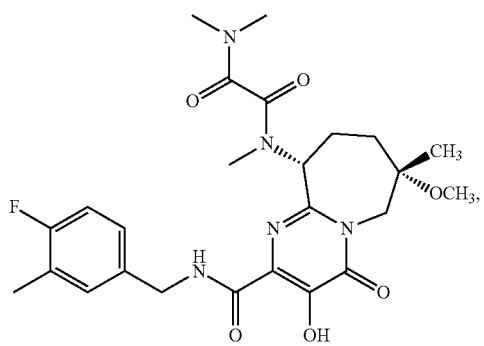 [SMILES: CO[C@@]1(C)CC[C@@H](N(C)C(=O)C(=O)N(C)C)c2nc(C(=O)NCc3ccc(F)c(C)c3)c(O)c(=O)n2C1]

135
-continued
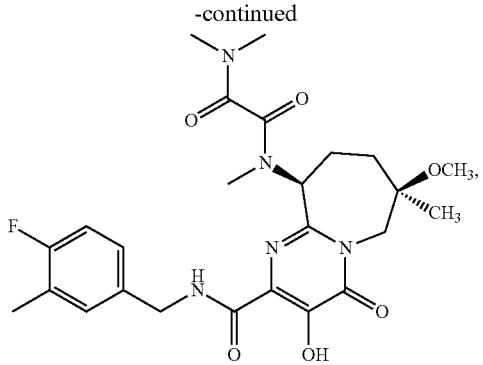
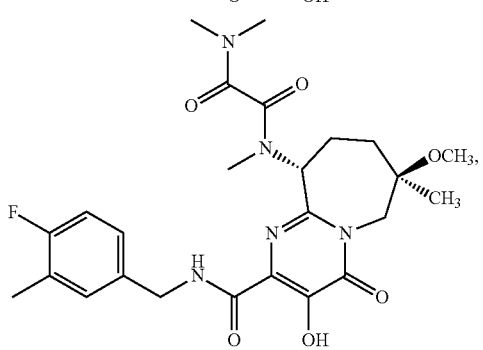
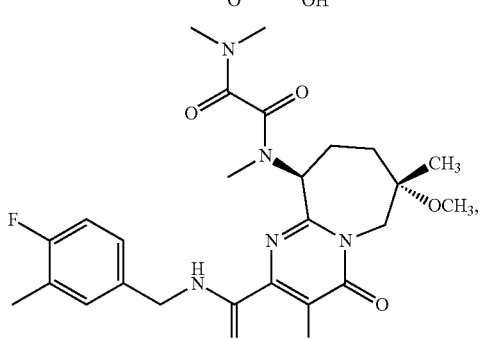
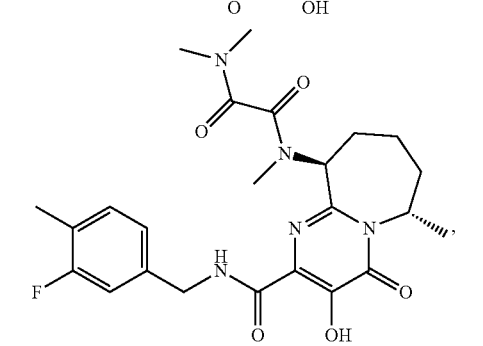
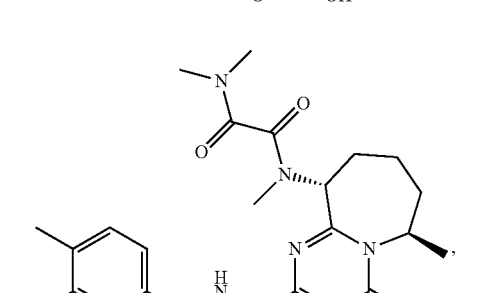
136
-continued
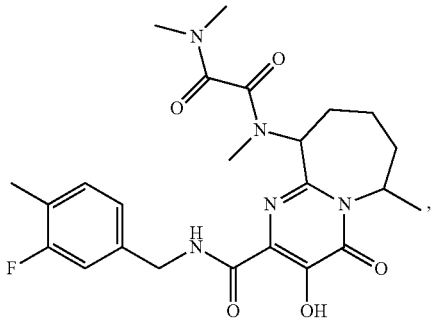
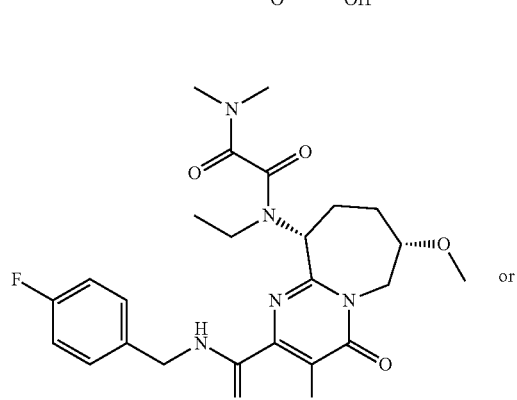
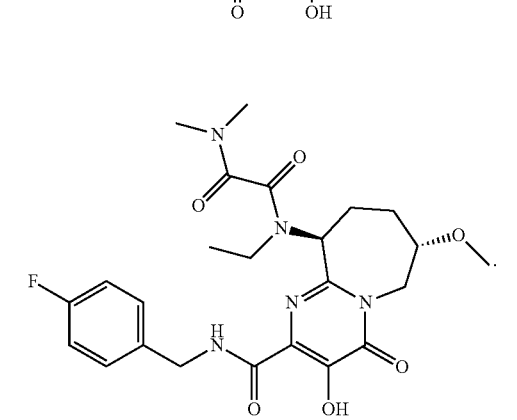
or
7. A compound according to claim 6, or a pharmaceutically acceptable salt thereof, wherein the compound is
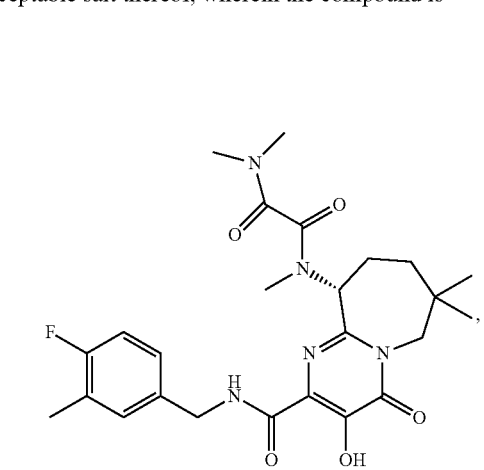

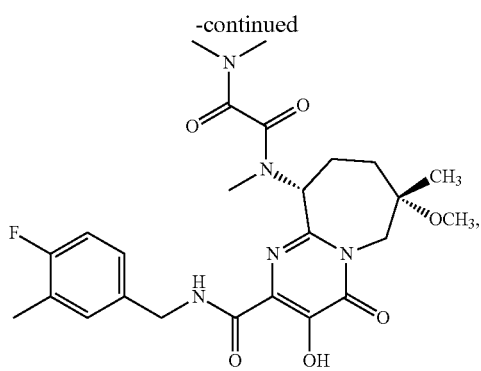

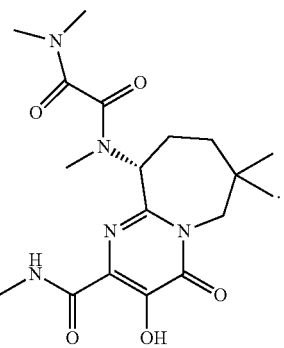

9. A compound according to claim 7, or a pharmaceutically acceptable salt thereof, wherein the compound is

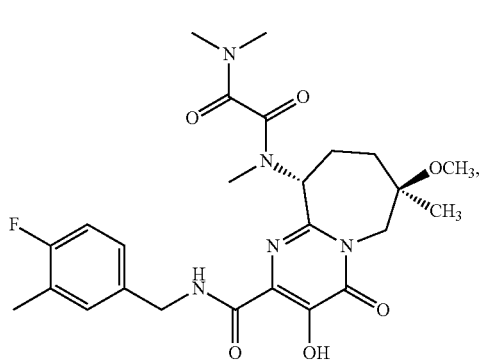

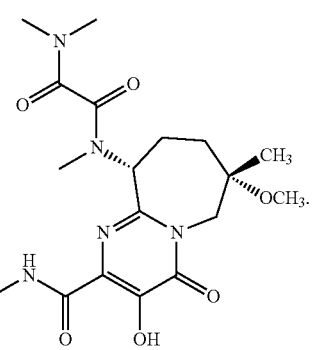

10. A crystalline form of the compound of claim 9, wherein the crystalline form is characterized by an X-ray powder diffraction pattern obtained using copper $K_\alpha$ radiation which comprises 2Θ values in degrees of about 8.5, 9.3, 13.3, 17.0, 18.8 and 20.8.

11. A compound according to claim 7, or a pharmaceutically acceptable salt thereof, wherein the compound is

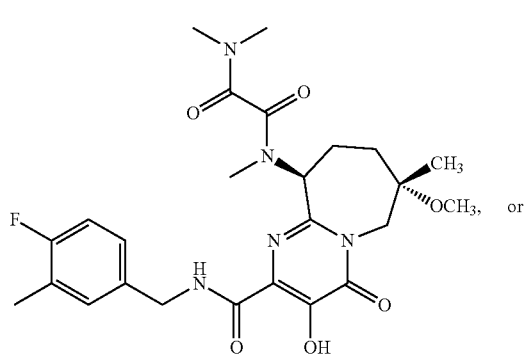 or

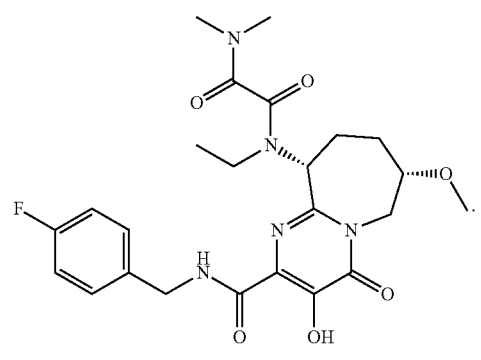

8. A compound according to claim 7, or a pharmaceutically acceptable salt thereof, wherein the compound is

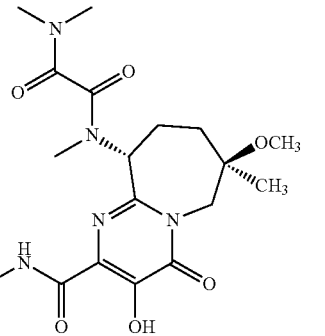 or

-continued

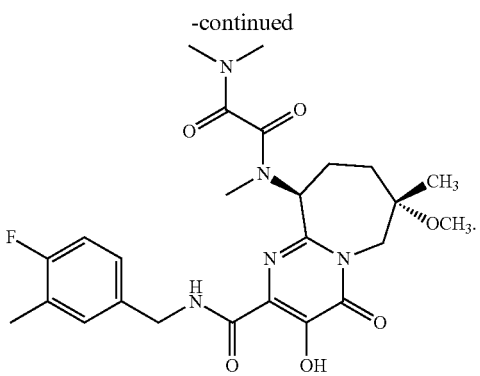

12. A compound according to claim 7, or a pharmaceutically acceptable salt thereof, wherein the compound is

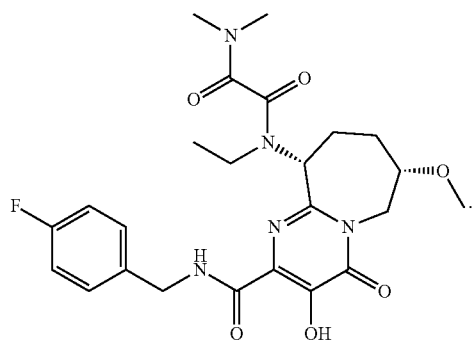

13. A crystalline form of the compound of claim 12, wherein the crystalline form is characterized by an X-ray powder diffraction pattern obtained using copper $K_\alpha$ radiation which comprises 2Θ values in degrees of about 10.6, 14.2, 17.4 18.8 and 20.4.

14. A compound according to claim 7, wherein the compound is stereomerically pure.

15. A pharmaceutical composition comprising an effective amount of a compound according to claim 1, or a pharmaceutically acceptable salt thereof, and a pharmaceutically acceptable carrier.

16. A method for the treatment or prophylaxis of infection by HIV in a subject in need thereof, which comprises administering to the subject an effective amount of the compound according to claim 1 or a pharmaceutically acceptable salt thereof.

17. A process for preparing a hexahydropyrimidoazepine compound of Formula S-III:

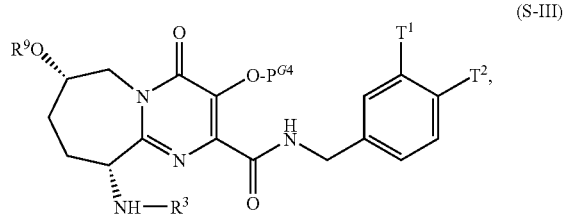

which comprises:
(S-B) hydrogenating a compound of Formula S-II

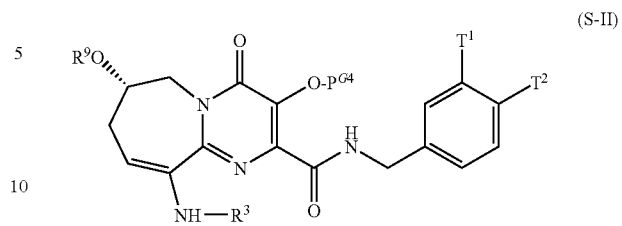

in the presence of a catalystic amount of a cationic rhodium complex having a chiral bidentate or monodentate phosphine ligand; and which optionally further comprises either:
(S-Aa) contacting a compound of Formula S-Ia:

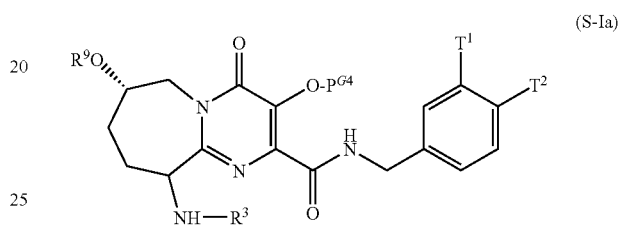

first with an oxidizing agent and then with tertiary amine base to obtain Compound S-II; or
(S-Ab) contacting a compound of Formula S-Ib:

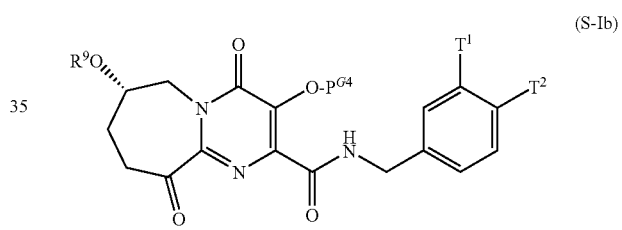

with an amine of Formula $R^3$—$NH_2$ in the presence of an acid to obtain Compound S-II;
wherein:
$R^3$ is $CH_3$ or $CH_2CH_3$;
$R^9$ is $CH_3$ or $CH_2CH_3$;
$P^{G4}$ is a hydroxy protective group; and
$T^1$ and $T^2$ are each independently selected from the group consisting of H, Cl, Br, F and $CH_3$, with the proviso that no more than one of $T^1$ and $T^2$ is H.

18. A pharmaceutical composition comprising an effective amount of a compound according to claim 6, or a pharmaceutically acceptable salt thereof, and a pharmaceutically acceptable carrier.

19. A pharmaceutical composition comprising an effective amount of a compound according to claim 12, or a pharmaceutically acceptable salt thereof, and a pharmaceutically acceptable carrier.

20. A method for the treatment of infection by HIV in a subject in need thereof, which comprises administering to the subject an effective amount of the compound according to claim 6, or a pharmaceutically acceptable salt thereof.

21. A method for the treatment of infection by HIV in a subject in need thereof, which comprises administering to the subject an effective amount of the compound according to claim 12, or a pharmaceutically acceptable salt thereof.

* * * * *